United States Patent
Takahashi et al.

(10) Patent No.: US 11,993,585 B2
(45) Date of Patent: *May 28, 2024

(54) POLY-ADP RIBOSE POLYMERASE (PARP) INHIBITORS

(71) Applicant: Mitobridge, Inc., Cambridge, MA (US)

(72) Inventors: Taisuke Takahashi, Tsukuba (JP); Arthur Kluge, Lincoln, MA (US); Bharat Lagu, Acton, MA (US); Nan Ji, Arlington, MA (US)

(73) Assignee: Mitobridge, Inc., Cambridge, MA (US)

( * ) Notice: Subject to any disclaimer, the term of this patent is extended or adjusted under 35 U.S.C. 154(b) by 184 days.

This patent is subject to a terminal disclaimer.

(21) Appl. No.: 17/342,873

(22) Filed: Jun. 9, 2021

(65) Prior Publication Data
US 2022/0033380 A1    Feb. 3, 2022

Related U.S. Application Data

(63) Continuation of application No. 16/473,127, filed as application No. PCT/US2017/068636 on Dec. 28, 2017, now Pat. No. 11,034,670.

(60) Provisional application No. 62/440,581, filed on Dec. 30, 2016.

(51) Int. Cl.
| | | |
|---|---|---|
| *C07D 401/14* | (2006.01) | |
| *A61P 13/12* | (2006.01) | |
| *C07D 401/06* | (2006.01) | |
| *C07D 403/06* | (2006.01) | |
| *C07D 403/14* | (2006.01) | |
| *C07D 405/14* | (2006.01) | |
| *C07D 417/14* | (2006.01) | |
| *C07D 471/04* | (2006.01) | |
| *C07D 487/04* | (2006.01) | |
| *C07D 495/04* | (2006.01) | |

(52) U.S. Cl.
CPC ............ *C07D 401/14* (2013.01); *A61P 13/12* (2018.01); *C07D 401/06* (2013.01); *C07D 403/06* (2013.01); *C07D 403/14* (2013.01); *C07D 405/14* (2013.01); *C07D 417/14* (2013.01); *C07D 471/04* (2013.01); *C07D 487/04* (2013.01); *C07D 495/04* (2013.01)

(58) Field of Classification Search
CPC ............................ A61P 13/12; C07D 401/14
See application file for complete search history.

(56) References Cited

U.S. PATENT DOCUMENTS

| | | | |
|---|---|---|---|
| 6,953,857 B2 | 10/2005 | Nazare et al. | |
| 7,799,775 B2 | 9/2010 | Sato et al. | |
| 7,935,706 B2 | 5/2011 | Masui et al. | |
| 8,039,674 B2 | 10/2011 | Habashita et al. | |
| 8,349,850 B2 | 1/2013 | Tworowski et al. | |
| 9,353,067 B2 | 5/2016 | Kogan et al. | |
| 9,901,577 B2 | 2/2018 | Dorsch et al. | |
| 11,034,670 B2* | 6/2021 | Takahashi | A61P 21/00 |
| 2002/0082268 A1 | 6/2002 | Gao et al. | |
| 2003/0087917 A1 | 5/2003 | Strack et al. | |
| 2004/0077667 A1 | 4/2004 | Matsuoka et al. | |
| 2006/0063767 A1 | 3/2006 | Javaid et al. | |
| 2007/0032502 A1 | 2/2007 | Mallams et al. | |
| 2019/0194163 A1 | 6/2019 | Heffernan et al. | |

FOREIGN PATENT DOCUMENTS

| | | |
|---|---|---|
| CN | 102838600 A | 12/2012 |
| CN | 105924434 A | 9/2016 |
| WO | 2006/003146 A1 | 1/2006 |
| WO | 2012/064973 A2 | 5/2012 |
| WO | 2014/036022 A1 | 3/2014 |
| WO | 2015/014442 A1 | 2/2015 |
| WO | 2015/169421 A1 | 11/2015 |

OTHER PUBLICATIONS

Giannini et al., Novel PARP-1 inhibitors based on a 2-propanoyl-3H-quinazolin-4-one scaffold. Bioorg Med Chem Lett. Jan. 15, 2014;24(2):462-6.
Kaya et al., Synthesis and biological evaluation of novel piperazine containing hydrazone derivatives. J Chem. Aug. 10, 2016;2016(Article ID 5878410):1-7.
McMahon, VEGF receptor signaling in tumor angiogenesis. Oncologist. 2000;5 Suppl 1:3-10.
Pinedo et al., Translational research: the role of VEGF in tumor angiogenesis. Oncologist. 2000;5 Suppl 1:1-2.
International Preliminary Report on Patentability for Application No. PCT/US2017/068636, dated Mar. 5, 2019, 6 pages.
International Search Report and Written Opinion for Application No. PCT/US2017/068636, dated Mar. 6, 2018, 11 pages.

* cited by examiner

*Primary Examiner* — Paul V Ward
(74) *Attorney, Agent, or Firm* — McCarter & English, LLP; Wei Song; James M. Alburger

(57) ABSTRACT

The present invention is related to a pharmaceutical composition comprising a pharmaceutically acceptable carrier or diluent and a compound represented by the following structural formula:

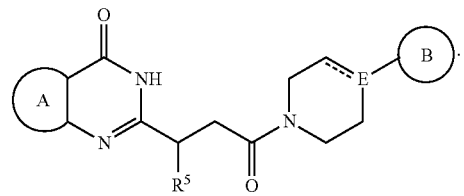

The present invention is also related a method of treating a subject with a disease which can be ameliorated by inhibition of poly(ADP-ribose)polymerase (PARP). The definitions of the variables are provided herein.

20 Claims, 1 Drawing Sheet

PARP1 inhibitors Example 29 and Example 30 reduce kidney injury
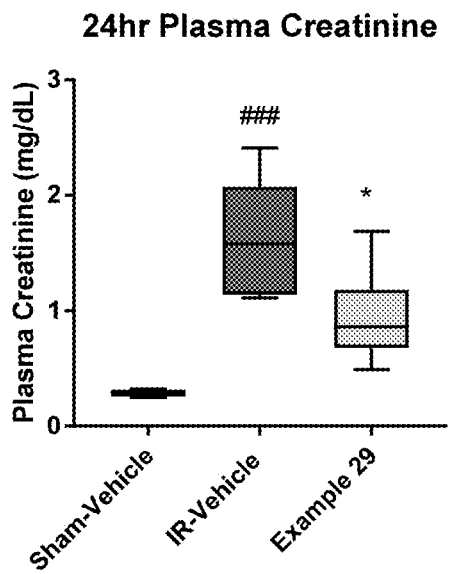
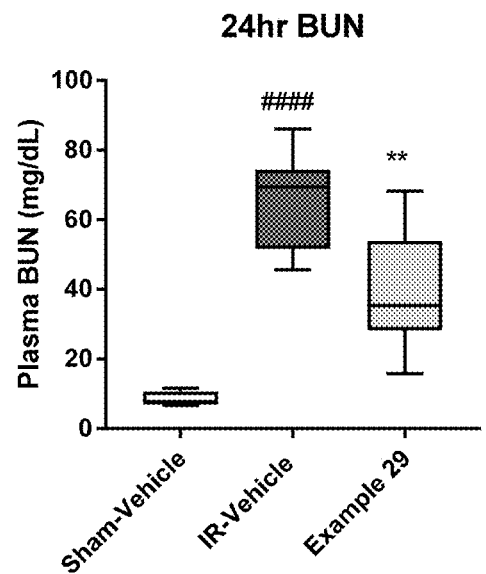
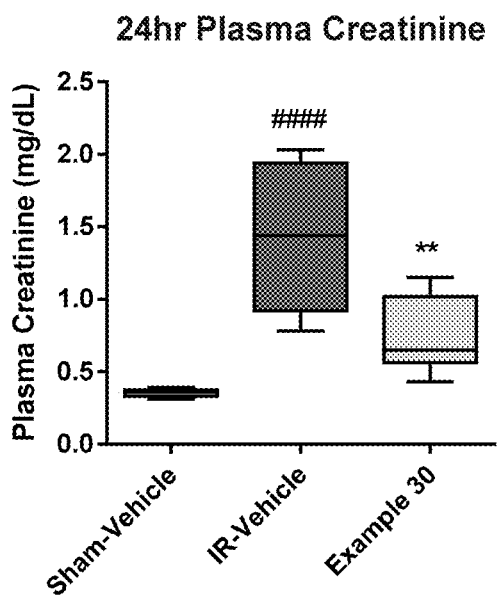
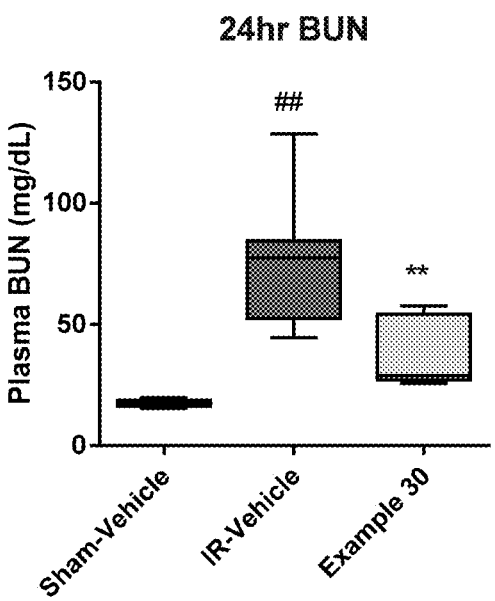

POLY-ADP RIBOSE POLYMERASE (PARP) INHIBITORS

CROSS-REFERENCES TO RELATED APPLICATIONS

This application is Continuation Application of U.S. application Ser. No. 16/473,127, filed on Jun. 24, 2019, which is the U.S. national stage filing, under 35 U.S.C. § 371(c), of International Application No. PCT/US2017/068636, filed on Dec. 28, 2017, which claims the benefit of U.S. Provisional Application No. 62/440,581, filed on Dec. 30, 2016. The entire teachings of the aforementioned applications are incorporated herein by reference.

FIELD OF THE INVENTION

This application is directed to inhibitors of poly(ADP-ribose)polymerase (PARP), particularly PARP-1 inhibitors, and methods for their use, such as to treat or prevent one or more PARP-related diseases.

BACKGROUND OF THE INVENTION

The nuclear enzyme poly(ADP-ribose) polymerase-1 (PARP-1) is a member of the PARP enzyme family. This growing family of enzymes consists of PARPs such as, for example: PARP-1, PARP-2, PARP-3 and Vault-PARP.

PARP plays a role in the repair of DNA strand breaks and its inhibition is therefore an established approach to cancer treatment. PARP inhibition can be especially effective when combined with DNA damaging treatment, such as with ionizing radiation or after treatment with DNA damaging agents such as methylating agents, topoisomerases I inhibitors and other chemotherapeutic agents such as cisplatin and bleomycin. The inhibition of PARP enzymatic activity should lead to an enhanced sensitivity of the tumor cells towards DNA damaging treatments. PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways.

The inhibition of PARP-2 can provide protection against oxidative stress (see Szanto, et al., *Cell Mol. Life Sci.* 69:4079 (2012)). As such, PARP inhibitors can be used to treat diseases characterized by oxidative stress (e.g., ischemia-reperfusion injury, inflammatory diseases, burn, Parkinsonism, Huntington's diseases, Alzheimer's disease and toxic insults).

PARP-1 and PARP-2 are pro-inflammatory (see Rosado et al., *Immunology* 139:428 (2013)). Their inhibition, as such, can be used to treat, for example, asthma, arthritis, colitis, chronic obstructive pulmonary disease (COPD), acute respiratory distress syndrome (ARDS), atherosclerosis, cardia remodeling after myocardial infarction, sepsis, endotoxic shock, hemorrhagic shock, graft-versus-host disease, encephalomyelitis and autoimmune nephritis.

PARP inhibition can also protect against viral infections (see Atasheva et al., *J. Virol.* 88:2116 (2014) and Virag and Szabo *Pharmacol. Rev.* 54:375 (2002)), e.g., against human immune deficiency virus 1, Venezuelan equine encephalitis virus, herpes simplex virus, human hepatitis B virus, and human cytomegalovirus infections (Virag and Szabo *Pharmacol. Rev.* 54:375 (2002)).

PARPs are involved in the control of glucose homeostasis (see Bai and Canto *Cell Metab.* 16:290 (2012), Riffel et al., *Nat. Rev. Drug Discovery* 11:923 (2012) and Yeh et al., *Diabetes* 58:2476 (2009). For example, PARP-1 inhibition improves glucose disposal and insulin sensitivity (see Bai and Canto *Cell Metab.* 16:290 (2012) and Pirinen et al., *Cell Metab.* 19:1034 (2014)). As such, PARP inhibition is useful for treating disease and conditions such as metabolic syndrome and type II diabetes and their subsequent complications such as diabetic neurological, renal and ocular complications.

As such, there is a need for new and improved PARP inhibitors for these and other therapeutic indications.

SUMMARY OF THE INVENTION

Applicant has now discovered novel compounds which are effective inhibitors of PARP (see Examples 1-53). In particular, they have selective inhibitory activities against PARP-1 over PARP-2 (see Example 54). Additionally, it has been demonstrated that certain of these PARP inhibitors are useful for increasing the amount of NAD$^+$ in cells (see Example 55).

In a first embodiment, the invention provides a pharmaceutical composition comprising a pharmaceutically acceptable carrier or diluent and a compound represented by the following structural formula:

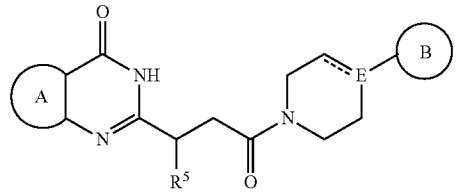

or a pharmaceutically acceptable salt thereof, wherein:
Ring A is optionally substituted phenyl or an optionally substituted 5-6 membered heteroaryl;
Ring B is aryl, 5-6 membered heteroaryl or 5-6 membered heterocyclyl, each optionally substituted with one or more substituents represented by R$^3$;
"----" is absent or a bond;
E is N or CH when "----" is absent or E is C when "-----" is a bond;

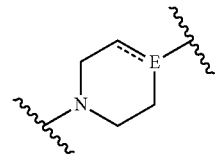

is optionally substituted with (C$_1$-C$_5$)alkyl or hydroxy (C$_1$-C$_5$)alkyl;
each R$^3$ is independently selected from the group consisting of -halogen, —CN, —NO$_2$, —OR$^d$, —NR$^e$R$^f$, —S(O)$_i$R$^e$, —C(=NR$^e$)NR$^e$R$^f$, —NR$^e$S(O)$_i$R$^f$, —S(O)$_i$ NR$^e$R$^f$, —C(=O)OR$^e$, —OC(=O)OR$^e$, —C(=S)OR$^e$, —O(C=S)R$^e$, —C(=O)NR$^e$R$^f$, —NR$^e$C(=O)R$^f$, —C(=S)NR$^e$R$^f$, —NR$^e$C(=S)R$^f$, —NR$^e$(C=O)OR$^f$, —O(C=O)NR$^e$R$^f$, —NR$^e$(C=S)OR$^f$, —O(C=S)NR$^e$R$^f$, —NR$^e$(C=O)NR$^e$R$^f$, —NR$^e$(C=S)NR$^e$R$^f$, —C(=S)R$^e$, —C(=O)R$^e$, halo(C$_1$-C$_5$)

alkyl, and $(C_1-C_5)$alkyl, wherein the $(C_1-C_5)$alkyl represented by $R^3$ is optionally substituted with —CN, —NO$_2$, —OR$^e$, —NR$^e$R$^f$, —S(O)$_i$R$^e$, —NR$^e$S(O)$_i$R$^f$, —S(O)$_i$NR$^e$R$^f$, —C(=O)OR$^e$, —OC(=O)OR$^e$, —C(=S)OR$^e$, —O(C=S)R$^e$, —C(=O)NR$^e$R$^f$, —NR$^e$C(=O)R$^f$, —C(=S)NR$^e$R$^f$, —NR$^e$C(=S)R$^f$, —NR$^e$(C=O)OR$^f$, —O(C=O)NR$^e$R$^f$, —NR$^e$(C=S)OR$^f$, —O(C=S)NR$^e$R$^f$, —NR$^e$(C=O)NR$^e$R$^f$, —NR$^e$(C=S)NR$^e$R$^f$, —C(=S)R$^e$, or —C(=O)R$^e$;

$R^d$ is —H, halo$(C_1-C_5)$alkyl or $(C_1-C_5)$alkyl, wherein the $(C_1-C_5)$alkyl is optionally substituted with hydroxyl or $(C_1-C_3)$alkoxy;

each $R^e$ is independently selected from the group consisting of —H and $(C_1-C_5)$alkyl optionally substituted with hydroxyl or $(C_1-C_3)$alkoxy;

each R is independently selected from the group consisting of —H, $(C_1-C_5)$alkyl optionally substituted with hydroxyl or $(C_1-C_3)$alkoxy, $(C_3-C_6)$cycloalkyl optionally substituted with $(C_1-C_2)$ alkyl, and 4-6 membered oxygen-containing heterocyclyl optionally substituted with $(C_1-C_2)$ alkyl; or —NR$^e$R$^f$ taken together is a 4-6 membered heterocyclyl optionally substituted with $(C_1-C_2)$ alkyl; or —C(=NR$^e$)NR$^e$R$^f$ taken together is a 4-6 membered heterocyclyl optionally substituted with R$^e$;

$R^5$ is —H or $(C_1-C_5)$alkyl; and i is 0, 1, or 2.

In a second embodiment, the invention provides a pharmaceutical composition according to the previous embodiment, wherein the compound is represented by the following structural formula:

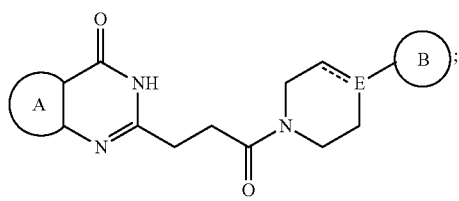

or a pharmaceutically acceptable salt thereof, wherein:

Ring A is optionally substituted phenyl or an optionally substituted 5-6 membered heteroaryl;

Ring B is aryl, 5-6 membered heteroaryl or 5-6 membered heterocyclyl, each optionally substituted with one or more substituents represented by $R^3$;

"----" is absent or a bond;

E is N or CH when "----" is absent or E is C when "-----" is a bond;

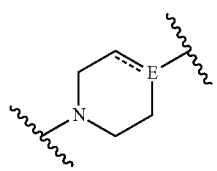

is optionally substituted with $(C_1-C_5)$alkyl or hydroxy $(C_1-C_5)$alkyl;

each $R^3$ is independently selected from the group consisting of -halogen, —CN, —NO$_2$, —OR$^d$, —NR$^e$R$^f$, —S(O)$_i$R$^e$, —C(=NR$^e$)NR$^e$R$^f$, —NR$^e$S(O)$_i$R$^f$, —S(O)$_i$ NR$^e$R$^f$, —C(=O)OR$^e$, —OC(=O)OR$^e$, —C(=S)OR$^e$, —O(C=S)R$^e$, —C(=O)NR$^e$R$^f$, —NR$^e$C(=O)R$^f$, —C(=S)NR$^e$R$^f$, —NR$^e$C(=S)R$^f$, —NR$^e$(C=O)OR$^f$, —O(C=O)NR$^e$R$^f$, —NR$^e$(C=S)OR$^f$, —O(C=S)NR$^e$R$^f$, —NR$^e$(C=O)NR$^e$R$^f$, —NR$^e$(C=S)NR$^e$R$^f$, —C(=S)R$^e$, —C(=O)R$^e$, halo$(C_1-C_5)$ alkyl and $(C_1-C_5)$alkyl, wherein the $(C_1-C_5)$alkyl represented by $R^3$ is optionally substituted with —CN, —NO$_2$, —OR$^e$, —NR$^e$R$^f$, —S(O)$_i$R$^e$, —NR$^e$S(O)$_i$R$^f$, —S(O)$_i$NR$^e$R$^f$, —C(=O)OR$^e$, —OC(=O)OR$^e$, —C(=S)OR$^e$, —O(C=S)R$^e$, —C(=O)NR$^e$R$^f$, —NR$^e$C(=O)R$^f$, —C(=S)NR$^e$R$^f$, —NR$^e$C(=S)R$^f$, —NR$^e$(C=O)OR$^f$, —O(C=O)NR$^e$R$^f$, —NR$^e$(C=S)OR$^f$, —O(C=S)NR$^e$R$^f$, —NR$^e$(C=O)NR$^e$R$^f$, —NR$^e$(C=S)NR$^e$R$^f$, —C(=S)R$^e$, or —C(=O)R$^e$;

$R^d$ is —H, halo$(C_1-C_5)$alkyl or $(C_1-C_5)$alkyl, wherein the $(C_1-C_5)$alkyl is optionally substituted with hydroxyl or $(C_1-C_3)$alkoxy;

each $R^e$ is independently selected from the group consisting of —H and $(C_1-C_5)$alkyl optionally substituted with hydroxyl or $(C_1-C_3)$alkoxy;

each $R^f$ is independently selected from the group consisting of —H, $(C_1-C_5)$alkyl optionally substituted with hydroxyl or $(C_1-C_3)$alkoxy, $(C_3-C_6)$cycloalkyl optionally substituted with $(C_1-C_2)$ alkyl, and 4-6 membered oxygen-containing heterocyclyl optionally substituted with $(C_1-C_2)$ alkyl; or —NR$^e$R$^f$ taken together is a 4-6 membered heterocyclyl optionally substituted with $(C_1-C_2)$ alkyl; or —C(=NR$^e$)NR$^e$R$^f$ taken together is a 4-6 membered heterocyclyl optionally substituted with R$^e$, wherein the remainder of the variables (e.g., i) are defined in the first embodiment.

In a third embodiment, the invention provides a pharmaceutical composition according to the first or second embodiment, wherein the compound is represented by the following structural formula:

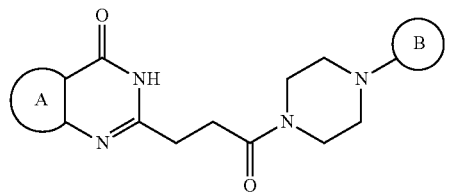

or a pharmaceutically acceptable salt thereof, wherein:

Ring A is optionally substituted phenyl or an optionally substituted 5-6 membered heteroaryl;

Ring B is aryl, 5-6 membered heteroaryl or 5-6 membered heterocyclyl, each optionally substituted with one or more substituents represented by $R^3$; and

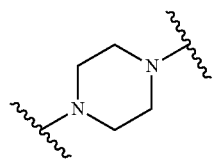 [SMILES: *N1CCN(*)CC1]

is optionally substituted with $(C_1-C_5)$alkyl or hydroxy $(C_1-C_5)$alkyl, wherein the remainder of the variables (e.g., $R^3$) are as defined in the first, or second embodiment.

In a fourth embodiment, the invention provides a pharmaceutical composition according to the first, second, or third embodiment, wherein the compound is represented by a structural formula selected from the group consisting of:

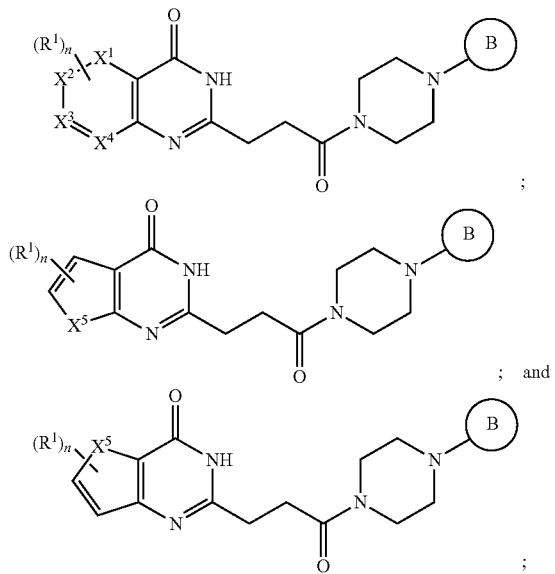

or a pharmaceutically acceptable salt thereof, wherein:

$X^1$, $X^2$, $X^3$ and $X^4$ are each independently selected from the group consisting of N and CH, provided no more than two of $X^1$, $X^2$, $X^3$ and $X^4$ is N;

$X^5$ is $NR^2$, O, or S;

Ring B is aryl, 5-6 membered heteroaryl or 5-6 membered heterocyclyl, each optionally substituted with one or more substituents represented by $R^3$;

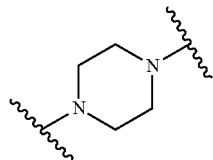 [SMILES: *N1CCN(*)CC1]

is optionally substituted with $(C_1\text{-}C_5)$alkyl or hydroxy $(C_1\text{-}C_5)$alkyl;

each $R^1$ is independently selected from the group consisting of -halogen, —CN, —NO$_2$, —OR$^c$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, —C(=O)R$^b$, halo(C$_1$-C$_5$)alkyl and (C$_1$-C$_5$)alkyl, wherein the (C$_1$-C$_5$)alkyl represented by R$^1$ is optionally substituted with —CN, —NO$_2$, —OR$^c$, —NR$^a$R$^b$, —S(O)$_i$R$^a$, —NR$^a$S(O)R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=)OR$^b$, —O(C=O) NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, or —C(=O)R$^a$;

$R^2$ is —H, C$_{1\text{-}5}$ alkyl, phenyl, —C(O)(C$_{1\text{-}5}$ alkyl), —C(O) (phenyl), —C(O)O(C$_{1\text{-}5}$ alkyl), —C(O)O(phenyl), —S(O)$_2$(C$_{1\text{-}5}$ alkyl) or —S(O)$_2$(phenyl), wherein each alkyl in the groups represented by R$^2$ independently is optionally substituted with one or more substituents selected from the group consisting of halogen, hydroxy, cyano, phenyl, 5-6 membered heteroaryl, (C$_1$-C$_5$) alkoxy, and halo(C$_1$-C$_5$)alkoxy, and wherein each phenyl in the groups represented by R$^2$ independently is optionally substituted with one or more substituents selected from the group consisting of halogen, hydroxy, nitro, cyano, amino, (C$_1$-C$_5$)alkyl, halo(C$_1$-C$_5$)alkyl, (C$_1$-C$_5$)alkoxy and halo(C$_1$-C$_5$)alkoxy;

each R$^a$ and each R$^b$ are independently selected from the group consisting of —H and (C$_1$-C$_5$)alkyl optionally substituted with hydroxyl or (C$_1$-C$_3$)alkoxy;

R$^c$ is —H, halo(C$_1$-C$_5$)alkyl or (C$_1$-C$_5$)alkyl, wherein the (C$_1$-C$_5$)alkyl is optionally substituted with hydroxyl or (C$_1$-C$_3$)alkoxy;

i is 0, 1, or 2; and n is 0, 1 or 2, wherein the remainder of the variables (e.g., R$^3$) are as defined in the first, second, or third embodiment.

In a fifth embodiment, the invention provides a pharmaceutical composition according to the first, second, third, or fourth embodiment, wherein the compound is represented by a structural formula selected from the group consisting of:

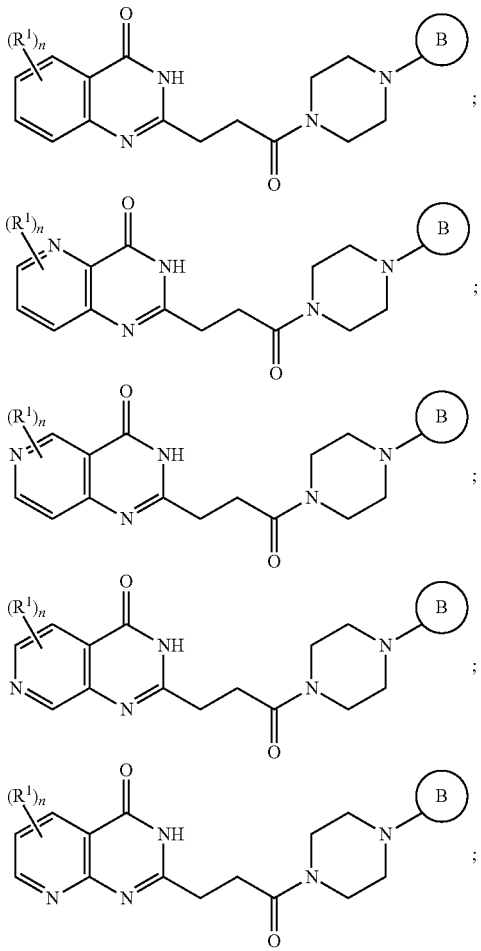

-continued

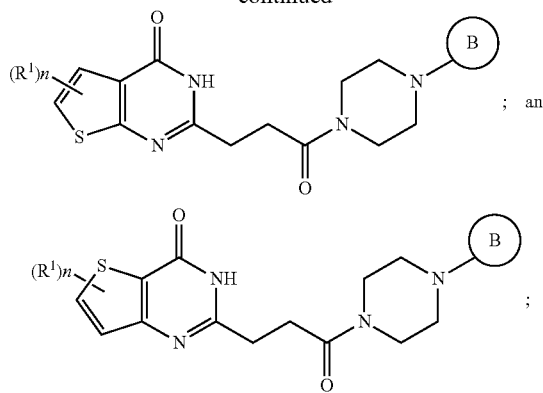

; and

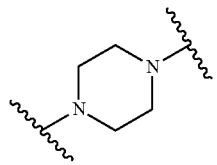 [SMILES: *N1CCN(*)CC1]

;

or a pharmaceutically acceptable salt thereof, wherein:

Ring B is aryl, 5-6 membered heteroaryl or 5-6 membered heterocyclyl, each optionally substituted with one or more substituents represented by $R^3$; and

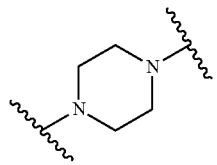 [SMILES: *N1CCN(*)CC1]

is optionally substituted with $(C_1-C_5)$alkyl or hydroxy $(C_1-C_5)$alkyl, wherein the remainder of the variables (e.g., $R^3$) are as defined in the first, second, third, or fourth embodiment.

In a sixth embodiment, the invention provides a pharmaceutical composition according to the first, second, third, fourth, or fifth embodiment, wherein Ring B is selected from the group consisting of

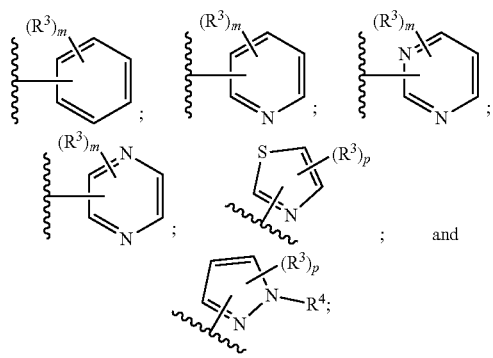

each $R^4$ is —H, $(C_1-C_5)$alkyl, or hydroxy$(C_1-C_5)$alkyl;
each p is independently 0 or 1; and
each m is 0 or 1, or 2, wherein the remainder of the variables (e.g., $R^3$) are as defined in the first, second, third, fourth, or fifth embodiment.

In a seventh embodiment, the invention provides a pharmaceutical composition according to the sixth embodiment, wherein Ring B is selected from the group consisting of

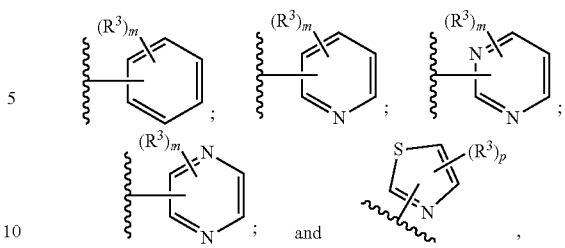

; and wherein the remainder of the variables are as defined in the first, second, third, fourth, fifth, or sixth embodiment.

In an eighth embodiment, the invention provides a pharmaceutical composition according to the fourth, fifth, sixth, or seventh embodiment, wherein:

each $R^1$ is independently halogen, $(C_1-C_5)$alkyl, halo$(C_1-C_5)$alkyl, $(C_1-C_5)$alkoxy, halo$(C_1-C_5)$alkoxy or cyano;
each $R^3$ is independently selected from the group consisting of -halogen, —CN, —C(=NR$^e$)NHR$^f$, —C(=NR$^d$)NR$^e$R$^f$, —S(O)$_i$NR$^e$R$^f$, —C(=O)NR$^e$R$^f$, —C(=S)NR$^e$R$^f$, —O(C=O)NR$^e$R$^f$, —O(C=S)NR$^e$R$^f$, —NR$^d$(C=O)NR$^e$R$^f$, —NR$^d$(C=S)NR$^e$R$^f$ and $(C_1-C_5)$alkyl, wherein the remainder of the variables are as defined in the first, second, third, fourth, fifth, sixth, or seventh embodiment.

In a ninth embodiment, the invention provides a pharmaceutical composition according to the fourth, fifth, sixth, seventh, or eighth embodiment, wherein:

each $R^1$ is independently halogen or $(C_1-C_5)$alkyl;
each $R^3$ is independently selected from the group consisting of -halogen, —CN, —C(=NR$^d$)NR$^e$R$^f$, —C(=O)NR$^e$R$^f$, —C(=NR$^e$)NHR$^f$ and $(C_1-C_5)$alkyl, wherein the remainder of the variables are as defined in the first, second, third, fourth, fifth, sixth or seventh embodiment.

In a tenth embodiment, the invention provides a pharmaceutical composition according to the fourth, fifth, sixth, seventh, or eighth embodiment, wherein:

each $R^1$ is independently chloro, fluoro or methyl;
each $R^3$ is independently selected from the group consisting of chloro, fluoro, —CN, —C(=NR$^d$)NR$^e$R$^f$, —C(=O)NR$^e$R$^f$ and methyl;
the

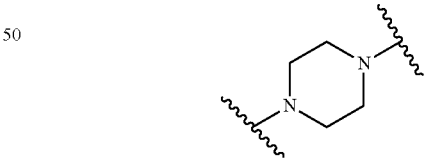

group is optionally substituted with methyl or hydroxymethyl, wherein the remainder of the variables are as defined in the first, second, third, fourth, fifth, sixth, seventh, or eighth embodiment.

In an eleventh embodiment, the invention provides a pharmaceutical composition according to the sixth, seventh, eighth, ninth, or tenth embodiment, wherein each $R^e$ and each $R^f$ are independently selected from the group consisting of —H and methyl; or $R^e$ is —H and $R^f$ is $(C_3-C_6)$cycloalkyl or 4-6 membered oxygen-containing heterocyclyl each optionally substituted with $(C_1-C_2)$ alkyl, wherein the remainder of the variables are as defined in the first, second, third, fourth, fifth, sixth, seventh, eighth, ninth, or tenth embodiment.

In a twelfth embodiment, the invention provides a pharmaceutical composition according to the sixth, seventh, eighth, ninth or tenth embodiment, wherein each $R^e$ and each $R^f$ are independently selected from the group consisting of —H and methyl; or $R^e$ is —H and $R^f$ is cyclopropyl, cyclobutyl or oxetanyl each optionally substituted with methyl, wherein the remainder of the variables are as defined in the first, second, third, fourth, fifth, sixth, seventh, eighth, ninth, tenth or eleventh embodiment.

In a thirteenth embodiment, the invention provides a pharmaceutical composition according to the sixth, seventh, eighth, ninth or tenth embodiment, wherein each $R^3$ is independently selected from the group consisting of chloro, fluoro, —CN, —C(O)NH(cyclopropyl), —C(O)NH$_2$, —C(O)NH(CH$_3$), —C(O)N(CH$_3$)$_2$,

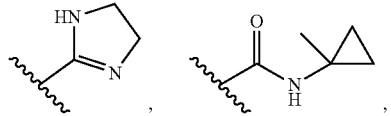

,

—C(O)NH(cyclobutyl),

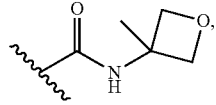 [SMILES: *C(=O)NC1(C)COC1]

—C(=NH)NHCH$_3$, and methyl, wherein the remainder of the variables are as defined in the first, second, third, fourth, fifth, sixth, seventh, eighth, ninth, tenth, eleventh or twelfth embodiment.

In a fourteenth embodiment, the invention provides a pharmaceutical composition according to the fourth embodiment, wherein $R^2$ is —H or (C$_1$-C$_5$)alkyl, preferably, —H or methyl, wherein the remainder of the variables are as defined in the first, second, third, fourth, fifth, sixth, seventh, eighth, ninth, tenth, eleventh, twelfth or thirteenth embodiment.

In a fifteenth embodiment, the invention provides a pharmaceutical composition according to the first or second embodiment, wherein the compound is 6-[(3S)-4-[3-(6-fluoro-4-oxo-3H-quinazolin-2-yl)propanoyl]-3-methyl-piperazin-1-yl]pyridine-3-carbonitrile or a pharmaceutically acceptable salt thereof.

In a sixteenth embodiment, the invention provides a pharmaceutical composition according to the first or second embodiment, wherein the compound is 6-[(3R)-4-[3-(6-fluoro-4-oxo-3H-quinazolin-2-yl)propanoyl]-3-methyl-piperazin-1-yl]pyridine-3-carbonitrile or a pharmaceutically acceptable salt thereof.

In a seventeenth embodiment, the invention provides a pharmaceutical composition according to the first or second embodiment, wherein the compound is 6-[(3S)-4-[3-(5-fluoro-4-oxo-3H-quinazolin-2-yl)propanoyl]-3-methyl-piperazin-1-yl]pyridine-3-carbonitrile or a pharmaceutically acceptable salt thereof.

In an eighteenth embodiment, the invention also includes any one of the compounds disclosed in the Exemplification or the Table in Example 55. Both pharmaceutically acceptable salts of these compounds and the corresponding neutral form of the compounds are included.

In a nineteenth embodiment, a compound of the following structural formula:

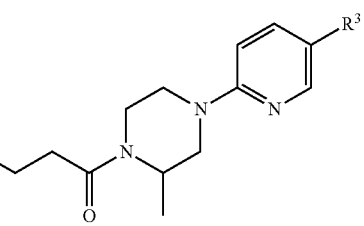

or a pharmaceutically acceptable salt thereof, wherein:
$R^1$ is F or methyl; and
$R^3$ is —CN, —C(=NH)NHCH$_3$,

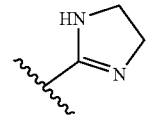

or methyl.

In a twentieth embodiment, the invention provides the compound according to the nineteenth embodiment, wherein: $R^1$ is F; and $R^3$ is —CN.

In a twenty-first embodiment, the invention provides the compound according to the twentieth embodiment, wherein the compound is 6-[(3S)-4-[3-(6-fluoro-4-oxo-3H-quinazolin-2-yl)propanoyl]-3-methyl-piperazin-1-yl]pyridine-3-carbonitrile or a pharmaceutically acceptable salt thereof.

In a twenty-second embodiment, the invention provides the compound according to the twentieth embodiment, wherein the compound is 6-[(3R)-4-[3-(6-fluoro-4-oxo-3H-quinazolin-2-yl)propanoyl]-3-methyl-piperazin-1-yl]pyridine-3-carbonitrile or a pharmaceutically acceptable salt thereof.

In a twenty-third embodiment, the invention provides the compound according to the twentieth embodiment, wherein the compound is 6-[(3S)-4-[3-(5-fluoro-4-oxo-3H-quinazolin-2-yl)propanoyl]-3-methyl-piperazin-1-yl]pyridine-3-carbonitrile or a pharmaceutically acceptable salt thereof.

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

The present invention also provides a method of treating a subject with a disease which can be ameliorated by inhibition of poly(ADP-ribose)polymerase (PARP), comprising administering to the subject an effective amount of one or more disclosed compounds, or a pharmaceutically acceptable salt thereof, or the pharmaceutical composition according to any one of the foregoing embodiments.

Also provided herein is the use of one or more of the disclosed compounds, or a pharmaceutically acceptable salt thereof, or the pharmaceutical composition according to any one of the foregoing embodiments, for the preparation of a medicament for the treatment of a disease which can be ameliorated by inhibition of PARP.

In another embodiment provided herein, the disclosed compounds, or a pharmaceutically acceptable salt thereof, or the pharmaceutical composition according to any one of the foregoing embodiments are for use in treating a disease which can be ameliorated by inhibition of PARP.

In one embodiment, the present invention provides a method of treating a subject with acute kidney injury, comprising administering to the subject an effective amount of one or more disclosed compounds, or a pharmaceutically acceptable salt thereof, or the pharmaceutical composition according to any one of the foregoing embodiments.

Also provided herein is the use of one or more of the disclosed compounds, or a pharmaceutically acceptable salt thereof, or the pharmaceutical composition according to any one of the foregoing embodiments, for the preparation of a medicament for the treatment of acute kidney injury.

In another embodiment provided herein, the disclosed compounds, or a pharmaceutically acceptable salt thereof, or the pharmaceutical composition according to any one of the foregoing embodiments are for use in treating acute kidney injury.

In another embodiment, the present invention provides a method of treating a subject with cancer, comprising administering to the subject an effective amount of one or more disclosed compounds, or a pharmaceutically acceptable salt thereof, or the pharmaceutical composition according to any one of the foregoing embodiments.

Also provided herein is the use of one or more of the disclosed compounds, or a pharmaceutically acceptable salt thereof, or the pharmaceutical composition according to any one of the foregoing embodiments, for the preparation of a medicament for the treatment of cancer.

In another embodiment, provided herein the disclosed compounds, or a pharmaceutically acceptable salt thereof, or the pharmaceutical composition according to any one of the foregoing embodiments are for use in treating cancer.

BRIEF DESCRIPTION OF THE DRAWINGS

FIG. 1 shows that PARP1 inhibitors Example 29 and Example 30 reduced after 24 hour plasma creatinine and blood urea nitrogen (BUN) in an animal model of kidney injury.

DETAILED DESCRIPTION

Definitions

The term "halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-5 carbon atoms, i.e. $(C_1-C_5)$alkyl. As used herein, a "$(C_1-C_5)$alkyl" group means a radical having from 1 to 5 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "$(C_1-C_4)$alkoxy" includes methoxy, ethoxy, propoxy, and butoxy.

The terms "haloalkyl" and "haloalkoxy" means alkyl or alkoxy, as the case may be, substituted with one or more halogen atoms.

The term "cycloalkyl" refers to a monocyclic saturated hydrocarbon ring system. For example, a $C_{3-6}$ cycloalkyl includes cyclopropyl, cyclobutyl, cyclopentyl and cyclohexyl. Unless otherwise described, a "cycloalkyl" has from three to six carbon atoms.

The term "heteroaryl", "heteroaromatic", "heteroaryl ring", "heteroaryl group", "heteroaromatic ring", and "heteroaromatic group", used alone or as part of a larger moiety as in "heteroaralkyl" or "heteroarylalkoxy", refers to monocyclic aromatic ring groups having five or six ring atoms (i.e., "5-6 membered") selected from carbon and at least one (typically 1 to 4, more typically 1 or 2) heteroatoms (e.g., oxygen, nitrogen or sulfur).

Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl.

The term "heterocyclyl" refers to a monocyclic non-aromatic ring radical containing from 4-6 ring atoms (i.e., "4-6 membered") selected from carbon atom and 1 or 2 heteroatoms. Each heteroatom is independently selected from nitrogen, quaternary nitrogen, oxidized nitrogen (e.g., NO); oxygen; and sulfur, including sulfoxide and sulfone. Representative heterocyclyl groups include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A "substituted heterocylyl group" is substituted at any one or more substitutable ring atom, which is a ring carbon or ring nitrogen atom bonded to a hydrogen.

As used herein, many moieties (e.g., alkyl, alkylene, cycloalkyl, cycloalkylene, aryl, arylene, heteroaryl, heteroarylene, heterocyclyl or heterocyclylene) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Suitable substituents are those which do not have a significant adverse effect on the ability of the compound to inhibit PARP. Where suitable substituents are not specifically enumerated, exemplary substituents include, but are not limited to: $(C_1-C_5)$alkyl, $(C_1-C_5)$hydroxyalkyl, $(C_1-C_5)$ haloalkyl, $(C_1-C_5)$ alkoxy, $(C_1-C_5)$ haloalkoxy, halogen, hydroxyl, cyano, amino, —CN, —NO$_2$, —OR$^c$, —NR$^a$R$^b$, —S(O)$_i$R$^a$, —NR$^a$S(O)R$^b$, —S(O)$_i$NR$^a$R$^b$, —C(=O)OR$^a$, —OC(=O)OR$^a$, —C(=S)OR$^a$, —O(C=S)R$^a$, —C(=O) NR$^a$R$^b$, —NR$^a$C(=O)R$^b$, —C(=S)NR$^a$R$^b$, —NR$^a$C(=S) R$^b$, —NR$^a$(C=O)OR$^b$, —O(C=O)NR$^a$R$^b$, —NR$^a$(C=S) OR$^b$, —O(C=S)NR$^a$R$^b$, —NR$^a$(C=O) NR$^a$R$^b$, —NR$^a$ (C=S)NR$^a$R$^b$, —C(=S)R$^a$, —C(=O)R$^a$, phenyl, or 5-6 membered heteroaryl. Each R$^a$ and each R$^b$ are independently selected from —H and $(C_1-C_5)$alkyl, optionally substituted with hydroxyl or $(C_1-C_3)$alkoxy; R$^c$ is —H, $(C_1-C_5)$ haloalkyl or $(C_1-C_5)$alkyl, wherein the $(C_1-C_5)$alkyl is optionally substituted with hydroxyl or $(C_1-C_3)$alkoxy.

Certain of the compounds described herein may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, geometric isomers, including essentially pure stereo or geometric isomers, as well as combination thereof.

In certain instances tautomeric forms of the disclosed compounds exist, such as the tautomeric structures shown below:

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure (also referred to as "enantiomerically pure"). Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

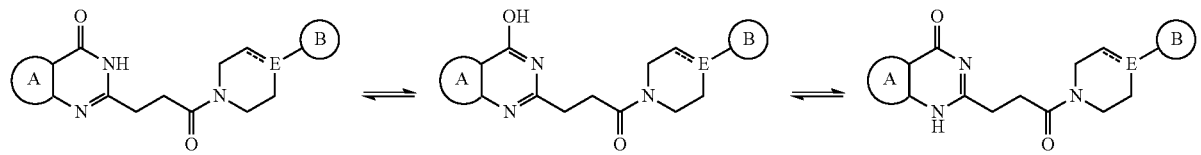

It is to be understood that when a compound herein is represented by a structural formula or designated by a chemical name herein, all other tautomeric forms which may exist for the compound are encompassed by the structural formula.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. "Geometric isomers" are stereoisomers that differ in the orientation of substituent atoms in relationship to a carbon-carbon double bond, to a carbocyclyl ring, or to a bridged bicyclic system.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture.

When a disclosed compound is named or depicted by structure without indicating the stereochemistry and e.g., the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

Pharmaceutical Compositions

The compounds disclosed therein are PARP inhibitors (e.g., PARP-1 inhibitors). The pharmaceutical composition of the present invention comprises one or more PARP inhibitors (e.g., PARP-1 inhibitors), or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

PARPs are involved in a wide array of cellular functions, including DNA repair, mitochondrial homeostasis, protection against oxidative stress, inflammation, metabolic regulation, circadian rhythms, differentiation and aging. See, for example, Peter Bai, *Molecular Cell* 58:947 (2015). As such, PARP inhibitors have the potential to treat a wide range ailments, and a number of PARP inhibitors have been approved for the treatment of cancer.

The present invention provides a method of treating a subject with a disease which can be ameliorated by inhibition of PARP, by administering to the subject an effective amount of one or more disclosed compounds, or a pharmaceutically acceptable salt thereof, or the corresponding pharmaceutical composition.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In one embodiment, the diseases which can be ameliorated by inhibition of PARP are a muscle structure disorder, a neuronal activation disorder, a muscle fatigue disorder, a muscle mass disorder, a beta oxidation disease, a metabolic disease, a cancer, a vascular disease, an ocular vascular disease, a muscular eye disease, or a renal disease.

In one aspect of this embodiment, the muscle structure disorder is selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In another aspect of the embodiment, the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In another aspect of this embodiment, the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy;

In another aspect of this embodiment, the muscle mass disorder is cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In another aspect of this embodiment, the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In yet another aspect of this embodiment, the metabolic disease is selected from hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In another aspect of this embodiment, the vascular disease is selected from peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In another aspect of this embodiment, the ocular vascular disease is selected from age-related macular degeneration (AMD), stargardt disease, hypertensive retinopathy, diabetic retinopathy, retinopathy, macular degeneration, retinal haemorrhage, and glaucoma.

In a further aspect of this embodiment, the muscular eye disease is selected from strabismus, progressive external ophthalmoplegia, esotropia, exotropia, a disorder of refraction and accommodation, hypermetropia, myopia, astigmatism, anisometropia, presbyopia, a disorders of accommodation, and internal ophthalmoplegia.

In a final aspect of this embodiment, the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure (also known as acute kidney injury), chronic renal failure, diabetic nephropathy, and Bartter's syndrome.

In another embodiment, the disease which can be ameliorated by inhibition of PARP includes genetic lipodystrophy, non-alcoholic fatty liver disease (NAFLD), non-alcoholic steatohepatitis (NASH), renal ischemia/reperfusion injury (IRI), Duchenne & Becker muscular dystrophy, diabetes (type I or type II), obesity, and sarcopenia.

In another embodiment, the disease which can be ameliorated by inhibition of PARP includes Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy. In yet another embodiment, the disease which can be ameliorated by inhibition of PARP is acute kidney injury.

In certain embodiments, the invention provides methods for using the compounds of the invention and pharmaceutical compositions thereof. The compounds of the invention and pharmaceutical compositions thereof may be useful for a variety of therapeutic applications including, for example, treating and/or reducing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of one or more compounds of the invention and/or pharmaceutical compositions thereof.

In another embodiment, the compounds of the invention and pharmaceutical compositions thereof may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated using the compounds of the invention and pharmaceutical compositions thereof prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with the nicotinamide riboside chloride preparations or pharmaceutical compositions of the invention, or may have a subset of cells/tissue treated locally with the compounds of the invention and pharmaceutical compositions thereof. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, the compounds of the invention and/or a pharmaceutical composition thereof can be used to treat skin conditions. Exemplary skin conditions that may be treated in accordance with the methods described herein include disorders or diseases associated with or caused by inflammation, sun damage or natural aging. For example, the compositions find utility in the treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, the compounds of the invention and pharmaceutical compositions thereof may be used for the treatment of wounds and/or burns to promote healing, including, for example, first-, second- or third-degree burns and/or thermal, chemical or electrical burns.

The compounds of the invention and pharmaceutical compositions thereof can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

The compounds of the invention and pharmaceutical compositions thereof can also be administered to a subject suffering from an acute disease, e.g., damage to an organ or tissue, e.g., a subject suffering from stroke or myocardial infarction or a subject suffering from a spinal cord injury. The compounds of the invention and pharmaceutical compositions thereof may also be used to repair an alcoholic's liver.

In another embodiment, the invention provides a method for treating a cardiovascular disease by administering to a subject in need thereof one or more of the compounds of the invention and/or a pharmaceutical composition thereof. Cardiovascular diseases that can be treated using the compounds of the invention and pharmaceutical compositions thereof include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated include those related to platelet aggregation, the retinal arterioles, the glomerular arterioles, the vasa nervorum, cardiac arterioles, and associated capillary beds of the eye, the kidney, the heart, and the central and peripheral nervous systems. The compounds of the invention and pharmaceutical compositions thereof may also be used for increasing HDL levels in plasma of an individual.

Methods of Administration and Dosage Forms

The precise amount of compound administered to provide an "effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, the disclosed PARP inhibitors can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a a PARP mediated disease using the disclosed PARP inhibitors (e.g., PARP-1 inhibitors) for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

EXEMPLIFICATION

Abbreviations

Me methyl
Et ethyl
Boc tert-butyloxycarbonyl
Ac acetyl

Ph phenyl
Tf trifluoromethanesulfonyl
DIPEA diisopropylethylamine
EDC 3-(3-dimethylaminopropyl)-1-ethylcarbodiimide
HOBt 1-hydroxybenzotriazole
DCM dichloromethane
DMF N,N-dimethylformamide
DMSO dimethylsulfoxide
TFA trifluoroacetic acid
THE tetrahydrofuran
TMS trimethyl silane
TMSOTf trimethylsilyl trifluoromethanesulfonate
aq aqueous
M concencetration expressed in mol/L
RT room temperature
TLC thin layer chromatography
HPLC high-performance liquid chromatography
NMI 1-methyl imidazole
LCMS liquid chromatography-mass spectrometry
ESI+ m/z values in mass spectroscopy (Ionization ESI)
ESI− m/z values in mass spectroscopy (Ionization ESI)
$^1$H NMR (DMSO-d$_6$) δ (ppm) of peak in $^1$H NMR in DMSO-d$_6$
s singlet (spectrum)
d doublet (spectrum)
t triplet (spectrum)
q quartet (spectrum)
dd double doublet (spectrum)
br broad line (spectrum)
m multiplet (spectrum).
4-ANI 4-Amino-1,8-naphthalimide
ADP Adenosine diphosphate
CPM counts per minute
DNA Deoxyribonucleic acid
DTT DL-Dithiothreitol
FB Flat Bottom
mg milli gram
mM milli molar
NAD Nicotinamide-Adenine Dinucleotide
nM nano molar
ng nano gram
PARP 1 Poly (ADP-ribose) polymerase-1
SPA Scintillation Proximity Assay
µCi micro curie
µL microliter
T3P propylphosphonic anhydride
NMM 4-methylmorpholine
CDI 1,1'-carbonyldiimidazole
EtOAc ethyl acetate
TEMPO 2,2,6,6-Tetramethyl-1-piperidinyloxy
MTBE tert-butyl methyl ether
HATU 3-1-[Bis(dimethylamino)methylene]-1H-1,2,3-triazolo[4,5-b]pyridinium oxid hexafluorophosphate
IPA isopropyl alcohol
DMA N,N-dimethylacetamide
BINAP 1,1'-binaphthalene-2,2'-diyl)bis(diphenylphosphine
NMP 1-methyl-2-pyrrolidinone
Dppf 1,1'-bis(diphenylphosphino)ferrocene
DMAP 4-(dimethylamino)pyridine
DIEA N,N-diisopropylethylamine Example 1—Synthesis of 3-chloro-4-(4-(3-(8-chloro-4-oxo-3,4-dihydroquinazolin-2-yl)propanoyl)piperazin-1-yl)-N-cyclopropylbenzamide Step-1

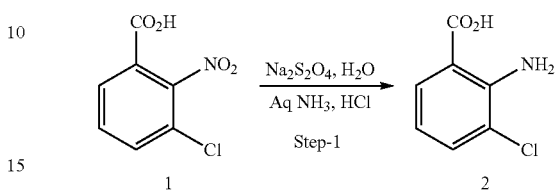

To a stirred solution of 3-chloro-2-nitro-benzoic acid (15 g, 0.074 mol) in water (105 mL), 30% aq. NH$_3$ (6 mL) and aqueous solution of sodium dithionite (52 g, 0.298 mol) were added at RT and stirred for 1 h (TLC indicated complete consumption of starting material). The reaction mixture was acidified with conc. HCl (30 mL) till pH=3, extracted with EtOAc (2×500 mL), washed with water (2×100 mL) and brine (150 mL). The combined organic extracts were dried over Na$_2$SO$_4$, concentrated under reduced pressure to give the crude product which was washed with Et$_2$O (50 mL) to furnish 2-amino-3-chlorobenzoic acid (9 g, 70%) as an off-white solid.

LCMS: m/z: 172.3 [M+H]$^+$.

Step-2

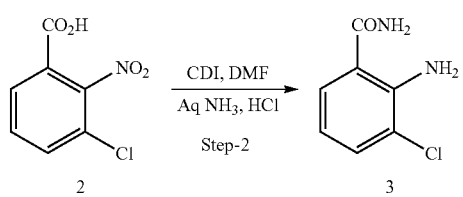 [SMILES: O=C(O)c1cccc(Cl)c1[N+](=O)[O-] ; NC(=O)c1cccc(Cl)c1N]

The stirred solution of 2-amino-3-chloro-benzoic acid (9 g, 0.052 mol) and CDI (9 g, 0.055 mol) in DMF (180 mL) was heated to 70° C. for 1 h. Then 30% aq. NH$_3$ (144 mL) was added maintaining the temperature at 70° C. and stirred for 16 h (TLC indicated complete consumption of starting material). The reaction mixture was brought to RT, poured into ice water (1 L) and extracted with EtOAc (2×250 mL). The combined organic extracts were washed with water (2×100 mL), brine (100 mL), dried over Na$_2$SO$_4$ and concentrated under reduced pressure to give the crude product which was washed with Et$_2$O (2×30 mL) to provide 2-amino-3-chloro-benzamide (5.4 g, 60%) as an off-white solid.

LCMS: m/z: 171.3 [M+H]$^+$.

Step: 3

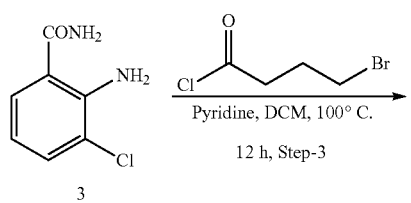

To a stirred solution of 2-amino-3-chloro-benzamide (2 g, 11.76 mmol) dissolved in pyridine (15 mL), taken in a sealed tube, 4-bromobutanoyl chloride (3.3 g, 17.64 mmol) in DCM (5 mL) was added at 0° C. The reaction mixture was heated to 100° C. and stirred for 12 h (TLC indicated complete consumption of starting material). The reaction mixture was brought to RT, diluted with water (150 mL) and extracted with EtOAc (2×150 mL). The combined organic extracts were washed with saturated aqueous NH$_4$Cl solution (2×50 mL), brine (50 mL), dried over Na$_2$SO$_4$, concentrated under reduced pressure to give the crude compound which was washed with toluene (20 mL), ether (2×10 mL) to afford 8-chloro-2-(3-hydroxypropyl)-3H-quinazolin-4-one (600 mg, 21%) as an off-white solid.

LCMS: m/z: 239.4 [M+1]$^+$.

Step-4

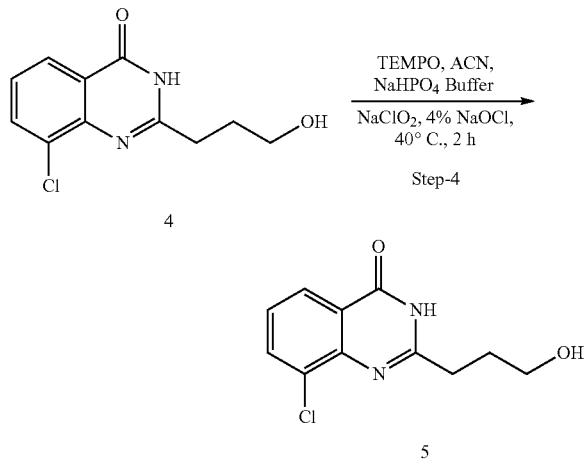

To a stirred solution of 8-chloro-2-(3-hydroxypropyl)-3H-quinazolin-4-one (500 mg, 2.10 mmol) in ACN (10 mL), TEMPO (65 mg, 0.414 mmol) and sodium phosphate buffer solution (8 mL, pH=6.5) were added at RT and heated to 40° C. Then sodium chlorite (3.75 g in 15 mL water) and sodium chlorite solution (4% in H$_2$O, 15 mL) were added portion wise at 40° C. The reaction mixture was brought to RT, basified with 1 N NaOH solution till pH=8, poured into 1 N Na$_2$S$_2$O$_3$ solution (50 mL), washed with MTBE (2×25 mL). The aqueous layer was acidified with 1 N HCl till pH=1 and extracted with EtOAc (3×50 mL). The combined organic extracts were washed with brine (50 mL), dried over Na$_2$SO$_4$, concentrated under reduced pressure to give 3-(8-chloro-4-oxo-3H-quinazolin-2-yl)propanoic acid (250 mg, 47%) which was used for the next step without any further purification.

LCMS: m/z: 253.3 [M+1]$^+$.

Step-5

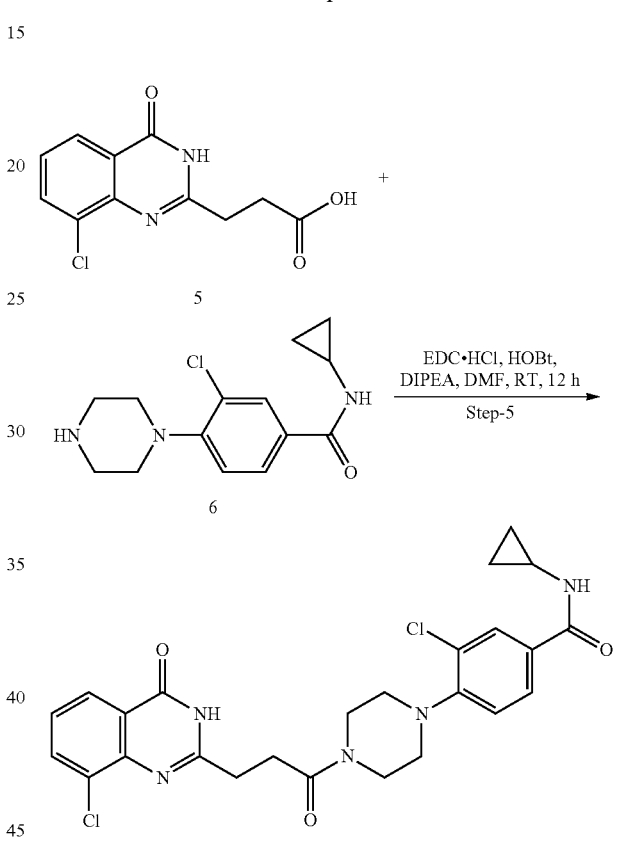

To a stirred solution of 3-(8-chloro-4-oxo-3H-quinazolin-2-yl)propanoic acid (285 mg, 1.13 mmol) and 3-chloro-N-cyclopropyl-4-piperazin-1-yl-benzamide (308 mg, 1.1 mmol) in DMF (2.6 mL), EDC·HCl (432 mg, 2.26 mmol), HOBt (305 mg, 2.26 mmol) and DIPEA (0.96 mL, 5.65 mmol) were added at RT and stirred for 12 h (TLC indicated complete consumption of starting material). The reaction mixture was diluted with cold water (50 mL), extracted with EtOAc (3×25 mL). The combined organic layers were washed with water (25 mL), brine (25 mL), dried over Na$_2$SO$_4$, concentrated under reduced pressure and the residue was purified by Teledyne-ISCO Combiflash (5-7% MeOH-DCM, 4 gm cartridge) to get 3-chloro-4-(4-(3-(8-chloro-4-oxo-3,4-dihydroquinazolin-2-yl)propanoyl)piperazin-1-yl)-N-cyclopropylbenzamide (100 mg, 85% LCMS) which was further purified by Prep-HPLC to afford pure compound (25 mg, 5%) as a white solid.

$^1$H NMR [300 MHz, DMSO-d$_6$]: δ 12.54 (brs, 1H), 8.42 (d, J=3.9 Hz, 1H), 8.05-8.02 (m, 1H), 7.93-7.88 (m, 2H), 7.76 (dd, J=8.1, 1.8 Hz, 1H), 7.42 (t, J=7.8 Hz, 1H), 7.16 (d, J=8.4 Hz, 1H), 3.70 (m, 2H), 3.61 (m, 2H), 3.08-2.92 (m, 2H), 2.8-2.79 (m, 7H), 0.71-0.62 (m, 2H), 0.60-0.52 (m, 2H).

LCMS: m/z: 514.4 [M+H]⁺.

Example 2—Synthesis of 3-chloro-4-[4-[3-(4-oxo-3H-quinazolin-2-yl)propanoyl]piperazin-1-yl]benzamide

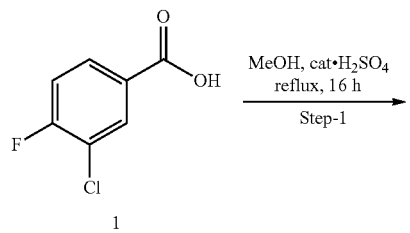

A round bottomed flask was charged with 3-chloro-4-fluoro-benzoic acid (2.0 g, 11.4 mmol), sulfuric acid (0.33 g, 3.4 mmol), MeOH (20 mL) and refluxed for 16 h (TLC indicated complete consumption of starting material). The volatiles were removed under reduced pressure; the residue was diluted with water (15 mL) and extracted with EtOAc (3×50 mL). The combined organic extracts were washed with brine (50 mL), dried over Na₂SO₄ and concentrated in vacuo to give the crude residue which was purified by column chromatography (100-200 silica gel, 40 g, 10% EtOAc-hexane) to afford methyl 3-chloro-4-fluoro-benzoate (1.5 g, 69%) as a light yellow oil.

¹H NMR [300 MHz, CDCl₃]: δ 8.08 (dd, J=6.9, 2.1 Hz, 1H), 7.94-7.89 (m, 1H), 7.18 (t, J=8.7 Hz, 1H), 3.90 (s, 3H).

Step-2

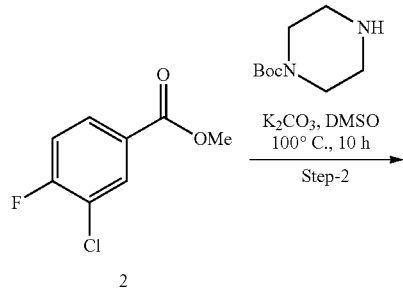

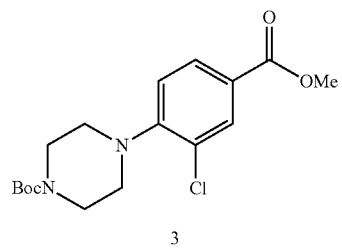

Methyl 3-chloro-4-fluoro-benzoate (1.5 g, 7.9 mmol) was taken in a sealed tube, piperazine-1-carboxylic acid tert-butyl ester (1.48 g, 7.9 mmol) followed by K₂CO₃ (3.29 g, 23 mmol) and DMSO (15 mL) were added and stirred at 100° C. for 10 h (TLC indicated complete consumption of starting material). The reaction mixture was poured into ice-cold water (150 mL) and extracted with EtOAc (2×100 mL). The combined organic extracts were washed with brine (2×75 mL), dried over Na₂SO₄ and concentrated under reduced pressure to give the crude residue which was purified by column chromatography (100-200 silica gel, 30 g, 10% EtOAc-hexane) to afford tert-butyl 4-(2-chloro-4-methoxycarbonyl-phenyl)piperazine-1-carboxylate (2.1 g, 74%) as a white solid.

LCMS: m/z: 355.4 [M+H]⁺.

Step-3

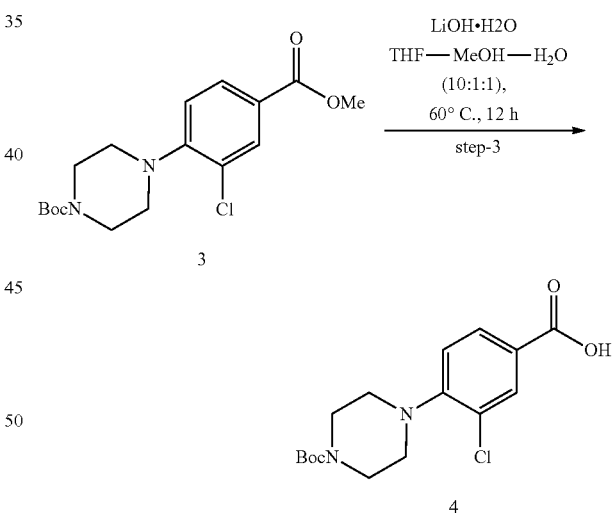

To a stirred solution of tert-butyl 4-(2-chloro-4-methoxycarbonyl-phenyl)piperazine-1-carboxylate (2 g, 5.6 mmol) in THF:MeOH:H₂O (10:1:1, 24 mL), LiOH·H₂O (0.47 g, 11.2 mmol) was added, heated at 60° C. for 12 h (TLC indicated complete consumption of the starting material) and concentrated under reduced pressure. The residue was dissolved in water (30 mL), cooled to 0° C., acidified with 1 N HCl till pH=2-3. The solid precipitated was filtered and dried in vacuo to afford 4-(4-tert-butoxycarbonylpiperazin-1-yl)-3-chloro-benzoic acid (1.4 g, 73%) as a white solid.

LCMS: m/z: 341.4 [M+H]⁺.

Step-4

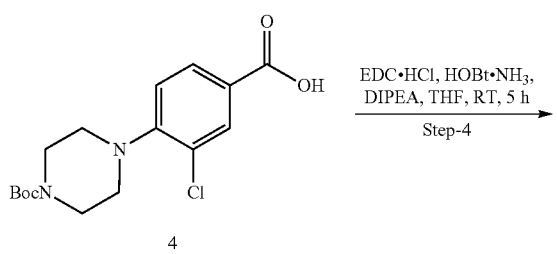

To a stirred solution of 4-(4-tert-butoxycarbonylpiperazin-1-yl)-3-chloro-benzoic acid (0.5 g, 1.4 mmol) in THF (5 mL), EDC·HCl (0.42 g, 2.2 mmol), HOBt-NH$_3$ (0.33 g, 2.2 mmol) and DIPEA (0.75 mL, 4.4 mmol) were added under argon atmosphere and stirred at RT for 5 h (TLC indicated the complete consumption of starting material). The volatiles were removed under reduced pressure and the residue was diluted with ice water (100 mL) and EtOAc (150 mL). The organic layer was separated, washed with brine (2×50 mL), dried over Na$_2$SO$_4$ and concentrated under reduced pressure. The crude residue was washed with Et$_2$O (3×5 mL), pentane (3×5 mL), dried under high vacuo to afford tert-butyl 4-(4-carbamoyl-2-chloro-phenyl)piperazine-1-carboxylate (0.4 g, 80%) as a white solid.

LCMS: m/z: 340.4 [M+H]$^+$.

Step-5

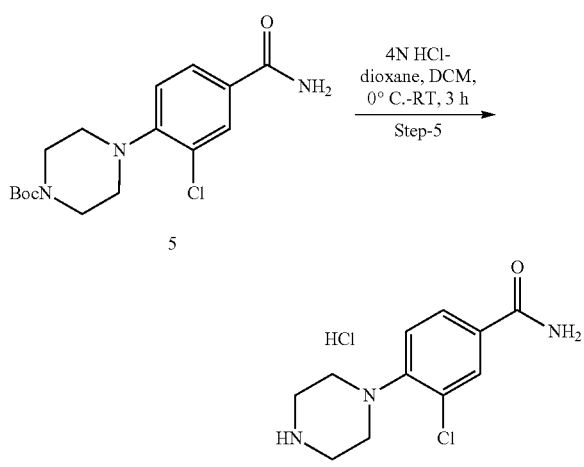

To a stirred solution of tert-butyl 4-(4-carbamoyl-2-chloro-phenyl)piperazine-1-carboxylate (0.4 g, 1.0 mmol) in DCM (4 mL), cooled to 0° C., 4 N HCl-dioxane (0.4 mL) was added and stirred at RT for 3 h (TLC indicated the complete consumption of the starting material). The volatiles were removed under reduced pressure and the residue was washed with Et$_2$O (3×10 mL), pentane (2×5 mL) and dried under high vacuo to afford 3-chloro-4-piperazin-1-yl-benzamide (300 mg, quant.) as a white solid.

LCMS: m/z: 240.4 [M+H]$^+$.

Step-6

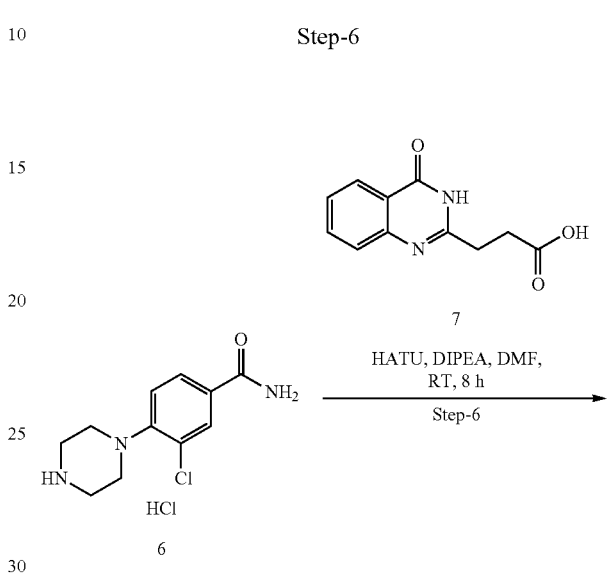

To a stirred solution of 3-chloro-4-piperazin-1-yl-benzamide (0.1 g, 0.45 mmol) in DMF (1 mL), 3-(4-oxo-3H-quinazolin-2-yl)propanoic acid (0.13 g, 0.50 mmol), HATU (0.26 g, 0.68 mmol) and DIPEA (0.23 mL, 1.37 mmol) were added under argon atmosphere and stirred at RT for 8 h (TLC indicated the complete consumption of starting material). The reaction mixture was poured into ice-cold water (10 mL) during which solid precipitated which was filtered, washed with Et$_2$O (3×5 mL), pentane (3×5 mL), MeOH (2×5 mL), dried under high vacuo to furnish 3-chloro-4-[4-[3-(4-oxo-3H-quinazolin-2-yl)propanoyl]piperazin-1-yl]benzamide (0.04 g, 20%) as an off-white solid.

$^1$H NMR [300 MHz, DMSO-d$_6$]: δ 12.22 (brs, 1H), 8.07 (dd, J=8.1, 1.2 Hz, 1H), 7.98 (brs, 1H), 7.93 (d, J=1.8 Hz, 1H), 7.83-7.78 (m, 2H), 7.76 (d, J=1.2 Hz, 1H), 7.74-7.48 (m, 1H), 7.47 (brs, 1H), 7.44 (d, J=7.2 Hz, 1H), 3.69-3.61 (m, 4H), 3.07-2.97 (m, 4H), 2.89 (brs, 4H).

LCMS: m/z: 440.4 [M+H]$^+$.

Example 3—Synthesis of 3-chloro-N-methyl-4-[4-[3-(4-oxo-3H-quinazolin-2-yl)propanoyl]piperazin-1-yl]benzamide Step-1

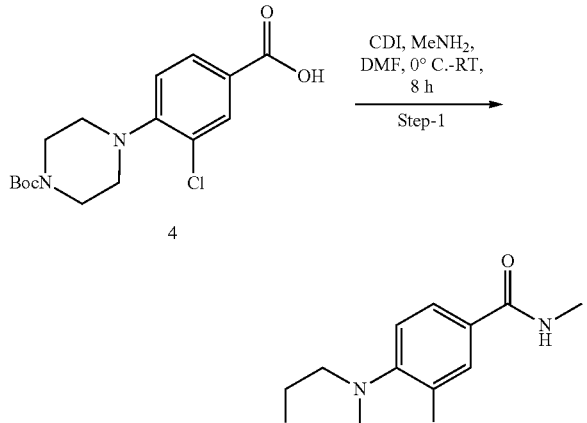

To a stirred solution of 4-(4-tert-butoxycarbonylpiperazin-1-yl)-3-chloro-benzoic acid (0.5 g, 1.4 mmol) in DMF (5 mL), CDI (0.35 g, 2.2 mmol) was added, cooled to 0° C., stirred at RT for 10 min and Methylamine solution (1 M solution in THF, 1.46 mL, 1.4 mmol) was added. The reaction mixture was warmed to RT, stirred for 8 h (TLC indicated complete consumption of starting material), poured into ice-cold water (50 mL) and extracted into EtOAc (2×50 mL). The combined organic extracts were washed with water (50 mL), brine (2×50 mL), dried over Na$_2$SO$_4$ and concentrated under reduced pressure. The crude residue was washed with Et$_2$O (3×10 mL) and pentane (3×10 mL), dried under high vacuo to provide tert-butyl 4-[2-chloro-4-(methylcarbamoyl)phenyl]piperazine-1-carboxylate (0.4 g, 77%) as a light brown solid.

$^1$H NMR [300 MHz, DMSO-d$_6$]: δ 8.44 (br, 1H), 7.88 (d, J=2.1 Hz, 1H), 7.78-7.75 (m, 1H), 7.19 (d, J=8.4 Hz, 1H), 3.47 (t, J=4.2 Hz, 4H), 2.98 (d, J=4.8 Hz, 4H), 2.75 (d, J=4.5 Hz, 3H), 1.42 (s, 9H).

LCMS: m/z: 354.4 [M+H]$^+$.

Step-2

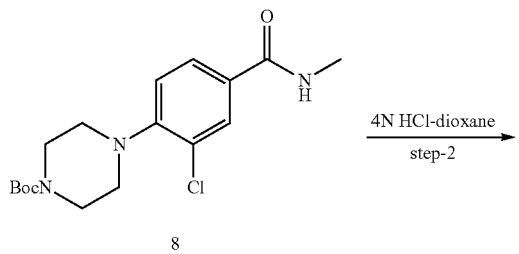

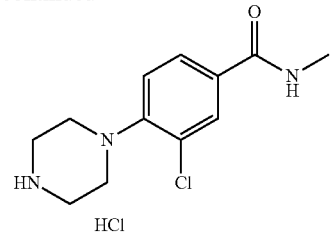

To a stirred solution of tert-butyl 4-[2-chloro-4-(methylcarbamoyl)phenyl]piperazine-1-carboxylate (0.4 g, 1.0 mmol) in DCM (4 mL), cooled to 0° C., 4 N HCl-dioxane (1.1 mL) was added, warmed to RT and stirred for 5 h (TLC indicated the complete consumption of starting material). The volatiles were removed under reduced pressure and the residue was washed with Et$_2$O and (2×5 mL) and pentane (2×5 mL) and dried under vacuo to give 3-chloro-N-methyl-4-piperazin-1-yl-benzamide (300 mg, 91%) as a white solid.

LCMS: m/z: 254.4 [M+H]$^+$.

Step-3

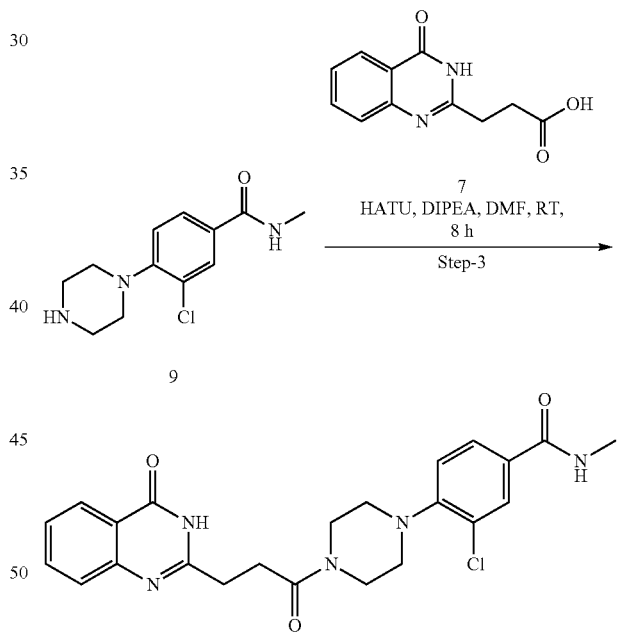

To a stirred solution of 3-chloro-N-methyl-4-piperazin-1-yl-benzamide (0.1 g, 0.45 mmol) in DMF (1 mL), 3-(4-oxo-3H-quinazolin-2-yl)propanoic acid (0.14 g, 0.50 mmol), HATU (0.26 g, 0.68 mmol) and DIPEA (0.23 mL, 1.37 mmol) were added under Argon atmosphere and stirred at RT for 8 h (TLC indicated the complete consumption of starting material). The reaction mixture was poured into ice-water and extracted with EtOAc (2×50 mL). The combined organic extracts were separated, washed with water (30 mL), brine (50 mL), dried over Na$_2$SO$_4$ and concentrated under reduced pressure. The crude residue was washed with Et$_2$O (3×5 mL), pentane (3×5 mL), 10% MeOH-DCM (3×5 mL) and dried under vacuo to afford 3-chloro-N-methyl-4-[4-[3-(4-oxo-3H-quinazolin-2-yl)propanoyl]piperazin-1-yl]benzamide (0.04 g, 19%) as an off-white solid.

¹H NMR [300 MHz, DMSO-d₆]: δ 12.21 (brs, 1H), 8.45-8.44 (br, 1H), 8.07 (dd, J=7.8, 1.2 Hz, 1H), 7.89 (d, J=2.1 Hz, 1H), 7.79-7.73 (m, 2H), 7.57 (d, J=7.8 Hz, 1H), 7.47-7.42 (m, 1H), 7.18 (d, J=8.4 Hz, 1H), 3.69-3.59 (m, 4H), 3.07-2.97 (m, 4H), 2.89 (br s, 4H), 2.76 (d, J=4.5 Hz, 3H).

LCMS: m/z: 454.4 [M+H]⁺.

Example 4—Synthesis of 3-chloro-N-cyclopropyl-4-[4-[3-(4-oxo-3H-quinazolin-2-yl)propanoyl]piperazin-1-yl]benzamide Step-1

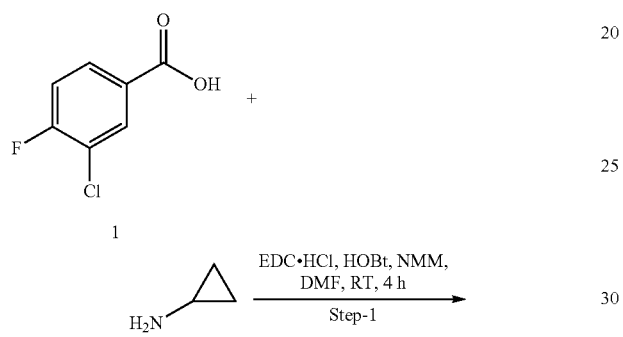

To a stirred solution of 3-chloro-4-fluoro-benzoic acid (1 g, 5.73 mmol) and cyclopropanamine (0.47 mL, 6.76 mmol) in dry DMF (10 mL), EDC·HCl (1.64 g, 8.56 mmol), HOBt (1.2 g, 8.89 mmol) and NMM (3.1 mL, 28.24 mmol) were added at RT under argon atmosphere and stirred for 4 h. After completion of the reaction (monitored by TLC), the reaction mixture was diluted with cold water (25 mL) and stirred for 15 minutes. The solid formed was filtered off which was washed with water (50 mL) and dried under vacuum to afford 3-chloro-N-cyclopropyl-4-fluoro-benzamide (0.85 g, 70% yield) as a white solid.

LCMS: m/z: 214.3 [M+H]⁺.

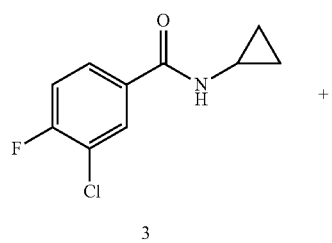

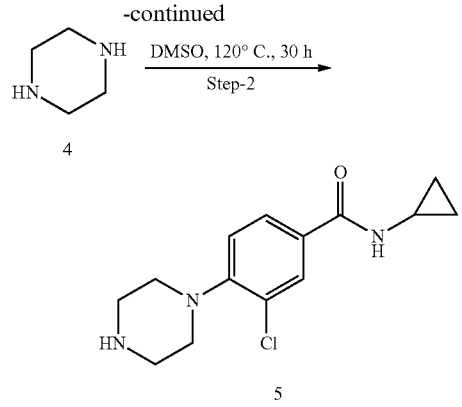

To a stirred solution of 3-chloro-N-cyclopropyl-4-fluoro-benzamide (3.1 g, 14.55 mmol) in dry DMSO (25 mL), piperazine (6.26 g, 72.77 mmol) was added at RT under argon atmosphere and stirred at 120° C. for 30 h (TLC indicated complete consumption of starting material). After cooling to RT, the reaction mass was diluted with water (20 mL) and extracted with 10% IPA-DCM (5×100 mL). The combined organic extracts were dried over anhydrous Na₂SO₄ and concentrated under reduced pressure. The residue was washed with Et₂O (2×20 mL) to afford 3-chloro-N-cyclopropyl-4-piperazin-1-yl-benzamide (3.9 g, 96% yield) as a white solid.

LCMS: m/z: 280.4 [M+H]⁺.

Step-3

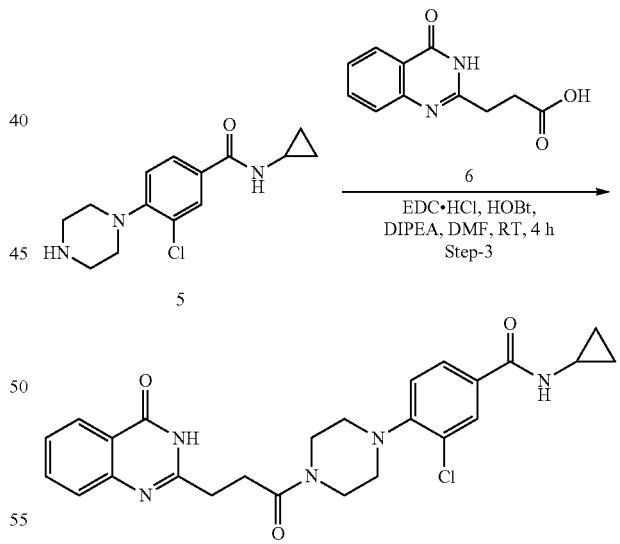

To a stirred solution of 3-chloro-N-cyclopropyl-4-piperazin-1-yl-benzamide (100 mg, 0.36 mmol) and 3-(4-oxo-3H-quinazolin-2-yl)propanoic acid (94 mg, 0.43 mmol) in dry DMF (2 mL), EDC·HCl (103 mg, 0.54 mmol), HOBt (73 mg, 0.54 mmol) and DIPEA (0.2 mL, 1.15 mmol) were added at RT under argon atmosphere and stirred for 4 h. After completion of the reaction (monitored by TLC), the reaction mixture was quenched with cold water (20 mL) and stirred for 15 minutes. The solid formed was filtered off, washed with water (50 mL) followed by Et₂O (2×5 mL) to give compound 3-chloro-N-cyclopropyl-4-[4-[3-(4-oxo-3H-quinazolin-2-yl)propanoyl]piperazin-1-yl]benzamide (80 mg, 47% yield) as a white Solid.

1H NMR [300 MHz, DMSO-d$_6$]: δ 12.31 (brs, 1H), 8.41 (brs, 1H), 8.08 (d, J=8.1 Hz, 1H), 7.89 (s, 1H), 7.79-7.40 (m, 2H), 7.57 (d, J=8.1 Hz, 1H), 7.45 (t, J=7.8 Hz, 1H), 7.17 (d, J=8.4 Hz, 1H), 3.69 (s, 2H), 3.62 (s, 2H), 3.07 (s, 2H), 2.97 (s, 2H), 2.88 (s, 4H), 2.85-2.81 (m, 1H), 0.71-0.65 (m, 2H), 0.56-0.55 (m, 2H).

LCMS: m/z: 480.5 [M+H]$^+$.

Example 5—Synthesis of 3-chloro-N-cyclobutyl-4-[4-[3-(4-oxo-3H-quinazolin-2-yl)propanoyl]piperazin-1-yl]benzamide Step-1

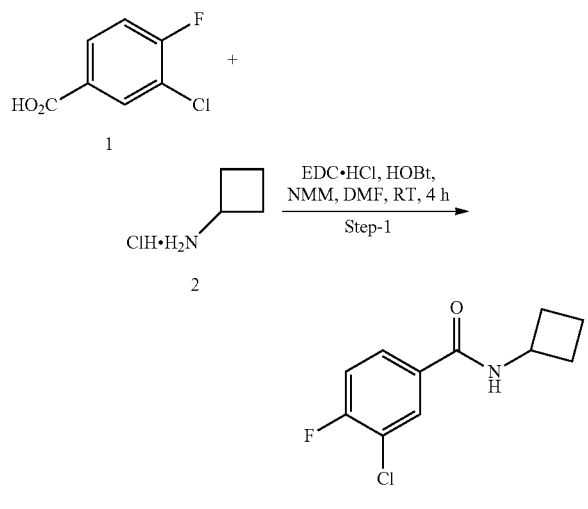

To the stirred solution of 3-chloro-4-fluoro-benzoic acid (500 mg, 2.865 mmol) in DMF (5 mL), cyclobutanamine hydrochloride (369 mg, 3.438 mmol), EDC HCl (820 mg, 4.297 mmol), HOBt (580 mg, 4.297 mmol) and NMM (1.6 mL, 14.325 mmol) were added at RT and stirred for 4 h (TLC indicated complete consumption of starting material). The reaction mixture was diluted with cold water (60 mL) and extracted with EtOAc (3×60 mL). The combined organic extracts were washed with cold water (50 mL), dried over Na$_2$SO$_4$, concentrated under reduced pressure to afford 3-chloro-N-cyclobutyl-4-fluoro-benzamide (550 mg, 84%) which was carried to the next step without any further purification.

LCMS: m/z: 228.22 [M+H]$^+$.

Step-2

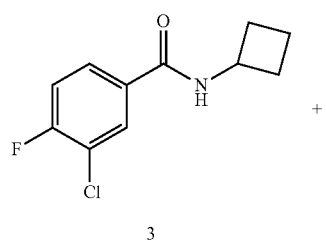

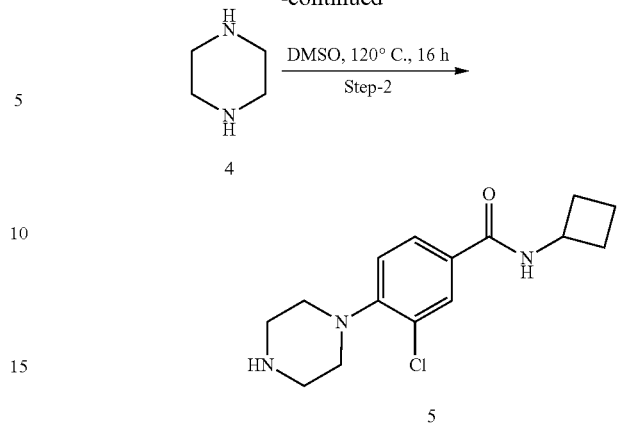

To the stirred solution of 3-chloro-N-cyclobutyl-4-fluoro-benzamide (550 mg, 2.422 mmol) in DMSO (5.5 mL), piperazine (1.04 g, 12.114 mmol) was added at RT and heated at 120° C. for 16 h (TLC indicated complete consumption of starting material). The reaction mixture was poured into ice-cold water (40 mL), solid was precipitated out which was filtered under argon atmosphere to afford crude 3-chloro-N-cyclobutyl-4-piperazin-1-yl-benzamide (410 mg, 58%). The crude material was carried to the next step without any purification.

LCMS: m/z: 294.39 [M+H]$^+$.

Step-3

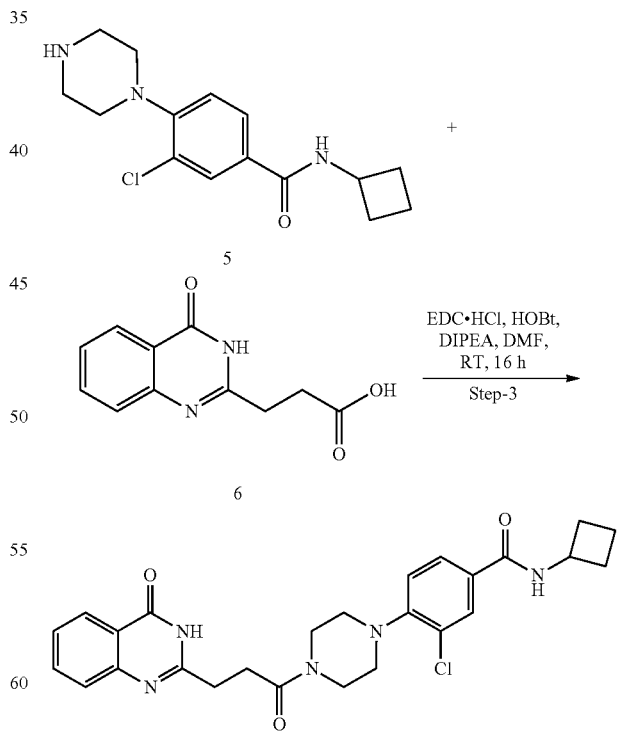

To the stirred solution of 3-(4-oxo-3H-quinazolin-2-yl) propanoic acid (100 mg, 0.458 mmol) in DMF (2 mL), 3-chloro-N-cyclobutyl-4-piperazin-1-yl-benzamide (134 mg, 0.458 mmol), EDC HCl (131 mg, 0.687 mmol), HOBt (92 mg, 0.687 mmol) and DIPEA (0.16 mL, 0.916 mmol) were added at RT and stirred for 16 h (TLC indicated complete consumption of the starting material). The reaction mixture was poured into ice-water (20 mL) during which the solid was precipitated out which was filtered, washed with Et$_2$O (20 mL) and dried under vacuum to get 3-chloro-N-cyclobutyl-4-[4-[3-(4-oxo-3H-quinazolin-2-yl)propanoyl]piperazin-1-yl]benzamide (90 mg, 40%) as a white solid.

$^1$H NMR [300 MHz, DMSO-d$_6$]: δ 12.2 (s, 1H), 8.60 (d, J 7.2 Hz, 1H), 8.07 (d, J=7.7 Hz, 1H), 7.92 (s, 1H), 7.80-7.73 (m, 2H), 7.56 (d, J=8.1 Hz, 1H), 7.45 (t, J=7.5 Hz, 1H), 7.17 (d, J=8.4 Hz, 1H), 4.42-4.37 (m, 1H), 3.65 (d, J=22.5 Hz, 4H), 3.07 (brs, 2H), 2.97 (brs, 2H), 2.89 (s, 4H), 2.18 (brs, 2H), 2.07-1.98 (m, 2H), 1.67-1.65 (m, 2H).

LCMS: m/z: 494.70 [M+H]$^+$.

Example 6—Synthesis of 3-chloro-N-(1-methylcyclopropyl)-4-[4-[3-(4-oxo-3H-quinazolin-2-yl)propanoyl]piperazin-1-yl]benzamide Step-1

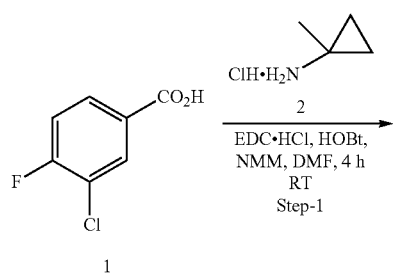

Step-2

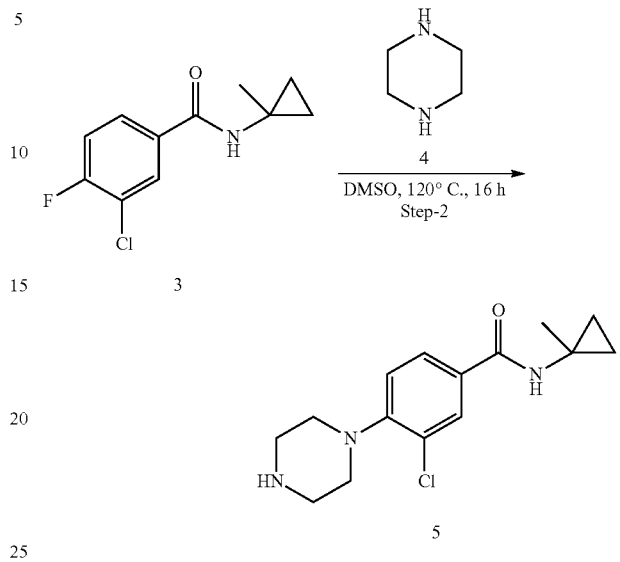

A stirred solution of 3-chloro-4-fluoro-N-(1-methylcyclopropyl)benzamide (500 mg, 2.21 mmol) and piperazine (951 mg, 11.06 mmol) in DMSO (5 mL) was heated at 120° C. for 16 hours (TLC indicated complete consumption of starting material). The reaction mixture was diluted with EtOAc (200 mL), washed with water (1×100 mL) and brine solution (1×100 mL). The organic layer was separated, dried over Na$_2$SO$_4$, volatiles were removed under reduced pressure to afford the crude 3-chloro-N-(1-methylcyclopropyl)-4-piperazin-1-yl-benzamide (800 mg) which was carried to the next step without purification.

LCMS: m/z: 294.35 [M+H]$^+$.

Step-3

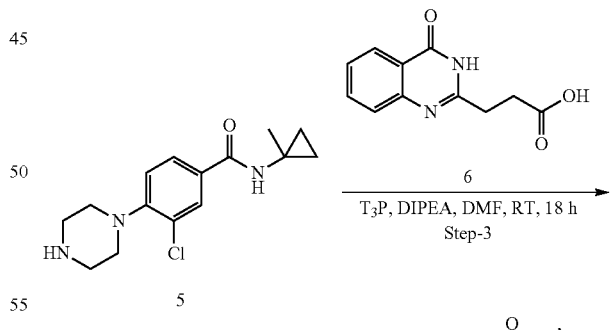

To a stirred solution of 3-chloro-4-fluoro-benzoic acid (50 mg, 0.29 mmol) in DMF (2 mL), 1-methylcyclopropanamine hydrochloride (36 mg, 0.34 mmol), EDC HCl (82 mg, 0.429 mmol), HOBt (58 mg, 0.429 mmol) and NMM (0.16 mL, 1.43 mmol) were added at RT and stirred for 4 h (TLC indicated complete consumption of starting material). The reaction mixture was diluted with water (25 mL) during which solid precipitated out which was filtered. The solid was washed with water (20 mL) and dried under high vacuum to afford 3-chloro-4-fluoro-N-(1-methylcyclopropyl)benzamide (50 mg, 78%) as an off-white solid.

LCMS: m/z: 228.19 [M+H]$^+$.

To a stirred solution of 3-(4-oxo-3H-quinazolin-2-yl)propanoic acid (300 mg, 1.37 mmol) in DMF (5 mL), 3-chloro- N-(1-methylcyclopropyl)-4-piperazin-1-yl-benzamide (604 mg, 2.06 mmol), T₃P (0.87 mL, 2.75 mmol, 50% in DMF) and DIPEA (0.75 mL, 4.12 mmol) were added at room temperature and stirred at RT for 18 hours (TLC indicated complete consumption of starting material). The reaction mixture was diluted with EtOAc (200 mL), washed with water (1×100 mL) and brine solution (1×100 mL). The organic layer was separated, dried over Na₂SO₄, volatiles were evaporated under reduced pressure to afford the crude compound which was purified by prep HPLC to afford 3-chloro-N-(1-methylcyclopropyl)-4-[4-[3-(4-oxo-3H-quinazolin-2-yl)propanoyl]piperazin-1-yl]benzamide (140 mg, 20%) as a white solid.

¹H NMR [400 MHz, DMSO-d₆]: δ 12.20 (brs, 1H), 8.64 (brs, 1H), 8.07 (d, J=8.0 Hz, 1H), 7.87 (s, 1H), 7.76-7.75 (m, 2H), 7.57 (d, J=8.0 Hz, 1H), 7.45 (t, J=8.0 Hz, 1H), 7.15 (d, J=8.4 Hz, 1H), 3.69 (brs, 2H), 3.61 (brs, 2H), 3.06 (brs, 2H), 2.96 (brs, 2H), 2.89 (s, 4H), 1.34 (s, 3H), 0.71 (brs, 2H), 0.60 (brs, 2H).

LCMS: m/z: 494.50 [M+H]⁺.

Example 7—Synthesis of 3-chloro-N-(3-methyloxetan-3-yl)-4-[4-[3-(4-oxo-3H-quinazolin-2-yl)propanoyl]piperazin-1-yl]benzamide Step-1

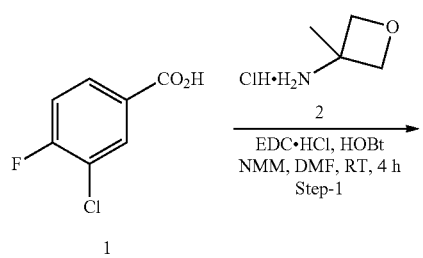

To a stirred solution of 3-chloro-4-fluoro-benzoic acid (500 mg, 2.86 mmol) in DMF (5 mL), 3-methyloxetan-3-amine hydrochloride (420 mg, 3.43 mmol), EDC HCl (820 mg, 4.29 mmol), HOBt (580 mg, 4.29 mmol) and NMM (1.6 mL, 14.32 mmol) were added at RT and stirred for 4 h (TLC indicated complete consumption of the starting material). The reaction mixture was diluted with EtOAc (200 mL), washed with water (1×100 mL), brine solution (1×100 mL). The organic layer was separated, dried over Na₂SO₄, volatiles were evaporated under reduced pressure and the residue was purified by column chromatography (100-200 silica gel, 7 g, 70% EtOAc-Hexane) to afford 3-chloro-4-fluoro-N-(3-methyloxetan-3-yl)benzamide (610 mg, 87%) as a cream color solid.

LCMS: m/z: 244.14 [M+H]⁺.

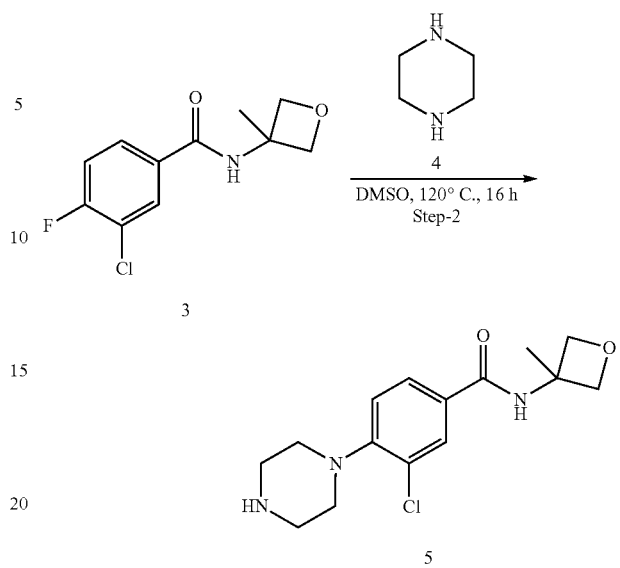

To a stirred solution of 3-chloro-4-fluoro-N-(3-methyloxetan-3-yl)benzamide (600 mg, 2.46 mmol) in DMSO (6 mL), piperazine (1 g, 12.34 mmol) was added at RT and heated at 120° C. for 16 h (TLC indicated complete consumption of the starting material). The reaction mixture was diluted with EtOAc (200 mL), washed with water (1×100 mL), brine solution (1×100 mL). The organic layer was separated, dried over Na₂SO₄, volatiles were evaporated under reduced pressure to afford the crude 3-chloro-N-(3-methyloxetan-3-yl)-4-piperazin-1-yl-benzamide (900 mg) which was carried to the next step without purification.

LCMS: m/z: 310.34 [M+H]⁺.

Step-3

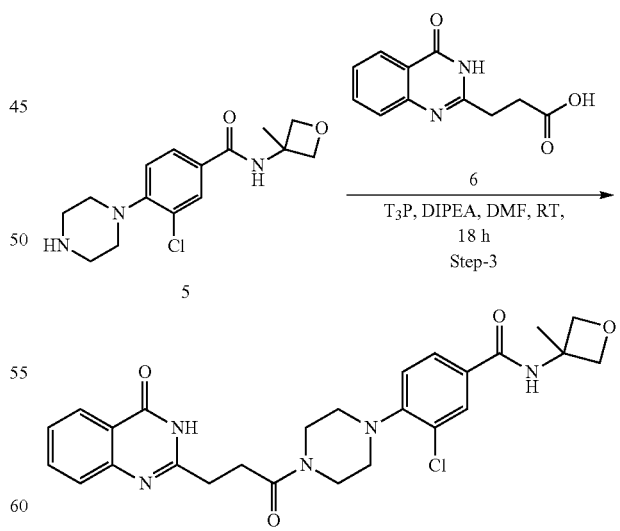

To a stirred solution of 3-(4-oxo-3H-quinazolin-2-yl)propanoic acid (200 mg, 0.917 mmol) in DMF (5 mL), 3-chloro-N-(3-methyloxetan-3-yl)-4-piperazin-1-yl-benzamide (425 mg, 1.37 mmol), T₃P (0.58 mL, 1.83 mmol, 50% solution in DMF) and DIPEA (0.5 mL, 2.75 mmol) were added at RT and stirred for 18 h (TLC indicated complete consumption of starting material). The reaction mixture was diluted with EtOAc (100 mL), washed with water (1×100 mL), brine solution (1×100 mL). The organic layer was separated, dried over Na₂SO₄, volatiles were evaporated under reduced pressure to afford the crude compound which was purified by prep HPLC to afford 3-chloro-N-(3-methyloxetan-3-yl)-4-[4-[3-(4-oxo-3H-quinazolin-2-yl)propanoyl]piperazin-1-yl]benzamide (100 mg, 21%) as a white solid.

$^1$H NMR [300 MHz, DMSO-$d_6$]: δ 12.30 (brs, 1H), 8.86 (brs, 1H), 8.08 (dd, J=8.1, 1.2 Hz, 1H), 7.92 (d, J=1.8 Hz, 1H), 7.81-7.73 (m, 2H), 7.57 (d, J=7.8 Hz, 1H), 7.47-7.42 (m, 1H), 7.19 (d, J=8.4 Hz, 1H), 4.69 (d, J=6.0 Hz, 2H), 4.36 (d, J=6.3 Hz, 2H), 3.70 (brs, 2H), 3.62 (brs, 2H), 3.08 (brs, 2H), 2.98 (brs, 2H), 2.90 (s, 4H), 1.58 (s, 3H).

LCMS: m/z: 510.69 [M+H]$^+$.

Example 8—Synthesis of 2-[3-oxo-3-(4-phenyl-1-piperidyl)propyl]-3H-quinazolin-4-one Step-1

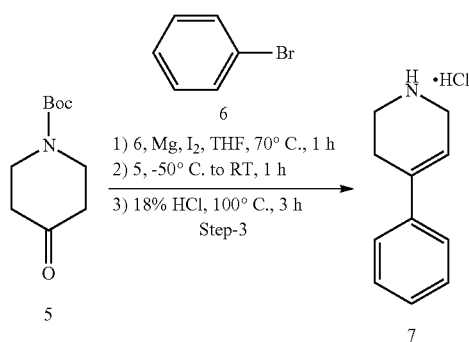 [SMILES: Brc1ccccc1 ; Cl ; CC(C)(C)OC(=O)N1CCC(=O)CC1 ; C1=C(c2ccccc2)CCNC1]

Step-2

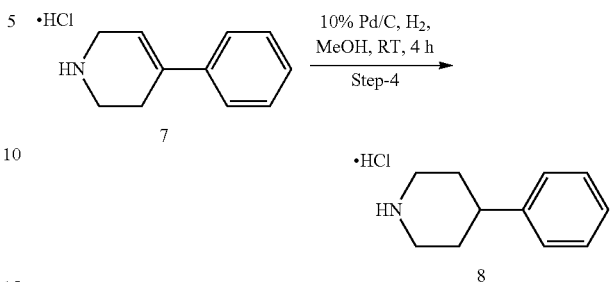

To a stirred solution of 4-phenyl-1,2,3,6-tetrahydropyridine hydrochloride (300 mg, 1.53 mmol) in MeOH (10 mL), 10% Pd—C (100 mg) was added at RT under argon atmosphere. The reaction mixture was flushed with H₂ (3 times) and stirred under H₂ atmosphere (balloon) for 4 h. After completion of the reaction (monitored by LCMS), the reaction mixture was filtered through a short pad of Celite and washed with MeOH (5 mL). The filtrate was concentrated under reduced pressure and the residue was washed with dry ether (2×5 mL) to give 4-phenylpiperidine hydrochloride (300 mg, 99%) as an off-white solid (hygroscopic).

LCMS: m/z: 162.3 [M+H]$^+$.

Step-3

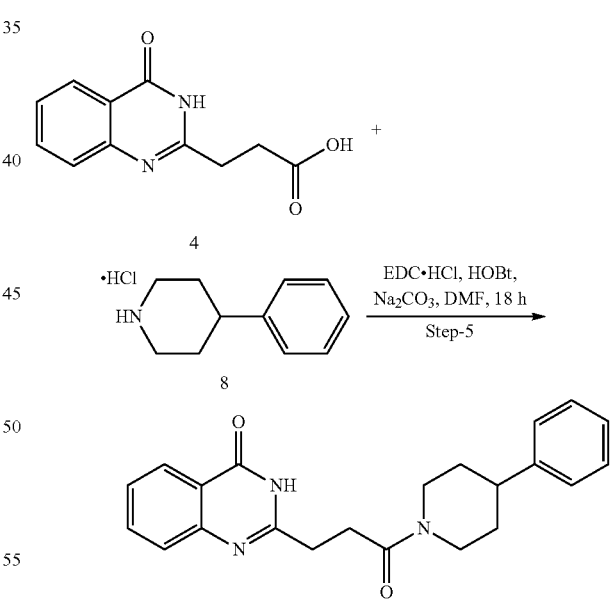

100 mL oven dried two neck round bottomed flask was charged with magnesium turnings (600 mg, 25 mmol) and dry THF (5 mL) at RT under argon atmosphere. To this mixture, iodine (20 mg) was added, heated to 70° C. with vigorous stirring and a solution of bromobenzene (1.57 g, 10 mmol) in dry THF (5 mL) was added maintaining the temperature at 70° C. and continued for 1 h under argon atmosphere. The reaction mixture was brought to RT and added dropwise to a pre-cooled (−50° C.) solution of tert-butyl 4-oxopiperidine-1-carboxylate (1 g, 5.0 mmol) in dry THF (5 mL) under argon atmosphere. The reaction mixture was allowed to warm to RT, stirred for 1 h (TLC indicated complete consumption of the starting material), quenched with saturated aqueous NH₄Cl solution (10 mL) and extracted with EtOAc (2×50 mL). The combined organic extracts were washed with water (10 mL), brine (25 mL) and dried over anhydrous Na₂SO₄. The volatiles were concentrated under reduced pressure; the crude product was taken in 18% aq. HCl solution (15 mL) and heated at 100° C. for 3 h (TLC indicated complete consumption of the starting material). The solvent was removed under reduced pressure and residue was washed with Et₂O (20 mL) and EtOAc (20 mL) to provide 4-phenyl-1,2,3,6-tetrahydropyridine hydrochloride (700 mg, 71%) as an off-white solid (hygroscopic).

LCMS: m/z: 160.3 [M+H]$^+$.

To a stirred solution of 3-(4-oxo-3H-quinazolin-2-yl)propanoic acid (200 mg, 0.917 mmol) and 4-phenylpiperidine hydrochloride (217 mg, 1.1 mmol) in dry DMF (1.5 mL), EDC HCl (264 mg, 1.375 mmol), HOBt (187 mg, 1.38 mmol) and Na₂CO₃ (292 mg, 2.75 mmol) were added at RT under argon atmosphere. The reaction mixture was stirred at RT for 18 h (TLC indicated complete consumption of starting material), quenched with ice cold water (15 mL) and stirred for 30 minutes. The precipitate was filtered and the solid was washed with water (10 mL) and dried under vacuum. The crude product was purified by column chromatography (100-200 silica gel, 25 g, 5% MeOH-DCM) to furnish the 2-[3-oxo-3-(4-phenyl-1-piperidyl)propyl]-3H-quinazolin-4-one (30 mg, 25%) as an off-white solid.

¹H NMR [300 MHz, DMSO-d₆]: δ 12.21 (s, 1H), 8.08 (d, J=6.6 Hz, 1H), 7.79-7.73 (m, 1H), 7.57-7.52 (m, 1H), 7.48-7.43 (m, 1H), 7.38-7.22 (m, 5H), 4.51 (d, J=12.6 Hz, 1H), 4.07 (d, J=13.8 Hz, 1H), 3.14 (t, J=12.6 Hz, 4H), 2.94-2.81 (m, 3H), 2.64-2.57 (m, 1H), 1.84-1.73 (m, 1H), 1.66-1.62 (m, 1H), 1.42-1.33 (m, 1H).

LCMS: m/z: 362.5 [M+H]⁺.

Example 9—Synthesis of 2-[3-oxo-3-(4-phenylpiperazin-1-yl)propyl]-3H-quinazolin-4-one Step-1

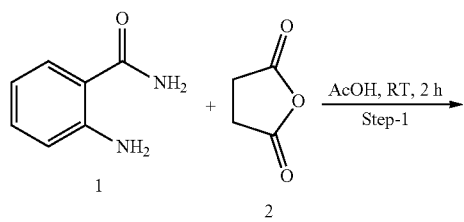

To a stirred solution of 2-aminobenzamide (5 g, 36.76 mmol) in AcOH 10 mL a solution of succinic anhydride (3.67 g, 36.76 mmol) in AcOH (10 mL) was added at RT. The reaction mixture was stirred at RT for 2 h (TLC indicated complete consumption of the starting material), diluted with cold water (100 mL) and stirred for 15 minutes. The precipitate was filtered, washed with cold water (30 mL) and dried under vacuum to afford 4-(2-carbamoylanilino)-4-oxo-butanoic acid (8 g, 92%) as a white solid.

LCMS: m/z: 237.4 [M+H]⁺.

Step-2

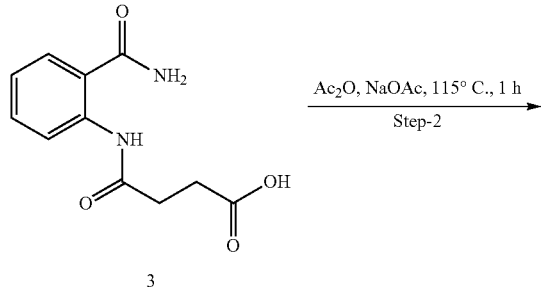

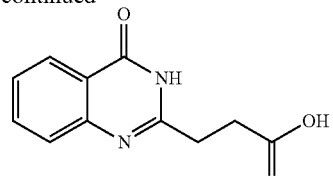

A stirred suspension of 4-(2-carbamoylanilino)-4-oxo-butanoic acid (8 g, 33.86 mmol) and NaOAc (2.78 g, 33.86 mmol) in Ac₂O (10 mL) was heated at 120° C. for 1 h (TLC indicated complete consumption of starting material). The reaction mixture was brought to RT, quenched with water (100 mL) and 1 N NaOH solution was added slowly till pH=10. The resulting mixture was washed with EtOAc (30 mL), the aqueous layer was separated and acidified with AcOH till pH=5, stirred for 1 h and filtered. The solid was washed with hexanes (3×20 mL) and dried under vacuum to afford 3-(4-oxo-3H-quinazolin-2-yl)propanoic acid (5.0 g, 68%) which was used for the next step without purification.

LCMS: m/z: 219.3 [M+H]⁺.

Step-3

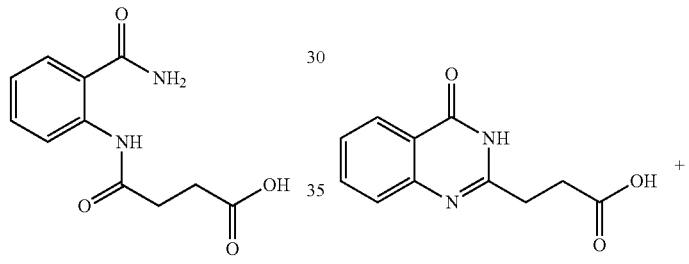

To a stirred solution of 3-(4-oxo-3H-quinazolin-2-yl)propanoic acid (100 mg, 0.458 mmol) and 1-phenylpiperazine (90 mg, 0.55 mmol) in dry DMF (1.5 mL), EDC HCl (132 mg, 0.687 mmol), HOBt (93 mg, 0.688 mmol) and Na₂CO₃ (146 mg, 1.37 mmol) were added at RT under argon atmosphere. The reaction mixture was stirred at RT for 18 h under argon (TLC indicated complete consumption of starting material), quenched with ice cold water (15 mL) and stirred for 30 minutes. The precipitate was filtered off, washed with water (10 mL) and dried under vacuum. The crude product was purified by column chromatography (100-200 silica gel, 50 g, 5% MeOH-DCM) to furnish 2-[3-oxo-3-(4-phenylpiperazin-1-yl)propyl]-3H-quinazolin-4-one (33 mg, 20%) as an off-white solid.

$^1$H NMR [300 MHz, DMSO-d$_6$]: δ 12.21 (s, 1H), 8.07 (dd, J=1.2, 8.1 Hz, 1H), 7.77-7.71 (m, 1H), 7.54 (d, J=7.8 Hz, 1H), 7.47-7.42 (m, 1H), 7.23 (t, J=7.5 Hz, 2H), 6.92 (d, J=8.1 Hz, 2H), 6.81 (t, J=7.2 Hz, 1H), 3.67-3.57 (m, 4H), 3.20-3.06 (m, 4H), 2.89 (s, 4H).

LCMS: m/z: 363.5 [M+H]$^+$.

Example 10—Synthesis of 2-[3-[4-(2-chlorophenyl) piperazin-1-yl]-3-oxo-propyl]-3H-quinazolin-4-one Step-1

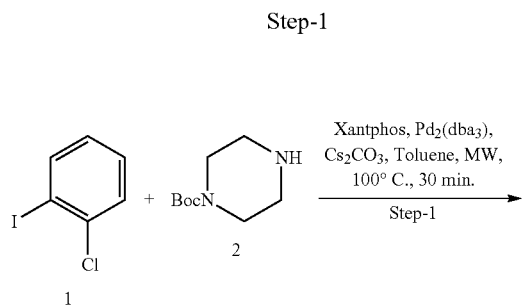

To a stirred solution of 1-chloro-2-iodo-benzene (140 mg, 0.590 mmol) and tert-butyl piperazine-1-carboxylate (100 mg, 0.537 mmol) in dry toluene (2 mL), xantphos (34 mg, 0.0590 mmol), Pd$_2$(dba)$_3$ (24 mg, 0.0262 mmol) and Cs$_2$CO$_3$ (261 mg, 0.80 mmol) were added at RT under argon atmosphere. The resulting mixture was irradiated at 100° C. for 30 minutes in CEM Microwave (TLC indicated the complete consumption of starting material). The solvent was evaporated under reduced pressure and the residue was diluted with water (20 mL), extracted with EtOAc (3×20 mL). The combined organic extracts were washed with brine (20 mL), dried over anhydrous Na$_2$SO$_4$ and concentrated in vacuo. The residue was purified by column chromatography (100-200 silica gel, 10 g, 5% EtOAc-hexane) to afford tert-butyl 4-(2-chlorophenyl)piperazine-1-carboxylate (100 mg, 63%) as an off-white solid.

$^1$H NMR [300 MHz, CDCl$_3$]: δ 7.37 (dd, J=7.8, 1.2 Hz, 1H), 7.22 (td, J=7.8, 1.2 Hz, 1H), 7.02-6.96 (m, 2H), 3.60 (t, J=5.1 Hz, 4H), 2.99 (t, J=5.1 Hz, 4H), 1.48 (s, 9H).

Step-2

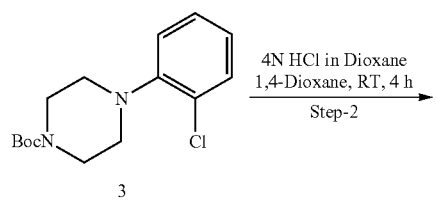

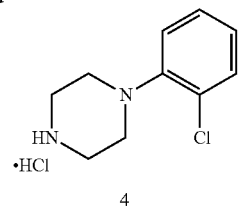

To a stirred solution of tert-butyl 4-(2-chlorophenyl) piperazine-1-carboxylate (250 mg, 0.844 mmol) in 1,4-dioxane (2 mL), 4 N HCl in 1,4-dioxane (0.9 mL, 3.60 mmol) was added dropwise at 0° C. The reaction mixture was allowed to warm to RT and stirred for 4 h (TLC indicated the complete consumption of starting material). The volatiles were removed under reduced pressure to give the crude compound, which was washed with diethyl ether (2×20 mL), and dried under high vacuum to afford 1-(2-chlorophenyl)piperazine hydrochloride (165 mg, 84%) as a white solid.

Step-3

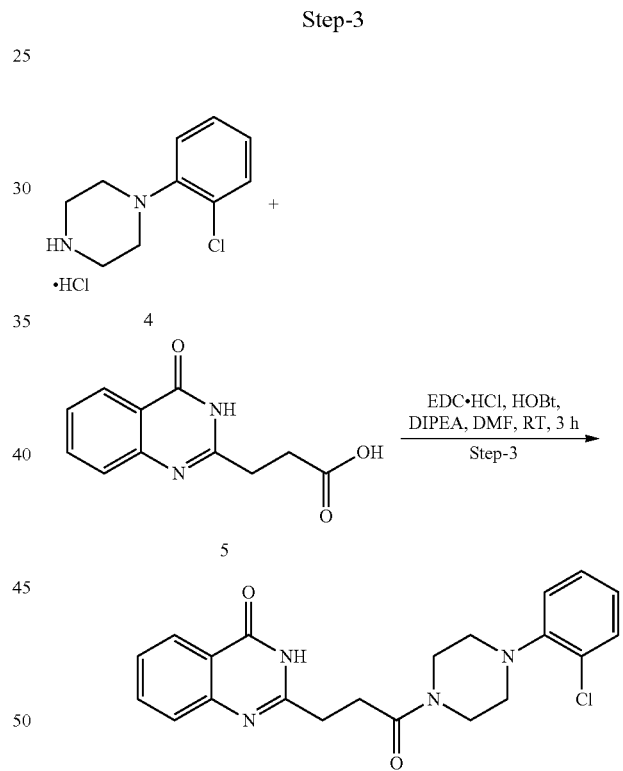

To a stirred solution of 1-(2-chlorophenyl)piperazine hydrochloride (119 mg, 0.510 mmol) and 3-(4-oxo-3H-quinazolin-2-yl)propanoic acid (111 mg, 0.509 mmol) in dry DMF (2 mL) EDC HCl (98 mg, 0.511 mmol), HOBt (69 mg, 0.510 mmol) and DIPEA (0.18 mL, 1.03 mmol) were added at RT and stirred for 3 h (TLC indicated the complete consumption of starting material). The reaction mixture was quenched with cold water (20 mL) and stirred for 15 minutes. The resultant precipitate was filtered off and the solid was washed with Et$_2$O (2×5 mL) to afford 2-[3-[4-(2-chlorophenyl)piperazin-1-yl]-3-oxo-propyl]-3H-quinazolin-4-one (90 mg, 44%) as a white solid.

$^1$H NMR [300 MHz, DMSO-d$_6$]: δ 12.20 (s, 1H), 8.08 (dd, J=7.8, 1.2 Hz, 1H), 7.76-7.73 (m, 1H), 7.57 (d, J=8.1

Hz, 1H), 7.48-7.41 (m, 2H), 7.31-7.28 (m, 1H), 7.15-7.04 (m, 2H), 3.68 (s, 2H), 3.61 (s, 2H), 3.00 (s, 4H), 2.89 (s, 4H). LCMS: m/z: 397.30 [M+H]+.

Example 11—Synthesis of 6-[4-[3-(4-oxo-3H-quinazolin-2-yl)propanoyl]piperazin-1-yl]pyridine-3-carbonitrile Step-1

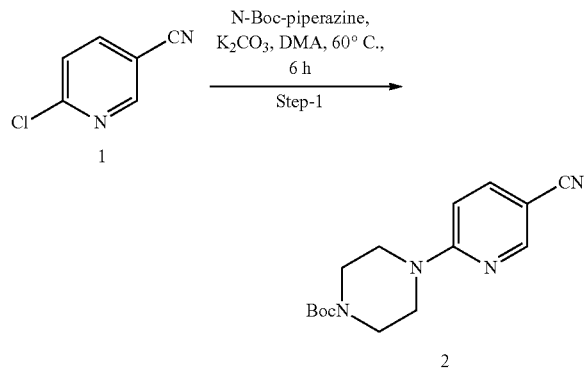

To a stirred solution of 6-chloropyridine-3-carbonitrile (2 g, 14.43 mmol) in DMA (20 mL), K$_2$CO$_3$ (3.4 g, 24.63 mmol), N-Boc-piperazine (2.7 g, 14.50 mmol) were added at RT under argon atmosphere and stirred for 3 h. The reaction mixture was heated at 60° C. for 3 h (TLC indicated complete consumption of starting material) and poured into ice-water (100 mL) during which solid precipitated out which was filtered, washed with Et$_2$O (3×10 mL), pentane (3×10 mL) and dried to afford tert-butyl 4-(5-cyano-2-pyridyl)piperazine-1-carboxylate (3 g, 73%) which was used without purification.

LCMS: m/z: 289.3 [M+H]+.

Step-2

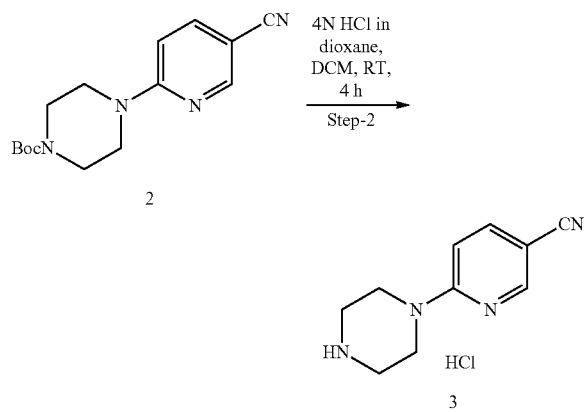

To a stirred solution of tert-butyl 4-(5-cyano-2-pyridyl)piperazine-1-carboxylate (0.5 g, 1.736 mmol) in DCM, 4 N HCl in dioxane (0.5 mL) was added dropwise and stirred at RT for 4 h under argon atmosphere (TLC indicated complete consumption of starting material). The reaction mixture was concentrated under reduced pressure to give the residue which was washed with Et$_2$O (2×5 mL), DCM (2×5 mL), pentane (2×5 mL) and dried under vacuo to afford 6-piperazin-1-ylpyridine-3-carbonitrile hydrochloride (0.3 g, 93% yield) which was carried for the next step without purification.

$^1$H NMR [300 MHz, DMSO-d$_6$]: δ 9.58 (brs, 2H), 8.54 (d, J=2.8 Hz, 1H), 7.91-7.33 (dd, J=3.2, 12.4 Hz, 1H), 7.02 (d, J=12.0 Hz, 1H), 3.91 (t, J=6.8 Hz, 4H), 3.14 (brs, 4H).

Step-3

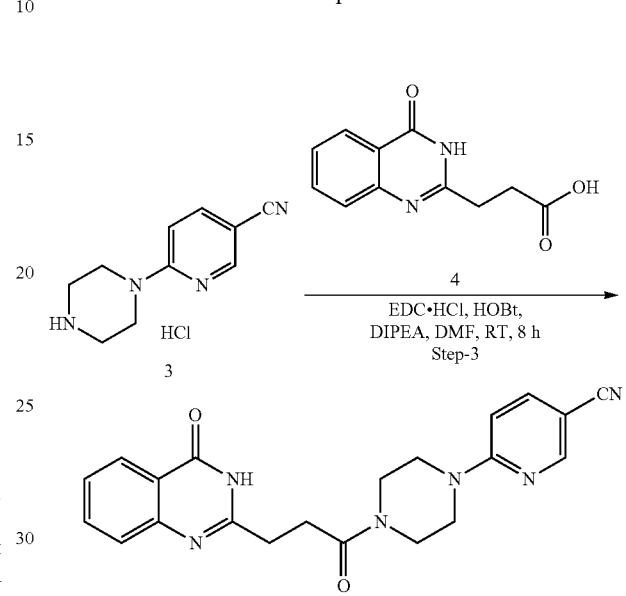

To a stirred solution of 6-piperazin-1-ylpyridine-3-carbonitrile hydrochloride (0.2 g, 0.974 mmol) and 3-(4-oxo-3H-quinazolin-2-yl)propanoic acid (0.2 g, 0.913 mmol) in DMF (2 mL), EDC HCl (0.35 g, 1.83 mmol), HOBt (0.24 g, 1.83 mmol) and DIPEA (0.8 mL, 4.59 mmol) were added at RT and stirred for 8 h (TLC indicated complete consumption of starting material). The reaction mixture was poured into ice-cold water (30 mL) and stirred for 15 min during which solid precipitated out which was filtered and purified by column chromatography (100-200 silica gel, 10 g, 5% MeOH in DCM) to afford 6-[4-[3-(4-oxo-3H-quinazolin-2-yl)propanoyl]piperazin-1-yl]pyridine-3-carbonitrile (0.025 g, 20%) as a white solid.

$^1$H NMR [300 MHz, DMSO-d$_6$]: δ 12.02 (s, 1H), 8.51 (d, J=3.2 Hz, 1H), 8.08-8.05 (dd, J=1.6, 10.4 Hz, 1H), 7.90-7.86 (dd, J=3.2, 12.0 Hz, 1H), 7.77-7.71 (m, 1H), 7.54 (d, J=10.4 Hz, 1H), 7.47-7.41 (m, 1H), 6.94 (d, J=12.0 Hz, 1H), 3.77-3.75 (m, 2H), 3.64 (d, J=4.8 Hz, 4H), 3.57-3.56 (m, 2H), 2.89 (s, 4H).

LCMS: m/z: 389.61 [M+H]+.

Example 12—Synthesis of 6-[4-[3-(4-oxo-3H-quinazolin-2-yl)propanoyl]piperazin-1-yl]pyridine-3-carboxamide

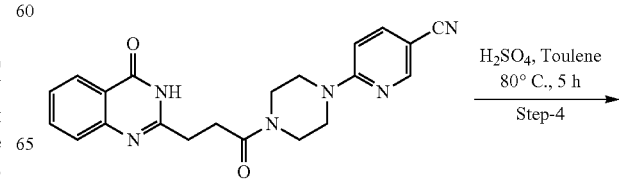

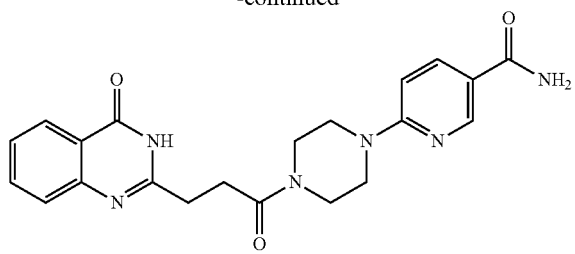

To a stirred solution of 6-[4-[3-(4-oxo-3H-quinazolin-2-yl)propanoyl]piperazin-1-yl]pyridine-3-carbonitrile (100 mg, 0.257 mmol) in toluene (1 mL), $H_2SO_4$ (127 mg, 1.285 mmol) was added at RT under argon atmosphere and heated at 80° C. for 5 h (TLC indicated complete consumption of starting material). The reaction mixture was concentrated under reduced pressure and co-distilled with toluene (3×5 mL), basified with 1 N NaOH solution till pH=9, extracted with 10% MeOH-DCM (3×10 mL), dried over $Na_2SO_4$ and concentrated under reduced pressure to give the residue which was purified by column chromatography (100-200 silica gel, 15 g, 10% MeOH in DCM) to afford 6-[4-[3-(4-oxo-3H-quinazolin-2-yl)propanoyl]piperazin-1-yl]pyridine-3-carboxamide (0.025 g, 20%) as a white solid.

$^1$H NMR [300 MHz, DMSO-$d_6$]: δ 12.02 (s, 1H), 8.63 (d, J=3.2 Hz, 1H), 8.08-8.05 (dd, J=1.6, 10.4 Hz, 1H), 8.00-7.96 (dd, J=3.2, 12.0 Hz, 1H), 7.79-7.71 (m, 2H), 7.54 (d, J=10.8 Hz, 1H), 7.44 (t, J=10.4 Hz, 1H), 7.17 (s, 1H), 6.86 (d, J=12 Hz, 1H), 3.69-3.64 (m, 4H), 3.56 (s, 4H), 2.89 (s, 4H).

LCMS: m/z: 407.5 [M+H]$^+$.

Example 13—Synthesis of 6-[4-[3-(5-methyl-4-oxo-3H-quinazolin-2-yl)propanoyl]piperazin-1-yl]pyridine-3-carbonitrile

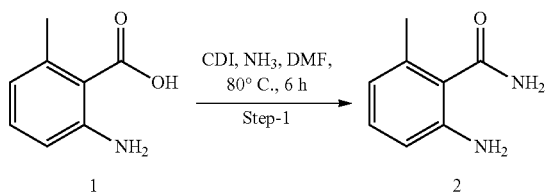

To a stirred solution of 2-amino-6-methyl-benzoic acid (0.5 g, 3.31 mmol) in DMF (5 mL) at RT, CDI (0.53 g, 3.31 mmol) was added. The reaction mixture was heated at 80° C. for 2 h and aq. ammonia (25%, 10 mL) was added carefully to the above reaction mixture maintaining the temperature at 80° C. and continued for 4 h (TLC indicated complete consumption of starting material). The reaction mixture was slowly brought to RT, diluted with water (30 mL) and extracted with EtOAc (3×100 mL). The combined organic extracts were washed with water (2×50 mL), brine (40 mL), dried over $Na_2SO_4$ and concentrated under reduced pressure to afford the crude residue which was washed with $Et_2O$ (10 mL) and dried under high vacuum to afford 2-amino-6-methyl-benzamide (200 mg, 40%) as a white solid.

LCMS (ESI+): m/z: 151.09 [M+H]$^+$.

Step-2

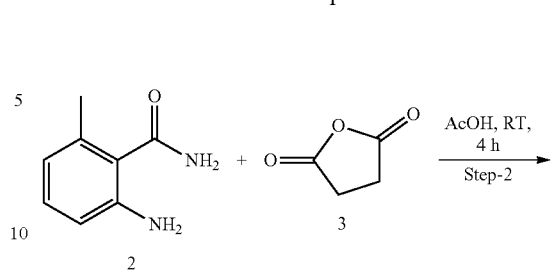

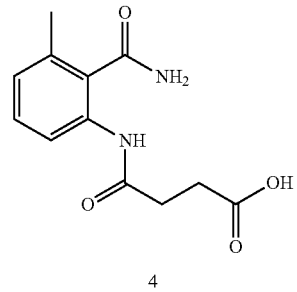

To a stirred solution of 2-amino-6-methyl-benzamide (0.2 g, 1.33 mmol) in AcOH (3 mL), succinic anhydride was added at RT and stirred for 4 h (TLC indicated complete consumption of starting material). The reaction mixture was poured into ice cold water (5 mL) and stirred for 30 min. during which solid precipitated out. The solid was filtered, washed with water (20 mL), cold acetone (5 mL) and dried under high vacuum to afford 4-(2-carbamoyl-3-methyl-anilino)-4-oxo-butanoic acid (250 mg, 75%) as a white solid.

LCMS (ESI+): m/z: 251.50 [M+H]$^+$.

Step-3

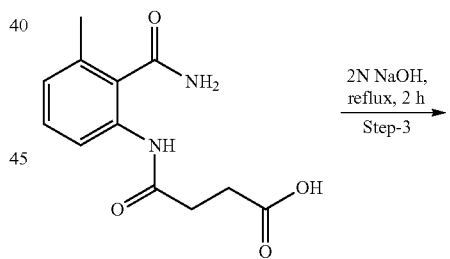

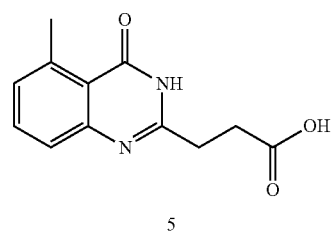

4-(2-carbamoyl-3-methyl-anilino)-4-oxo-butanoic acid (0.25 g, 1.0 mmol) was taken in 2 N aq. NaOH (5 mL) and stirred at 100° C. for 2 h (TLC indicated complete consumption of starting material). The reaction mixture was slowly cooled to 0° C. and acidified to pH=3-4 with 2 N aq. HCl during which white solid precipitated. The suspension was stirred at 0° C. for 30 min., filtered, washed with water (20 mL), cold acetone (2 mL) and dried under high vacuum to provide 3-(5-methyl-4-oxo-3H-quinazolin-2-yl)propanoic acid (150 mg, 64%) as an off-white solid.

LCMS (ESI+): m/z: 233.49 [M+H]+.

Step-4

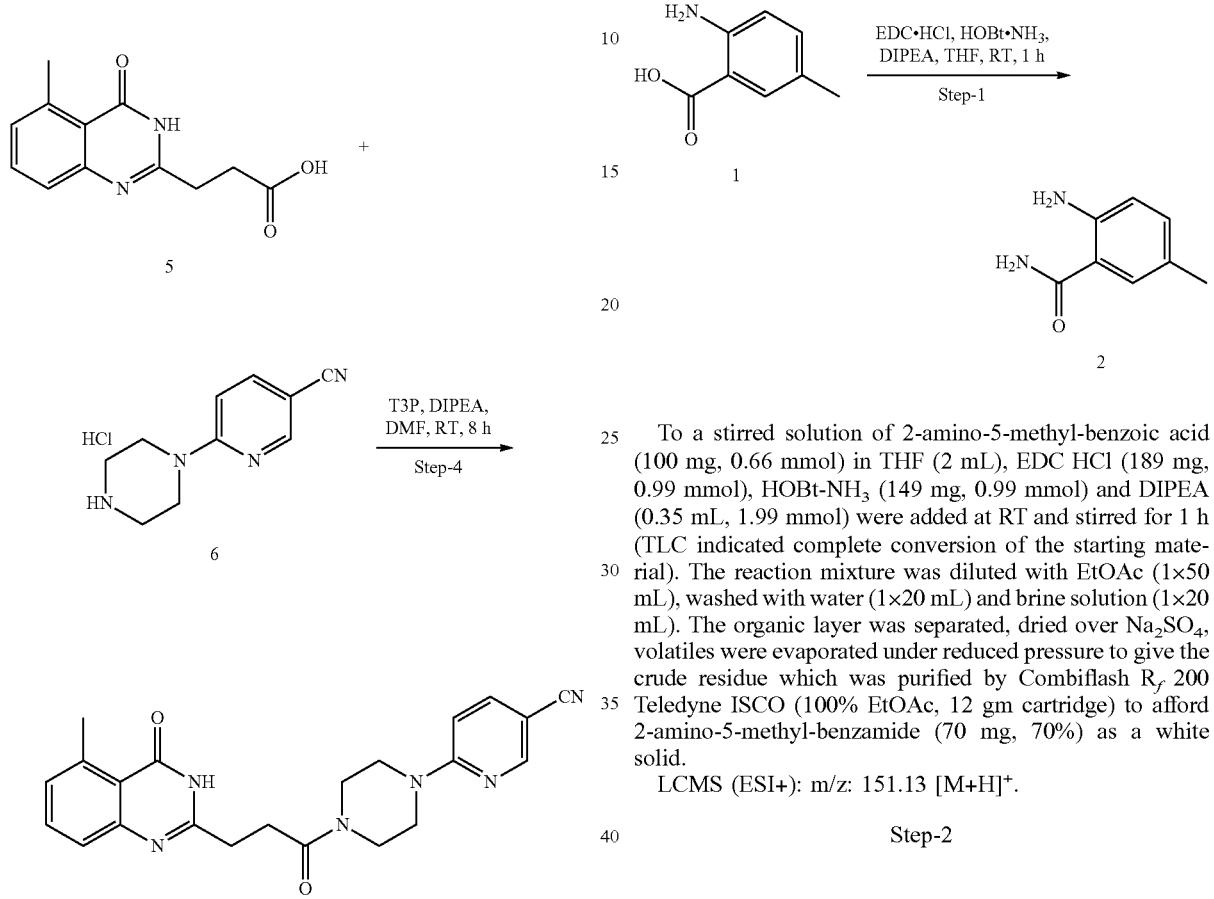

To a stirred solution of 3-(5-methyl-4-oxo-3H-quinazolin-2-yl)propanoic acid (150 mg, 0.65 mmol) and 6-piperazin-1-ylpyridine-3-carbonitrile hydrochloride (145 mg, 0.77 mmol) in DMF (2 mL), DIPEA (0.3 mL, 1.94 mmol) and T$_3$P (50% solution in EtOAc, 0.4 mL, 1.29 mmol) were added at RT and stirred for 8 h (TLC indicated complete consumption of starting material). The reaction mixture was quenched with water (10 mL) and extracted with EtOAc (3×40 mL). The combined organic extracts were washed with cold water (3×30 mL), brine (20 mL), dried over Na$_2$SO$_4$ and concentrated under reduced pressure to give the crude residue which was purified by column chromatography (100-200 silica gel, 10 g, 5% MeOH-DCM) to afford 6-[4-[3-(5-methyl-4-oxo-3H-quinazolin-2-yl)propanoyl]piperazin-1-yl]pyridine-3-carbonitrile (60 mg, 27%) as a white solid.

$^1$H NMR [300 MHz, DMSO-d$_6$]: δ 11.98 (brs, 1H), 8.51 (d, J=2.1 Hz, 1H), 7.88 (dd, J=9.0, 2.1 Hz 1H), 7.55 (t, J=7.8 Hz, 1H), 7.34 (d, J=7.8 Hz, 1H), 7.16 (d, J=7.2 Hz, 1H), 6.93 (d, J=9.0 Hz, 1H), 3.77-3.76 (m, 2H), 3.64-3.62 (m, 4H), 3.57-3.55 (m, 2H), 2.88-2.83 (m, 4H), 2.75 (s, 3H).

LCMS (ESI+): m/z: 403.66 [M+H]+.

Example 14—Synthesis of 6-[4-[3-(6-methyl-4-oxo-3H-quinazolin-2-yl)propanoyl]piperazin-1-yl]pyridine-3-carbonitrile Step-1

To a stirred solution of 2-amino-5-methyl-benzoic acid (100 mg, 0.66 mmol) in THF (2 mL), EDC HCl (189 mg, 0.99 mmol), HOBt-NH$_3$ (149 mg, 0.99 mmol) and DIPEA (0.35 mL, 1.99 mmol) were added at RT and stirred for 1 h (TLC indicated complete conversion of the starting material). The reaction mixture was diluted with EtOAc (1×50 mL), washed with water (1×20 mL) and brine solution (1×20 mL). The organic layer was separated, dried over Na$_2$SO$_4$, volatiles were evaporated under reduced pressure to give the crude residue which was purified by Combiflash R$_f$ 200 Teledyne ISCO (100% EtOAc, 12 gm cartridge) to afford 2-amino-5-methyl-benzamide (70 mg, 70%) as a white solid.

LCMS (ESI+): m/z: 151.13 [M+H]+.

Step-2

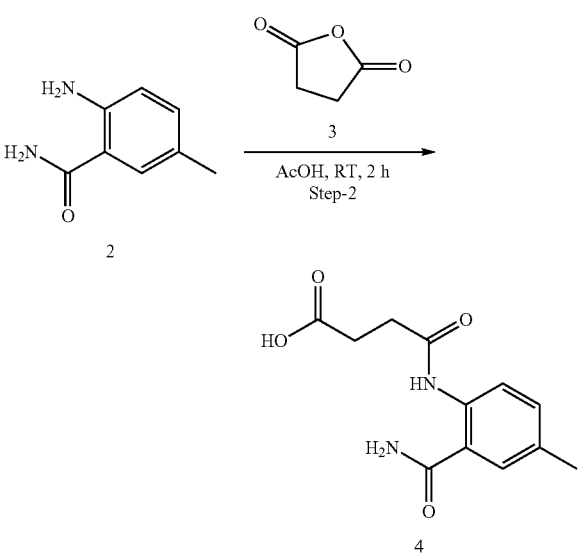

To a stirred solution of 2-amino-5-methyl-benzamide (600 mg, 4.0 mmol) in AcOH (6 mL), Succinic succinic anhydride (480 mg, 4.80 mmol) was added at RT and stirred for 2 h (TLC indicated complete conversion of starting material). The reaction mixture was diluted with ice cold water (1×50 mL), stirred for 30 min during which solid was precipitated out which was filtered, washed with water (1×50 mL), followed by cold acetone (1×20 mL) and dried under high vacuum to give 4-(2-carbamoyl-4-methyl-anilino)-4-oxo-butanoic acid (800 mg, 80%) as a white solid.

LCMS (ESI+): m/z: 273.56 [M+Na]$^+$.

Step-3

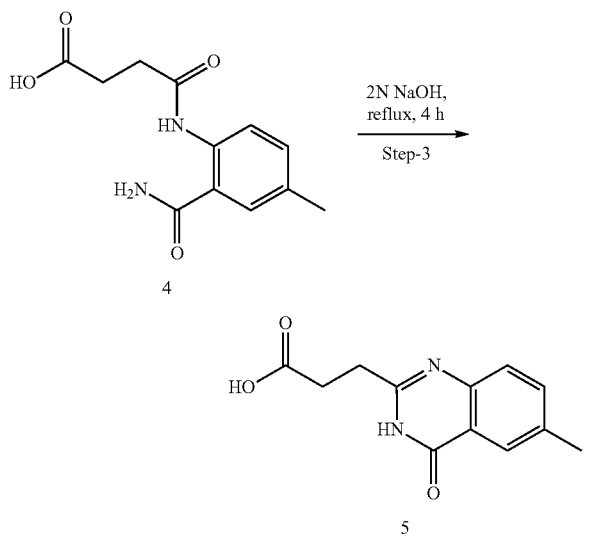

A stirred solution of 4-(2-carbamoyl-4-methyl-anilino)-4-oxo-butanoic acid (480 mg, 2.07 mmol) in aqueous 2 N NaOH (15 mL) was heated at 100° C. for 4 h (TLC indicated complete conversion of compound 4). The reaction mixture was cooled to 0° C., acidified with AcOH till pH=5 during which solid precipitated out. The solid was filtered, washed with water (1×80 mL), followed by cold acetone (1×20 mL) and dried under high vacuum to give 3-(6-methyl-4-oxo-3H-quinazolin-2-yl)propanoic acid (380 mg, 85%) as an off-white solid.

LCMS (ESI+): m/z: 233.45 [M+H]$^+$.

Step-4

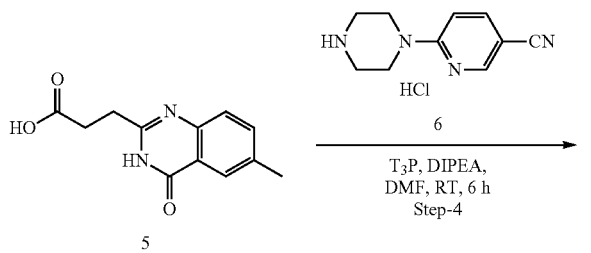

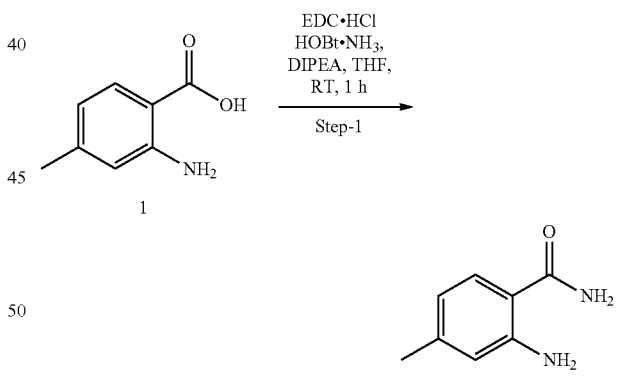

To a stirred solution of 3-(6-methyl-4-oxo-3H-quinazolin-2-yl)propanoic acid (250 mg, 1.077 mmol) in DMF (5 mL) at RT, 6-piperazin-1-ylpyridine-3-carbonitrile hydrochloride (289 mg, 1.293 mmol), T$_3$P (50% in DMF, 0.68 mL, 2.15 mmol) and DIPEA (0.57 mL, 3.23 mmol) were added and stirred for 6 hours (TLC indicated complete consumption of the starting material). The reaction mixture was diluted with water (1×80 mL), stirred for 5 min when solid precipitated out which was filtered. The solid was washed with water (1×70 mL) and dried under high vacuum to furnish 6-[4-[3-(6-methyl-4-oxo-3H-quinazolin-2-yl)propanoyl]piperazin-1-yl]pyridine-3-carbonitrile (170 mg, 39%) as an off-white solid.

$^1$H NMR [300 MHz, DMSO-d$_6$]: δ 12.10 (brs, 1H), 8.51 (s, 1H), 7.90-7.87 (m, 2H), 7.56 (d, J=8.1 Hz, 1H), 7.44 (d, J=8.4 Hz, 1H), 6.94 (d, J=9.3 Hz, 1H), 3.79-3.72 (m, 2H), 3.68-3.62 (m, 4H), 3.59-3.54 (m, 2H), 2.87 (s, 4H), 2.41 (s, 3H).

LCMS (ESI$^+$): m/z: 403.66 [M+H]$^+$.

Example 15—Synthesis of 6-[4-[3-(7-methyl-4-oxo-3H-quinazolin-2-yl)propanoyl]piperazin-1-yl]pyridine-3-carbonitrile Step-1

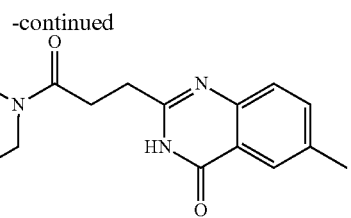

To a stirred solution of 2-amino-4-methyl-benzoic acid (300 mg, 1.99 mmol) in THF (6 mL), EDC HCl (569 mg, 2.98 mmol), HOBt-NH$_3$ (447 mg, 2.98 mmol) and DIPEA (1.06 mL, 5.96 mmol) were added at RT and stirred for 1 h (TLC indicated complete consumption of starting material). The reaction mixture was diluted with water (30 mL), extracted with EtOAc (3×25 mL). The combined organic extracts were dried over Na$_2$SO$_4$, concentrated under reduced pressure to give the crude compound which was purified by flash column chromatography (100-200 silica gel, 5 g, 50% EtOAc-Hexane) to afford 2-amino-4-methyl-benzamide (190 mg, 64%) as a white solid.

¹H NMR [300 MHz, DMSO-d₆]: δ 7.62 (brs, 1H), 7.42 (d, J=8.1 Hz, 1H), 6.93 (brs, 1H), 6.54-6.46 (m, 3H), 6.30-6.27 (m, 1H), 2.15 (s, 3H).

Step-2

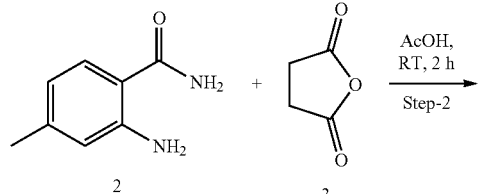

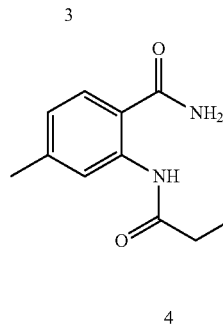

To a stirred solution of 2-amino-4-methyl-benzamide (190 mg, 1.27 mmol) in AcOH (5 mL), succinic anhydride (151 mg, 1.52 mmol) was added at RT and stirred for 2 h (TLC indicated complete consumption of starting material). The reaction mixture was diluted with water (20 mL), solid was precipitated out, filtered and dried under vacuum to get the required 4-(2-carbamoyl-5-methyl-anilino)-4-oxo-butanoic acid (250 mg, 89%) which was used for next step without further purification.

¹H NMR [300 MHz, DMSO-d₆]: δ 12.37 (brs, 1H), 11.88 (s, 1H), 8.33 (s, 1H), 8.20 (s, 1H), 7.70 (d, J=8.1 Hz, 1H), 7.64 (s, 1H), 6.91 (d, J=7.8 Hz, 1H), 2.53-2.50 (m, 4H), 2.31 (s, 3H).

LCMS: m/z: 273.50 [M+Na]⁺.

Step-3

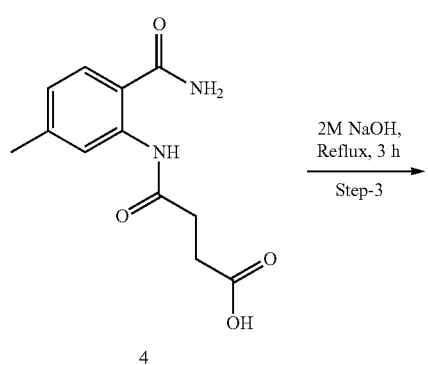

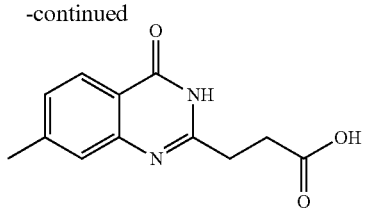

4-(2-Carbamoyl-5-methyl-anilino)-4-oxo-butanoic acid (250 mg, 1 mmol) was taken in 2 N NaOH (10 mL) and refluxed for 3 h (TLC indicated complete consumption of starting material), cooled to 0° C. and acidified with AcOH till pH=4 during which solid precipitated out. The solid was filtered & dried under vacuum to afford 3-(7-methyl-4-oxo-3H-quinazolin-2-yl)propanoic acid (220 mg, 95%) which was used for next step without further purification.

LCMS: m/z: 233.45 [M+H]⁺.

Step-4

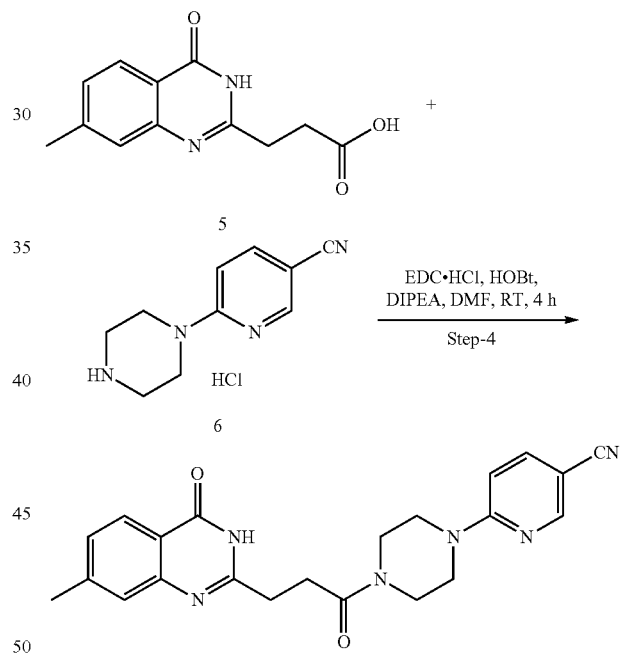

To a stirred solution of 3-(7-methyl-4-oxo-3H-quinazolin-2-yl)propanoic acid (150 mg, 0.65 mmol) and 6-piperazin-1-ylpyridine-3-carbonitrile hydrochloride (173 mg, 0.78 mmol) in DMF (4 mL), EDC HCl (185 mg, 0.97 mmol), HOBt (130 mg, 0.97 mmol) and DIPEA (0.46 mL, 2.58 mmol) were added at RT and stirred for 4 h (TLC indicated complete consumption of starting material). The reaction mixture was poured into cold water (25 mL), stirred for 10 min, during which solid was precipitated out. The solid was filtered, dried under vacuum, washed with Et₂O (20 mL) and hexane (20 mL) to obtain 6-[4-[3-(7-methyl-4-oxo-3H-quinazolin-2-yl)propanoyl]piperazin-1-yl]pyridine-3-carbonitrile (75 mg, 29%) as an off-white solid.

¹H NMR [300 MHz, DMSO-d₆]: δ 12.1 (s, 1H), 8.52 (s, 1H), 7.96-7.87 (m, 2H), 7.33 (s, 1H), 7.26 (d, J=8.1 Hz, 1H), 6.94 (d, J=9.3 Hz, 1H), 3.78 (brs, 2H), 3.65 (brs, 4H), 3.57 (brs, 2H), 2.87 (brs, 4H), 2.39 (s, 3H).
LCMS: m/z: 403.69 [M+H]⁺.

Example 16—Synthesis of 6-[4-[3-(8-methyl-4-oxo-3H-quinazolin-2-yl)propanoyl]piperazin-1-yl]pyridine-3-carbonitrile

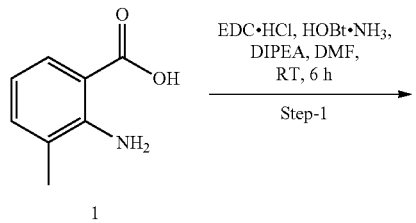

To a stirred solution of 2-amino-3-methyl-benzoic acid (0.5 g, 3.31 mmol) in THF (15 mL), EDC HCl (0.948 g, 4.97 mmol), HOBt-NH₃ (0.745 g, 4.97 mmol) and DIPEA (1.76 mL, 9.93 mmol) were added at RT and stirred for 6 h (TLC indicates complete conversion of starting material). The reaction mixture was diluted with water (30 mL) and extracted with EtOAc (3×100 mL). The combined organic extracts were washed with water (2×50 mL), brine (40 mL), dried over Na₂SO₄ and concentrated under reduced pressure to give the crude residue. The crude material was purified by column chromatography (100-200 silica gel, 20 g, 50% EtOAc-Hexane) to afford 2-amino-3-methyl-benzamide (0.3 g, 60%) as a white solid.
LCMS: m/z: 151.09 [M+H]⁺.

Step-2

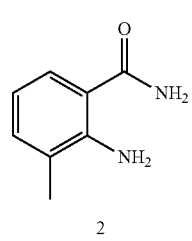

To a stirred solution of 2-amino-3-methyl-benzamide (0.3 g, 2.0 mmol) in AcOH (3 mL), succinic anhydride was added at RT and stirred for 4 h (TLC indicated complete consumption of starting material). The reaction mixture was poured into ice-cold water (10 mL) and stirred for 30 min. during which solid precipitated. The solid was filtered, washed with water (20 mL), cold acetone (5 mL) and dried under high vacuum to afford 4-(2-carbamoyl-6-methyl-anilino)-4-oxo-butanoic acid (280 mg, 56%) as a white solid.
LCMS: m/z: 251.48 [M+H]⁺.

Step-3

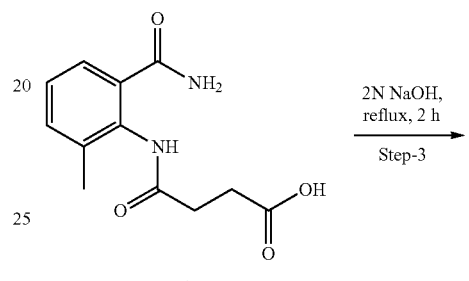

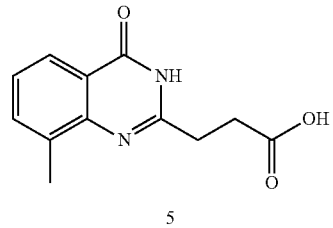

4-(2-Carbamoyl-6-methyl-anilino)-4-oxo-butanoic acid (0.28 g, 1.12 mmol) in 2 N aq. NaOH (5 mL) was stirred at 100° C. for 2 h (TLC indicated complete consumption of starting material). The reaction mixture was cooled to 0° C. and acidified with 2 N aq. HCl till pH=3-4 during which white solid precipitated. The suspension was stirred at 0° C. for 30 min., filtered, washed with water (20 mL), cold acetone (5 mL) and dried under high vacuum to provide 3-(8-methyl-4-oxo-3H-quinazolin-2-yl)propanoic acid (180 mg, 69%) as an off-white solid.
LCMS: m/z: 233.45 [M+H]⁺.

Step-4

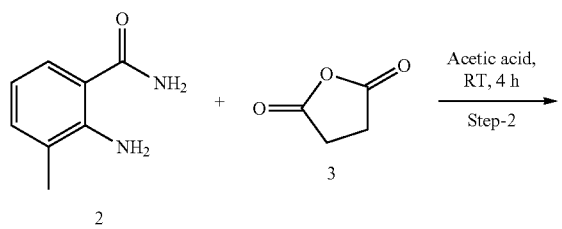

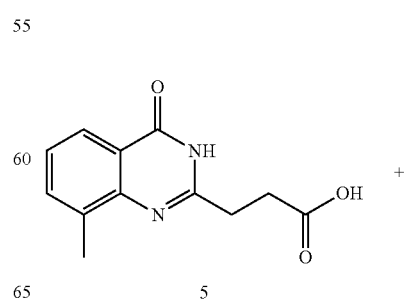

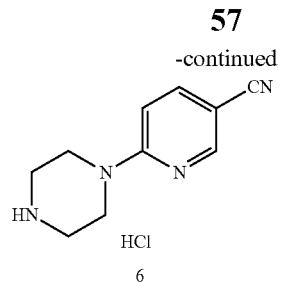

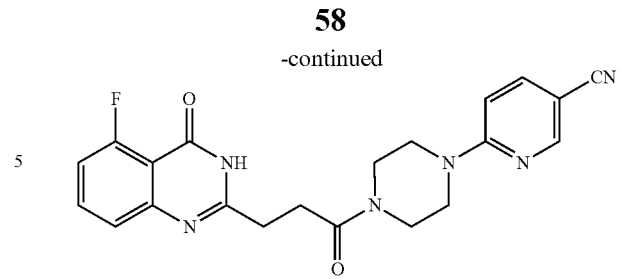

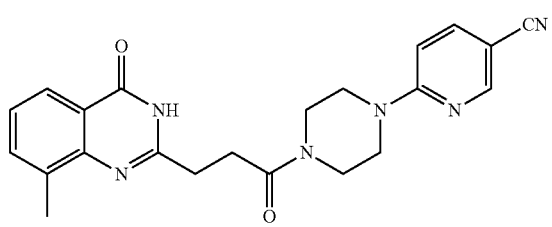

To a stirred solution of 3-(8-methyl-4-oxo-3H-quinazolin-2-yl)propanoic acid (100 mg, 0.43 mmol) and 6-piperazin-1-ylpyridine-3-carbonitrile hydrochloride (97 mg, 0.52 mmol) in DMF (3 mL), DIPEA (0.23 mL, 1.29 mmol) and T$_3$P (0.27 mL, 0.86 mmol) were added at RT and stirred for 3 h (TLC indicated complete consumption of starting material). The reaction mixture was quenched with water (10 mL) and extracted with EtOAc (3×60 mL). The combined organic extracts were washed with cold water (3×30 mL), brine (20 mL), dried over Na$_2$SO$_4$ and concentrated under reduced pressure to give the crude residue. The crude material was recrystallized from Acetonitrile (5 mL) to afford 6-[4-[3-(8-methyl-4-oxo-3H-quinazolin-2-yl)propanoyl]piperazin-1-yl]pyridine-3-carbonitrile (60 mg, 34%) as a white solid.

$^1$H NMR [300 MHz, DMSO-d$_6$]: δ 12.20 (brs, 1H), 8.51 (d, J=2.1 Hz, 1H), 7.92-7.86 (m, 2H), 7.60 (d, J=6.9 Hz, 1H), 7.31 (t, J=7.5 Hz, 1H), 6.93 (d, J=9.0 Hz, 1H), 3.77-3.75 (m, 2H), 3.66-3.65 (m, 4H), 3.59-3.57 (m, 2H), 2.90 (s, 4H), 2.46 (s, 3H).

LCMS: m/z: 403.68 [M+H]$^+$.

Example 17—Synthesis of 6-[4-[3-(5-fluoro-4-oxo-3H-quinazolin-2-yl)propanoyl]piperazin-1-yl]pyridine-3-carbonitrile

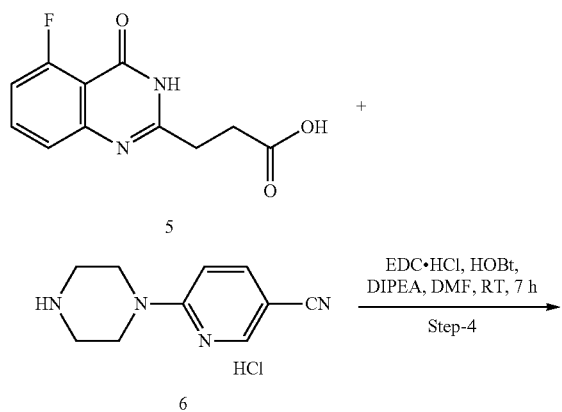

To a stirred solution of 3-(5-fluoro-4-oxo-3H-quinazolin-2-yl)propanoic acid (250 mg, 1.054 mmol) in DMF (5 mL), 6-piperazin-1-ylpyridine-3-carbonitrile hydrochloride (283 mg, 1.265 mmol), EDC HCl (302 mg, 1.582 mmol), HOBt (213 mg, 1.582 mmol) and DIPEA (0.56 mL, 3.164 mmol) were added at RT and stirred for 7 h (TLC indicated complete consumption of starting material). The reaction mixture was diluted with water (1×80 mL), stirred for 5 min at RT during which solid was precipitated out which was filtered, washed with water (1×70 mL), dried under high vacuum to provide 6-[4-[3-(5-fluoro-4-oxo-3H-quinazolin-2-yl)propanoyl]piperazin-1-yl]pyridine-3-carbonitrile (120 mg, 23%) as a pale yellow solid.

$^1$H NMR [300 MHz, DMSO-d$_6$]: δ 12.20 (brs, 1H), 8.51 (d, J=2.1 Hz, 1H), 7.88 (dd, J=9.3, 2.4 Hz, 1H), 7.73-7.67 (m, 1H), 7.35 (d, J=8.1 Hz, 1H) 7.21-7.15 (m, 1H), 6.94 (d, J=9.3 Hz, 1H), 3.81-3.74 (m, 2H), 3.68-3.62 (m, 4H), 3.58-3.53 (m, 2H), 2.87 (s, 4H).

LCMS: m/z: 407.60 [M+H]$^+$.

Example 18—Synthesis of 6-[4-[3-(6-fluoro-4-oxo-3H-quinazolin-2-yl)propanoyl]piperazin-1-yl]pyridine-3-carbonitrile

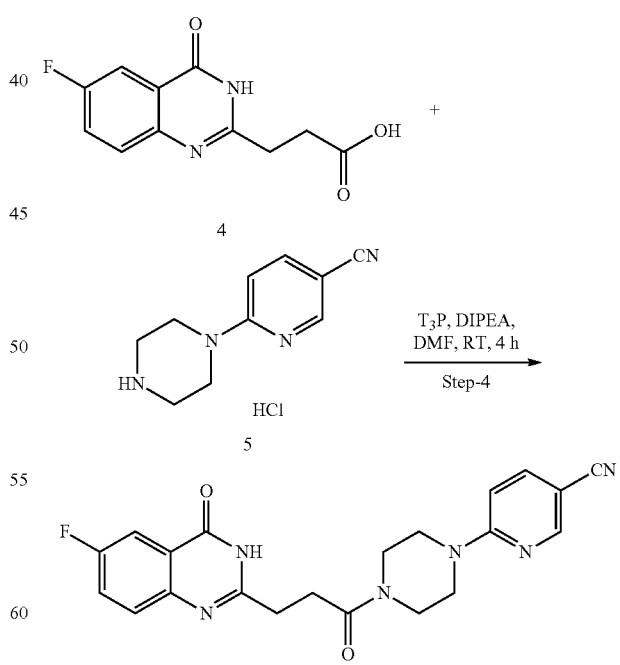

To a stirred solution of 3-(6-fluoro-4-oxo-3H-quinazolin-2-yl)propanoic acid (100 mg, 0.42 mmol) and 6-piperazin-1-ylpyridine-3-carbonitrile hydrochloride (95 mg, 0.51 mmol) in DMF (2 mL), DIPEA (0.2 mL, 1.27 mmol) and T₃P (0.3 mL, 0.85 mmol) were added at RT and stirred for 4 h (TLC indicates complete consumption of starting material). The reaction mixture was quenched with water (10 mL) and extracted into EtOAc (3×40 mL). The combined organic extracts were washed with cold water (3×30 mL), brine (20 mL), dried over Na₂SO₄ and concentrated under reduced pressure to give crude residue. The crude material was purified by column chromatography (100-200 silica gel, 10 g, 5% MeOH-DCM) to afford 6-[4-[3-(6-fluoro-4-oxo-3H-quinazolin-2-yl)propanoyl]piperazin-1-yl]pyridine-3-carbonitrile (60 mg, 35%) as a white Solid.

¹H NMR [400 MHz, DMSO-d₆]: δ 12.33 (brs, 1H), 8.51 (d, J=2.1 Hz, 1H), 7.88 (dd, J=9.0, 2.1 Hz, 1H), 7.74 (d, J=8.1 Hz, 1H), 7.64-7.62 (m, 2H), 6.93 (d, J=9.3 Hz, 1H), 3.77-3.56 (m, 8H), 2.88 (s, 4H).

LCMS: m/z: 407.61 [M+1]⁺.

Example 19—Synthesis of 6-[4-[3-(7-fluoro-4-oxo-3H-quinazolin-2-yl)propanoyl]piperazin-1-yl]pyridine-3-carbonitrile Step-1

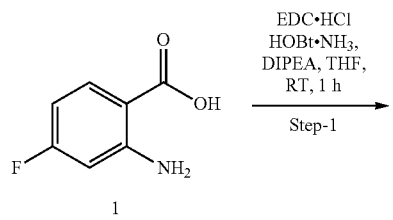

To a stirred solution of 2-amino-4-fluoro-benzoic acid (300 mg, 1.93 mmol) in THF (6 mL), EDC HCl (553 mg, 2.90 mmol), HOBt-NH₃ (435 mg, 2.90 mmol), DIPEA (1.03 mL, 5.79 mmol) were added at RT and stirred for 1 h (TLC indicated complete consumption of starting material). The reaction mixture was diluted with water (25 mL) and extracted with EtOAc (3×20 mL). The combined organic extracts were dried over Na₂SO₄, concentrated under reduced pressure to get the crude residue which was purified by flash column chromatography (100-200 mesh silica gel, 5 g, 50% EtOAc-Hexane) to furnish 2-amino-4-fluoro-benzamide (195 mg, 65%) as a white solid.

¹H NMR [300 MHz, DMSO-d₆]: δ 7.71 (brs, 1H), 7.61-7.56 (m, 1H), 7.07 (brs, 1H), 6.89 (s, 2H), 6.42 (dd, J=2.7, 12.0 Hz, 1H), 6.30-6.23 (m, 1H).

Step-2

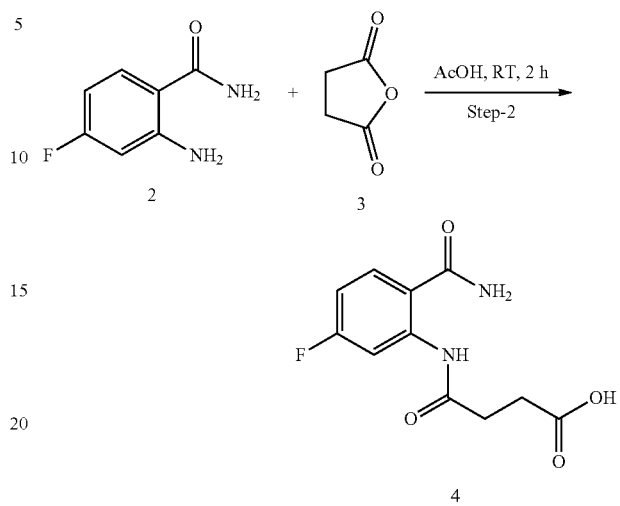

To a stirred solution of 2-amino-4-fluoro-benzamide (195 mg, 1.26 mmol) in AcOH (4 mL), succinic anhydride (151 mg, 1.51 mmol) was added at RT and stirred for 2 h (TLC indicated complete consumption of starting material). The reaction mixture was diluted with water (20 mL) during which solid was precipitated out. The solid was filtered, dried under vacuum to get 4-(2-carbamoyl-5-fluoro-anilino)-4-oxo-butanoic acid (260 mg, 81%) which was used for the next step without further purification.

¹H NMR [300 MHz, DMSO-d₆]: δ 12.10 (s, 1H), 8.40-8.26 (m, 3H), 7.92-7.87 (m, 1H), 7.79 (brs, 1H), 7.00-6.93 (m, 1H), 2.56-2.49 (m, 4H).

Step-3

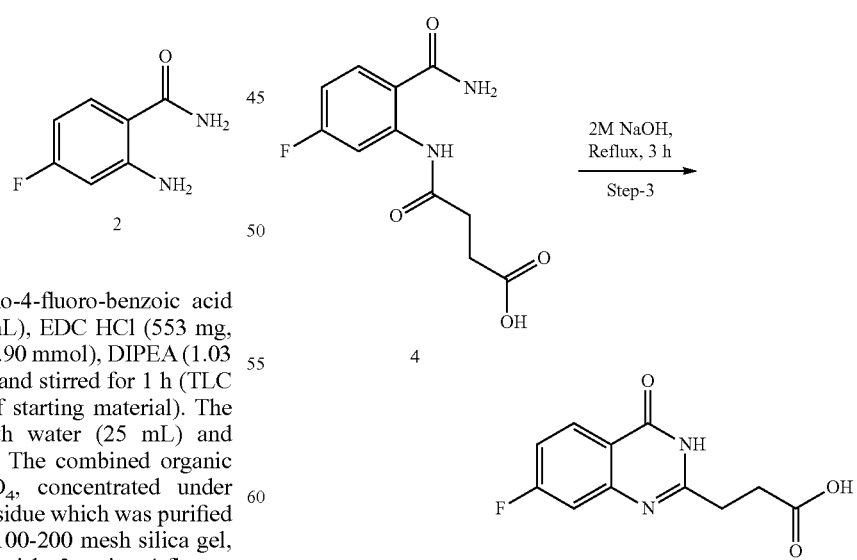

A stirred solution of 4-(2-carbamoyl-5-fluoro-anilino)-4-oxo-butanoic acid (250 mg, 0.98 mmol) in 2 N NaOH (10 mL) was refluxed for 3 h (TLC indicated complete consumption of starting material). The reaction mixture was cooled to 0° C., acidified with AcOH till pH=4 during which solid was precipitated out. The solid was filtered & dried under vacuum to afford 3-(7-fluoro-4-oxo-3H-quinazolin-2-yl)propanoic acid (210 mg, 90%) which was used for the next step without further purification.

LCMS: m/z: 237.43 [M+H]$^+$.

Step-4

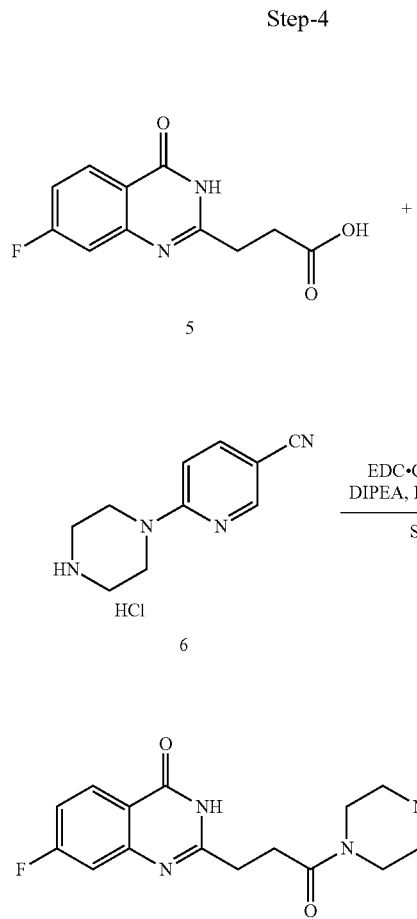

To a stirred solution of 3-(7-fluoro-4-oxo-3H-quinazolin-2-yl)propanoic acid (150 mg, 0.63 mmol) and 6-piperazin-1-ylpyridine-3-carbonitrile; hydrochloride (174 mg, 0.76 mmol) in DMF (4 mL), EDC HCl (181 mg, 0.95 mmol), HOBt (130 mg, 0.95 mmol) and DIPEA (0.45 mL, 2.54 mmol) were added at RT and stirred for 4 h (TLC indicated complete consumption of starting material). The reaction mixture was poured in cold water (25 mL) during which solid was precipitated out. The solid was filtered, dried under vacuum and washed with Et$_2$O (20 mL), hexane (20 mL), pentane (20 mL), EtOAc (15 mL) and again dried under vacuum to furnish 6-[4-[3-(7-fluoro-4-oxo-3H-quinazolin-2-yl)propanoyl]piperazin-1-yl]pyridine-3-carbonitrile (110 mg, 43%) as an off-white solid.

$^1$H NMR [300 MHz, DMSO-d$_6$]: δ 12.30 (s, 1H), 8.51 (d, J=2.1 Hz, 1H), 8.15-8.10 (m, 1H), 7.88 (dd, J=2.4, 9.6 Hz, 1H), 7.33-7.27 (m, 2H), 6.94 (d, J=9.0 Hz, 1H), 3.80-3.73 (m, 2H), 3.69-3.61 (m, 4H), 3.59-3.53 (m, 2H), 2.89 (s, 4H).

LCMS: m/z: 407.61 [M+H]$^+$.

Example 20—Synthesis of 6-[4-[3-(8-fluoro-4-oxo-3H-quinazolin-2-yl)propanoyl]piperazin-1-yl]pyridine-3-carbonitrile Step-1

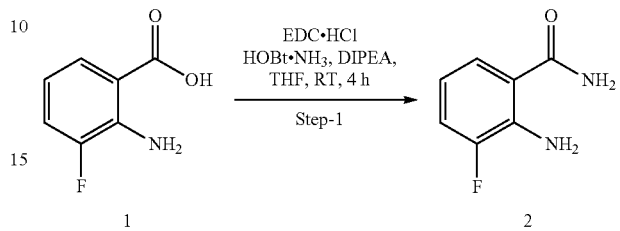

To a stirred solution of 2-amino-3-fluoro-benzoic acid (400 mg, 2.57 mmol) in THF (10 mL), EDC HCl (738 mg, 3.86 mmol), HOBt-NH$_3$ (580 mg, 3.86 mmol) and DIPEA (1.38 mL, 7.73 mmol) were added at RT and stirred for 4 h (TLC indicated complete consumption of starting material). The reaction mixture was diluted with water (30 mL) and extracted with EtOAc (3×40 mL). The combined organic extracts were dried over Na$_2$SO$_4$, concentrated under reduced pressure to get the crude compound which was purified by flash column chromatography (100-200 mesh silica gel, 5 g, 50% EtOAc-Hexane) to provide 2-amino-3-fluoro-benzamide (250 mg, 63%) as a white solid.

LCMS: m/z: 155.42 [M+H]$^+$.

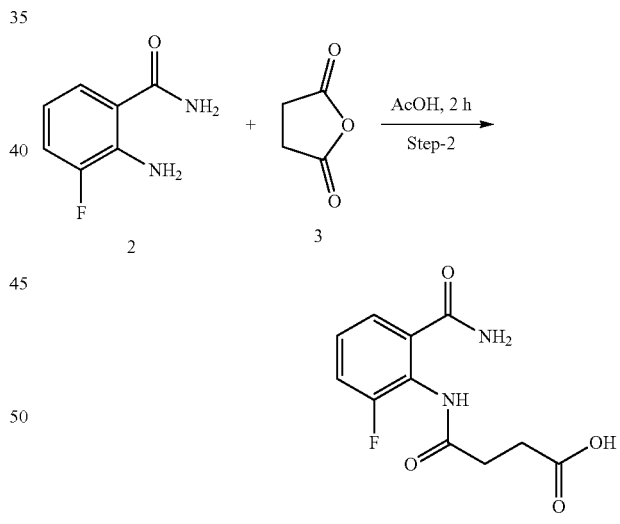

To a stirred solution of 2-amino-3-fluoro-benzamide (250 mg, 1.62 mmol) in AcOH (5 mL), succinic anhydride (389 mg, 3.89 mmol) was added at RT and stirred for 2 h (TLC indicated complete consumption of the starting material). The reaction mixture was diluted with water (20 mL) during which solid was precipitated out. The solid was filtered and dried under vacuum to get 4-(2-carbamoyl-6-fluoro-anilino)-4-oxo-butanoic acid (400 mg, 97%) which was used for the next step without further purification.

LCMS: m/z: 255.42 [M+H]$^+$.

Step-3

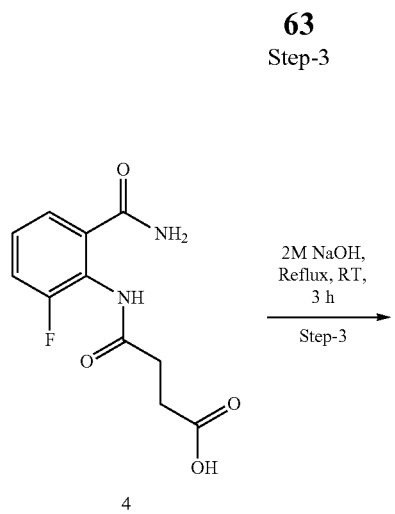

4-(2-Carbamoyl-6-fluoro-anilino)-4-oxo-butanoic acid (400 mg, 1.57 mmol) was taken in 2 N NaOH (10 mL) and heated at 100° C. for 3 h (TLC indicated complete consumption of starting material). After completion of the reaction, the reaction mixture was cooled to 0° C., acidified with AcOH till pH=4 during which solid was precipitated out. The solid was filtered & dried under vacuum to afford 3-(8-fluoro-4-oxo-3H-quinazolin-2-yl)propanoic acid (250 mg, 67%) which was used for the next step without further purification.

LCMS: m/z: 237.39 [M+H]$^+$.

Step-4

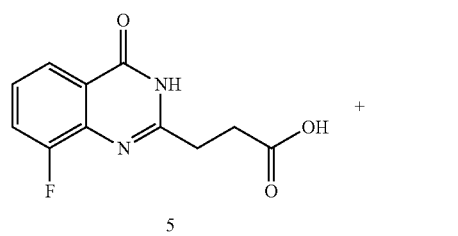

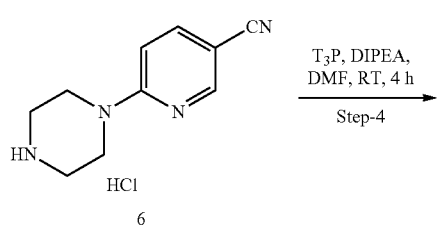

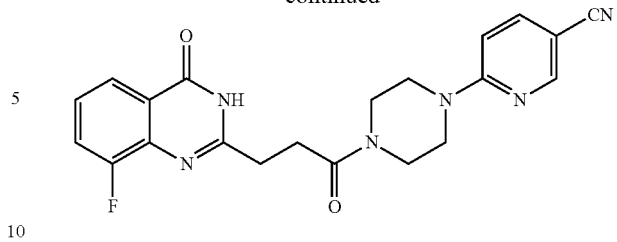

To a stirred solution of 3-(8-fluoro-4-oxo-3H-quinazolin-2-yl)propanoic acid (150 mg, 0.63 mmol) and 6-piperazin-1-ylpyridine-3-carbonitrile hydrochloride (170 mg, 0.76 mmol) in DMF (4 mL), T$_3$P (0.3 mL, 0.95 mmol) and DIPEA (0.45 ml, 2.54 mmol) were added at RT and stirred for 4 h (TLC indicated complete consumption of starting material). The reaction mixture was poured in cold water (25 mL) during which solid was precipitated out. The solid was filtered, dried under vacuum, washed with hexane (30 mL), chloroform (30 mL) and again dried under vacuum to furnish 6-[4-[3-(8-fluoro-4-oxo-3H-quinazolin-2-yl)propanoyl]piperazin-1-yl]pyridine-3-carbonitrile (80 mg, 23%) as an off-white solid.

$^1$H NMR [300 MHz, DMSO-d$_6$]: δ 8.51 (d, J=2.1 Hz, 1H), 7.90-7.87 (m, 2H), 7.65-7.59 (m, 1H), 7.46-7.39 (m, 1H), 6.93 (d, J=9.0 Hz, 1H), 3.77 (brs, 2H), 3.64 (brs, 4H), 3.57 (brs, 2H), 2.90 (s, 4H).

LCMS: m/z: 407.61 [M+H]$^+$.

Example 21—Synthesis of 6-[4-[3-(4-oxo-3H-pyrido[3,2-d]pyrimidin-2-yl)propanoyl]piperazin-1-yl]pyridine-3-carbonitrile Step-1

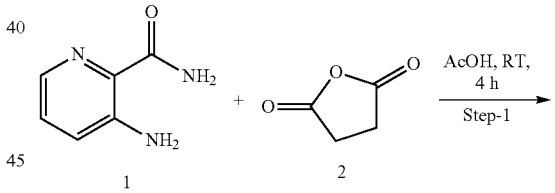

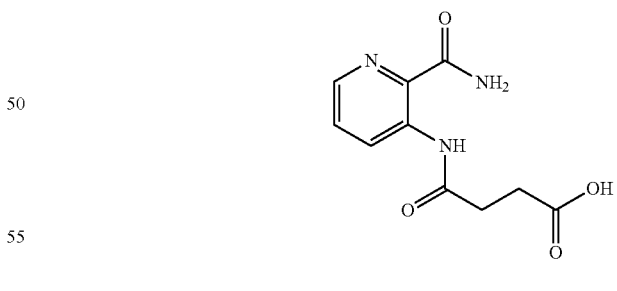

To a stirred solution of 3-aminopyridine-2-carboxamide (0.3 g, 2.19 mmol) in AcOH (3 mL), succinic anhydride (0.26 g, 2.63 mmol) was added at RT and stirred for 4 h (TLC indicated complete consumption of starting material). The reaction mixture was poured into ice cold water (5 mL) and stirred for 30 min during which solid precipitated out. The solid was filtered, washed with water (10 mL), cold acetone (5 mL) and dried under high vacuum to provide 4-[(2-carbamoyl-3-pyridyl)amino]-4-oxo-butanoic acid (320 mg, 61%) which was used for the next step without any purification.

LCMS: m/z: 238.41 [M+H]+.

Step-2

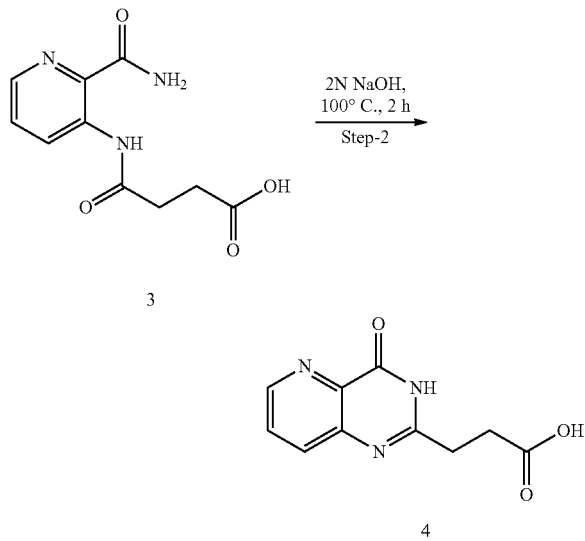

4-[(2-Carbamoyl-3-pyridyl)amino]-4-oxo-butanoic acid (300 mg, 1.27 mmol) was taken in 2 N aq. NaOH (5 mL) and stirred at 100° C. for 2 h (TLC indicated complete consumption of starting material). The reaction mixture was cooled to 0° C. and acidified with 2 N aq. HCl to pH=3-4 during which white solid precipitated out. The reaction mixture was stirred at 0° C. for 30 min. The solid was filtered, washed with water (10 mL), cold acetone (4 mL) and dried under high vacuum to afford 3-(4-oxo-3H-pyrido[3,2-d]pyrimidin-2-yl)propanoic acid (200 mg, 72%) which was used for the next step without any purification.

LCMS: m/z: 220.46 [M+H]+.

Step-3

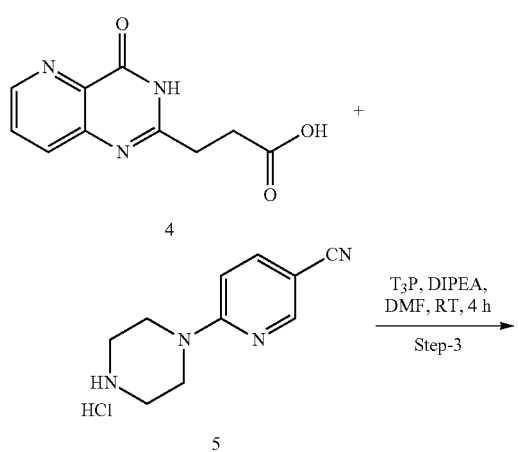

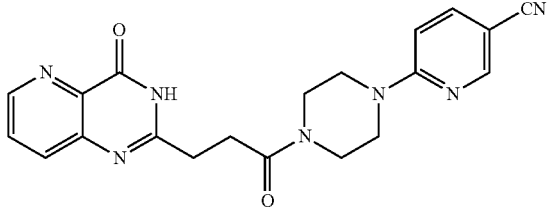

To a stirred solution of 3-(4-oxo-3H-pyrido[3,2-d]pyrimidin-2-yl)propanoic acid (100 mg, 0.46 mmol) and 6-piperazin-1-ylpyridine-3-carbonitrile hydrochloride (104 mg, 0.55 mmol) in DMF (3 mL), DIPEA (0.3 mL, 1.37 mmol) and T3P (0.23 mL, 0.92 mmol) were added at RT and stirred for 4 h (TLC indicates complete consumption of starting material). The reaction mixture was quenched with water (10 mL) and extracted with EtOAc (3×40 mL). The combined organic extracts were washed with cold water (3×20 mL), brine (20 mL), dried over Na2SO4 and concentrated under reduced pressure to give the crude residue. The crude material was purified by column chromatography (100-200 silica gel, 10 g, 5% MeOH-DCM to afford 6-[4-[3-(4-oxo-3H-pyrido[3,2-d]pyrimidin-2-yl)propanoyl]piperazin-1-yl]pyridine-3-carbonitrile (60 mg, 36%) as a white solid.

$^1$H NMR [400 MHz DMSO-d$_6$]: δ 12.50 (brs, 1H), 8.71 (dd, J=4.0, 1.2 Hz, 1H), 8.50 (d, J=2.0 Hz, 1H), 7.95 (dd, J=8.4, 1.6 Hz, 1H), 7.88 (dd, J=9.2, 1.6 Hz, 1H), 7.73 (dd, J=8.0, 4.0 Hz, 1H), 6.93 (d, J=9.2 Hz, 1H), 3.77-3.75 (m, 2H), 3.66-3.63 (m, 4H), 3.57-3.55 (m, 2H), 2.90 (s, 4H).

LCMS: m/z: 390.69 [M+H]+.

Example 22—Synthesis of 6-[4-[3-(4-oxo-3H-pyrido[3,4-d]pyrimidin-2-yl)propanoyl]piperazin-1-yl]pyridine-3-carbonitrile Step-1

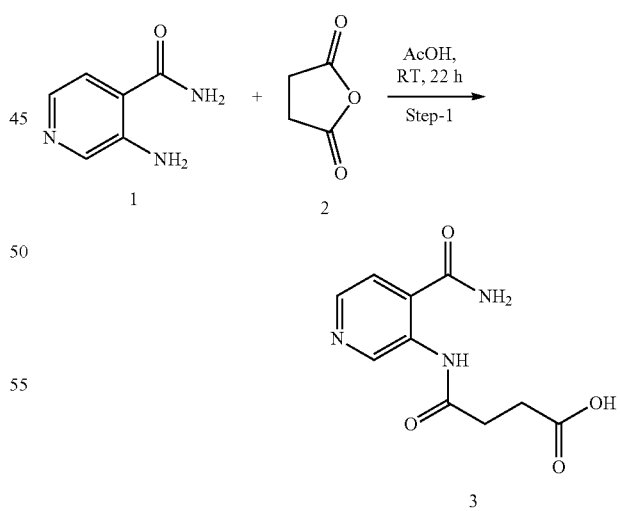

To a stirred solution of 3-aminopyridine-4-carboxamide (300 mg, 2.18 mmol) in AcOH (6 mL) succinic anhydride (262 mg, 2.62 mmol) was added at RT and stirred for 22 h (TLC indicated complete consumption of starting material). The reaction mixture was diluted with water (20 mL) during which solid was precipitated. The solid was filtered and dried under vacuum to obtain 4-[(4-carbamoyl-3-pyridyl) amino]-4-oxo-butanoic acid (430 mg, 83%) which was used for the next step without further purification.

LCMS: m/z: 238.52 [M+H]⁺.

Step-2

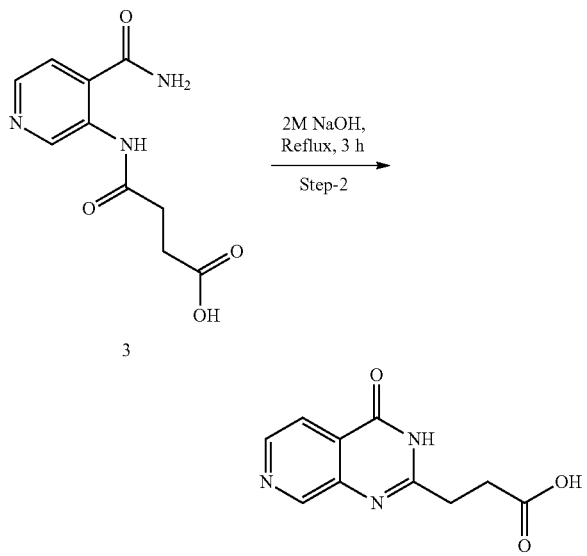

4-[(4-Carbamoyl-3-pyridyl)amino]-4-oxo-butanoic acid (430 mg, 1.81 mmol) was taken in 2 N NaOH (8.6 mL) and refluxed for 4 h (TLC indicated complete consumption of the starting material). After completion of reaction, the reaction mixture was cooled to 0° C., acidified with AcOH till pH=4, during which solid was precipitated out. The solid was filtered & dried under vacuum to provide 3-(4-oxo-3H-pyrido[3,4-d]pyrimidin-2-yl)propanoic acid (380 mg, 96%) which was used for the next step without further purification.

LCMS: m/z: 220.42 [M+H]⁺.

Step-3

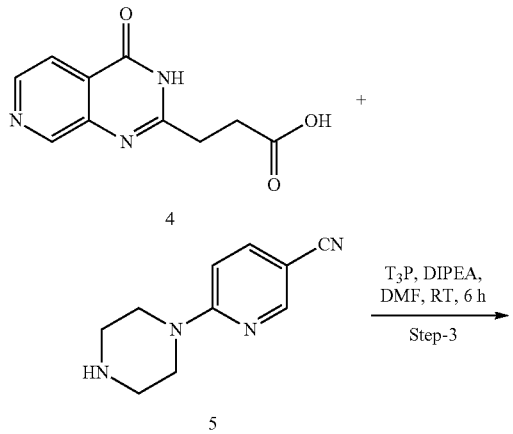

-continued

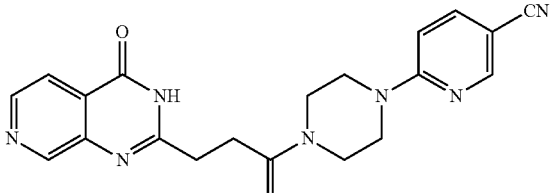

To a stirred solution of 3-(4-oxo-3H-pyrido[3,4-d]pyrimidin-2-yl)propanoic acid (200 mg, 0.91 mmol) and 6-piperazin-1-ylpyridine-3-carbonitrile hydrochloride (245 mg, 1.09 mmol) in DMF (5 mL), T₃P (0.87 mL, 1.36 mmol), DIPEA (0.64 mL, 3.65 mmol) were added at RT and stirred for 4 h (TLC indicated complete consumption of the starting material). The reaction mixture was diluted (30 mL), extracted with EtOAc (3×15 mL). The combined organic extracts were dried over Na₂SO₄, concentrated under reduced pressure to give the crude compound which was purified by column chromatography (100-200 mesh silica gel, 4 g, 5% MeOH-DCM) to afford 6-[4-[3-(4-oxo-3H-pyrido[3,4-d]pyrimidin-2-yl)propanoyl]piperazin-1-yl]pyridine-3-carbonitrile (45 mg, 13%) as a white solid.

¹H NMR [400 MHz, DMSO-d₆]: δ 12.55 (s, 1H), 8.94 (s, 1H), 8.59 (d, J=4.8 Hz, 1H), 8.51-8.50 (m, 1H), 7.91-7.87 (m, 2H), 6.94 (d, J=9.2 Hz, 1H), 3.77 (brs, 2H), 3.65 (brs, 4H), 3.56 (brs, 2H), 2.92 (brs, 4H).

LCMS: m/z: 390.70 [M+H]⁺.

Example 23—Synthesis of 6-[4-[3-(4-oxo-3H-thieno[2,3-d]pyrimidin-2-yl)propanoyl]piperazin-1-yl]pyridine-3-carbonitrile Step-1

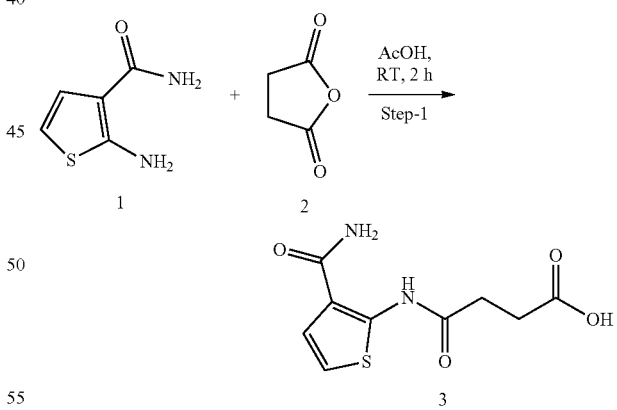

To a stirred solution of 2-aminothiophene-3-carboxamide (300 mg, 2.11 mmol) in acetic acid (3 mL) was added succinic anhydride (253 mg, 2.53 mmol) at RT. The reaction mixture was stirred at RT for 2 h. (TLC indicated complete consumption of starting material). The reaction mixture was then diluted with water (20 mL) and precipitation was formed. The mixture was filtered and the obtained solid was dried under vacuum to provide 4-[(3-carbamoyl-2-thienyl) amino]-4-oxo-butanoic acid (410 mg, 69%), which was used for next step without further purification.

¹H NMR [400 MHz, DMSO-d₆]: δ 12.20 (s, 1H), 12.14 (s, 1H), 7.89 (s, 1H), 7.50 (brs, 1H), 7.39 (d, J=5.6 Hz, 1H), 6.93 (d, J 6.0 Hz, 1H), 2.67 (t, J=6.4 Hz, 2H), 2.56 (t, J=6.8 Hz, 2H).

LCMS: m/z: 265.40 [M+Na]⁺.

Step-2

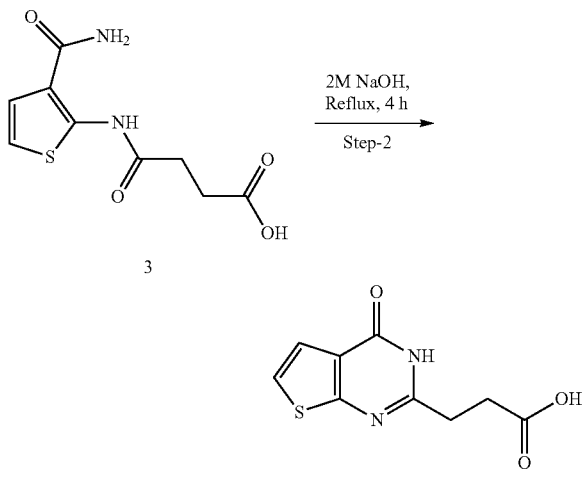

4-[(3-carbamoyl-2-thienyl)amino]-4-oxo-butanoic acid (350 mg, 1.44 mmol) was suspended in 2 N NaOH (7 mL) at RT. The resulting mixture was heated at 100° C. for 4 h. (TLC indicated complete consumption of starting material). After completion of reaction, reaction mixture was cooled to 0° C., acidified with AcOH (pH=4). Solids were formed, collected by filtration and dried under vacuum to afford 3-(4-oxo-3H-thieno[2,3-d]pyrimidin-2-yl)propanoic acid (290 mg, 90%), which was used for next step without further purification.

LCMS: m/z: 225.38 [M+H]⁺.

Step-3

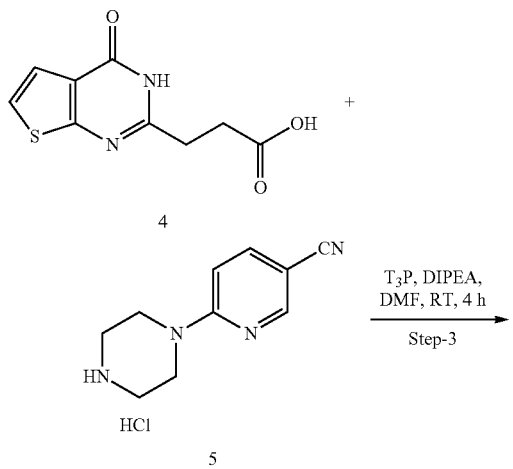

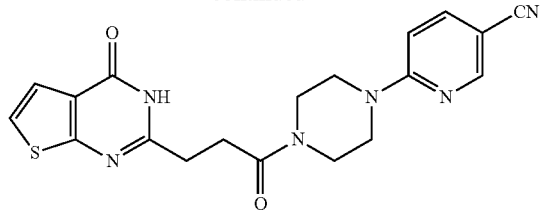

To a stirred solution of 3-(4-oxo-3H-thieno[2,3-d]pyrimidin-2-yl)propanoic acid (200 mg, 0.89 mmol) and 6-piperazin-1-ylpyridine-3-carbonitrile hydrochloride (239 mg, 1.07 mmol) in DMF (5 mL), was added T₃P (0.85 mL, 1.33 mmol), DIPEA (0.62 mL, 3.568 mmol) at RT. Stirred the reaction mixture at RT for 4 h. (TLC indicated complete consumption of starting material). The reaction mixture was diluted (30 mL), extracted with EtOAc (3×30 mL). The combined organic layers were dried over Na₂SO₄, evaporated the solvent under reduced pressure to get crude compound. The obtained crude was purified by column chromatography (100-200 silica gel, 4 g, 5% MeOH-DCM) to afford 6-[4-[3-(4-oxo-3H-thieno[2,3-d]pyrimidin-2-yl)propanoyl]piperazin-1-yl]pyridine-3-carbonitrile (80 mg, 22%) as a white solid.

¹H NMR [400 MHz, DMSO-d₆]: δ 12.38 (s, 1H), 8.50 (d, J=2.0 Hz, 1H), 7.88 (dd, J=2.4, 9.2 Hz, 1H), 7.45 (d, J=6.0 Hz, 1H), 7.32 (d, J=5.6 Hz, 1H), 6.93 (d, J=9.2 Hz, 1H), 3.77-3.74 (m, 2H), 3.65-3.62 (m, 4H), 3.57-3.55 (m, 2H), 2.92-2.84 (m, 4H).

LCMS: m/z: 395.62 [M+H]⁺.

Example 24—Synthesis of 6-[4-[3-(4-oxo-3H-thieno[3,2-d]pyrimidin-2-yl)propanoyl]piperazin-1-yl]pyridine-3-carbonitrile Step-1

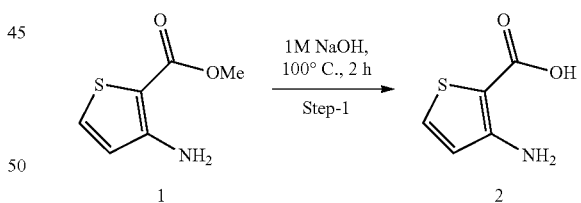

A stirred solution of methyl 3-aminothiophene-2-carboxylate (2 g, 12.72 mmol) in 1 M sodium hydroxide (14 mL, 14 mmol) was heated at 100° C. for 2 h (TLC indicated complete consumption of starting material). The reaction mixture was brought to RT, acidified with 1 N HCl till pH=2 and extracted with 50% THF-EtOAc (2×100 mL). The combined organic extracts were dried over Na₂SO₄, concentrated under reduced pressure to give the crude product which was washed with n-pentane (2×20 mL) to afford 3-aminothiophene-2-carboxylic acid (1.4 g, 77%) which was used for the next step without any purification.

LCMS (ESI+): m/z: 144.30 [M+H]⁺.

Step-2

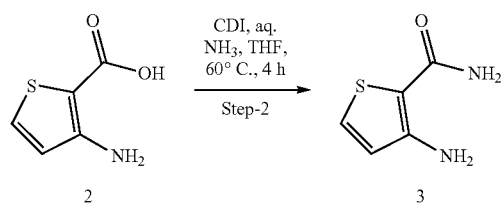 [SMILES: Nc1ccsc1C(=O)O ; NC(=O)c1sccc1N]

Step-4

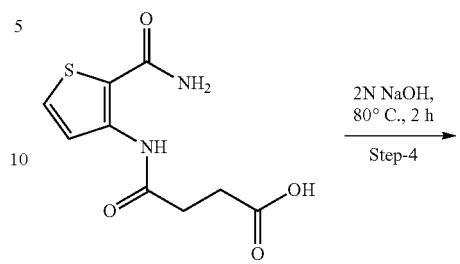

A solution of 3-aminothiophene-2-carboxylic acid (1 g, 6.99 mmol) and CDI (1.24 g, 7.69 mmol) in THF (20 mL) was heated at 60° C. for 1 h, then 25% aqueous ammonia solution (16 mL) was added and continued at 60° C. for 3 h (TLC indicated complete consumption of starting material). The reaction mixture was brought to RT and extracted with EtOAc (2×75 mL); the combined organic extracts were washed with brine (40 mL), dried over $Na_2SO_4$, concentrated under reduced pressure to give the crude residue which was purified by column chromatography (100-200 silica gel, 20 g, 50-75% EtOAc-Hexane) to furnish 3-aminothiophene-2-carboxamide (400 mg, 40%) as an off-white solid.

LCMS (ESI+): m/z: 143.33 [M+H]+.

Step-3

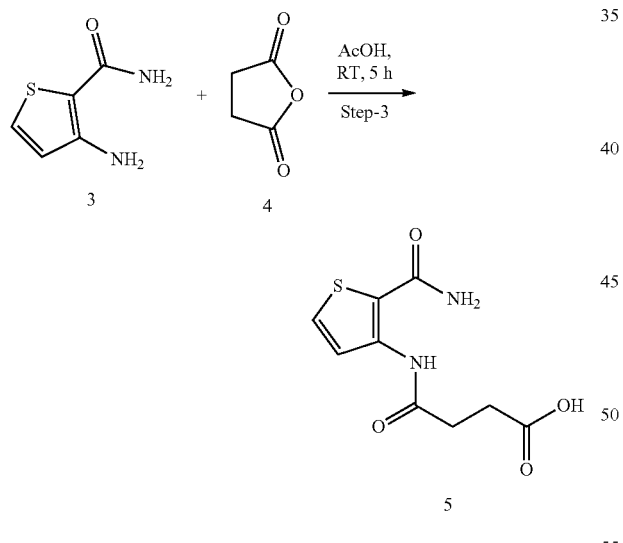

To a stirred suspension of 3-aminothiophene-2-carboxamide (390 mg, 2.74 mmol) in AcOH (10 mL), succinic anhydride (277 mg, 2.77 mmol) was added and stirred at RT for 2 h (TLC indicated complete consumption of starting material). The reaction mixture was quenched with water (40 mL), stirred for 15 min, precipitate was filtered, washed with water (10 mL) and dried to obtain 4-[(2-carbamoyl-3-thienyl)amino]-4-oxo-butanoic acid (585 mg, 88%) as a white solid.

LCMS (ESI+): m/z: 243.40 [M+H]+.

A solution of 4-[(2-carbamoyl-3-thienyl)amino]-4-oxo-butanoic acid (500 mg, 2.07 mmol) in 2 N sodium hydroxide solution (16 mL, 32 mmol) was stirred at 80° C. for 2 h (LCMS indicated complete consumption of starting material). The reaction mixture was brought to RT, acidified with AcOH till pH=5, white precipitate was filtered, washed with water (20 mL), dried under reduced pressure to give 3-(4-oxo-3H-thieno[3,2-d]pyrimidin-2-yl)propanoic acid (330 g, 72%) as a white solid.

LCMS (ESI+): m/z: 225.42 [M+H]+.

Step-5

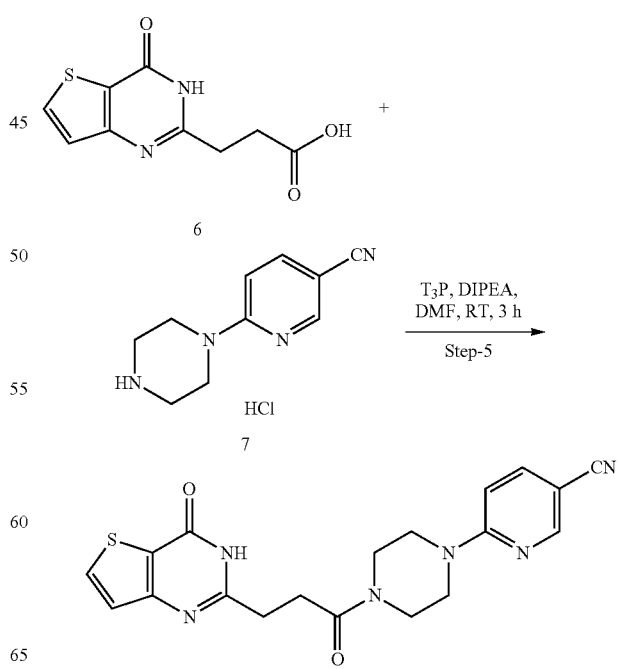

To a stirred solution of 3-(4-oxo-3H-thieno[3,2-d]pyrimidin-2-yl)propanoic acid (200 mg, 0.89 mmol), 6-piperazin-1-ylpyridine-3-carbonitrile hydrochloride (240 mg, 1.07 mmol) and DIPEA (0.31 mL, 1.78 mmol) in DMF (10 mL), 50% T₃P solution in EtOAc (0.85 mL, 1.34 mmol) were added at RT and stirred for 3 h (LCMS indicated complete consumption of starting material). The reaction mixture was quenched with water (60 mL) and extracted with DCM (2×50 mL). The combined organic extracts were washed with brine (20 mL), dried over Na₂SO₄ and concentrated under reduced pressure to give the crude product which was purified by column chromatography (100-200 silica gel, 20 g, 2-4% MeOH-DCM) to afford 6-[4-[3-(4-oxo-3H-thieno[3,2-d]pyrimidin-2-yl)propanoyl]piperazin-1-yl]pyridine-3-carbonitrile (60 mg, 17%) as an off-white solid.

¹H NMR [400 MHz, DMSO-d₆]: δ 12.37 (s, 1H), 8.50 (d, J=2.0 Hz, 1H), 8.12 (d, J=5.2 Hz, 1H), 7.88 (dd, J=5.6, 9.2 Hz, 1H), 7.29 (d, J=5.2 Hz, 1H), 6.93 (d, J=9.2 Hz, 1H), 3.80-3.72 (m, 2H), 3.68-3.61 (m, 4H), 3.59-3.55 (m, 2H), 2.92-2.85 (m, 4H).

LCMS (ESI+): m/z: 395.63 [M+H]⁺.

Example 25—Synthesis of 6-[(2S)-2-methyl-4-[3-(4-oxo-3H-quinazolin-2-yl)propanoyl]piperazin-1-yl]pyridine-3-carbonitrile Step-1

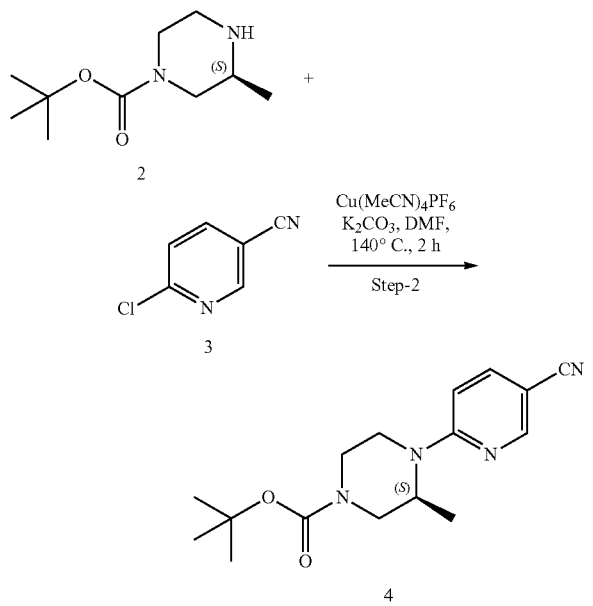

To a stirred solution of tert-butyl (3S)-3-methylpiperazine-1-carboxylate (500 mg, 2.50 mmol) and 6-chloropyridine-3-carbonitrile (415 mg, 3.0 mmol) in DMSO (10 mL), K₂CO₃ (863 mg, 6.25 mmol) and Cu(MeCN)₄PF₆ (18 mg, 0.05 mmol) were added. The reaction mixture was heated at 140° C. for 2 h (TLC indicated complete consumption of starting material). The reaction mixture was brought to RT, diluted with water (20 mL) and extracted with EtOAc (3×50 mL). The combined organic extracts were washed with water (2×30 mL) and brine (40 mL), dried over Na₂SO₄ and concentrated under reduced pressure to give the crude residue which was purified by column chromatography (100-200 silica gel, 15 g, 30% EtOAc-Hexane) to furnish tert-butyl (3S)-4-(5-cyano-2-pyridyl)-3-methyl-piperazine-1-carboxylate (260 mg, 34%) as an off-white solid.

LCMS: m/z: 303.60 [M+H]⁺.

Step-2

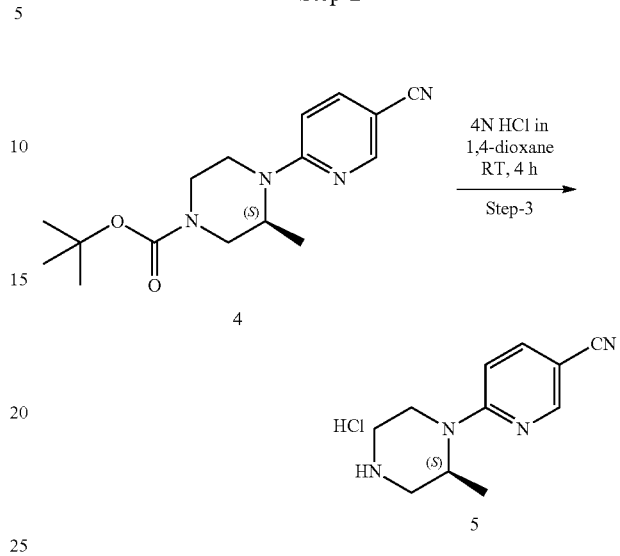

To a stirred solution of tert-butyl (3S)-4-(5-cyano-2-pyridyl)-3-methyl-piperazine-1-carboxylate (260 mg, 0.86 mmol) in DCM (5 mL), cooled to 0° C., 4 N HCl in dioxane (5 mL) was added. The reaction mixture was brought to RT and stirred for 4 h (TLC indicated complete consumption of starting material). The reaction mixture was concentrated under reduced pressure to give the crude residue which was washed with Et₂O (5 mL) and dried under high vacuum to furnish 6-[(2S)-2-methylpiperazin-1-yl]pyridine-3-carbonitrile hydrochloride (120 mg, 68%) as an off-white solid.

LCMS: m/z: 203.45 [M+H]⁺.

Step-3

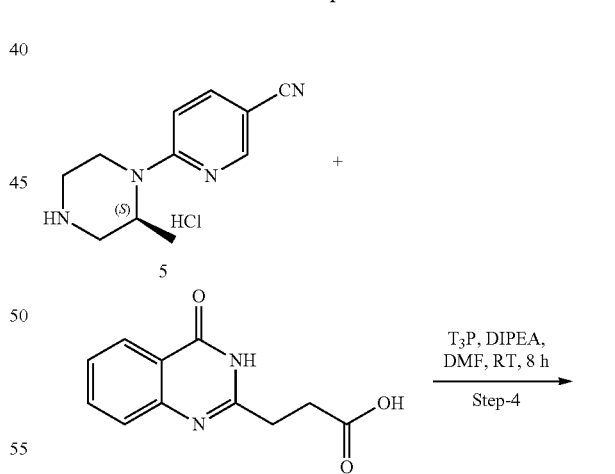

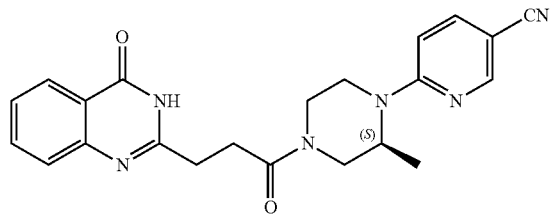

To a stirred solution of 6-[(2S)-2-methylpiperazin-1-yl]pyridine-3-carbonitrile hydrochloride (100 mg, 0.46 mmol) and 3-(4-oxo-3H-quinazolin-2-yl)propanoic acid (111 mg, 0.55 mmol) in DMF (5 mL), cooled to 0° C., T₃P (0.3 mL, 0.92 mmol, 50% in DMF) and DIPEA (0.25 mL, 1.38 mmol) were added. The reaction mixture was warmed to RT and stirred for 8 h (TLC indicated complete consumption of starting material). The reaction mixture was quenched with water (20 mL) and extracted with EtOAc (3×60 mL). The combined organic extracts were washed with cold water (3×30 mL), brine (40 mL), dried over Na₂SO₄ and concentrated under reduced pressure to give the crude residue which was purified by column chromatography (100-200 silica gel, 8 g, 5% MeOH-EtOAc) to provide 6-[(2S)-2-methyl-4-[3-(4-oxo-3H-quinazolin-2-yl)propanoyl]piperazin-1-yl]pyridine-3-carbonitrile (40 mg, 21%) as a white solid.

¹H NMR [300 MHz, DMSO-d₆]: δ 12.28 (s, 1H), 8.52 (d, J=1.8 Hz, 1H), 8.06 (d, J=7.5 Hz, 1H), 7.88 (dd, J=1.8 Hz, J=9.0 Hz, 1H), 7.76-7.17 (m, 1H), 7.51 (d, J=8.1 Hz, 1H), 7.44 (t, J=7.5 Hz, 1H), 6.90 (d, J=9.0 Hz, 1H), 4.66-4.58 (m, 1H), 4.25-4.14 (m, 2H), 4.05-3.87 (m, 1H), 3.47 (d, J=10.5 Hz, 1H), 3.12-2.99 (m, 2H), 2.91-2.84 (m, 4H), 1.20-0.98 (m, 3H).

LCMS: m/z: 403.66 [M+H]⁺.

Example 26—Synthesis of 6-[(2R)-2-methyl-4-[3-(4-oxo-3H-quinazolin-2-yl)propanoyl]piperazin-1-yl]pyridine-3-carbonitrile Step-1

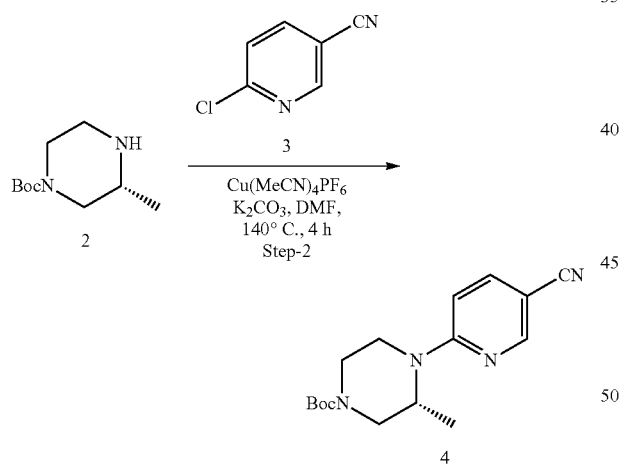

To a stirred solution of tert-butyl (3R)-3-methylpiperazine-1-carboxylate (500 mg, 2.5 mmol), 6-chloropyridine-3-carbonitrile (415 mg, 3 mmol) in DMSO (10 mL), potassium carbonate (690 mg, 5 mmol), Cu (MeCN)₄PF₆ (18 mg, 0.05 mmol) were added at RT. The reaction mixture was heated at 140° C. for 4 h (TLC indicated complete consumption of the starting materials), brought to RT, diluted with water (30 mL) and extracted with EtOAc (3×40 mL). The combined organic extracts were washed with water (30 mL), brine (40 mL), dried over Na₂SO₄ and concentrated under reduced pressure to afford the crude compound. The crude material was purified by column chromatography (100-200 mesh silica gel, 7 g, 30% EtOAc-hexane) to afford tert-butyl (3R)-4-(5-cyano-2-pyridyl)-3-methyl-piperazine-1-carboxylate (415 mg, 55%) as an off-white solid.

¹H NMR [300 MHz, CDCl₃]: δ 8.39 (d, J=2.4 Hz, 1H), 7.62-7.58 (m, 1H), 6.54 (d, J=9.0 Hz, 1H), 4.51 (brs, 1H), 4.13-3.89 (m, 3H), 3.27-3.13 (m, 2H), 3.00 (brs, 1H), 1.45 (s, 9H), 1.23-1.16 (m, 3H).

LCMS: m/z: 247.46 [M-tBu]⁺.

Step-2

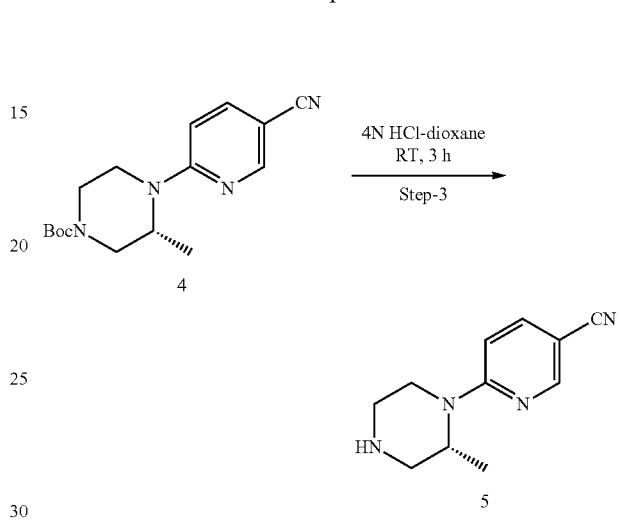

To a stirred solution of tert-butyl (3R)-4-(5-cyano-2-pyridyl)-3-methyl-piperazine-1-carboxylate (410 mg, 1.35 mmol) in 1,4-dioxane (4 mL), cooled to 0° C., 4 N HCl in dioxane (1.35 mL, 5.43 mmol) was added. The reaction slowly brought to RT and stirred for 3 h (TLC indicated complete consumption of starting material). The volatiles were removed under reduced pressure to give the crude 6-[(2R)-2-methylpiperazin-1-yl]pyridine-3-carbonitrile (310 mg, 96%) which was used for the next step without any purification.

LCMS: m/z: 203.41 [M+H]⁺.

Step-3

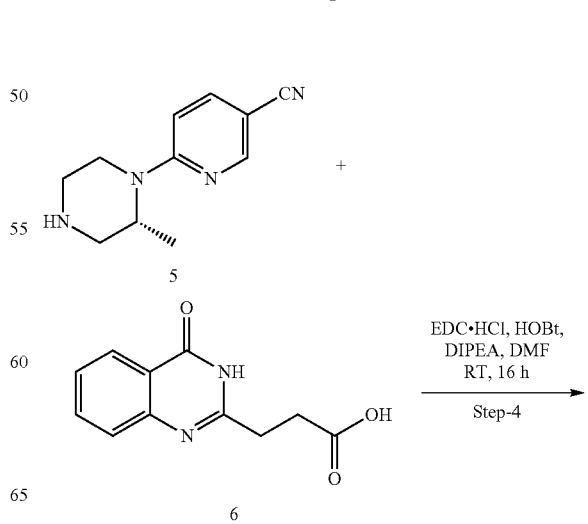

-continued

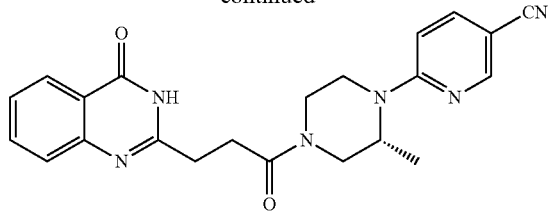

To a stirred solution of 3-(4-oxo-3H-quinazolin-2-yl)propanoic acid (100 mg, 0.45 mmol), 6-[(2R)-2-methylpiperazin-1-yl]pyridine-3-carbonitrile (93 mg, 0.45 mmol) in DMF (2 mL), EDC HCl (131 mg, 0.68 mmol), HOBt (92 mg, 0.68 mmol) and DIPEA (0.16 mL, 0.91 mmol) were added at RT and stirred for 16 h (TLC indicated complete consumption of starting materials). The reaction mixture was diluted with cold water (20 mL) and extracted with EtOAc (3×30 mL). The combined organic extracts were washed with cold water (1×30 mL), brine solution (40 mL), dried over Na$_2$SO$_4$ and concentrated under reduced pressure to give the crude compound. The crude residue was purified by column chromatography (100-200 mesh silica gel, 4 g, 3% of MeOH-DCM) to furnish 6-[(2R)-2-methyl-4-[3-(4-oxo-3H-quinazolin-2-yl)propanoyl]piperazin-1-yl]pyridine-3-carbonitrile (60 mg, 33%) as a pale pink Solid.

$^1$H NMR [300 MHz, DMSO-d$_6$]: δ 12.30 (brs, 1H), 8.52 (d, J=2.1 Hz, 1H), 8.06 (d, J=7.8 Hz, 1H), 7.88 (dd, J=9.0, 2.1 Hz, 1H), 7.76-7.71 (m, 1H), 7.51 (d, J=8.1 Hz, 1H), 7.44 (t, J=7.5 Hz, 1H), 6.89 (d, J=9.0 Hz, 1H), 4.66-4.58 (m, 1H), 4.24-4.14 (m, 2H), 4.05-3.87 (m, 1H), 3.34-3.31 (m, 1H), 3.05-2.72 (m, 6H), 1.20-0.98 (m, 3H).
LCMS: m/z: 403.66 [M+H]$^+$.

Example 27—Synthesis of 6-[(3R)-3-methyl-4-[3-(4-oxo-3H-quinazolin-2-yl)propanoyl]piperazin-1-yl]pyridine-3-carbonitrile Step-1

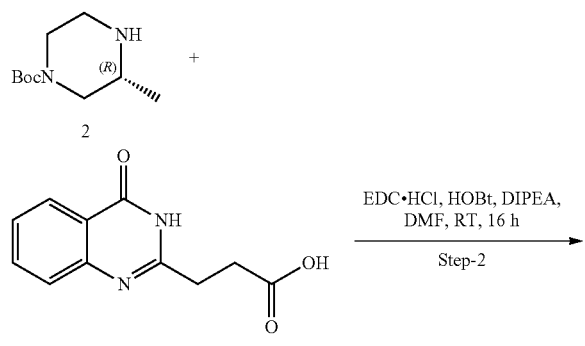

To a stirred solution of 3-(4-oxo-3H-quinazolin-2-yl)propanoic acid (1 g, 4.58 mmol), tert-butyl (3R)-3-methylpiperazine-1-carboxylate (917 mg, 4.58 mmol) in DMF (20 mL), EDC HCl (1.3 g, 6.88 mmol), HOBt (928 mg, 6.88 mmol) and DIPEA (1.6 mL, 9.17 mmol) were added and stirred at RT for 16 h (TLC indicated complete consumption of starting materials). The reaction mixture was diluted with cold water (40 mL) and extracted with EtOAc (3×40 mL). The combined organic extracts were washed with cold water (50 mL), brine (40 mL), dried over Na$_2$SO$_4$ and concentrated under reduced pressure give the crude compound. The crude compound was purified by column chromatography (100-200 mesh silica gel, 10 g, 3% of MeOH in DCM) to afford tert-butyl (3R)-3-methyl-4-[3-(4-oxo-3H-quinazolin-2-yl)propanoyl]piperazine-1-carboxylate (410 mg, 22%) as an off-white solid.
LCMS: m/z: 401.67 [M+H]$^+$.

Step-2

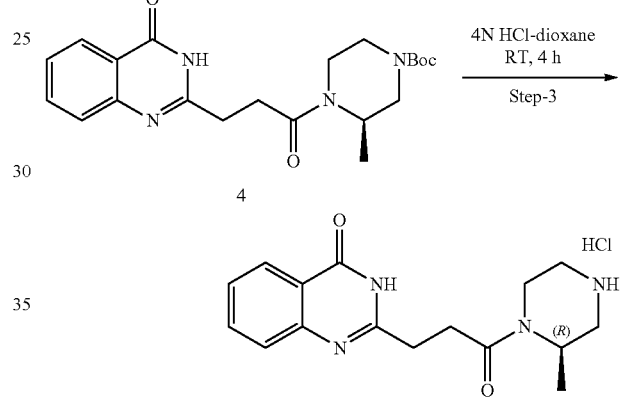

To a stirred solution of tert-butyl (3R)-3-methyl-4-[3-(4-oxo-3H-quinazolin-2-yl)propanoyl]piperazine-1-carboxylate (410 mg, 1 mmol) in 1,4-dioxane (4 mL), cooled to 0° C., 4 N HCl in dioxane (1.0 mL, 4 mmol) was added. The reaction was warmed to RT and stirred for 3 h (TLC indicated complete consumption of starting material). The volatiles were removed under reduced pressure to give the crude 2-[3-[(2R)-2-methylpiperazin-1-yl]-3-oxo-propyl]-3H-quinazolin-4-one hydrochloride (310 mg, quantitative) which was used for the next step without any purification.
LCMS: m/z: 301.61 [M+H]$^+$.

Step-3

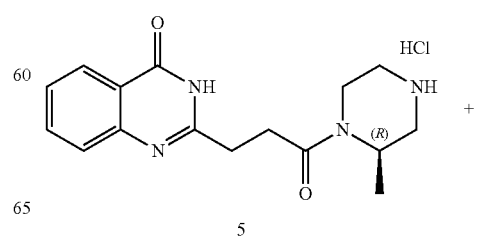

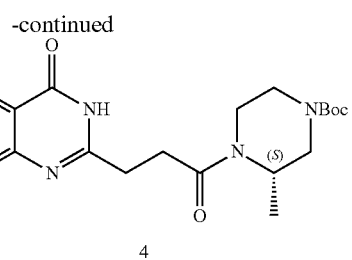

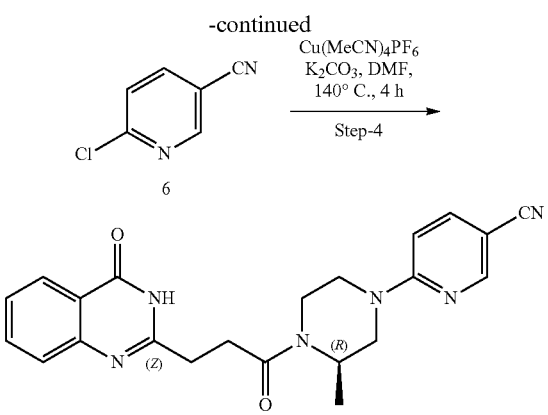

To a stirred solution of 2-[3-[(2R)-2-methylpiperazin-1-yl]-3-oxo-propyl]-3H-quinazolin-4-one hydrochloride (200 mg, 0.66 mmol), 6-chloropyridine-3-carbonitrile (110 mg, 0.79 mmol) in DMSO (4 mL), potassium carbonate (183 mg, 1.33 mmol), Cu(MeCN)$_4$PF$_6$ (5 mg, 0.013 mmol) was added at RT. The reaction mixture was heated at 140° C. for 4 h (TLC indicated complete consumption of the starting materials), slowly brought to RT, diluted with cold water (30 ml), extracted with EtOAc (3×40 mL). The combined organic extracts were washed with cold water (30 mL), brine (40 mL), dried over Na$_2$SO$_4$ and concentrated under reduced pressure to afford the crude compound. The crude material was purified by column chromatography (100-200 mesh silica gel, 4 g, 5% MeOH-DCM) to afford 6-[(3R)-3-methyl-4-[3-(4-oxo-3H-quinazolin-2-yl)propanoyl]piperazin-1-yl]pyridine-3-carbonitrile (65 mg, 24%) as an off-white solid.

$^1$H NMR [400 MHz, DMSO-d$_6$]: δ 12.20 (s, 1H), 8.48 (s, 1H), 8.06 (d, J=7.6 Hz, 1H), 7.86 (d, J=7.6 Hz, 1H), 7.73 (brs, 1H), 7.52 (m, 1H), 7.44 (t, J=2.0 Hz, 1H), 6.93 (brs, 1H), 4.56 (brs, 1H), 4.37-4.14 (m, 3H), 3.52-3.31 (m, 2H), 2.98-2.88 (m, 5H), 1.20-1.00 (m, 3H).

LCMS: m/z: 403.62 [M+H]$^+$.

Example 28—Synthesis of 6-[(3S)-3-methyl-4-[3-(4-oxo-3H-quinazolin-2-yl)propanoyl]piperazin-1-yl]pyridine-3-carbonitrile Step-1

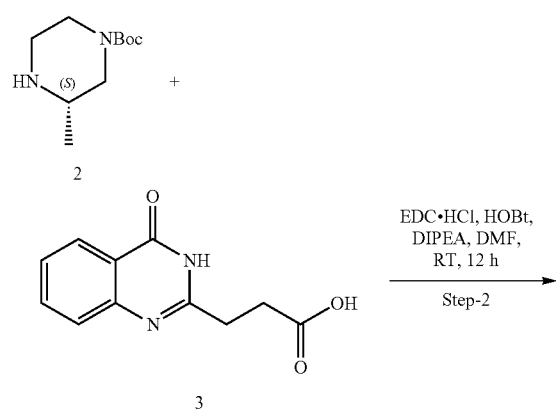

To a stirred solution of tert-butyl (2R)-2-methylpiperazine-1-carboxylate (0.55 g, 2.75 mmol) and 3-(4-oxo-3H-quinazolin-2-yl)propanoic acid (0.5 g, 2.29 mmol) in DMF (10 mL), cooled to 0° C., EDC HCl (0.657 g, 3.44 mmol), HOBt (0.464 g, 3.44 mmol) and DIPEA (1.2 mL, 6.88 mmol) were added. The reaction mixture was warmed to RT, stirred for 12 h (TLC indicated complete consumption of starting material), quenched with water (20 mL) and extracted with EtOAc (3×60 mL). The combined organic extracts were washed with cold water (3×30 mL), brine (40 mL), dried over Na$_2$SO$_4$ and concentrated under reduced pressure to give the crude compound. The crude material was purified by column chromatography (100-200 silica gel, 15 g, 5% MeOH-EtOAc) to furnish tert-butyl (3S)-3-methyl-4-[3-(4-oxo-3H-quinazolin-2-yl)propanoyl]piperazine-1-carboxylate (0.3 g, 32%).

LCMS: m/z: 401.67 [M+H]$^+$.

Step-2

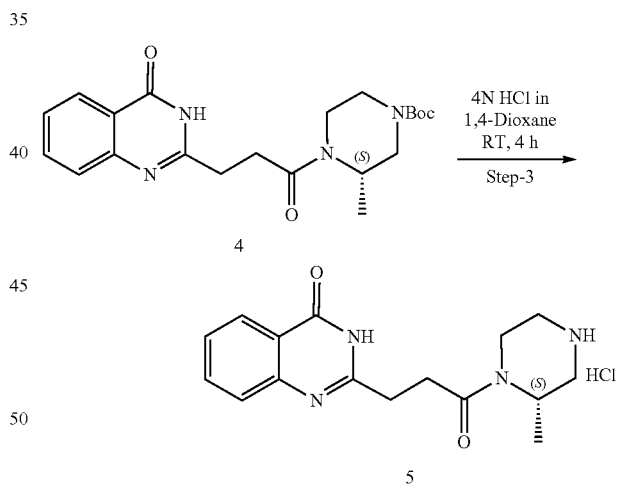

To a stirred solution of tert-butyl (3S)-3-methyl-4-[3-(4-oxo-3H-quinazolin-2-yl)propanoyl]piperazine-1-carboxylate (0.2 g, 0.5 mmol) in DCM (5 mL), cooled to 0° C., 4 N HCl in dioxane (5 mL) was added. The reaction mixture was slowly warmed to RT and stirred for 4 h (TLC indicated complete consumption of starting material). The reaction mixture was concentrated under vacuum to give the crude residue which was washed with Et$_2$O (5 mL) and dried under high vacuum to provide 2-[3-[(2S)-2-methylpiperazin-1-yl]-3-oxo-propyl]-3H-quinazolin-4-one hydrochloride (120 mg, 80%) as an off-white solid.

LCMS: m/z: 301.61 [M+H]$^+$.

Step-3

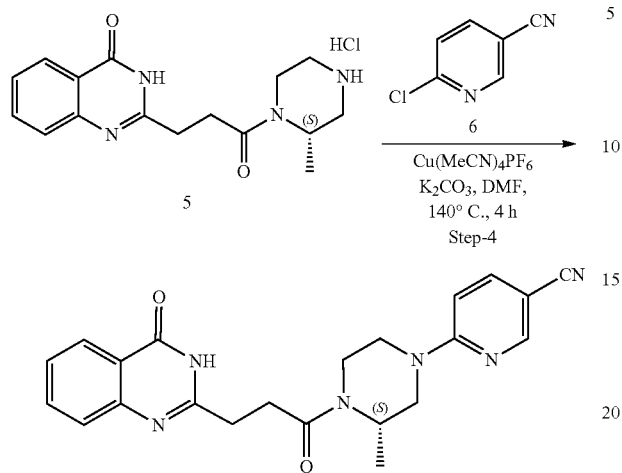

A solution of 2-[3-[(2S)-2-methylpiperazin-1-yl]-3-oxo-propyl]-3H-quinazolin-4-one hydrochloride (100 mg, 0.33 mmol), 6-chloropyridine-3-carbonitrile (55 mg, 0.39 mmol), $K_2CO_3$ (138 mg, 0.10 mmol) and $Cu(MeCN)_4PF_6$ (2 mg, 0.006 mmol) in DMSO (3 mL) was stirred at 140° C. for 4 h (TLC indicated complete consumption of starting material). The reaction mixture was brought to RT, diluted with water (20 mL) and extracted with EtOAc (3×50 mL). The combined organic extracts were washed with water (2×30 mL), brine (1×30 mL), dried over $Na_2SO_4$, and concentrated under reduced pressure to give the crude residue which was purified by column chromatography (100-200 silica gel, 10 g, 5% MeOH-EtOAc) to give 6-[(3S)-3-methyl-4-[3-(4-oxo-3H-quinazolin-2-yl)propanoyl]piperazin-1-yl]pyridine-3-carbonitrile (30 mg, 22%) as a white solid.

$^1$H NMR [300 MHz, DMSO-$d_6$]: δ 12.24 (s, 1H), 8.49 (d, J=2.1, 1H), 8.06 (d, J=7.2 Hz, 1H), 7.87 (dd, J=9.0, 2.4 Hz, 1H), 7.78-7.70 (m, 1H), 7.55-7.42 (m, 2H), 7.01-6.91 (m, 1H), 4.61-4.51 (m, 1H), 4.38-4.15 (m, 2H), 3.95-3.85 (d, J=12.9 Hz, 1H), 3.51-3.40 (m, 1H), 3.25-3.17 (m, 1H), 3.05-2.81 (m, 5H), 1.22-0.99 (m, 3H).

LCMS: m/z: 403.63 [M+H]$^+$.

Example 29—Synthesis of 6-[(3S)-4-[3-(6-fluoro-4-oxo-3H-quinazolin-2-yl)propanoyl]-3-methyl-piperazin-1-yl]pyridine-3-carbonitrile Step-1

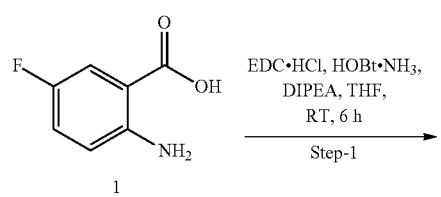

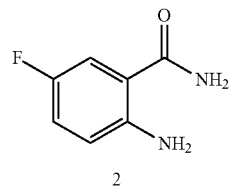

To a stirred solution of 2-amino-5-fluoro-benzoic acid (15 g, 96.69 mmol) in THF (300 mL), EDC HCl (27.70 g, 145.03 mmol), HOBt-$NH_3$ (21.75 g, 145.03 mmol) and DIPEA (51.0 mL, 290.07 mmol) were added at RT and stirred for 6 h (TLC indicated complete consumption of starting material). The reaction mixture was concentrated under reduced pressure to give the crude residue which was diluted with water (150 mL) and extracted with EtOAc (3×150 mL). The combined organic extracts were washed with water (2×100 mL), brine (1×100 mL), dried over $Na_2SO_4$, and concentrated under reduced pressure to give the crude residue. The crude material was purified by column chromatography (100-200 silica gel, 300 g, 40% EtOAc-Hexane) to provide 2-amino-5-fluoro-benzamide (10.0 g, 67%) as a pale yellow solid.

LCMS: m/z: 155.38 [M+H]$^+$.

Step-2

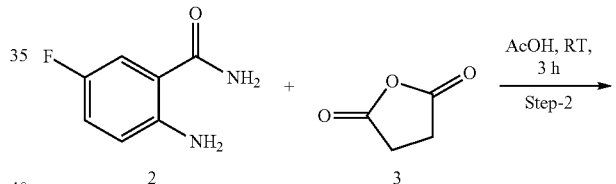

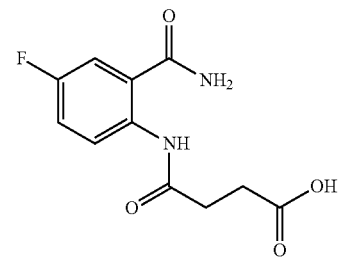

To a stirred solution of 2-amino-5-fluoro-benzamide (7.0 g, 45.45 mmol) in AcOH (35 mL), succinic anhydride (5.45 g, 54.54 mmol) was added at RT and stirred for 3 h (TLC indicated complete consumption of starting material). The reaction mixture was poured into ice cold water (250 mL), solid precipitated out was stirred for 30 min at RT, filtered, washed with water (50 mL), cold acetone (20 mL) and dried under high vacuum to furnish 4-(2-carbamoyl-4-fluoro-anilino)-4-oxo-butanoic acid (9.0 g, 77%) as a white solid.
LCMS: m/z: 255.57 [M+H]$^+$.

Step-3

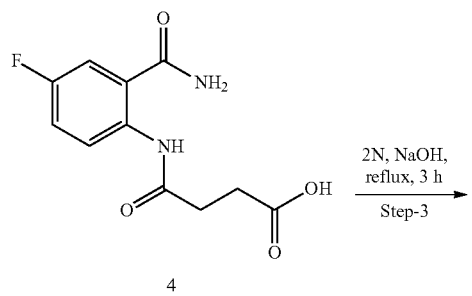

A stirred solution of 4-(2-carbamoyl-4-fluoro-anilino)-4-oxo-butanoic acid (9.0 g, 35.43 mmol) in 2 N aq. NaOH (100 mL) was heated at 100° C. for 3 h (TLC indicated complete consumption of starting material). The reaction mixture was cooled to 0° C. and acidified with 2 N aq. HCl till pH=4-5 during which white precipitate was formed. The suspension was stirred at 0° C. for 30 min., filtered, washed with water (2×50 mL) and cold acetone (20 mL). The solid was dried under high vacuum to afford 3-(6-fluoro-4-oxo-3H-quinazolin-2-yl)propanoic acid (7.0 g, 83%) as an off-white solid. LCMS: m/z: 237.43 [M+H]⁺.

Step-4

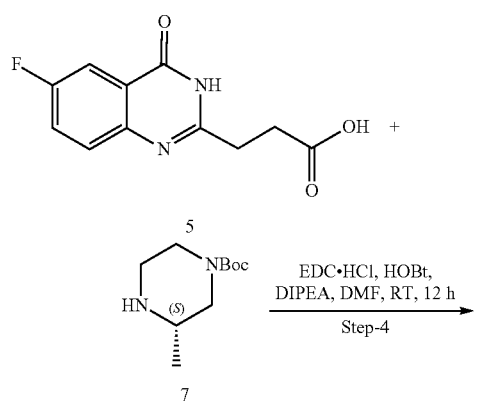

To a stirred solution of 3-(6-fluoro-4-oxo-3H-quinazolin-2-yl)propanoic acid (5.0 g, 21.19 mmol) and tert-butyl (3S)-3-methylpiperazine-1-carboxylate (4.2 g, 21.19 mmol) in DMF (50 mL), cooled to 0° C., EDC HCl (6.06 g, 31.78 mmol), HOBt (4.29 g, 31.78 mmol) and DIPEA (11.2 mL, 63.56 mmol) were added. The reaction mixture was warmed to RT, stirred for 12 h (TLC indicated complete consumption of starting material), quenched with water (100 mL) and extracted with EtOAc (3×200 mL). The combined organic extracts were washed with cold water (3×50 mL), brine (50 mL), dried over Na₂SO₄ and concentrated under reduced pressure to give the crude residue which was purified by column chromatography (100-200 silica gel, 80 g, 5% MeOH-DCM) to give tert-butyl (3S)-4-[3-(6-fluoro-4-oxo-3H-quinazolin-2-yl)propanoyl]-3-methyl-piperazine-1-carboxylate (4.0 g, 45%) as an off-white solid. LCMS: m/z: 419.73 [M+H]⁺.

Step-5

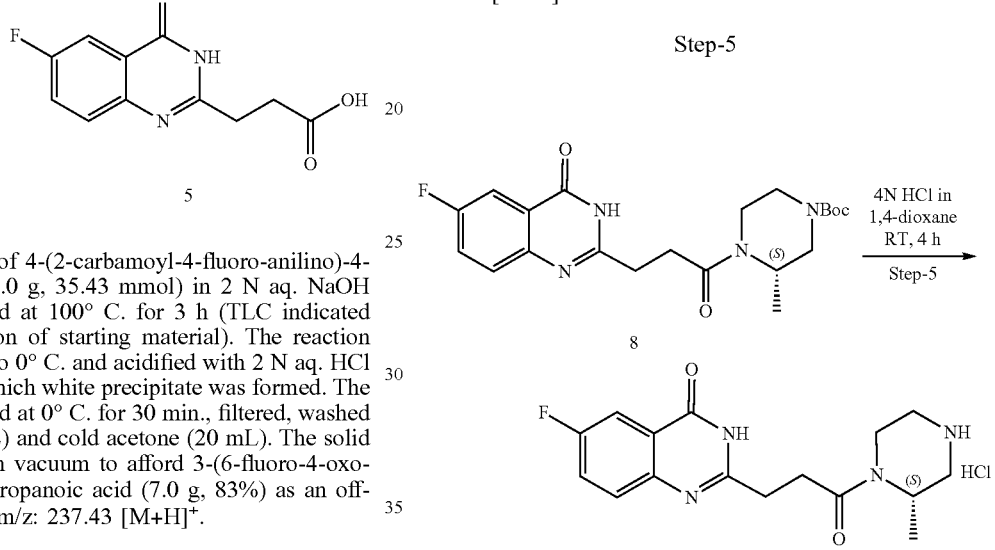

To a stirred solution of tert-butyl (3S)-4-[3-(6-fluoro-4-oxo-3H-quinazolin-2-yl)propanoyl]-3-methyl-piperazine-1-carboxylate (4.0 g, 9.57 mmol) in 1,4-dioxane (20 mL), cooled to 0° C., 4 N HCl in dioxane (10 mL, 40.0 mmol) was added. The reaction mixture was brought to RT and stirred for 4 h (TLC indicated complete consumption of starting material). The volatiles were concentrated under reduced pressure to give the crude residue which was washed with Et₂O (10 mL), dried under high vacuum to afford 6-fluoro-2-[3-[(2S)-2-methylpiperazin-1-yl]-3-oxo-propyl]-3H-quinazolin-4-one hydrochloride (2.0 g, 65%) and used for the next step without any purification. LCMS: m/z: 319.63 [M+H]⁺.

Step-6

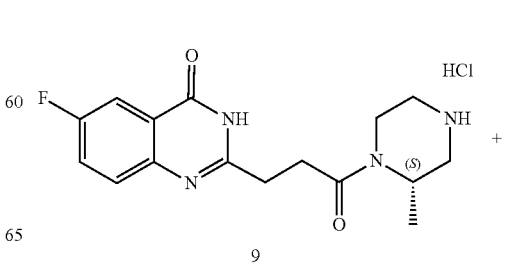

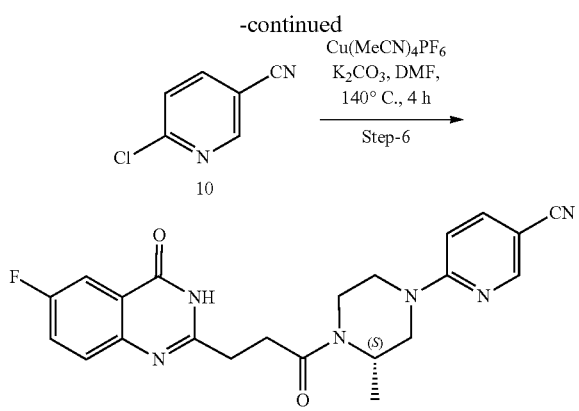

To a stirred solution of 6-fluoro-2-[3-[(2S)-2-methylpiperazin-1-yl]-3-oxo-propyl]-3H-quinazolin-4-one hydrochloride (2.5 g, 7.86 mmol), 6-chloropyridine-3-carbonitrile (1.08 g, 7.86 mmol), and K$_2$CO$_3$ (3.2 g, 23.58 mmol) in DMSO (20 mL), Cu(MeCN)$_4$PF$_6$ (58 mg, 0.16 mmol) was added and stirred at 140° C. for 4 h (TLC indicated complete consumption of starting material). The reaction mixture was brought to RT, diluted with water (50 mL) and extracted with EtOAc (3×150 mL). The combined organic extracts were washed with water (2×100 mL), brine (1×10 mL), dried over Na$_2$SO$_4$ and concentrated under reduced pressure to give the crude residue. The crude product was purified by column chromatography (100-200 silica gel, 40 g, 5% MeOH-DCM) to furnish compound 6-[(3S)-4-[3-(6-fluoro-4-oxo-3H-quinazolin-2-yl)propanoyl]-3-methyl-piperazin-1-yl]pyridine-3-carbonitrile (1.3 g, 40%) as a white solid.

$^1$H NMR [400 MHz, DMSO-d$_6$]: δ 12.31 (s, 1H), 8.48 (d, J=2.4 Hz, 1H), 7.86 (dd, J=8.8, 2.0 Hz, 1H), 7.73 (dd, J=8.8, 2.8 Hz, 1H), 7.68-7.55 (m, 2H), 6.97-6.88 (s, 1H), 4.56-4.36 (m, 1H), 4.30-4.14 (m, 3H), 3.51-3.44 (m, 1H), 3.24-3.17 (m, 1H), 2.98 (s, 1H), 2.95-2.80 (s, 4H), 1.25-0.94 (m, 3H).

LCMS: m/z: 421.72 [M+H]$^+$.

Example 29a—Synthesis of 6-[(3R)-4-[3-(6-fluoro-4-oxo-3H-quinazolin-2-yl)propanoyl]-3-methyl-piperazin-1-yl]pyridine-3-carbonitrile Step-1

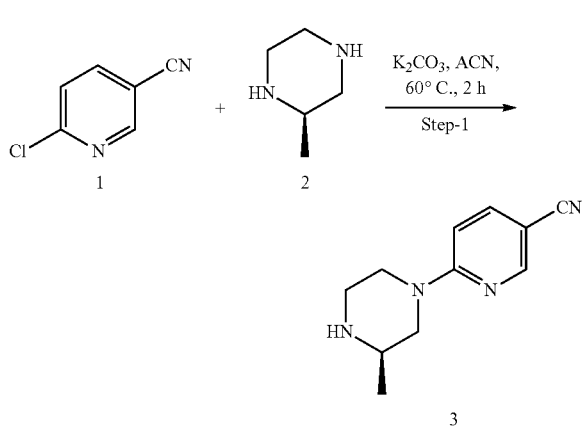

To a mixture of 6-chloropyridine-3-carbonitrile (10 g, 0.06 mol) and (2R)-2-methylpiperazine (6.35 g, 0.06 mol) in acetonitrile (80 mL), K$_2$CO$_3$ (12.0 g, 0.09 mol) was added at RT. The resulting mixture was stirred at 60° C. for 2 h (TLC indicated complete consumption of starting material). The reaction was brought to RT, quenched with water (150 mL) and extracted with EtOAc (3×80 mL). The combined organic extracts were dried over anhydrous Na$_2$SO$_4$ and concentrated under reduced pressure. The residue was purified by column chromatography (100-200 silica gel, 5% MeOH-DCM) to afford 6-[(3R)-3-methyl-piperazine-1-yl]-pyridine-3-carbonitrile (10.0 g, 69% yield).

Step-2

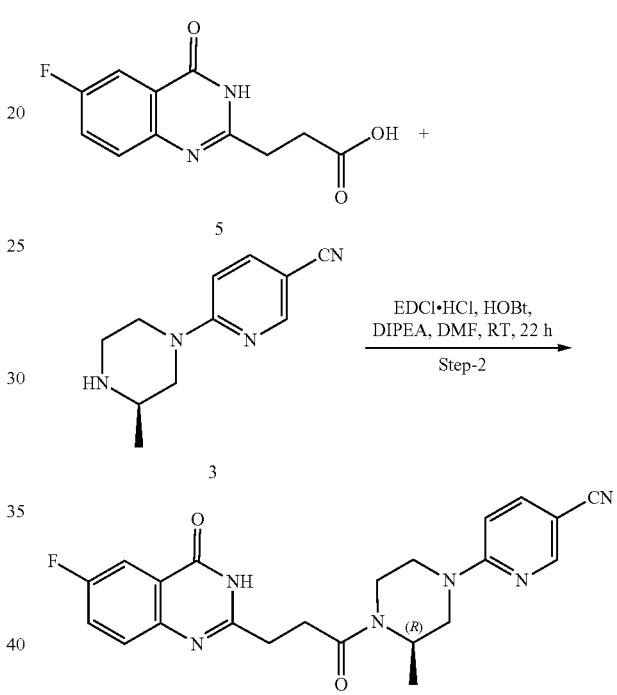

To a stirred solution of 3-(6-fluoro-4-oxo-3H-quinazolin-2-yl)propanoic acid (5.0 g, 21.19 mmol, obtained from Example 29, step 3) in dry DMF (40 mL, ~8 vol), 6-[(3R)-3-methyl-piperazine-1-yl]-pyridine-3-carbonitrile (4.06 g, 20 mmol), EDC·HCl (6.08 g, 31.6 mmol), HOBt (3.43 g, 25.4 mmol) and DIPEA (14.5 mL, 84.5 mol) were added at 10-15° C. and stirred for 22 h. The reaction mixture was quenched with ice cold water (500 mL) and extracted with EtOAc (3×70 mL). The combined organic layers were dried over anhydrous Na$_2$SO$_4$ and concentrated under reduced pressure to get crude compound. Crude compound was stirred with EtOAc (50 mL) for 1 hour at RT, filtered and suck dried. Solid obtained was again made slurry with EtOAc. Filtered the solid and washed with EtOAc (50 mL) to afford (50 mL) 6-[(3R)-4-[3-(6-fluoro-4-oxo-3H-quinazolin-2-yl)propanoyl]-3-methyl-piperazin-1-yl]pyridine-3-carbonitrile in 43% yield (3.8 g). Chiral HPLC was used to confirm that the compound is the enantiomer of compound 29. Column used: Lux, 5 micron, Cellulose-4 (250×4.6 mm, 5 micron, Mobile phase: 50:50 n-hexane: (0.1% HCOOH in 1:1 ethanol:methanol), Flow rate: 1.0 mL/min, Temperature: 25° C. Retention time for R-enantiomer=12.9 min; Retention time for compound 29=13.4 min.

Example 30—Synthesis of 6-[(3S)-4-[3-(5-fluoro-4-oxo-3H-quinazolin-2-yl)propanoyl]-3-methyl-piperazin-1-yl]pyridine-3-carbonitrile

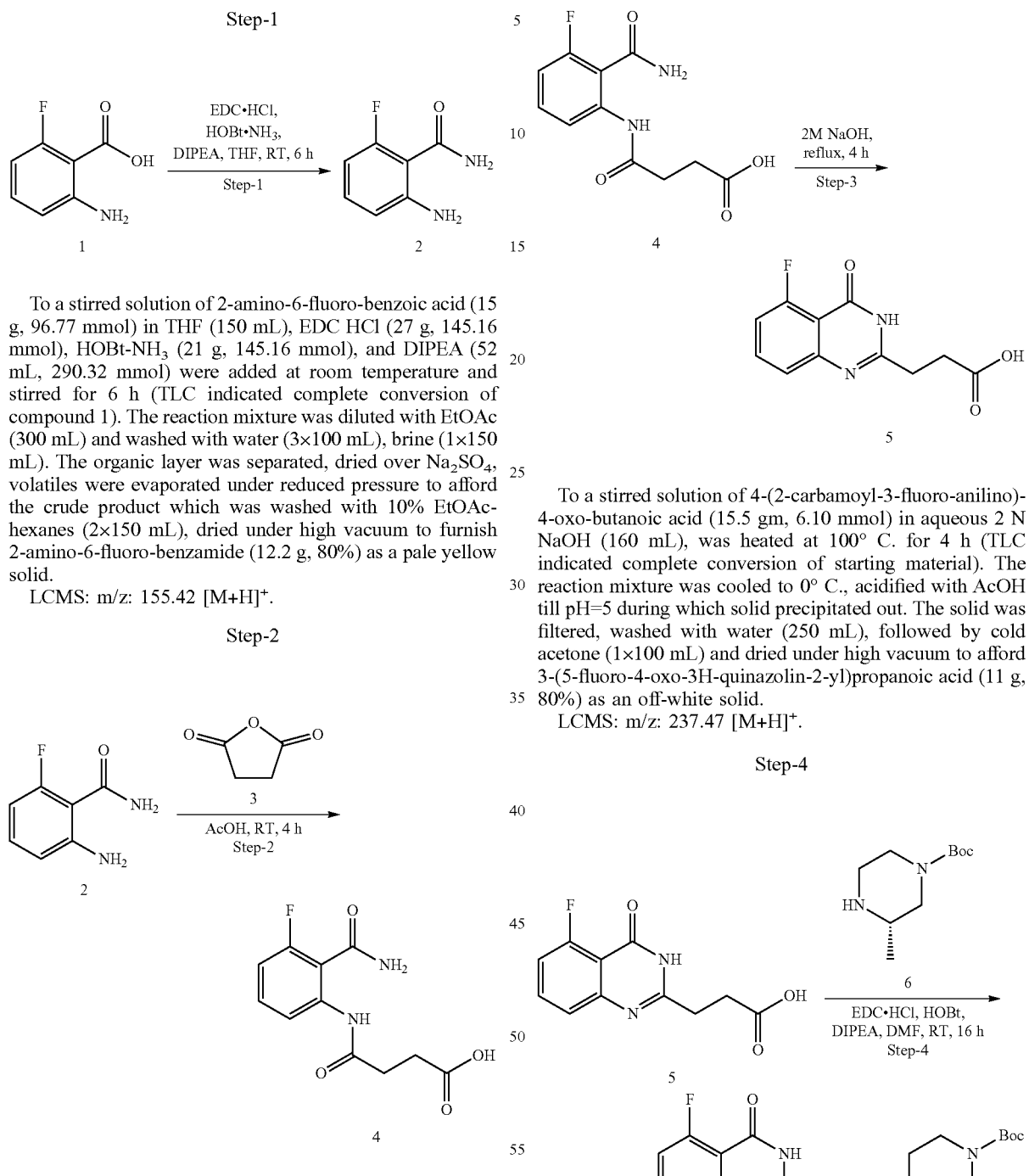

To a stirred solution of 2-amino-6-fluoro-benzoic acid (15 g, 96.77 mmol) in THF (150 mL), EDC HCl (27 g, 145.16 mmol), HOBt-NH₃ (21 g, 145.16 mmol), and DIPEA (52 mL, 290.32 mmol) were added at room temperature and stirred for 6 h (TLC indicated complete conversion of compound 1). The reaction mixture was diluted with EtOAc (300 mL) and washed with water (3×100 mL), brine (1×150 mL). The organic layer was separated, dried over Na₂SO₄, volatiles were evaporated under reduced pressure to afford the crude product which was washed with 10% EtOAc-hexanes (2×150 mL), dried under high vacuum to furnish 2-amino-6-fluoro-benzamide (12.2 g, 80%) as a pale yellow solid.

LCMS: m/z: 155.42 [M+H]⁺.

Step-2

To a stirred solution of 2-amino-6-fluoro-benzamide (12 g, 77.92 mmol) in AcOH (120 mL), succinic anhydride (9.3 g, 93.50 mmol) was added at RT and stirred for 4 h (TLC indicated complete conversion of starting material). The reaction mixture was diluted with ice cold water (1×200 mL), stirred for 30 min when solid was precipitated out. The solid was filtered, washed with water (1×150 mL), followed by cold acetone (1×100 mL) and dried under high vacuum to furnish 4-(2-carbamoyl-3-fluoro-anilino)-4-oxo-butanoic acid (16 g, 81%) as an off-white solid. LCMS: m/z: 277.46 [M+Na]⁺, 238.49 [M-NH₂]⁺.

Step-3

To a stirred solution of 4-(2-carbamoyl-3-fluoro-anilino)-4-oxo-butanoic acid (15.5 gm, 6.10 mmol) in aqueous 2 N NaOH (160 mL), was heated at 100° C. for 4 h (TLC indicated complete conversion of starting material). The reaction mixture was cooled to 0° C., acidified with AcOH till pH=5 during which solid precipitated out. The solid was filtered, washed with water (250 mL), followed by cold acetone (1×100 mL) and dried under high vacuum to afford 3-(5-fluoro-4-oxo-3H-quinazolin-2-yl)propanoic acid (11 g, 80%) as an off-white solid.

LCMS: m/z: 237.47 [M+H]⁺.

Step-4

To a stirred solution of 3-(5-fluoro-4-oxo-3H-quinazolin-2-yl)propanoic acid (5.2 g, 22 mmol) in DMF (52 mL), tert-butyl (3S)-3-methylpiperazine-1-carboxylate (6.6 g, 33.05 mmol), EDC HCl (6.2 g, 33.05 mmol), HOBt (4.4 g, 33.05 mmol) and DIPEA (12 mL, 66.10 mmol) were added at RT and stirred for 16 h (TLC indicates complete conversion of starting material). The reaction mixture was quenched with ice cold water (160 mL), stirred 30 min when solid was precipitated out which was filtered. The filtrate was extracted with EtOAc (3×200 mL) and the combined organic extracts were washed with water (1×200 mL), brine (1×200 mL), dried over Na$_2$SO$_4$ and concentrated under reduced pressure to give the crude residue which was purified by column chromatography (100-200 silica gel, 60 g, 5% MeOH-DCM) to afford tert-butyl (3S)-4-[3-(5-fluoro-4-oxo-3H-quinazolin-2-yl)propanoyl]-3-methyl-piperazine-1-carboxylate (4 g, 43%) as a cream color solid. LCMS: m/z: 419.73 [M+H]$^+$.

Step-5

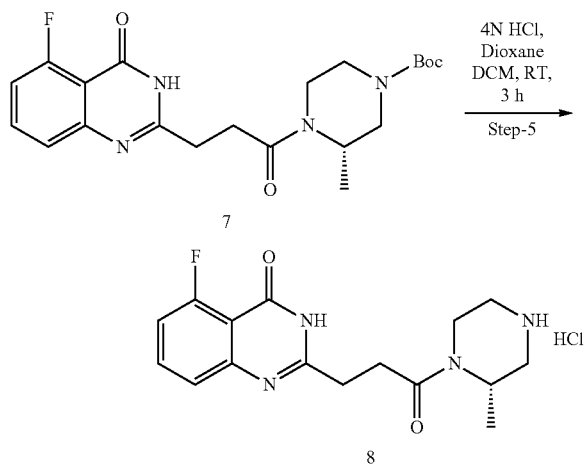

To a stirred solution of tert-butyl (3S)-4-[3-(5-fluoro-4-oxo-3H-quinazolin-2-yl)propanoyl]-3-methyl-piperazine-1-carboxylate (6 g, 14.35 mmol) in DCM (60 mL), 4 N HCl in dioxane (60 mL) was added at RT and stirred for 3 h (TLC indicated complete conversion of starting material). The volatiles were evaporated under reduced pressure, the crude residue was co-distilled with toluene (2×100 mL) and dried under high vacuum to afford 5-fluoro-2-[3-[(2S)-2-methylpiperazin-1-yl]-3-oxo-propyl]-3H-quinazolin-4-one hydrochloride (4.7 g, 94%) as a white solid. LCMS: m/z: 319.59 [M+H]$^+$.

Step-6

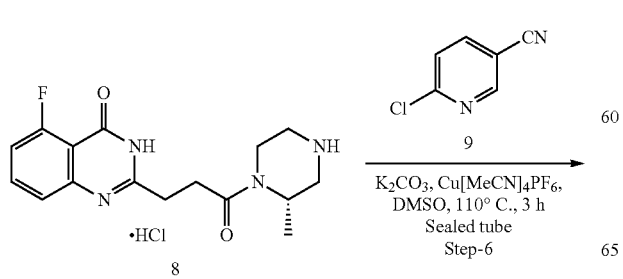

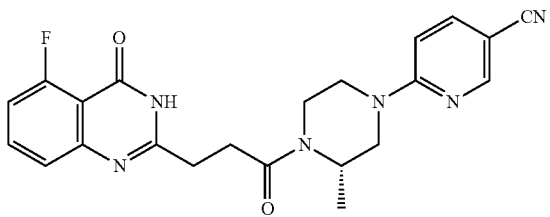

To a stirred solution of 5-fluoro-2-[3-[(2S)-2-methylpiperazin-1-yl]-3-oxo-propyl]-3H-quinazolin-4-one hydrochloride (5.2 g, 14.73 mmol) in DMSO (52 mL), taken in a sealed tune, K$_2$CO$_3$ (4 g, 29.40 mmol), 6-chloropyridine-3-carbonitrile (2 g, 14.73 mmol) and tetrakis(acetonitrile) copper (I) hexafluorophosphate (109 mg, 0.29 mmol) were added at RT. The reaction mixture was degassed with Argon for 5 min and stirred at 110° C. for 3 h (LCMS indicated complete conversion of starting material). The reaction mixture was quenched with water (300 mL) and extracted with EtOAc (3×200 mL). The combined organic extracts were washed with cold water (1×200 mL), brine (1×200 mL), organic layer was separated, dried over Na$_2$SO$_4$ and concentrated under reduced pressure to give the crude residue which was purified by column chromatography (100-200 silica gel, 60 g, 5% MeOH-DCM) to give off white solid. This solid was washed with 5% MeOH-EtOAc to provide 6-[(3S)-4-[3-(5-fluoro-4-oxo-3H-quinazolin-2-yl)propanoyl]-3-methyl-piperazin-1-yl]pyridine-3-carbonitrile (1.4 g, 23%) as a white solid.

$^1$H NMR [400 MHz, DMSO-d$_6$]: δ 12.22 (s, 1H), 8.47 (d, J=2.0 Hz, 1H), 7.85 (dd, J=9.2, 2.4 Hz, 1H), 7.73-7.65 (m, 1H), 7.32 (t, J=8.4 Hz, 1H), 7.19-7.14 (m, 1H), 6.91 (d, J=8.0 Hz, 1H), 4.55-4.35 (m, 1H), 4.29-4.11 (m, 3H), 3.48 (t, J=9.2 Hz, 1H), 3.26-3.18 (m, 1H), 3.04-2.94 (m, 1H), 2.91-2.84 (m, 4H), 1.21-0.98 (m, 3H). LCMS: m/z: 421.72 [M+H]$^+$.

Example 31—Synthesis of 6-[3-(hydroxymethyl)-4-[3-(4-oxo-3H-quinazolin-2-yl)propanoyl]piperazin-1-yl]pyridine-3-carbonitrile Step-1

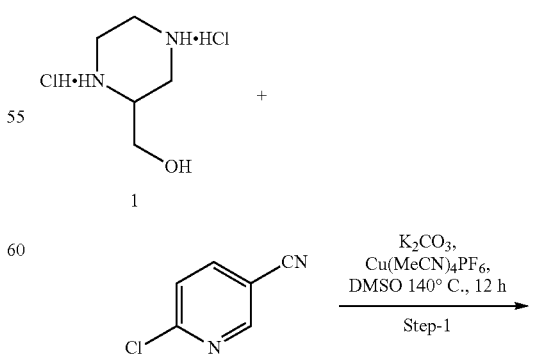

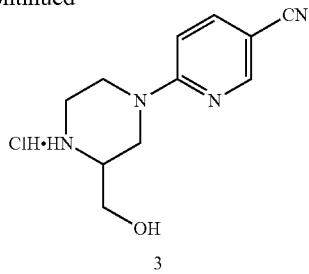

3

To a stirred solution of piperazin-2-ylmethanol dihydrochloride (100 mg, 0.53 mmol) in DMSO (3 mL), 6-chloropyridine-3-carbonitrile (88 mg, 0.63 mmol), $K_2CO_3$ (146 mg, 1.062 mmol) and $Cu(MeCN)_4PF_6$ (3.9 mg, 0.01 mmol) were added at RT. The reaction mixture was heated at 140° C. for 12 h (TLC indicated complete consumption of starting material), quenched with water (10 mL) and extracted with EtOAc (3×10 mL). The combined organic extracts were dried over $Na_2SO_4$, concentrated under reduced pressure to give the crude residue which was purified by column chromatography (100-200 silica gel, 5 g, 5% MeOH-DCM) to provide 6-[3-(hydroxymethyl)piperazin-1-yl]pyridine-3-carbonitrile hydrochloride (50 mg, 32%) as a white Solid. LCMS: m/z: 219 [M+H]⁺.

Step-2

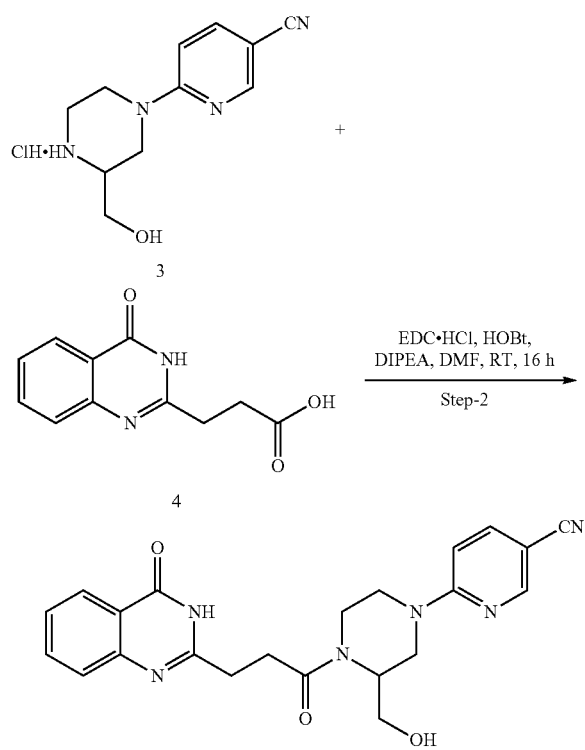

To a stirred solution of 6-[3-(hydroxymethyl)piperazin-1-yl]pyridine-3-carbonitrile hydrochloride (120 mg, 0.55 mmol) and 3-(4-oxo-3H-quinazolin-2-yl)propanoic acid (120 mg, 0.55 mmol) in dry DMF (2 mL), EDC HCl (157 mg, 0.825 mmol), HOBt (113 mg, 0.825 mmol) and DIPEA (0.2 mL, 1.1 mmol) were added at RT and stirred for 16 h (TLC indicated complete consumption of starting material). The reaction mixture was quenched with cold water (20 mL) and extracted with EtOAc (3×10 mL). The combined organic extracts were dried over $Na_2SO_4$, concentrated under reduced pressure to give the residue which was purified by preparative HPLC to afford 6-[3-(hydroxymethyl)-4-[3-(4-oxo-3H-quinazolin-2-yl)propanoyl]piperazin-1-yl]pyridine-3-carbonitrile (26 mg, 11%) as a white solid.

$^1$H NMR [400 MHz, DMSO-d$_6$]: δ 12.17 (s, 1H), 8.49 (d, J=1.6 Hz, 1H), 8.08-8.06 (m, 1H), 7.88-7.85 (m, 1H), 7.74 (t, J=8 Hz, 1H), 7.53 (d, J=8.4 Hz, 1H), 7.46-7.42 (m, 1H), 6.93-6.86 (m, 1H), 5.0-4.82 (m, 2H), 4.42-3.88 (m, 4H), 3.56-3.47 (m, 2H), 2.99-2.89 (m, 6H).

LCMS: m/z: 419.76 [M+H]⁺.

Example 32—Synthesis of 6-[4-[3-(6-fluoro-4-oxo-3H-quinazolin-2-yl)propanoyl]-3-(hydroxymethyl)piperazin-1-yl]pyridine-3-carbonitrile

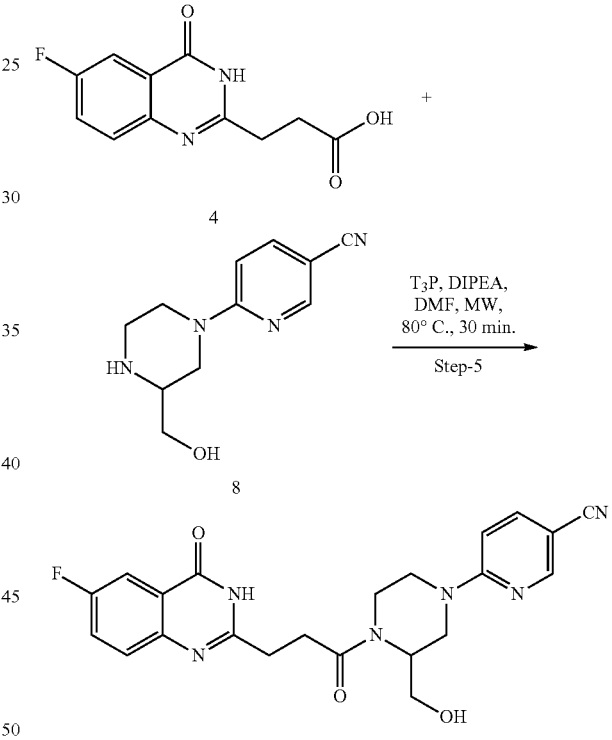

To a stirred solution of 3-(6-fluoro-4-oxo-3H-quinazolin-2-yl)propanoic acid (300 mg, 1.27 mmol) and 6-[3-(hydroxymethyl)piperazin-1-yl]pyridine-3-carbonitrile (277 mg, 1.27 mmol) in DMF (4 mL), DIPEA (0.68 mL, 3.81 mmol), $T_3P$ (0.8 mL, 2.54 mmol) were added at RT. The reaction mixture was heated at 80° C. in CEM Microwave for 30 min (TLC indicated complete consumption of the starting material), slowly brought to RT, quenched with water (10 mL) and extracted with EtOAc (3×60 mL). The combined organic extracts were washed with cold water (3×30 mL), brine (20 mL), dried over $Na_2SO_4$ and concentrated under reduced pressure to give the crude residue. The crude residue was purified by column chromatography (100-200 silica gel, 15 g, 5-10% MeOH-DCM) to furnish 6-[4-[3-(6-fluoro-4-oxo-3H-quinazolin-2-yl)propanoyl]-3-(hydroxymethyl)piperazin-1-yl]pyridine-3-carbonitrile (90%

LCMS, 300 mg) which was repurified by Prep HPLC to afford pure compound (154 mg, 27%) as a white Solid.

$^1$H NMR [400 MHz, DMSO-d$_6$]: δ 12.31 (brs, 1H), 8.48 (s, 1H), 7.85 (dd, J=9.2, 2.4 Hz, 1H), 7.74 (dd, J=8.8, 2.4 Hz, 1H), 7.66-7.61 (m, 2H), 6.92-6.86 (m, 1H), 5.07-4.84 (m, 2H), 4.44-4.37 (m, 1H), 4.33-4.16 (m, 4H), 3.94-3.86 (m, 1H), 3.12-2.78 (m, 6H).

LCMS: m/z: 437.75 [M+H]$^+$.

Example 33—Synthesis of 6-[4-[3-(5-fluoro-4-oxo-3H-quinazolin-2-yl)propanoyl]-3-(hydroxymethyl)piperazin-1-yl]pyridine-3-carbonitrile

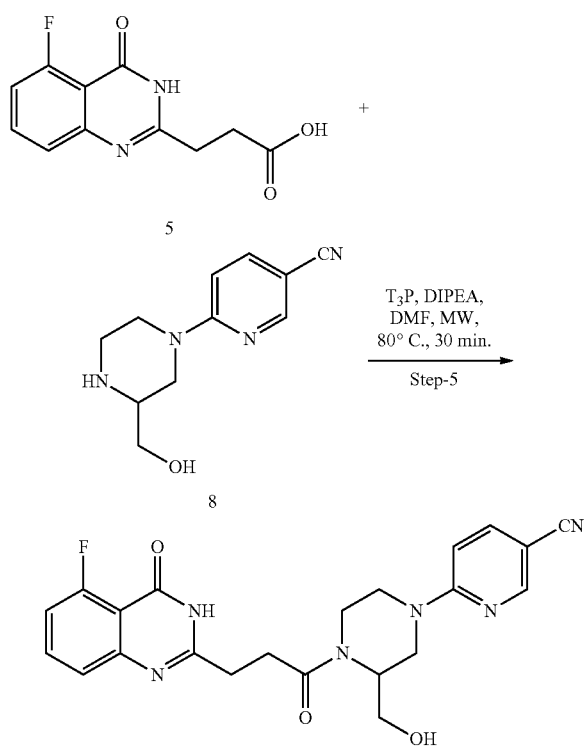

To a stirred solution of 3-(5-fluoro-4-oxo-3H-quinazolin-2-yl)propanoic acid (400 mg, 1.69 mmol) and 6-[3-(hydroxymethyl)piperazin-1-yl]pyridine-3-carbonitrile (369 mg, 1.69 mmol) in DMF (4 mL) at RT, DIPEA (0.88 mL, 5.08 mmol) followed by T$_3$P (1.0 mL, 3.39 mmol) was added. The reaction mixture was heated at 80° C. for 30 min in CEM microwave (TLC indicated complete consumption of the starting material), slowly brought to RT, quenched with water (10 mL) and extracted with EtOAc (3×60 mL). The combined organic extracts were washed with cold water (3×30 mL), brine (20 mL), dried over Na$_2$SO$_4$ and concentrated under reduced pressure to give the crude residue. The residue was purified by column chromatography (100-200 silica gel, 15 g, 5-10% MeOH-DCM) to give 6-[4-[3-(5-fluoro-4-oxo-3H-quinazolin-2-yl)propanoyl]-3-(hydroxymethyl)piperazin-1-yl]pyridine-3-carbonitrile (90% LCMS, 300 mg) which was purified by Prep-HPLC to afford pure compound (160 mg, 21%) as a white Solid.

$^1$H NMR [400 MHz, DMSO-d$_6$]: δ12.36 (brs, 1H), 8.49 (s, 1H), 7.86 (dd, J=8.8, 2.0 Hz, 1H), 7.70 (q, J=8.0 Hz, 1H), 7.34 (d, J=8.4 Hz, 1H), 7.20-7.15 (m, 2H), 6.93-6.86 (m, 1H), 5.02-4.81 (m, 1H), 4.42-4.39 (m, 1H), 4.33-3.88 (m, 3H), 3.53-3.41 (m, 2H), 2.95-2.87 (m, 6H).

LCMS: m/z: 437.75 [M+H]$^+$.

Example 34—Synthesis of 2-[3-oxo-3-[4-(2-pyridyl)piperazin-1-yl]propyl]-3H-quinazolin-4-one Step-1

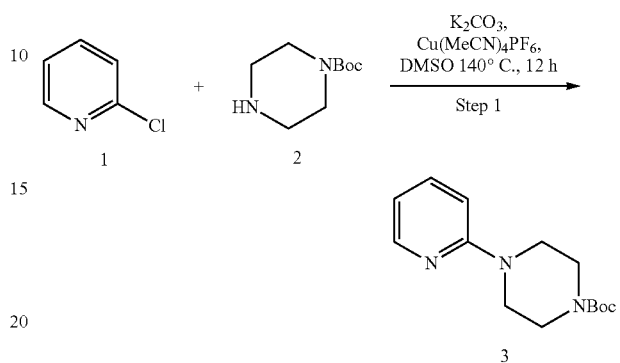

To a stirred solution of 2-chloropyridine (750 mg, 6.60 mmol) in DMSO (10 mL), tert-butyl piperazine-1-carboxylate (1.4 g, 7.92 mmol), K$_2$CO$_3$ (1.8 g, 13.27 mmol) and Cu(MeCN)$_4$PF$_6$ (49 mg, 0.132 mmol) were added at RT and heated at 140° C. for 12 h (TLC indicated complete consumption of starting material). The reaction mixture was quenched with water (40 mL) and extracted with EtOAc (3×60 mL). The combined organic extracts were dried over Na$_2$SO$_4$, concentrated under reduced pressure to give the crude compound which was purified by flash chromatography (100-200 silica gel, 8 g, 20% of EtOAc-hexanes) to provide tert-butyl 4-(2-pyridyl)piperazine-1-carboxylate (350 mg, 20%) as a yellow oil.

LCMS: m/z: 264.55 [M+H]$^+$.

Step-2

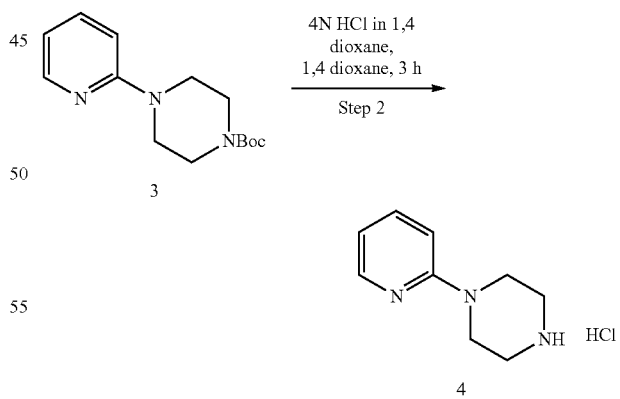

To the stirred solution of tert-butyl 4-(2-pyridyl)piperazine-1-carboxylate (350 mg, 1.32 mmol) in 1,4-dioxane (4 mL), 4 N HCl in dioxane (1.3 mL, 5.30 mmol) was added at 0° C. under argon atmosphere. The reaction mixture was slowly warmed to RT and stirred for 3 h (TLC indicated complete consumption of starting material). The volatiles were removed under reduced pressure to give the crude compound which was washed with Et$_2$O (50 mL) to furnish 1-(2-pyridyl)piperazine hydrochloride (210 mg, 96%) as a white solid.

LCMS: m/z: 164.48 [M+H]$^+$.

Step-3

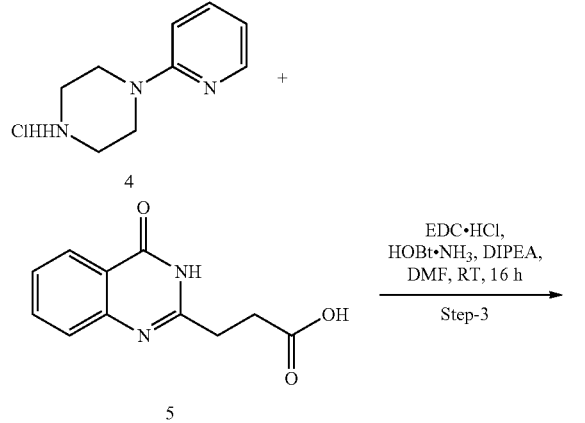

To a stirred solution of 1-(2-pyridyl)piperazinehydrochloride (100 mg, 0.609 mmol) and 3-(4-oxo-3H-quinazolin-2-yl)propanoic acid (121 mg, 0.609 mmol) in dry DMF (2 mL), EDC HCl (174 mg, 0.913 mmol), HOBt (123 mg, 0.913 mmol) and DIPEA (0.2 mL, 1.2 mmol) were added at RT and stirred for 16 h (TLC indicated the complete consumption of starting material). The reaction mixture was quenched with cold water (20 mL), stirred for 15 min, solid precipitated out, which was filtered, washed with Et$_2$O (2×5 mL) and dried under vacuum to give 2-[3-oxo-3-[4-(2-pyridyl)piperazin-1-yl]propyl]-3H-quinazolin-4-one (55 mg, 24%) as a white solid.

$^1$H NMR [300 MHz, DMSO-d$_6$]: δ 12.20 (s, 1H), 8.13-8.11 (dd, J=4.8, 1.5 Hz, 1H), 8.08 (dd, J=7.8, 1.2 Hz, 1H), 7.76-7.74 (m, 1H), 7.58-7.52 (m, 2H), 7.46-7.41 (m, 1H), 6.84 (d, J=8.7 Hz, 1H), 6.68-6.64 (m, 1H), 3.62 (s, 2H), 3.59-3.51 (m, 4H), 3.46-3.46 (m, 2H), 2.89 (brs, 4H).

LCMS: m/z: 364.62 [M+H]$^+$.

Example 35—Synthesis of 2-[3-[4-(5-methyl-2-pyridyl)piperazin-1-yl]-3-oxo-propyl]-3H-quinazolin-4-one Step-1

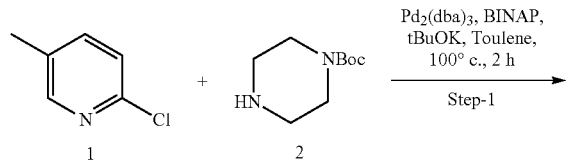

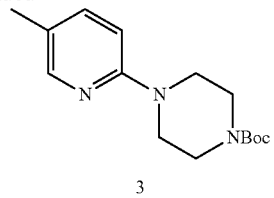

To a stirred solution of 2-chloro-5-methyl-pyridine (500 mg, 2.68 mmol) in toluene (10 mL), tert-butyl piperazine-1-carboxylate (409 mg, 3.22 mmol), Pd$_2$(dba)$_3$ (122 mg, 0.13 mmol), BINAP (167 mg, 0.27 mmol) and t-BuOK (903 mg, 8.06 mmol) were added at RT and heated at 100° C. for 2 h (TLC indicated complete consumption of starting material). The reaction mixture was quenched with water (30 mL) and extracted with EtOAc (3×30 mL). The combined organic extracts were dried over Na$_2$SO$_4$, concentrated under reduced pressure and the residue was purified by flash chromatography (100-200 silica gel, 8 g, 30% of EtOAc-hexanes) to provide tert-butyl 4-(5-methyl-2-pyridyl)piperazine-1-carboxylate (560 mg, 92%) as a yellow oil.

Step-2

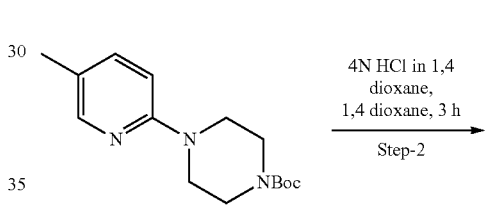

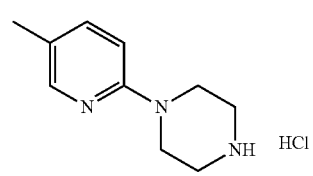

To a stirred solution of 1-(5-methyl-2-pyridyl)piperazine; hydrochloride (560 mg, 1.80 mmol) in 1,4-dioxane (5 ml), cooled to 0° C., 4 N HCl in dioxane (1.8 ml, 7.22 mmol) was added under argon atmosphere and stirred for 3 h (TLC indicated complete consumption of starting material). The volatiles were removed under reduced pressure to give the residue which was washed with Et$_2$O (50 ml) and dried to give 1-(5-methyl-2-pyridyl)piperazine hydrochloride (350 mg, 98%) as a white solid.

$^1$H NMR [300 MHz, DMSO-d$_6$]: δ 9.64 (brs, 2H), 7.95 (s, 1H), 7.85 (d, J=8.7 Hz, 1H), 7.25 (d, J=8.7 Hz, 1H), 3.90 (m, 4H), 3.22 (m, 4H), 2.22 (s, 3H).

Step-3

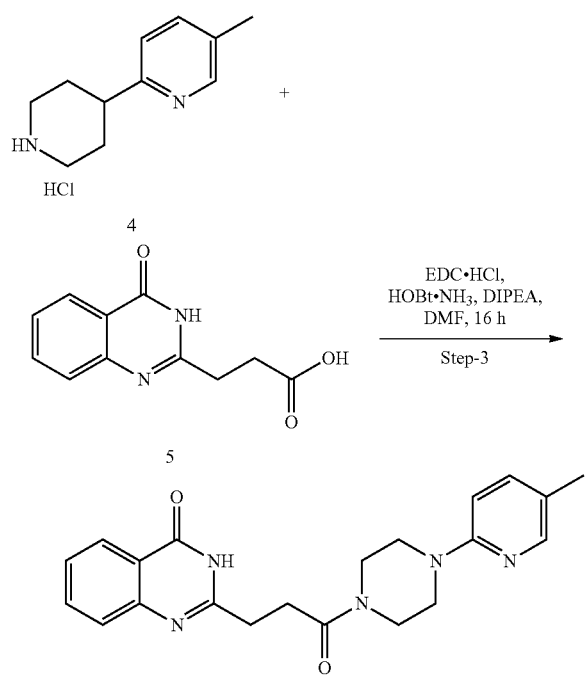

To a stirred solution of 1-(5-methyl-2-pyridyl)piperazine hydrochloride (100 mg, 0.56 mmol) and 3-(4-oxo-3H-quinazolin-2-yl)propanoic acid (135 mg, 0.67 mmol) in dry DMF (2 mL), EDC HCl (161 mg, 0.84 mmol), HOBt (114 mg, 0.84 mmol) and DIPEA (0.2 mL, 1.1 mmol) were added at RT and stirred for 16 h (TLC indicated the complete consumption of starting material). The reaction mixture was quenched with water (10 mL) and extracted with DCM (3×10 mL). The combined organic extracts were dried over Na$_2$SO$_4$, concentrated under reduced pressure and the residue was purified by flash chromatography (100-200 silica gel, 4 g, 5% MeOH-DCM) to obtain compound 2-[3-[4-(5-methyl-2-pyridyl)piperazin-1-yl]-3-oxo-propyl]-3H-quinazolin-4-one (50 mg, 23%) as a white solid.

$^1$H NMR [400 MHz, DMSO-d$_6$]: δ 12.18 (s, 1H), 8.07 (dd, J=6, 0.9 Hz, 1H), 7.96 (s, 1H), 7.75-7.71 (m, 1H), 7.54 (d, J=6 Hz, 1H), 7.46-7.38 (m, 2H), 6.78 (d, J=6.6 Hz, 1H), 3.62-3.61 (m, 2H), 3.59-3.51 (m, 4H), 3.39-3.38 (m, 2H), 2.88 (brs, 4H), 2.14 (brs, 3H).

LCMS: m/z: 378.37 [M+H]$^+$.

Example 36—Synthesis of 2-[3-[4-(3-methyl-2-pyridyl)piperazin-1-yl]-3-oxo-propyl]-3H-quinazolin-4-on

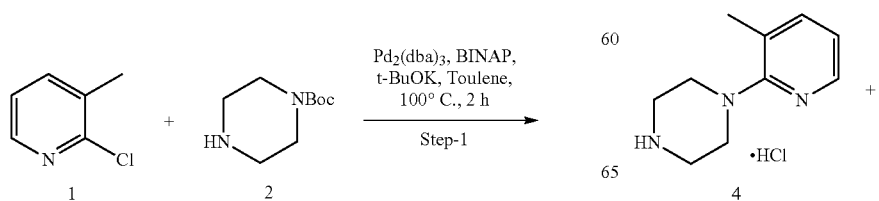

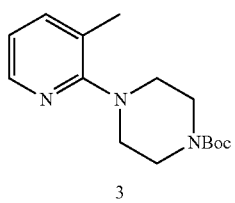

To a stirred solution of 2-chloro-3-methyl-pyridine (500 mg, 2.68 mmol) in toluene (10 mL), tert-butyl piperazine-1-carboxylate (409 mg, 3.22 mmol), Pd$_2$(dba)$_3$ (122 mg, 0.13 mmol), BINAP (167 mg, 0.26 mmol) and t-BuOK (903 mg, 8.06 mmol) were added at RT and heated at 100° C. for 2 h (TLC indicated complete consumption of starting material). The reaction mixture was quenched with water (30 mL) and extracted with EtOAc (3×30 mL). The combined organic extracts were dried over Na$_2$SO$_4$, concentrated under reduced pressure to give the residue which was purified by flash chromatography (100-200 silica gel, 8 g, 30% EtOAc-Hexane) to furnish tert-butyl 4-(3-methyl-2-pyridyl)piperazine-1-carboxylate (560 mg, 92%) as a yellow oil.

Step-2

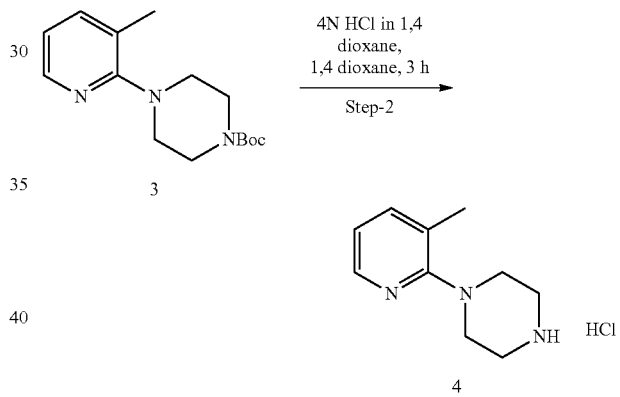

To the stirred solution of tert-butyl 4-(3-methyl-2-pyridyl)piperazine-1-carboxylate (560 mg, 1.80 mmol) in 1,4-dioxane (5 mL), cooled to 0° C., 4 N HCl in dioxane (1.8 mL, 7.2 mmol) was added under argon atmosphere. The reaction mixture was slowly warmed to RT and stirred for 3 h (TLC indicated complete consumption of starting material). The volatiles were removed under reduced pressure and the residue was washed with Et$_2$O (50 mL) to give 1-(3-methyl-2-pyridyl)piperazine hydrochloride (350 mg, 98%) which was used for the next step without any purification.

Step-3

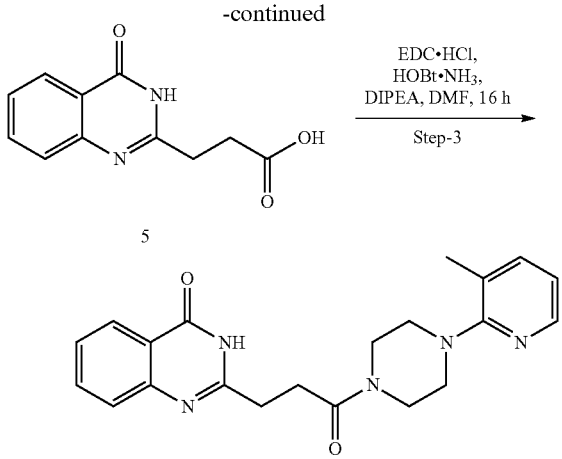

To a stirred solution of 1-(3-methylpyridin-2-yl)piperazine hydrochloride (100 mg, 0.46 mmol) and 3-(4-oxo-3H-quinazolin-2-yl)propanoic acid (135 mg, 0.67 mmol) in dry DMF (2 mL), EDC HCl (161 mg, 0.84 mmol), HOBt (114 mg, 0.84 mmol) and DIPEA (0.2 mL, 1.1 mmol) were added at RT and stirred for 16 h (TLC indicated the complete consumption of starting material). The reaction mixture was quenched with water (10 mL) and extracted with EtOAc (3×10 mL). The combined organic extracts were dried over Na$_2$SO$_4$, concentrated under reduced pressure to give the residue which was purified by flash chromatography (100-200 silica gel, 3 g, 5% MeOH-DCM) to afford compound 2-[3-[4-(3-methyl-2-pyridyl)piperazin-1-yl]-3-oxo-propyl]-3H-quinazolin-4-one (50 mg, 23%) as a white solid.

$^1$H NMR [400 MHz, DMSO-d$_6$]: δ 12.18 (s, 1H), 8.12-8.06 (m, 2H), 7.77-7.73 (m, 1H), 7.59-7.57 (m, 1H), 7.53-7.51 (m, 1H), 7.46-7.42 (m, 1H), 6.96-6.93 (m, 1H), 3.66 (brs, 2H), 3.59 (brs, 2H), 3.11 (brs, 2H), 2.98 (brs, 2H), 2.89 (s, 4H), 2.26 (s, 3H).

LCMS: m/z: 378.61 [M+H]$^+$.

Example 37—Synthesis of 2-[3-[4-(6-methyl-2-pyridyl)piperazin-1-yl]-3-oxo-propyl]-3H-quinazolin-4-one Step-1

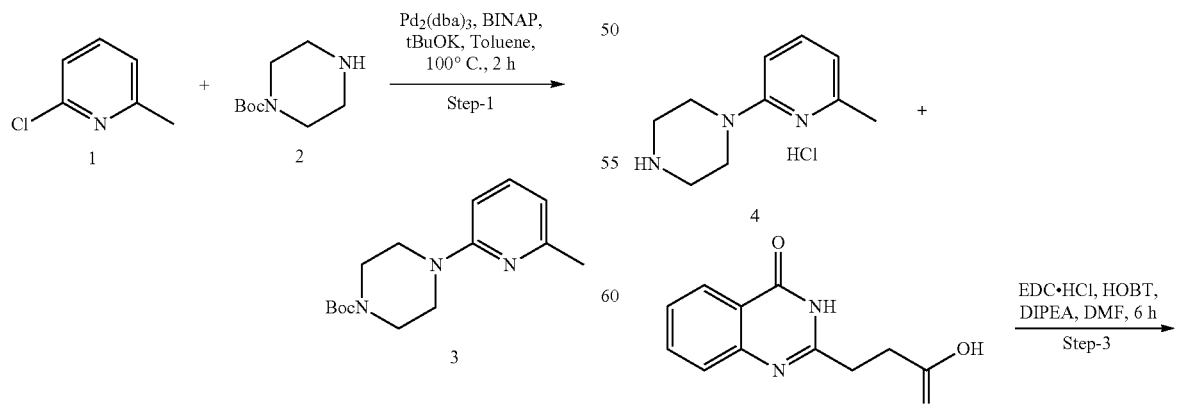

To a stirred solution of 2-chloro-6-methyl-pyridine (500 mg, 2.68 mmol) in toluene (10 mL), tert-butyl piperazine-1-carboxylate (409 mg, 3.22 mmol), Pd$_2$(dba)$_3$ (122 mg, 0.13 mmol), BINAP (167 mg, 0.26 mmol), tBuOK (903 mg, 8.06 mmol) were added at RT. The reaction mixture was heated at 100° C. for 2 h (TLC indicated complete consumption of starting material), diluted with water (20 mL), extracted with EtOAc (3×30 mL). The combined organic extracts were dried over Na$_2$SO$_4$, concentrated under reduced pressure to give the crude compound which was purified by flash chromatography (100-200 silica gel, 8 g, 30% EtOAc-Hexane) to give tert-butyl 4-(6-methyl-2-pyridyl)piperazine-1-carboxylate (560 mg, 75%) as a yellow solid.

LCMS: m/z: 278.59 [M+H]$^+$.

Step-2

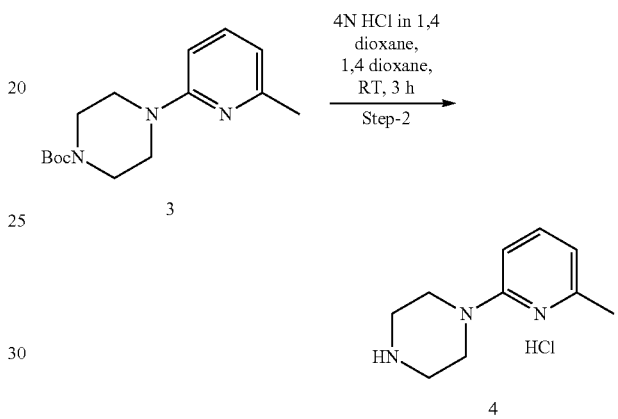

To the stirred solution of tert-butyl 4-(6-methyl-2-pyridyl)piperazine-1-carboxylate (560 mg, 1.80 mmol) in 1,4-dioxane (5 mL), cooled to 0° C., 4 N HCl in dioxane (1.8 mL, 7.22 mmol) was added under argon atmosphere. The reaction mixture was slowly brought to RT and stirred for 3 h (TLC indicated complete consumption of starting material). The volatiles were removed under reduced pressure and the residue was washed with Et$_2$O (50 mL) and EtOAc (50 mL) to obtain 1-(6-methyl-2-pyridyl)piperazine hydrochloride (350 mg, 98%) as an off-white solid.

LCMS: m/z: 178.48 [M+H]$^+$.

Step-3

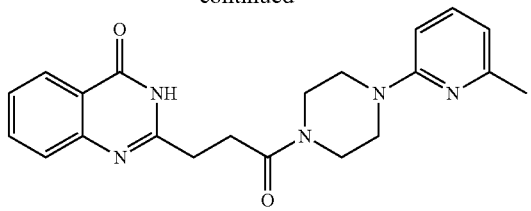

To a stirred solution of compound 5 (100 mg, 0.45 mmol), 1-(6-methyl-2-pyridyl)piperazine hydrochloride (81 mg, 0.45 mmol) in DMF (2 mL), EDC HCl (131 mg, 0.68 mmol), HOBt (92 mg, 0.68 mmol) and DIPEA (0.16 ml, 0.91 mmol) were added. The reaction mixture was stirred at RT for 6 h (TLC indicated the complete consumption of starting material), diluted with cold water (30 mL) and stirred for 10 min during which solid was precipitated out. The solid was filtered, washed with EtOAc (3×10 mL) and dried under vacuum to afford 2-[3-[4-(6-methyl-2-pyridyl)piperazin-1-yl]-3-oxo-propyl]-3H-quinazolin-4-one (62 mg, 36%) as a white solid.

$^1$H NMR [400 MHz, DMSO-d$_6$]: δ 12.19 (s, 1H), 8.07 (dd, J=7.6, 1.2 Hz, 1H), 7.76-7.72 (m, 1H), 7.545 (d, J=8.0 Hz, 1H), 7.44 (t, J=7.6 Hz, 2H), 6.62 (d, J=8.8 Hz, 1H), 6.53 (d, J=7.2 Hz, 1H), 3.63-3.61 (m, 2H), 3.57-3.53 (m, 4H), 3.45-3.43 (m, 2H), 2.89 (s, 4H), 2.31 (s, 3H).

LCMS: m/z: 378.57 [M+H]$^+$.

Example 38—Synthesis of 2-[3-[4-(4-methyl-2-pyridyl)piperazin-1-yl]-3-oxo-propyl]-3H-quinazolin-4-one Step-1

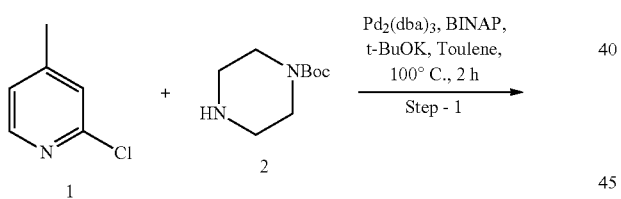

To a stirred solution of 2-chloro-4-methyl-pyridine (200 mg, 1.07 mmol) in DMSO (3 mL), tert-butyl piperazine-1-carboxylate (161 mg, 1.29 mmol), Pd$_2$(dba)$_3$ (49 mg, 0.05 mmol), BINAP (66 mg, 0.107 mmol) and t-BuOK (360 mg, 3.22 mmol) were added at RT. The reaction mixture was heated at 100° C. for 2 h (TLC indicated complete consumption of starting material), quenched with water (30 mL) and extracted with EtOAc (3×30 mL). The combined organic extracts were dried over Na$_2$SO$_4$, concentrated under reduced pressure and the residue was purified by flash chromatography (100-200 silica gel, 10 g, 30% of EtOAc-Hexane) to provide tert-butyl 4-(4-methyl-2-pyridyl)piperazine-1-carboxylate (240 mg, 80%) as a yellow oil.

Step-2

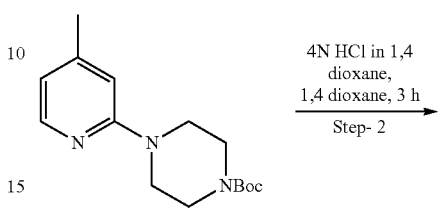

To the stirred solution of tert-butyl 4-(4-methyl-2-pyridyl)piperazine-1-carboxylate (560 mg, 1.805 mmol) in 1,4-dioxane (5 mL), cooled to 0° C., 4 N HCl in dioxane (1.8 mL, 7.220 mmol) was added under argon atmosphere. The reaction mixture was warmed to RT and stirred for 3 h (TLC indicated complete consumption of starting material). The volatiles were removed under reduced pressure, the residue was washed with Et$_2$O (50 ml) and dried to obtain 1-(4-methyl-2-pyridyl)piperazine hydrochloride (350 mg, 98% yield) as a white solid.

Step-3

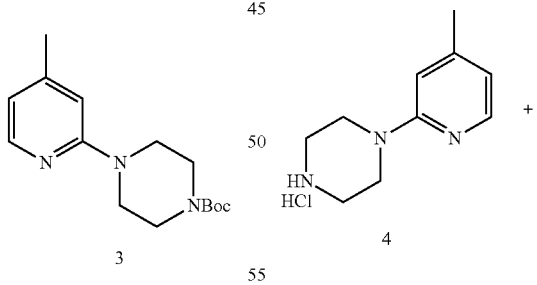

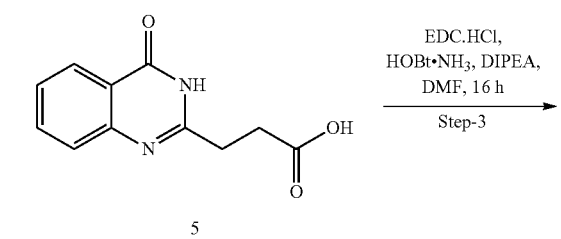

-continued

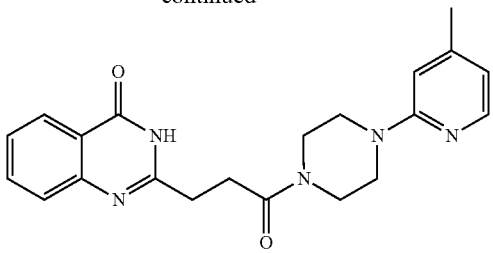

To a stirred solution of 1-(4-methyl-2-pyridyl)piperazine hydrochloride (100 mg, 0.564 mmol) and 3-(4-oxo-3H-quinazolin-2-yl)propanoic acid (135 mg, 0.677 mmol) in dry DMF (2 mL), EDC HCl (161 mg, 0.84 mmol), HOBt (114 mg, 0.84 mmol) and DIPEA (0.2 mL, 1.1 mmol) were added at RT and stirred for 16 h (TLC indicated the complete consumption of starting material). The reaction mixture was quenched with water (10 mL) and extracted with DCM (3×10 mL). The combined organic extracts were dried over $Na_2SO_4$, concentrated under reduced pressure to give the crude residue which was purified by flash chromatography (100-200 silica gel, 8 g, 5% MeOH-DCM) to afford 2-[3-[4-(4-methyl-2-pyridyl)piperazin-1-yl]-3-oxo-propyl]-3H-quinazolin-4-one (50 mg, 23%) as a white solid.

$^1$H NMR [400 MHz, DMSO-$d_6$]: δ 12.18 (s, 1H), 8.08-8.06 (d, J=9.2 Hz, 1H), 7.99-7.97 (d, J=5.2 Hz, 1H), 7.77-7.73 (m, 1H), 7.54 (d, J=8 Hz, 1H), 7.46-7.42 (m, 1H), 6.67 (s, 1H), 6.51 (d, J=5.2 Hz, 1H), 3.62-3.43 (m, 8H), 2.89 (s, 4H), 2.22 (s, 3H).

LCMS: m/z: 378.63 [M+H]$^+$.

Example 39—Synthesis of 5-[4-[3-(4-oxo-3H-quinazolin-2-yl)propanoyl]piperazin-1-yl]pyrazine-2-carbonitrile Step-1

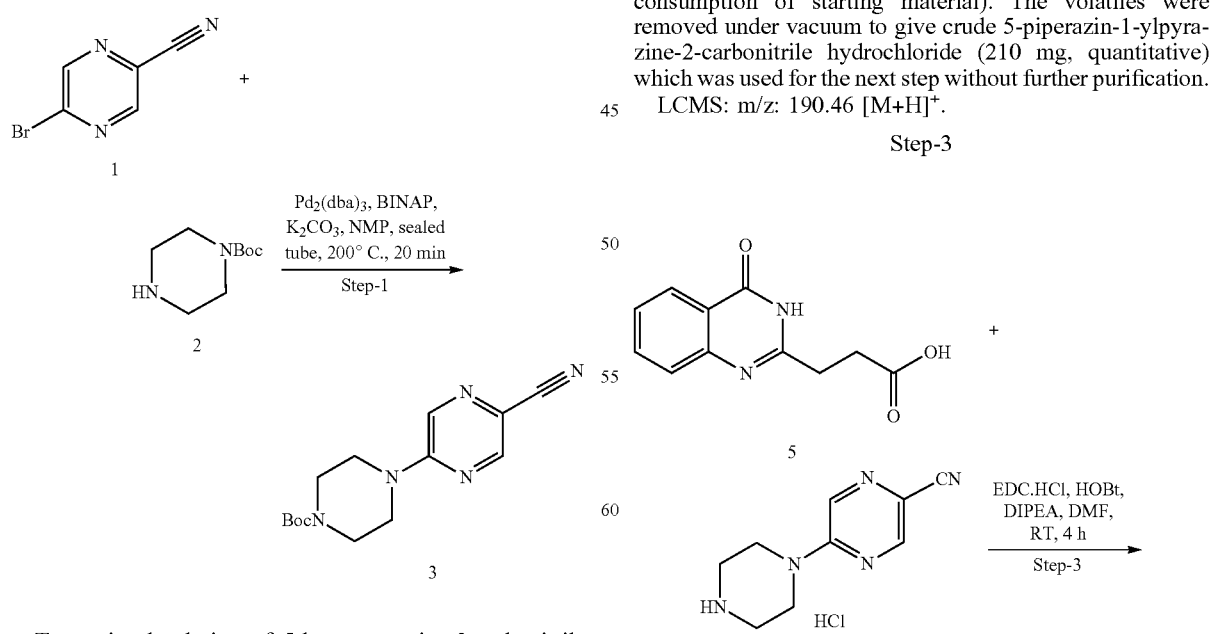

To a stirred solution of 5-bromopyrazine-2-carbonitrile (350 mg, 1.90 mmol) in NMP (4 mL), tert-butyl piperazine-1-carboxylate (424 mg, 2.28 mmol), Pd$_2$(dba)$_3$ (35 mg, 0.04 mmol), X-Phos (72 mg, 0.152 mmol) and K$_2$CO$_3$ (367 mg, 2.66 mmol) was added at RT. The reaction mixture was heated at 200° C. for 20 min (TLC indicated complete consumption of the starting material). After completion of reaction, the reaction mixture was diluted with EtOAc (50 mL), washed with cold water (2×20 mL), the organic layer was dried over $Na_2SO_4$ and concentrated under reduced pressure to give the crude compound. The crude material was purified by flash chromatography (100-200 silica gel, 5 g, 30% EtOAc-Hexane) to provide tert-butyl 4-(5-cyanopyrazin-2-yl)piperazine-1-carboxylate (320 mg, 58%) as a white solid.

LCMS: m/z: 290.61 [M+H]$^+$.

Step-2

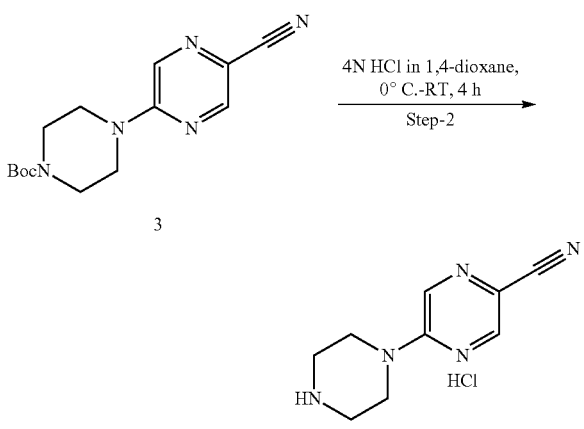

To a stirred solution of tert-butyl 4-(5-cyanopyrazin-2-yl)piperazine-1-carboxylate (310 mg, 1.07 mmol) in 1,4-dioxane (4 mL), cooled to 0° C., 4 N HCl in 1,4-dioxane (1.07 mL, 4.29 mmol) was added. The reaction mixture was warmed to RT and stirred for 4 h (TLC indicated complete consumption of starting material). The volatiles were removed under vacuum to give crude 5-piperazin-1-ylpyrazine-2-carbonitrile hydrochloride (210 mg, quantitative) which was used for the next step without further purification.

LCMS: m/z: 190.46 [M+H]$^+$.

Step-3

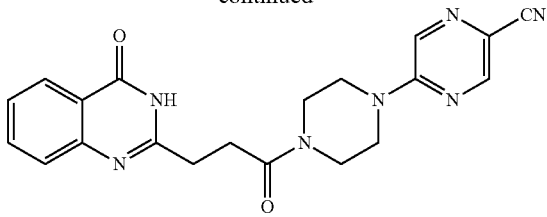

To a stirred solution of 3-(4-oxo-3H-quinazolin-2-yl)propanoic acid (200 mg, 0.917 mmol) and 5-piperazin-1-ylpyrazine-2-carbonitrile hydrochloride (208 mg, 1.10 mmol) in DMF (4 mL), EDC HCl (262 mg, 1.37 mmol), HOBt (185 mg, 1.37 mmol) and DIPEA (0.64 mL, 3.66 mmol) were added at RT and stirred for 4 h (TLC indicated complete consumption of starting material). The reaction mixture was diluted with cold water (40 mL) and extracted with EtOAc (3×40 mL). The combined organic extracts were dried over $Na_2SO_4$, concentrated under reduced pressure to give the crude compound which was purified by flash chromatography (100-200 silica gel, 5 g, 5% MeOH-DCM) to furnish 5-[4-[3-(4-oxo-3H-quinazolin-2-yl)propanoyl]piperazin-1-yl]pyrazine-2-carbonitrile (70 mg, 20%) as an off-white solid.

$^1$H NMR [400 MHz, DMSO-$d_6$]: δ 12.19 (s, 1H), 8.58 (d, J=1.2 Hz, 1H), 8.43 (d, J=1.2 Hz, 1H), 8.07 (dd, J=1.6, 8.0 Hz, 1H), 7.77-7.72 (m, 1H), 7.55 (d, J=8.0 Hz, 1H), 7.47-7.43 (m, 1H), 3.87-3.83 (m, 2H), 3.76-3.66 (m, 4H), 3.63-3.57 (m, 2H), 2.90 (s, 4H).

LCMS: m/z: 390.68 $[M+H]^+$.

Example 40—Synthesis of 2-[4-[3-(4-oxo-3H-quinazolin-2-yl)propanoyl]piperazin-1-yl]thiazole-5-carbonitrile Step-1

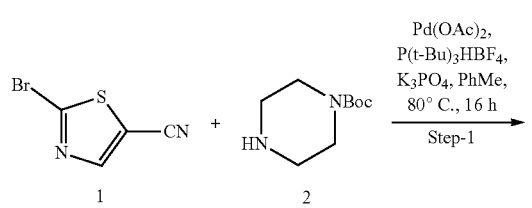

To a stirred solution of 2-bromothiazole-5-carbonitrile (200 mg, 1.05 mmol), tert-butyl piperazine-1-carboxylate (800 mg, 4.3 mmol), potassium phosphate tribasic (260 mg, 1.22 mmol), palladium acetate trimer (40 mg, 0.06 mmol), tri-tert-butylphosphine tetrafluoroborate (20 mg, 0.06 mmol) in toluene (4 mL), taken in a microwave vial under argon atmosphere was irradiated for 30 min at 80° C. (TLC indicated complete consumption of starting material). The reaction mixture was diluted with water (10 mL) and extracted with EtOAc (3×30 mL). The combined organic extracts were washed with brine (10 mL), dried over $Na_2SO_4$ and concentrated under reduced pressure. The crude product obtained was purified by column chromatography (100-200 silica gel, 20 g, 10-30% EtOAc-Hexane) to afford tert-butyl 4-(5-cyanothiazol-2-yl)piperazine-1-carboxylate (200 mg, 64%) as a white solid.

LCMS (ESI+): m/z: 295.60 $[M+H]^+$.

Step-2

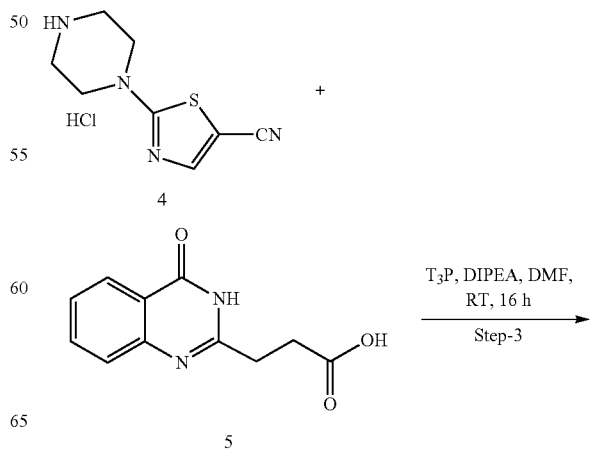

To a stirred solution of tert-butyl 4-(5-cyanothiazol-2-yl)piperazine-1-carboxylate (200 g, 0.680 mmol) in dioxane (10 mL), 4 N HCl in dioxane (5 mL) was added at RT and stirred for 4 h (TLC indicated complete consumption of starting material). The volatiles were removed under reduced pressure to give the crude product which was washed with EtOAc (2×15 mL), followed by diethyl ether (15 mL) to afford 2-piperazin-1-ylthiazole-5-carbonitrile hydrochloride (155 mg, 98%) as a white solid.

LCMS (ESI+): m/z: 195.44 $[M+H]^+$.

Step-3

-continued

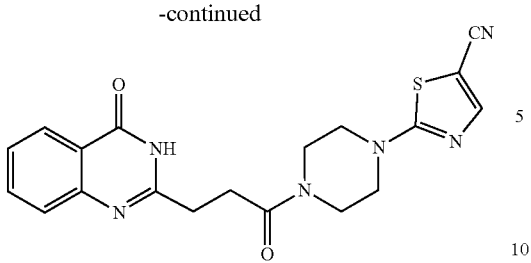

To a stirred solution of 2-piperazin-1-ylthiazole-5-carbonitrile hydrochloride (155 mg, 0.55 mmol) in anhydrous DMF, DIPEA (0.3 mL, 1.74 mmol), 3-(4-oxo-3H-quinazolin-2-yl)propanoic acid (120 mg, 0.67 mmol) and 50% $T_3P$ solution in EtOAc (0.53 mL, 0.82 mmol) were added stirred at RT for 16 h (LCMS indicated complete consumption of starting material). The reaction mixture was quenched with ice-water (60 mL), extracted with DCM (2×50 mL), the combined organic extracts were washed with brine (25 mL), dried over $Na_2SO_4$ and concentrated under reduced pressure. The crude residue was purified by column chromatography (100-200 silica gel, 200 g, 2-5% MeOH-DCM) to afford 2-[4-[3-(4-oxo-3H-quinazolin-2-yl)propanoyl]piperazin-1-yl]thiazole-5-carbonitrile (50 mg, 23%) as a pale yellow solid.

$^1$H NMR [400 MHz, DMSO-$d_6$]: δ 12.18 (brs, 1H), 8.09-8.05 (m, 2H), 7.77-7.72 (m, 1H), 7.55 (d, J=8.0 Hz, 1H), 7.45 (t, J=7.2 Hz, 1H), 3.75-3.55 (m, 6H), 3.53-3.50 (m, 2H), 2.89 (s, 4H).

LCMS (ESI+): m/z: 395.62 [M+H]$^+$.

Example 41—Synthesis of 6-[4-[3-(4-oxo-3H-pyrido[4,3-d]pyrimidin-2-yl)propanoyl]piperazin-1-yl]pyridine-3-carbonitrile Step-1

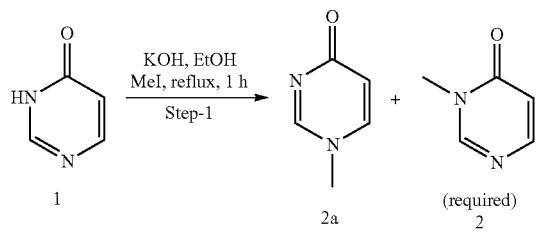

To a stirred solution of KOH (5.82 g, 0.104 mol) in EtOH (80 mL), 1H-pyrimidin-6-one (10 g, 0.104 mol) followed by MeI (7.20 mL, 0.114 mol) were added at RT. The reaction mixture was refluxed for 2 h (TLC indicated 10-15% of unreacted starting material). Additional amount of MeI (1.5 g, 0.01 mol) was added refluxed for 1 h (TLC indicated complete consumption of the starting material) and slowly brought to RT. The reaction mixture was filtered, washed with DCM (100 mL) and the filtrate was concentrated under reduced pressure to give the crude product which was purified by column chromatography (100-200 silica gel, 200 g, 2-5% MeOH-DCM) to give 3-methylpyrimidin-4-one (4.5 g, 39%) as an off-white solid.

LCMS (ESI+): m/z: 111.30 [M+H]$^+$.

Step-2

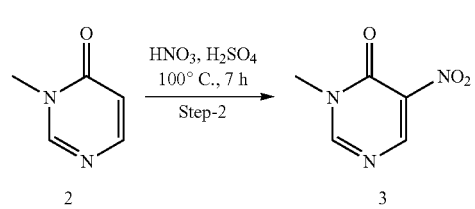

To Sulfuric acid (50 mL), cooled to 10° C., 3-methylpyrimidin-4-one (5.5 g, 50.00 mol) followed by fuming nitric acid (6.6 mL, 157.15 mol) was added. The reaction mixture was slowly brought to RT, heated at 100° C. for 4 h (TLC indicated complete consumption of starting material), again brought to RT and poured into crushed ice (500 g); then 50% aqueous sodium hydroxide solution was added slowly till pH=5. The reaction mixture was extracted with $CHCl_3$ (3×250 mL); the combined organic extracts were dried over $Na_2SO_4$ and concentrated under reduced pressure to give the crude compound which was re-crystallized from EtOH (15 mL) to afford 3-methyl-5-nitro-pyrimidin-4-one (2 g, 26%) as a yellow solid.

LCMS (ESI+): m/z: 156.36 [M+H]$^+$.

Step-3

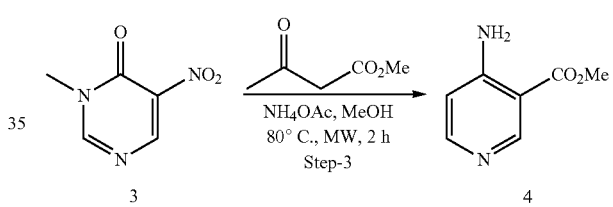

In a CEM microwave vial, 3-methyl-5-nitro-pyrimidin-4-one (300 mg, 1.94 mmol), methyl acetoacetate (2.7 g, 23.27 mmol), ammonium acetate (1.79 g, 23.22 mmol) and MeOH (8.0 mL) were added and irradiated at 80° C. for 2 h (TLC indicated complete consumption of starting material). The reaction mixture was concentrated under reduced pressure to give the crude product which was purified by column chromatography (100-200 silica gel, 40 g, 5-10% MeOH-DCM) to afford methyl 4-aminopyridine-3-carboxylate; this reaction mixture was carried out in 6 batches (300 mg each), the crude material after work-up was combined and purified to afford methyl 4-aminopyridine-3-carboxylate (900 mg, 51%) as a yellow solid.

LCMS (ESI+): m/z: 153.43 [M+H]$^+$.

Step-4

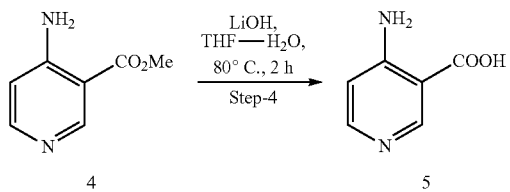

To a stirred solution of methyl 4-aminopyridine-3-carboxylate (2 g, 13.15 mmol) in EtOH-water (120 mL, 1:1), LiOH·H$_2$O (1.21 g, 28.80 mmol) was added at RT and heated at 80° C. for 2 h (TLC indicated complete consumption of starting material). The volatiles were removed under reduced pressure to give the crude compound which was dissolved in water (30 mL), washed with EtOAc (2×25 mL) to remove the non-polar impurities. The aqueous layer was acidified with 1 N HCl till pH=1, and extracted with EtOAc (2×10 mL). The combined organic extracts were concentrated under reduced pressure to give the crude residue which was crystallized from MeOH (20 mL) to obtain 4-aminopyridine-3-carboxylic acid (1 g, 55%) as an off-white solid.

LCMS (ESI+): m/z: 139.31 [M+H]$^+$.

Step-5

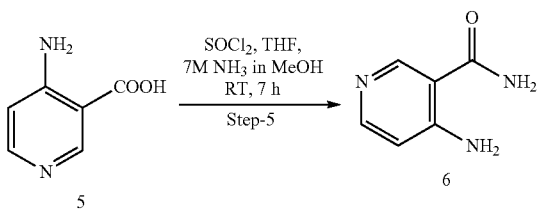 [SMILES: Nc1ccncc1C(=O)O ; NC(=O)c1cnccc1N]

To a stirred solution of 4-aminopyridine-3-carboxylic acid (3 g, 0.013 mol) in THF (50 mL), SOCl$_2$ (3.6 mL, 0.045 mol) and catalytic DMF (30 μL) were added at RT and stirred for 3 h under argon atmosphere (TLC indicated complete consumption of the starting material). The volatiles were removed under reduced pressure to give the crude product which was dissolved in THF (30 mL), cooled to 0° C. and 7 N NH$_3$-methanol (22 mL) was added. The reaction mixture was slowly warmed to RT and stirred for 4 h, the precipitate was filtered, the filtrate was concentrated under reduced pressure to give the crude compound which was purified by column chromatography (100-200 silica gel, 60 g, 10% MeOH-10% NH$_4$OH-DCM) to provide 4-aminopyridine-3-carboxamide (475 mg, 27%) which was used for the next step without any purification.

LCMS (ESI+): m/z: 138.33 [M+H]$^+$.

Step-6

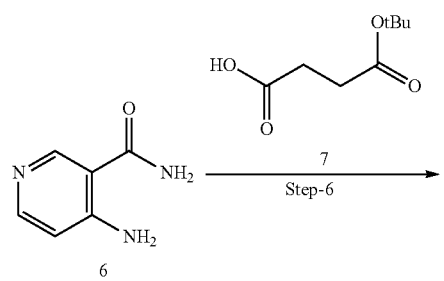

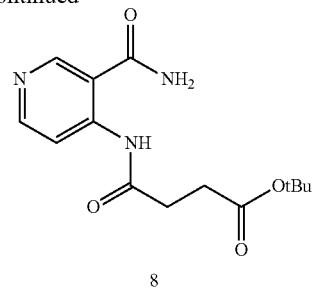

To a stirred solution of 4-aminopyridine-3-carboxamide (500 mg, 3.65 mmol), 4-tert-butoxy-4-oxo-butanoic acid (762 mg, 4.38 mmol), TEA (1 mL, 7.29 mmol) in DMF (10 mL), 50% T$_3$P solution in EtOAc (3.5 mL, 5.5 mmol) was added at RT and stirred for 12 h (TLC indicated complete consumption of starting material). The reaction mixture was quenched with water (50 mL) and extracted with DCM (2×35 mL). The combined organic extracts were washed with brine (30 mL), dried over Na$_2$SO$_4$, concentrated under reduced pressure to give the crude product which was purified by column chromatography (100-200 silica gel, 20 g, 10% MeOH-10% NH$_4$OH-DCM) to afford tert-butyl 4-[(3-carbamoyl-4-pyridyl)amino]-4-oxo-butanoate (500 mg, 47%) as a yellow solid.

$^1$H NMR [400 MHz, CDCl$_3$]: δ 11.74 (s, 1H), 9.07 (s, 1H), 8.69 (d, J=5.2 Hz, 1H), 8.52 (d, J=5.2 Hz, 1H), 7.11 (brs, 1H), 5.83 (brs, 1H), 2.75-2.70 (m, 2H), 2.68-2.63 (m, 2H), 1.44 (s, 9H).

LCMS (ESI+): m/z: 316.59 [M+Na]$^+$.

Step-7

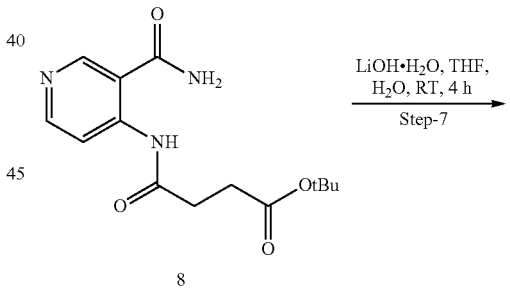

To a stirred solution of tert-butyl 4-[(3-carbamoyl-4-pyridyl)amino]-4-oxo-butanoate (900 mg, 3.071 mmol) in THF (31 mL), water (0.9 mL), LiOH·H$_2$O (645 mg, 15.35 mmol) were added at 0° C. The reaction mixture was slowly brought to RT, stirred for 2 h (TLC indicated complete consumption of starting material) and extracted with EtOAc (2×30 mL). The combined organic extracts were washed with brine (30 mL) dried over Na$_2$SO$_4$, concentrated under reduced pressure to give the crude product which was washed with pentane (2×15 mL) to obtain tert-butyl 3-(4-oxo-3H-pyrido[4,3-d]pyrimidin-2-yl)propanoate (700 mg, 83%) as a pale yellow solid.

LCMS (ESI+): m/z: 276.48 [M+H]$^+$.

Step-8

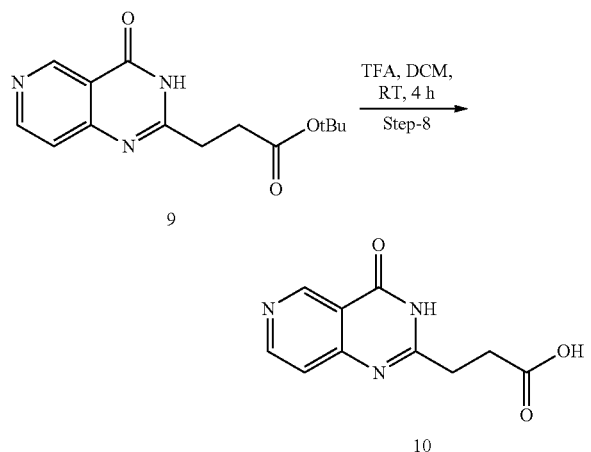

To a stirred solution of tert-butyl 3-(4-oxo-3H-pyrido[4,3-d]pyrimidin-2-yl)propanoate (700 mg, 2.545 mmol) in DCM (26 mL), TFA (5.7 mL, 74.50 mmol) was added at RT and stirred for 4 h (LCMS indicated complete consumption of starting material). The volatiles were removed under reduced pressure, the residue was co-distilled with toluene (2×10 mL) to give the crude product which was triturated with pentane (2×20 mL) to give 3-(4-oxo-3H-pyrido[4,3-d]pyrimidin-2-yl)propanoic acid (351 mg, 63%) as a pale-yellow solid.

LCMS (ESI+): m/z: 220.42 [M+H]$^+$.

Step-9

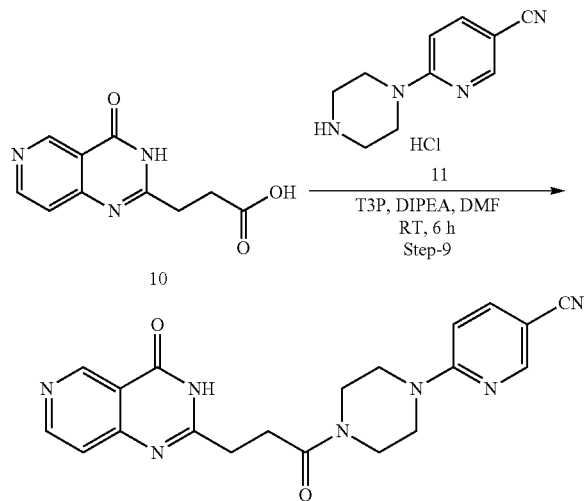

To a stirred solution of 3-(4-oxo-3H-pyrido[4,3-d]pyrimidin-2-yl)propanoic acid (250 mg, 1.141 mmol), 6-piperazin-1-ylpyridine-3-carbonitrile hydrochloride (256 mg, 1.361 mmol) in DMF (2.5 mL), DIPEA (0.4 mL, 2.325 mmol) and 50% T$_3$P solution in EtOAc (0.75 mL, 1.711 mmol) were added. The reaction mixture was stirred at RT for 4 h (TLC indicated complete consumption of starting material). The reaction mixture was quenched with water (25 mL), extracted with DCM (3×30 mL), the combined organic extracts were washed with brine (10 mL) and dried over Na$_2$SO$_4$. The solvent was concentrated under reduced pressure to give the crude product which was purified by column chromatography (100-200 silica gel, 10 g, 10% MeOH-5% NH$_4$OH-DCM) to afford 6-[4-[3-(4-oxo-3H-pyrido[4,3-d]pyrimidin-2-yl)propanoyl]piperazin-1-yl]pyridine-3-carbonitrile (45 mg, 10%) as an off-white solid.

$^1$H NMR [400 MHz, DMSO-d$_6$]: δ 12.57 (brs, 1H), 9.22 (s, 1H), 8.74 (d, J=5.6 Hz, 1H), 8.50 (d, J=2.0 Hz, 1H), 7.88 (dd, J=8.8, 2.0 Hz, 1H), 7.45 (d, J=5.6 Hz, 1H), 6.94 (d, J=9.2 Hz, 1H), 3.78-3.76 (m, 2H), 3.64 (t, J=4.8 Hz, 4H), 3.57-3.54 (m, 2H), 3.31 (s, 4H).

LCMS (ESI+): m/z: 390.63 [M+H]$^+$.

Example 42—Synthesis of 6-[4-[3-(4-oxo-3H-pyrido[2,3-d]pyrimidin-2-yl)propanoyl]piperazin-1-yl]pyridine-3-carbonitrile Step-1

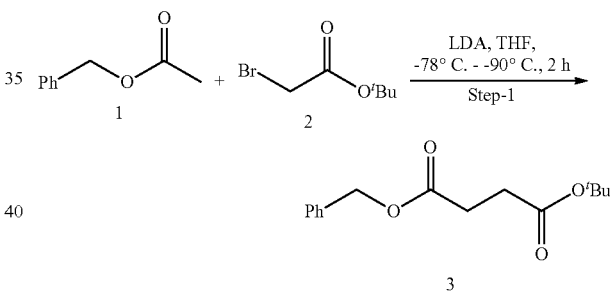

A solution of DIPEA (4.16 mL, 29.3 mmol) in dry THF (60 mL) was cooled to −78° C. in a dry ice-acetone bath. n-BuLi in hexanes (1.6 M, 18.3 mL, 29.3 mmol) was added dropwise at −78° C. and stirred for 30 min. Benzyl acetate (3.8 mL, 26.6 mmol) in dry THF (30 mL) was added dropwise to the reaction flask, maintaining the temperature below −78° C. When addition was complete, the flask was transferred to a dry ice-Et$_2$O bath and stirred until the temperature dropped below −90° C. tert-Butyl 2-bromoacetate (5.9 mL, 40.0 mmol) in THF (30 mL) was added dropwise to the above solution and stirred for 1 h at −90° C. The reaction mixture was quenched by slow addition of water (100 mL), warmed to RT and extracted with Et$_2$O (2×150 mL). The combined organic extracts were dried over Na$_2$SO$_4$, filtered, and concentrated under reduced pressure to give the crude residue which was purified by column chromatography (100-200 silica gel, 60 g, 5% EtOAc-Hexane) to afford benzyl tert-butyl butanedioate (2.3 g, 27%) as a pale yellow oil.

LCMS: m/z: 287.6 [M+Na]$^+$.

Step-2

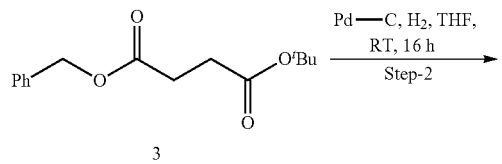

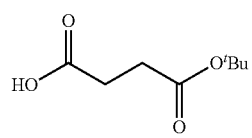

To a stirred solution of benzyl tert-butyl butanedioate (2.3 g, 8.71 mmol) in dry THF (30 mL), 10% Pd—C (0.23 g) was added and stirred under $H_2$ atmosphere (balloon) for 16 h (TLC indicated complete consumption of starting material). The reaction mixture was filtered through Celite and washed with $CHCl_3$ (100 mL). The filtrate was concentrated in vacuo to give crude residue which was purified by column chromatography (100-200 silica gel, 30 g, 35% EtOAc-Hexane) to afford 4-tert-butoxy-4-oxo-butanoic acid (0.8 g, 52%) as a colorless oil.

$^1$H NMR [400 MHz, $CDCl_3$]: δ 2.65-2.61 (m, 2H), 2.56-2.52 (m, 2H), 1.44 (s, 9H).

Step-3

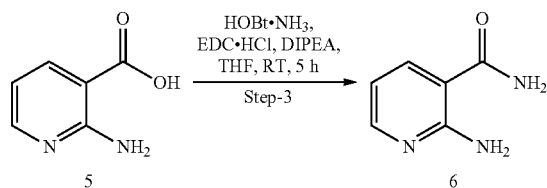 [SMILES: Nc1ncccc1C(=O)O ; NC(=O)c1cccnc1N]

To a stirred solution of 2-aminopyridine-3-carboxylic acid (0.9 g, 6.52 mmol) in THF (15 mL), was added EDC HCl (1.86 g, 9.78 mmol), HOBt-$NH_3$ (1.46 g, 9.78 mmol) and DIPEA (4.67 mL, 26.08 mmol) at RT. The reaction mixture was stirred at RT for 5 h (TLC indicated complete consumption of starting material), diluted with water (30 mL) and extracted with EtOAc (3×75 mL). The combined organic extracts were washed with cold water (2×40 mL), brine (40 mL), separated, dried over $Na_2SO_4$ and concentrated under reduced pressure to give the crude residue which was purified by column chromatography (100-200 silica gel, 20 g, 60% EtOAc-Hexane) to afford 2-aminopyridine-3-carboxamide (0.4 g, 45%) as a white solid.

LCMS: m/z: 138.3 [M+H]$^+$.

Step-4

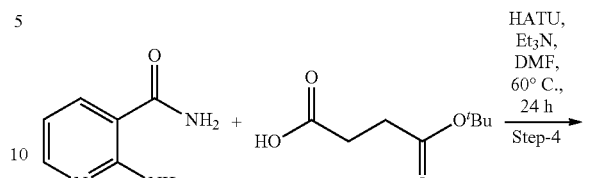

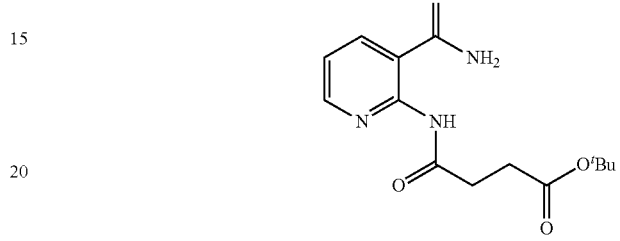

To a stirred solution of 2-aminopyridine-3-carboxamide (0.35 g, 2.55 mmol) in DMF (15 mL), 4-tert-butoxy-4-oxo-butanoic acid (0.66 g, 3.83 mmol), HATU (1.45 g, 3.83 mmol) and $Et_3N$ (0.7 mL, 5.04 mmol) were added at RT. The resultant reaction mixture was stirred at 60° C. for 24 h (TLC indicated complete consumption of SM). The reaction mixture was diluted with water (30 mL) and extracted with EtOAc (3×50 mL). The combined organic extracts were washed with cold water (2×30 mL), brine (30 mL), dried over $Na_2SO_4$ and concentrated under reduced pressure to give the crude residue which was purified by column chromatography (100-200 silica gel, 10 g, 2% MeOH-DCM) to furnish tert-butyl 4-[(3-carbamoyl-2-pyridyl)amino]-4-oxo-butanoate (0.22 g, 26%) as a pale yellow solid.

LCMS: m/z: 294.6 [M+H]$^+$.

Step-5

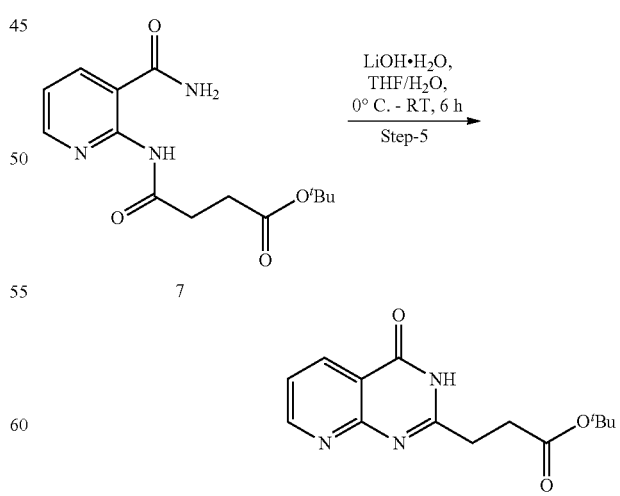

To a stirred solution of tert-butyl 4-[(3-carbamoyl-2-pyridyl)amino]-4-oxo-butanoate (0.22 g, 0.75 mmol) in THF (8 mL) and water (0.3 mL) at 0° C., LiOH·H₂O (0.16 g, 3.88 mmol) was added. The reaction mixture was brought to RT, stirred for 6 h (TLC indicated complete consumption of starting material), diluted with water (10 mL) and extracted with EtOAc (2×75 mL). The combined organic extracts were washed with brine (20 mL), dried over Na₂SO₄ and concentrated under reduced pressure to provide tert-butyl 3-(4-oxo-3H-pyrido[2,3-d]pyrimidin-2-yl)propanoate (140 mg, 63%) as a pale yellow solid.

LCMS: m/z: 276.4 [M+H]⁺.

Step-6

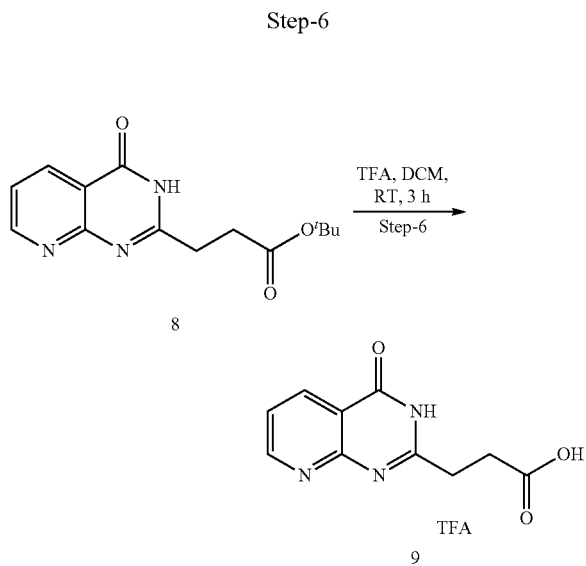

To a stirred solution of tert-butyl 3-(4-oxo-3H-pyrido[2,3-d]pyrimidin-2-yl)propanoate (0.14 g, 0.50 mmol) in DCM (5 mL), TFA (1.1 mL, 15.0 mmol) was added at RT and stirred for 3 h (TLC indicated complete consumption of starting material). The reaction mixture was concentrated under reduced pressure to give 3-(4-oxo-3H-pyrido[2,3-d]pyrimidin-2-yl)propanoic acid trifluoroacetic acid salt (0.14 g, 75%), which was carried to the next step without further purification as a pale yellow liquid.

LCMS: m/z: 220.3 [M+H]⁺.

Step-7

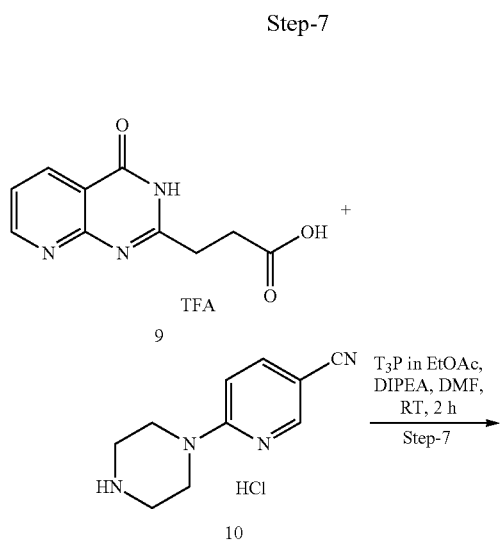

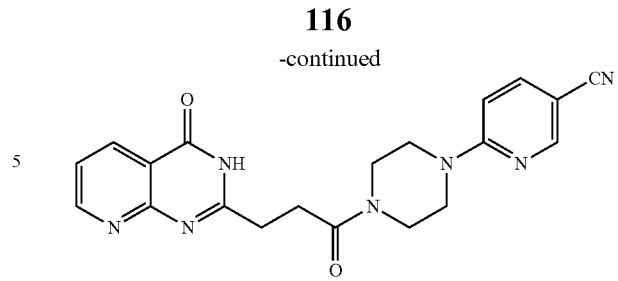

To a stirred solution of 3-(4-oxo-3H-pyrido[2,3-d]pyrimidin-2-yl)propanoic acid trifluoroacetic acid salt (0.087 g, 0.39 mmol) and 6-piperazin-1-ylpyridine-3-carbonitrile hydrochloride (0.133 g, 0.59 mmol) in DMF (4 mL), DIPEA (0.14 mL, 0.79 mmol) and 50% T₃P solution in EtOAc (0.5 mL, 0.78 mmol) were added at RT and stirred for 2 h (TLC indicated complete consumption of starting material). The reaction mixture was quenched with water (10 mL) and extracted with DCM (3×30 mL). The combined organic extracts were washed with brine (10 mL), dried over Na₂SO₄ and concentrated to give the crude product (150 mg, 54% LCMS) which was prep purified to afford 6-[4-[3-(4-oxo-3H-pyrido[2,3-d]pyrimidin-2-yl)propanoyl]piperazin-1-yl]pyridine-3-carbonitrile (29 mg, 18%) as a white solid.

¹H NMR [400 MHz, DMSO-d₆]: δ 12.49 (brs, 1H), 8.86 (dd, J=4.0, 1.6 Hz, 1H), 8.50 (d, J=2.4 Hz, 1H), 8.45 (dd, J=7.6, 1.6 Hz, 1H), 7.88 (dd, J=8.8, 2.0 Hz, 1H), 7.47 (dd, J=8.0, 4.8 Hz, 1H), 6.94 (d, J=9.2 Hz, 1H), 3.83-3.77 (m, 2H), 3.69-3.62 (m, 4H), 3.58-3.53 (m, 2H), 2.93 (s, 4H).

LCMS: m/z: 390.67 [M+H]⁺.

Example 43—Synthesis of 6-[4-[3-(4-oxo-3H-quinazolin-2-yl)butanoyl]piperazin-1-yl]pyridine-3-carbonitrile Step-1

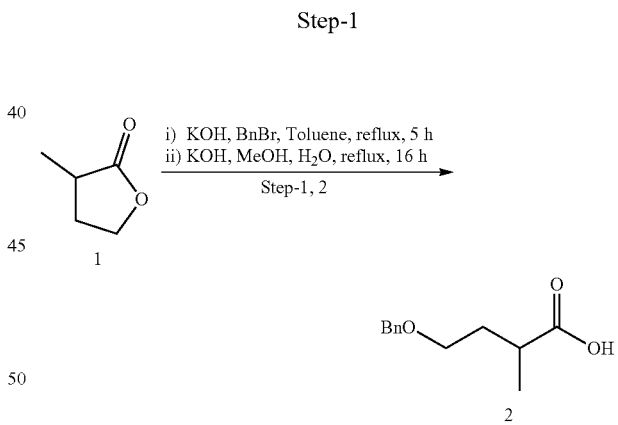

Powdered KOH (6.0 g, 0.10 mol) was added to a solution of 3-methyltetrahydrofuran-2-one (2.0 g, 0.02 mol) and benzyl bromide (14.0 g, 0.08 mol) in toluene (36 mL). The resultant reaction mixture was stirred at 110° C. for 5 h and toluene was removed under vacuum to give the crude residue which was dissolved in MeOH (40 mL). KOH (2.0 g, 0.035 mol) and water (20 mL) were added to the above solution and the reaction mixture was refluxed for 16 h. The reaction mixture was brought to RT, washed with Et₂O (2×50 mL), the aqueous layer was acidified to pH=2-3 with conc. HCl, and extracted with DCM (3×50 mL). The combined organic extracts were dried over Na₂SO₄, filtered, and concentrated under vacuum to afford 4-benzyloxy-2-methylbutanoic acid (3.4 g, 81%) as a pale yellow oil.

¹H NMR [400 MHz, CDCl₃]: δ 7.37-7.26 (m, 5H), 4.53-4.50 (m, 2H), 3.54 (t, J=6.4 Hz, 2H), 2.73-2.64 (m, 1H), 2.09-2.00 (m, 1H), 1.76-1.68 (m, 1H), 1.21 (d, J=7.2 Hz, 3H).

Step-2

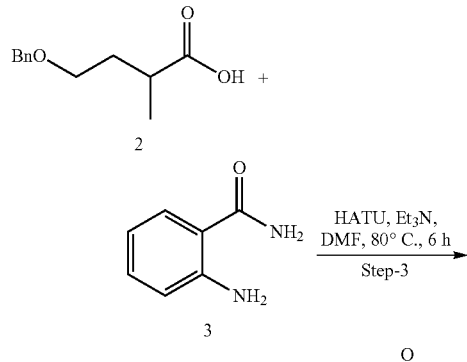

To a stirred solution of 2-aminobenzamide (0.3 g, 2.20 mmol) in DMF (5 mL), 4-benzyloxy-2-methyl-butanoic acid (0.59 g, 2.83 mmol), HATU (1.25 g, 3.28 mmol) and Et₃N (0.61 mL, 4.35 mmol) were added at RT. The resultant reaction mixture was stirred at 80° C. for 6 h (TLC indicated complete consumption of starting material). The reaction mixture was diluted with water (30 mL) and extracted with EtOAc (3×50 mL). The combined organic extracts were washed with cold water (2×30 mL), brine (30 mL), dried over Na₂SO₄ and concentrated under reduced pressure to give crude residue which was purified by column chromatography (100-200 silica gel, 20 g, 30% EtOAc-hexanes) to provide 2-[(4-benzyloxy-2-methyl-butanoyl)amino]benzamide (0.63 g, 79%) as a colorless liquid.

LCMS: m/z: 327.6 [M+H]⁺.

Step-3

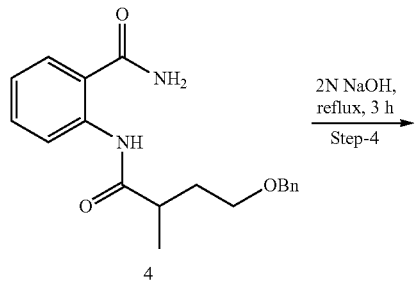

-continued

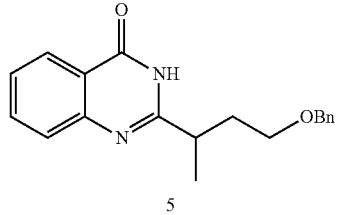

2-[(4-Benzyloxy-2-methyl-butanoyl)amino]benzamide (0.63 g, 1.93 mmol) in 2 N aq. NaOH (12 mL) was stirred at 100° C. for 3 h (TLC indicated complete consumption of starting material). The reaction mixture was cooled to 0° C. and acidified with 2 N aq. HCl till to pH=3-4 and extracted with EtOAc (3×50 mL). The combined organic extracts were washed with brine (30 mL), dried over Na₂SO₄ and concentrated under reduced pressure to give 2-(3-benzyloxy-1-methyl-propyl)-3H-quinazolin-4-one (450 mg, 67%) which was used for the next step without any purification.

LCMS: m/z: 309.5 [M+H]⁺.

Step-4

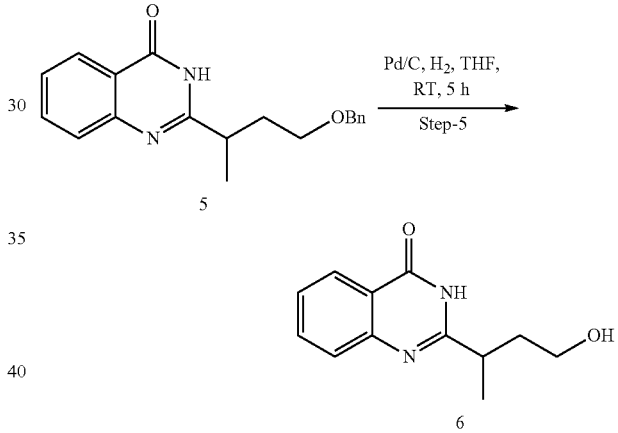

To a stirred solution of 2-(3-benzyloxy-1-methyl-propyl)-3H-quinazolin-4-one (0.55 g, 1.78 mmol) in THF (15 mL) 10% Pd—C catalyst (50% wet, 1.0 g) was added and stirred under H₂ atmosphere (balloon) for 5 h (TLC indicated complete consumption of starting material). The reaction mixture was filtered through Celite, and was washed with THF (30 mL). The filtrate was concentrated in vacuo to afford 2-(3-hydroxy-1-methyl-propyl)-3H-quinazolin-4-one (0.3 g, 78%) as an off-white solid.

LCMS: m/z: 219.49 [M+H]⁺.

Step-5

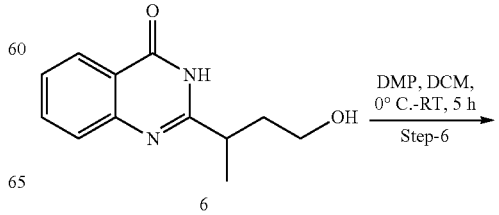

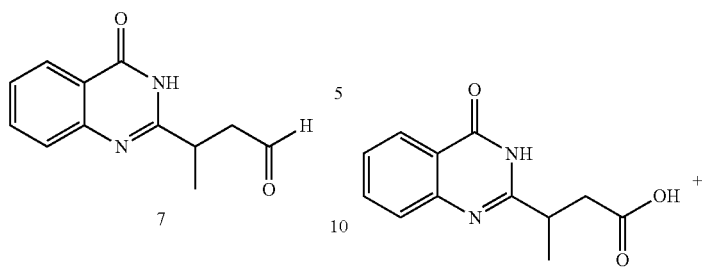

To a stirred solution of 2-(3-hydroxy-1-methyl-propyl)-3H-quinazolin-4-one (0.40 g, 1.83 mmol) in DCM (25 mL), cooled to 0° C., Dess-Martin periodinane (0.85 g, 2.00 mmol) was added. The reaction mixture was slowly warmed to RT and stirred for 5 h (TLC indicated complete consumption of the starting material). The reaction mixture was quenched with saturated aq. $Na_2S_2O_3$ and extracted with EtOAc (2×30 mL). The combined organic extracts were washed with brine (25 mL), dried over $Na_2SO_4$ and concentrated in vacuo to give the crude residue which was purified by silica gel column chromatography (100-200 silica gel, 10 g, 15% EtOAc-Hexane) to provide 3-(4-oxo-3H-quinazolin-2-yl)butanal (220 mg, 56%) as a white solid.

LCMS: m/z: 217.5 [M+H]$^+$.

Step-6

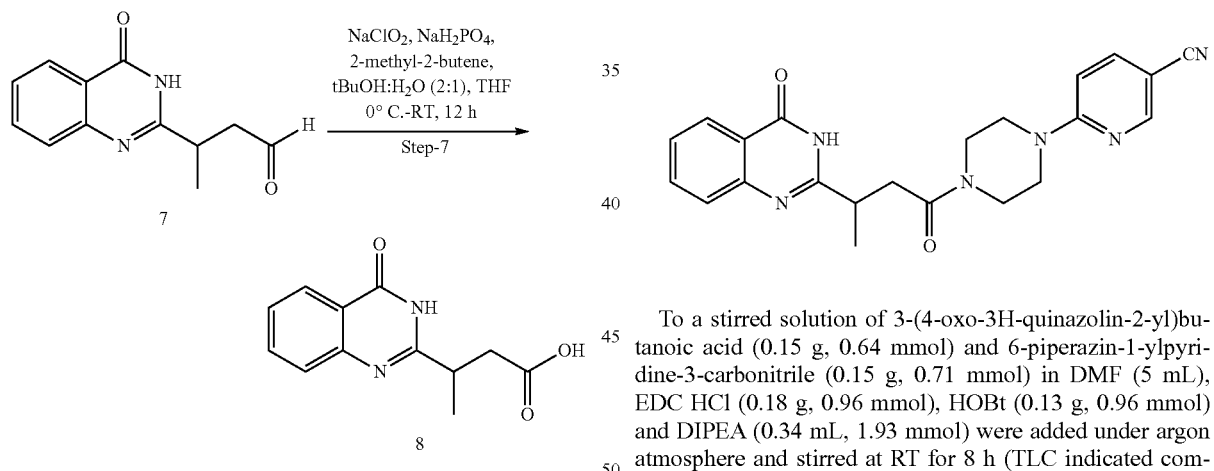

To a stirred solution of the 3-(4-oxo-3H-quinazolin-2-yl) butanal (0.20 g, 0.92 mmol) in THF (10 mL), at 5° C., t-BuOH (5 mL), water (1.5 mL) and 2-methyl-2-butene (0.51 g, 7.28 mmol) were added followed by $NaClO_2$ (0.25 g, 2.77 mmol) and $NaH_2PO_4$—$H_2O$ (0.43 g, 2.75 mmol). The reaction mixture was slowly brought to RT, stirred for 12 h, diluted with water (15 mL) and extracted with EtOAc (2×30 mL). The combined organic extracts were washed with brine (25 mL), dried over $Na_2SO_4$ and concentrated in vacuo to give the crude residue which was purified by column chromatography (100-200 silica gel, 10 g, 10% MeOH-DCM) to furnish 3-(4-oxo-3H-quinazolin-2-yl)butanoic acid (150 mg, 52%) which was carried to the next step without further purification.

LCMS: m/z: 233.4 [M+H]$^+$.

Step-7

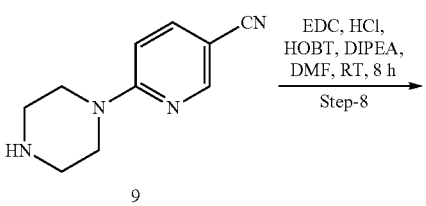

To a stirred solution of 3-(4-oxo-3H-quinazolin-2-yl)butanoic acid (0.15 g, 0.64 mmol) and 6-piperazin-1-ylpyridine-3-carbonitrile (0.15 g, 0.71 mmol) in DMF (5 mL), EDC HCl (0.18 g, 0.96 mmol), HOBt (0.13 g, 0.96 mmol) and DIPEA (0.34 mL, 1.93 mmol) were added under argon atmosphere and stirred at RT for 8 h (TLC indicated complete consumption of starting material). The volatiles were removed under reduced pressure and the residue was diluted with water (30 mL) and extracted with EtOAc (3×50 mL). The combined organic extracts were washed with cold water (2×25 mL), brine (20 mL), dried over $Na_2SO_4$ and concentrated under reduced pressure to give the crude residue (100 mg, 71% LCMS), which was prep purified to provide 6-[4-[3-(4-oxo-3H-quinazolin-2-yl)butanoyl]piperazin-1-yl]pyridine-3-carbonitrile (28 mg, 9%) as a white solid.

$^1$H NMR [400 MHz, DMSO-d$_6$]: δ 12.19 (brs, 1H), 8.50 (d, J=2.4 Hz, 1H), 8.06 (d, J=7.6 Hz, 1H), 7.87 (dd, J=8.8, 2.4 Hz, 1H), 7.75-7.70 (m, 1H), 7.53 (d, J=8.0 Hz, 1H), 7.43 (t, J=8.0 Hz, 1H), 6.92 (d, J=9.2 Hz, 1H), 3.76-3.66 (m, 4H), 3.62-3.51 (m, 4H), 3.25-3.08 (m, 2H), 2.64-2.59 (m, 1H), 1.26 (d, J=7.2 Hz, 3H).

LCMS: m/z: 403.7 [M+H]$^+$.

Example 44—Synthesis of 6-[(3S)-4-[3-(5,6-difluoro-4-oxo-3H-quinazolin-2-yl)propanoyl]-3-methyl-piperazin-1-yl]pyridine-3-carbonitrile

Step-1

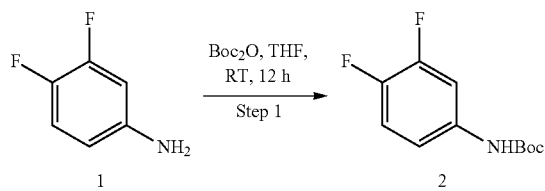 [SMILES: Nc1ccc(F)c(F)c1 ; CC(C)(C)OC(=O)Nc1ccc(F)c(F)c1]

Di-tert-butyl dicarbonate (3.0 g, 23.2 mmol) was added to 3,4-difluoroaniline (5.5 g, 25.2 mmol) in dry THF (45 mL) and the resultant reaction mixture was stirred at RT for 12 h (TLC indicated complete consumption of starting material). Volatiles were removed under reduced pressure and the residue was washed with hexanes (15 mL). The white solid obtained was dried under high vacuum to afford tert-butyl N-(3,4-difluorophenyl)carbamate (5 g, 93%) which was used for the next step without any purification.

$^1$H NMR [400 MHz, CDCl$_3$]: δ 7.45-7.40 (m, 1H), 7.08-7.01 (m, 1H), 6.92-6.89 (m, 1H), 6.45 (brs, 1H), 1.51 (s, 9H).

LCMS: m/z: 174.4 [M+H−56]$^+$.

Step-2

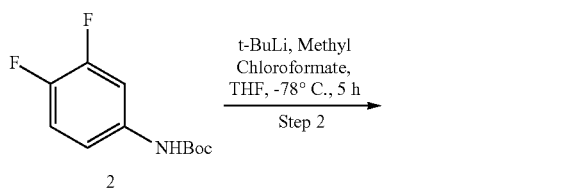

To a stirred solution of tert-butyl N-(3,4-difluorophenyl) carbamate (1 g, 4.36 mmol) in THF (30 mL) at −78° C., t-BuLi (7.54 mL, 9.82 mmol) was added dropwise and stirred for 3 h. Ethyl chloroformate (0.48 g, 5.1 mmol) was added slowly to the reaction mixture at −78° C. and stirred for 1 h (TLC indicated complete consumption of the starting material). The reaction mixture was brought to 0° C., treated with saturated aqueous ammonium chloride solution (24 mL) over a period of 10 min then warmed to room temperature and diluted with EtOAc (100 mL) and water (50 mL). The layers were separated and the aqueous phase was extracted with EtOAc (2×30 mL). The combined organic extracts were washed with brine (50 mL), dried over Na$_2$SO$_4$, filtered and concentrated under reduced pressure to give the crude residue which was purified by column chromatography (100-200 silica gel, 20 g, 2% EtOAc-Hexane) to furnish ethyl 6-(tert-butoxycarbonylamino)-2,3-difluoro-benzoate (0.5 g, 38%) as a white solid.

$^1$H NMR [400 MHz, CDCl$_3$]: δ 9.44 (brs, 1H), 8.11-8.08 (m, 1H), 7.30-7.23 (m, 1H), 4.45 (q, J=6.8 Hz, 2H), 1.51 (s, 9H), 1.41 (t, J=7.2 Hz, 3H).

LCMS: m/z: 202.4 [M+H−100]$^+$.

Step-3

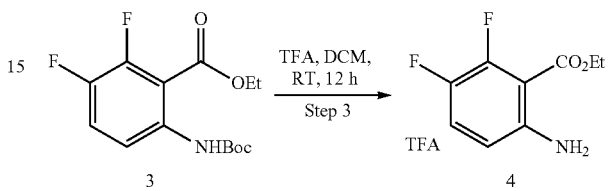

To a stirred solution of ethyl 6-(tert-butoxycarbonylamino)-2,3-difluoro-benzoate (0.5 g, 1.66 mmol) in DCM (14 mL), TFA (2.27 mL) was added drop wise at RT and stirred for 12 h (TLC indicated complete consumption of the starting material). The reaction mixture was concentrated under reduced pressure to afford ethyl 6-amino-2,3-difluoro-benzoate (0.43 g, 89%), which was carried to the next step without further purification.

LCMS: m/z: 202.3 [M+H]$^+$.

Step-4

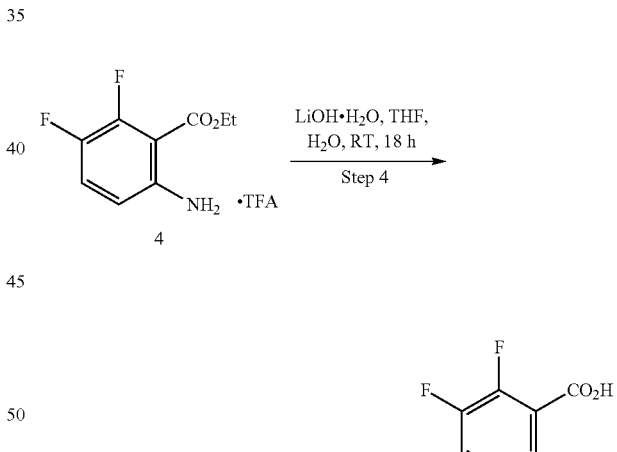

To a stirred solution of ethyl 6-amino-2,3-difluoro-benzoate (0.43 g, 1.44 mmol) in THF:H$_2$O (2:1, 15 mL), LiOH·H$_2$O (0.46 g, 14.3 mmol) was added. The resultant reaction mixture was stirred at RT for 18 h (TLC indicated complete consumption of the starting material), acidified with 1 N HCl till pH=4-5 and extracted with EtOAc (50 mL). The organic layer was separated, dried over anhydrous Na$_2$SO$_4$ and concentrated under reduced pressure to afford 6-amino-2,3-difluoro-benzoic acid (0.2 g, 80%) which was carried to the next step without further purification.

LCMS: m/z: 174.39 [M+H]$^+$.

Step-5

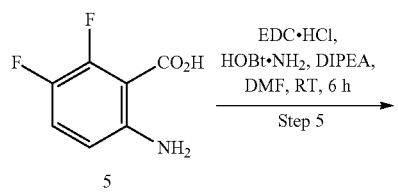

To a stirred solution of 6-amino-2,3-difluoro-benzoic acid (0.7 g, 4.0 mmol) in THF (15 mL), EDC HCl (1.15 g, 6.0 mmol), HOBt-NH₃ (0.91 g, 6.0 mmol) and DIPEA (2.17 mL, 12.0 mmol) were added under argon atmosphere and stirred at RT for 6 h (TLC indicated complete consumption of starting material). The volatiles were removed under reduced pressure and the residue was diluted with cold water (40 mL) and EtOAc (100 mL). The organic layer was separated, washed with cold water (2×20 mL), brine (2×20 mL), dried over Na₂SO₄ and concentrated under reduced pressure to give the crude residue which was purified by column chromatography (100-200 silica gel, 20 g, 25% EtOAc-Hexane) to give 6-amino-2,3-difluoro-benzamide (0.45 g, 65%) as a white solid.

LCMS: m/z: 173.4 [M+H]⁺.

Step-6

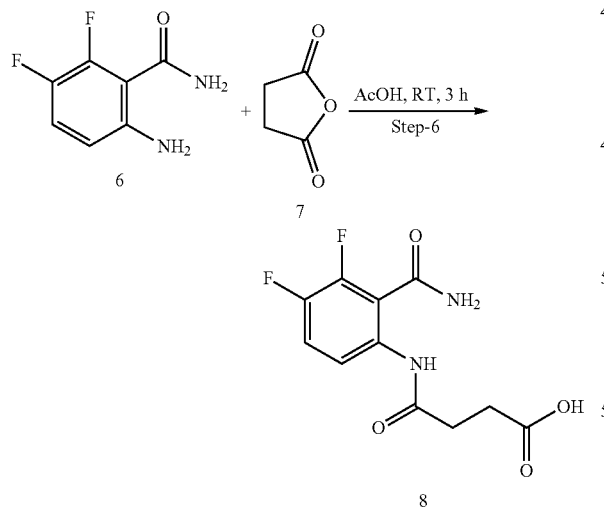

To a stirred solution of 6-amino-2,3-difluoro-benzamide (0.45 g, 2.61 mmol) in AcOH (4.5 mL) at RT, succinic anhydride (0.31 g, 3.13 mmol) was added and stirred at RT for 3 h (TLC indicated complete consumption of starting material). The reaction mixture was poured into ice cold water (10 mL) and stirred for 30 min at RT. The solid precipitated was filtered, washed with water (10 mL), cold acetone (5 mL) and dried under high vacuum to afford 4-(2-carbamoyl-3,4-difluoro-anilino)-4-oxo-butanoic acid (500 mg, 70%) which was used for the next step without further purification.

LCMS: m/z: 273.5 [M+H]⁺.

Step-7

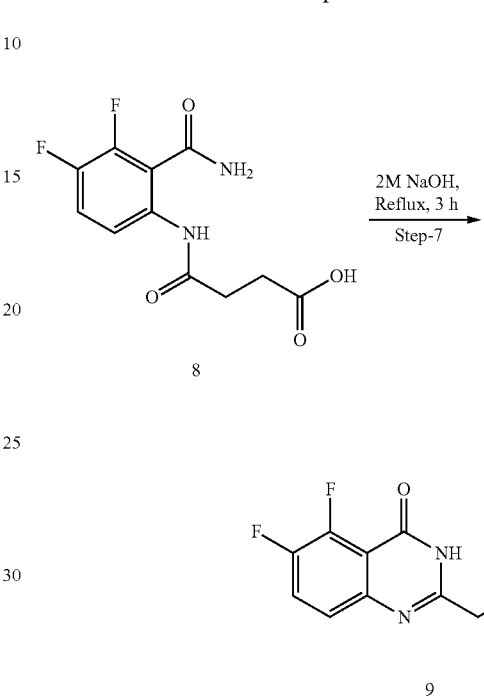

4-(2-Carbamoyl-3,4-difluoro-anilino)-4-oxo-butanoic acid (0.50 g, 1.83 mmol) in 2 N aq. NaOH (5 mL) was stirred at 100° C. for 3 h (TLC indicated complete consumption of starting material). The reaction mixture was cooled to 0° C. and acidified with 2 N aq. HCl till pH=3-4 during which white solid precipitated. The suspension was stirred at 0° C. for 30 min., filtered, washed with water (10 mL), cold acetone (2 mL) and dried under high vacuum to afford 3-(5,6-difluoro-4-oxo-3H-quinazolin-2-yl)propanoic acid (300 mg, 65%) which was used for the next step without any purification.

LCMS: m/z: 255.46 [M+H]⁺.

Step-8

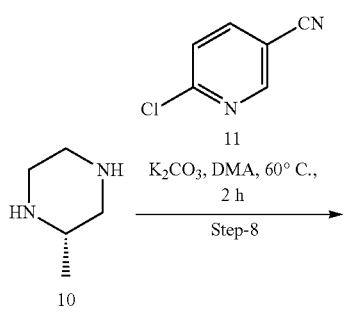

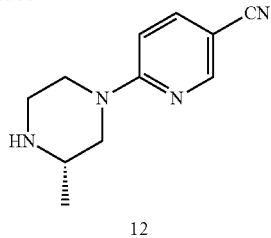

To a stirred solution of (2S)-2-methylpiperazine (0.30 g, 2.1 mmol) in DMA (6 mL), 6-chloropyridine-3-carbonitrile (0.29 g, 2.3 mmol) and K₂CO₃ were added. The resultant reaction mixture was heated to 60° C. for 2 h (TLC indicated complete consumption of starting material). The reaction mixture was diluted with cold water (20 mL) and extracted with EtOAc (3×25 mL). The combined organic extracts were washed with cold water (20 mL) and brine (2×20 mL). The organic layer was separated, dried over Na₂SO₄ and concentrated under reduced pressure to give the crude residue which was purified by column chromatography (100-200 silica gel, 10 g, 10% MeOH-DCM) to furnish 6-[(3S)-3-methylpiperazin-1-yl]pyridine-3-carbonitrile (0.29 g, 67%) as an off-white solid.

LCMS: m/z: 203.4 [M+H]⁺.

Step-9

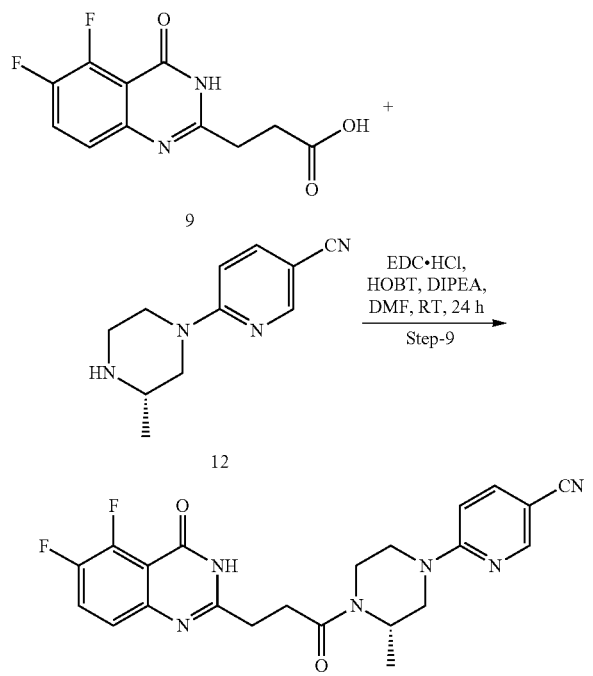

To a stirred solution of 3-(5,6-difluoro-4-oxo-3H-quinazolin-2-yl)propanoic acid (0.25 g, 1.0 mmol) and 6-[(3S)-3-methylpiperazin-1-yl]pyridine-3-carbonitrile (0.19 g, 1.0 mmol) in DMF (5 mL), EDC HCl (0.28 g, 1.4 mmol), HOBt (0.22 g, 1.4 mmol) and DIPEA (0.5 mL, 2.9 mmol) were added under Argon atmosphere and stirred at RT for 24 h (TLC indicated complete consumption of starting material). The volatiles were removed under reduced pressure and the residue was diluted with ice water (30 mL) and EtOAc (50 mL). The organic layer was separated, washed with ice water (2×15 mL), brine (2×15 mL), dried over Na₂SO₄ and concentrated under reduced pressure to give the crude residue (200 mg, 47% LCMS) which was prep purified to furnish 6-[(3S)-4-[3-(5,6-difluoro-4-oxo-3H-quinazolin-2-yl)propanoyl]-3-methyl-piperazin-1-yl]pyridine-3-carbonitrile (40 mg, 9%) as a white solid.

¹H NMR [400 MHz, CDCl₃]: δ 12.33 (brs, 1H), 8.48 (d, J=2.4 Hz, 1H), 7.86 (dd, J=9.2, 2.4 Hz, 1H), 7.84-7.76 (m, 1H), 7.39-7.33 (m, 1H), 6.95-6.91 (m, 1H), 4.55-4.34 (m, 1H), 4.30-3.86 (m, 3H), 3.49-3.42 (m, 1H), 3.23-3.15 (m, 1H), 3.05-2.94 (m, 1H), 2.89-2.78 (m, 4H), 1.20-0.98 (m, 3H).

LCMS: m/z: 439.7 [M+H]⁺.

Example 45—Synthesis of 2-[4-[3-(4-oxo-3H-quinazolin-2-yl)propanoyl]piperazin-1-yl]pyrimidine-5-carbonitrile Step-1

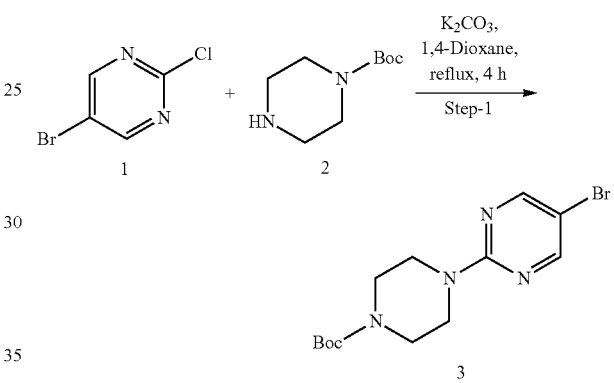

To a solution of 5-bromo-2-chloro-pyrimidine (0.5 g, 2.58 mmol) in 1,4-dioxane (20 mL), tert-butyl piperazine-1-carboxylate (0.722 g, 3.88 mmol) and K₂CO₃ (0.713 g, 5.17 mmol) were added at RT. The reaction mixture was refluxed for 4 h (TLC indicated complete consumption of starting material). The reaction mixture was brought to RT, diluted with water (20 mL) and extracted with EtOAc (3×50 mL). The combined organic extracts were washed with water (2×40 mL), brine (1×40 mL), dried over Na₂SO₄ and concentrated under reduced pressure to give the residue. The residue was further purified by column chromatography (100-200 silica gel, 15 g, 10% EtOAc-Hexane) to afford tert-butyl 4-(5-bromopyrimidin-2-yl)piperazine-1-carboxylate (0.7 g, 78%) as a white solid.

¹H NMR [400 MHz, CDCl₃]: δ 8.29 (s, 2H), 3.75 (t, J=4.8 Hz, 4H), 3.47 (t, J=5.2 Hz, 4H), 1.47 (s, 9H).

LCMS: m/z: 287.44 [M−ᵗBu]⁺.

Step-2

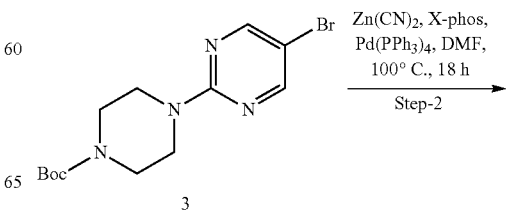

-continued

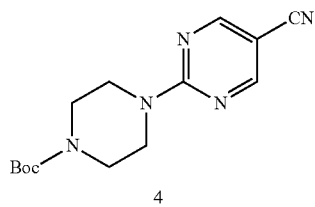

To a stirred solution of tert-butyl 4-(5-bromopyrimidin-2-yl)piperazine-1-carboxylate (500 mg, 1.46 mmol) in DMF (15 mL), Zn(CN)$_2$ (513 mg, 4.37 mmol) and X-phos (84 mg, 0.15 mmol) were added at RT. The reaction mixture was degassed with argon gas for 20 min, then Pd(PPh$_3$)$_4$ (168 mg, 0.15 mmol) was added and heated at 100° C. for 18 h (TLC indicated complete consumption of starting material). The reaction mixture was slowly brought to RT, diluted with water (20 mL) and extracted with EtOAc (3×100 mL). The combined organic extracts were washed with water (2×40 mL), brine (1×40 mL), dried over Na$_2$SO$_4$ and concentrated under reduced pressure to give the crude material. The crude material was purified by column chromatography (100-200 silica gel, 12 g, 10% EtOAc-Hexane) to give tert-butyl 4-(5-cyanopyrimidin-2-yl)piperazine-1-carboxylate (300 mg, 71%) as a white solid.

LCMS: m/z: 290.49 [M+H]$^+$.

Step-3

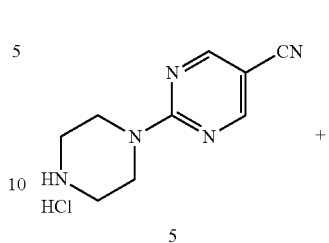

To a stirred solution of tert-butyl 4-(5-cyanopyrimidin-2-yl)piperazine-1-carboxylate (300 mg, 0.5 mmol) in DCM (5 mL) at 0° C., 4 N HCl in dioxane (5 mL) was added. The reaction mixture was warmed to RT and stirred for 4 h (TLC indicated complete consumption of starting material). The reaction mixture was concentrated under reduced pressure to give the crude residue which was washed with Et$_2$O (5 mL) and dried under vacuum to provide 2-piperazin-1-ylpyrimidine-5-carbonitrile; hydrochloride (200 mg, 80%) as a white solid.

LCMS: m/z: 190.46 [M+H]$^+$.

Step-4

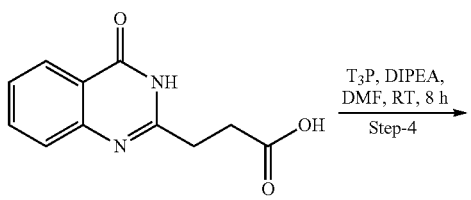

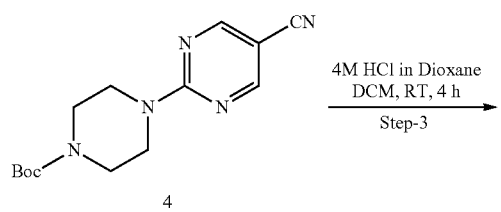

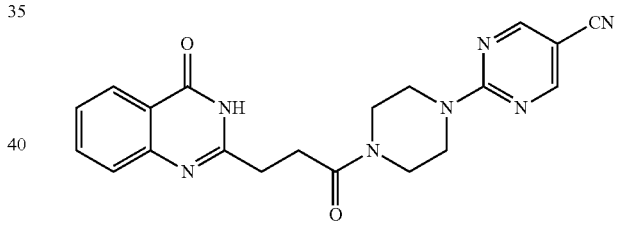

To a stirred solution of 2-piperazin-1-ylpyrimidine-5-carbonitrile hydrochloride (130 mg, 0.69 mmol) and 3-(4-oxo-3H-quinazolin-2-yl)propanoic acid (100 mg, 0.46 mmol) in DMF (2 mL), DIPEA (0.3 mL, 1.38 mmol) and T$_3$P (291 mg, 0.92 mmol) were added at RT and stirred for 8 h (TLC indicated complete consumption of starting material). The reaction mixture was quenched with water (10 mL) and extracted into EtOAc (3×40 mL). The combined organic extracts were washed with cold water (3×20 mL), brine (20 mL), dried over Na$_2$SO$_4$ and concentrated under reduced pressure to give the residue. The crude residue was purified by column chromatography (100-200 silica gel, 10 g, 5% MeOH-DCM) to furnish 2-[4-[3-(4-oxo-3H-quinazolin-2-yl)propanoyl]piperazin-1-yl]pyrimidine-5-carbonitrile (30 mg, 16%) as a white solid.

$^1$H NMR [400 MHz DMSO-d$_6$]: δ 12.20 (s, 1H), 8.79 (s, 2H), 8.06 (dd, J=7.6, 1.2 Hz, 1H), 7.78-7.73 (m, 1H), 7.57 (d, J=8.0 Hz, 1H), 7.47-7.43 (m, 1H), 3.93 (t, J=4.4 Hz, 2H), 3.81 (t, J=4.4 Hz, 2H), 3.66 (t, J=4.8 Hz, 2H), 3.57 (t, J=5.6 Hz, 2H), 2.90 (s, 4H).

LCMS: m/z: 390.67 [M+H]$^+$.

Example 46—Synthesis of 2-methyl-5-[4-[3-(4-oxo-3H-quinazolin-2-yl)propanoyl]piperazin-1-yl]pyrazole-3-carbonitrile

Step-1

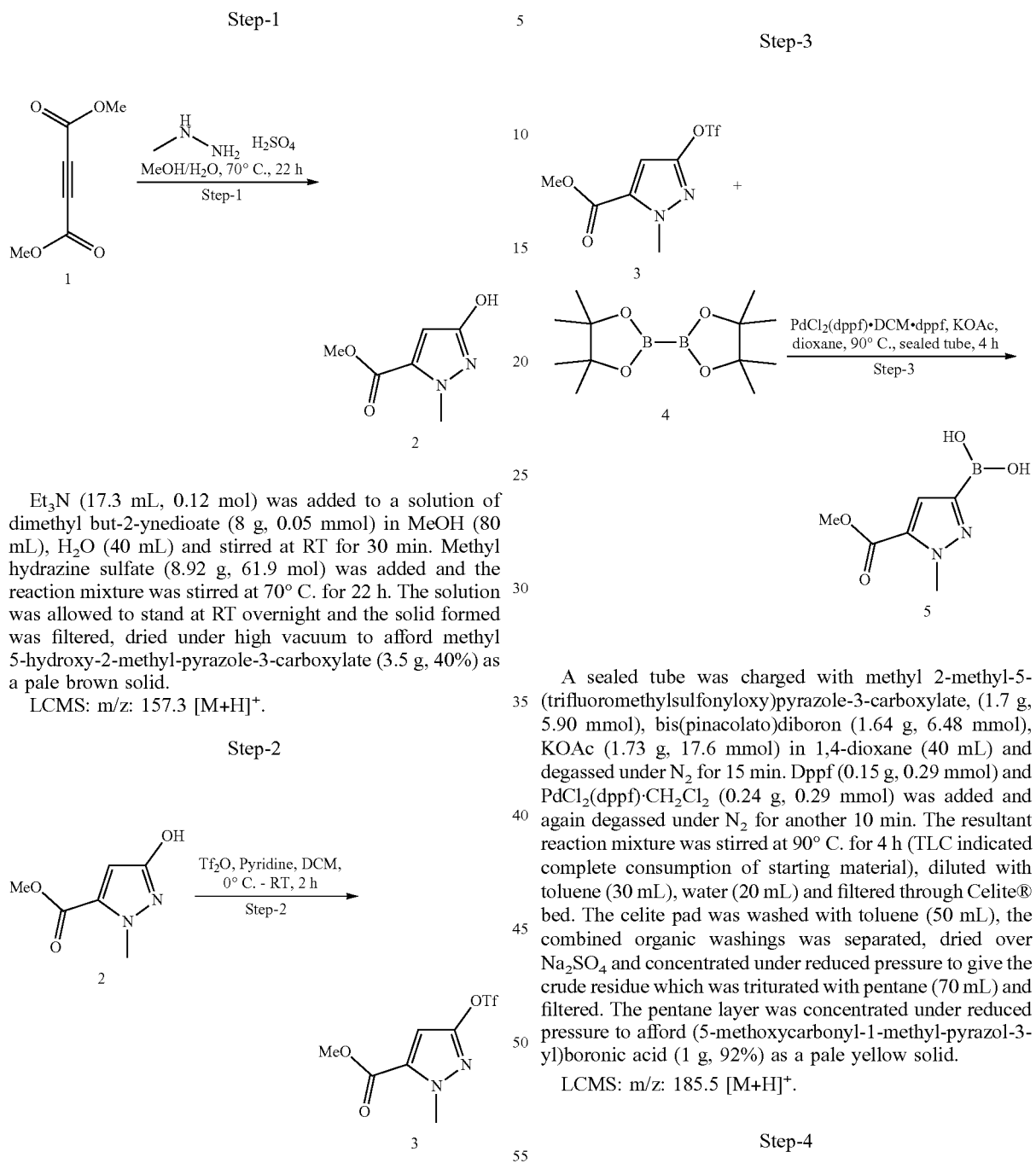

Et₃N (17.3 mL, 0.12 mol) was added to a solution of dimethyl but-2-ynedioate (8 g, 0.05 mmol) in MeOH (80 mL), H₂O (40 mL) and stirred at RT for 30 min. Methyl hydrazine sulfate (8.92 g, 61.9 mol) was added and the reaction mixture was stirred at 70° C. for 22 h. The solution was allowed to stand at RT overnight and the solid formed was filtered, dried under high vacuum to afford methyl 5-hydroxy-2-methyl-pyrazole-3-carboxylate (3.5 g, 40%) as a pale brown solid.

LCMS: m/z: 157.3 [M+H]⁺.

Step-2

To a stirred solution of methyl 5-hydroxy-2-methyl-pyrazole-3-carboxylate (0.3 g, 1.92 mmol) in DCM (30 mL) at 0° C., Pyridine (0.18 g, 2.30 mmol) followed by Tf₂O (0.59 g, 2.11 mmol) was added dropwise. The reaction mixture was slowly warmed to RT and stirred for 2 h (TLC indicated complete consumption of starting material). The reaction mixture was slowly diluted with water (15 mL) and extracted with DCM (2×30 mL). The combined organic extracts were washed with brine (25 mL), dried over Na₂SO₄ and concentrated under reduced pressure to afford methyl 2-methyl-5-(trifluoromethylsulfonyloxy)pyrazole-3-carboxylate (580 mg, 93%), which was carried to the next step without further purification.

LCMS: m/z: 289.4 [M+H]⁺.

Step-3

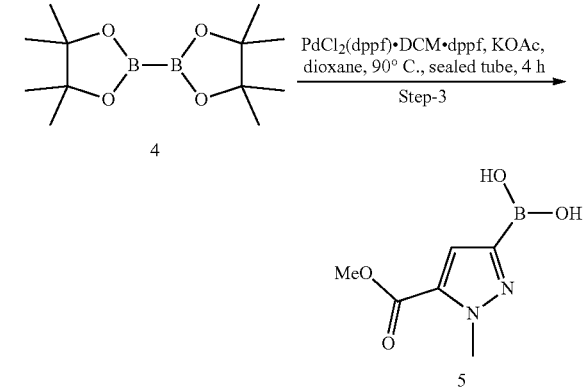

A sealed tube was charged with methyl 2-methyl-5-(trifluoromethylsulfonyloxy)pyrazole-3-carboxylate, (1.7 g, 5.90 mmol), bis(pinacolato)diboron (1.64 g, 6.48 mmol), KOAc (1.73 g, 17.6 mmol) in 1,4-dioxane (40 mL) and degassed under N₂ for 15 min. Dppf (0.15 g, 0.29 mmol) and PdCl₂(dppf)·CH₂Cl₂ (0.24 g, 0.29 mmol) was added and again degassed under N₂ for another 10 min. The resultant reaction mixture was stirred at 90° C. for 4 h (TLC indicated complete consumption of starting material), diluted with toluene (30 mL), water (20 mL) and filtered through Celite® bed. The celite pad was washed with toluene (50 mL), the combined organic washings was separated, dried over Na₂SO₄ and concentrated under reduced pressure to give the crude residue which was triturated with pentane (70 mL) and filtered. The pentane layer was concentrated under reduced pressure to afford (5-methoxycarbonyl-1-methyl-pyrazol-3-yl)boronic acid (1 g, 92%) as a pale yellow solid.

LCMS: m/z: 185.5 [M+H]⁺.

Step-4

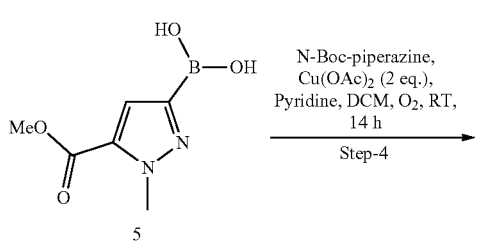

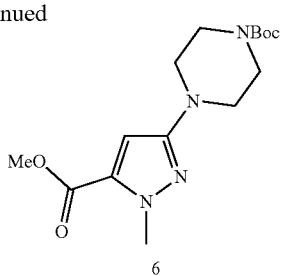

To a stirred solution of (5-methoxycarbonyl-1-methyl-pyrazol-3-yl)boronic acid (1.05 g, 5.64 mmol) and N-Boc-piperazine (0.8 g, 4.34 mmol) in DCM (20 mL) at RT, pyridine (1.03 g, 13.03 mmol), 4 Å molecular sieves and Cu(OAc)$_2$ (1.57 g, 8.67 mmol) were added. The reaction mixture was stirred under 02 atmosphere (balloon pressure) at RT for 14 h (TLC indicated complete consumption of starting material). The reaction mixture was diluted with water (10 mL) and extracted with DCM (2×30 mL). The combined organic extracts were washed with brine (20 mL), dried over Na$_2$SO$_4$ and concentrated under reduced pressure to give the crude residue (41% purity) which was purified by column chromatography (100-200 silica, 30 g, 15% EtOAc-Hexane) to furnish tert-butyl 4-(5-methoxycarbonyl-1-methyl-pyrazol-3-yl)piperazine-1-carboxylate (0.43 g, 60% LCMS) as a white solid.

LCMS: m/z: 325.7 [M+H]$^+$.

Step-5

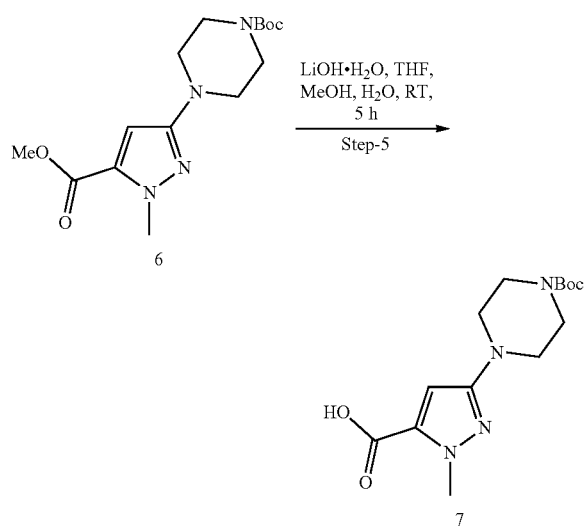

To a stirred solution of tert-butyl 4-(5-methoxycarbonyl-1-methyl-pyrazol-3-yl)piperazine-1-carboxylate (0.43 g, 1.32 mmol) in THF:MeOH:H$_2$O (1:1:1, 15 mL), LiOH·H$_2$O (0.27 g, 6.63 mmol) was added at RT and stirred for 5 h (TLC indicated complete consumption of the starting material). The reaction mixture was acidified with 1 N HCl till pH=4-5 and extracted with EtOAc (2×30 mL). The combined organic extracts were washed with brine (20 mL), dried over anhydrous Na$_2$SO$_4$ and concentrated under reduced pressure to afford 5-(4-tert-butoxycarbonylpiperazin-1-yl)-2-methyl-pyrazole-3-carboxylic acid (0.24 g, 58%) as a white solid.

LCMS: m/z: 311.4 [M+H]$^+$.

Step-6

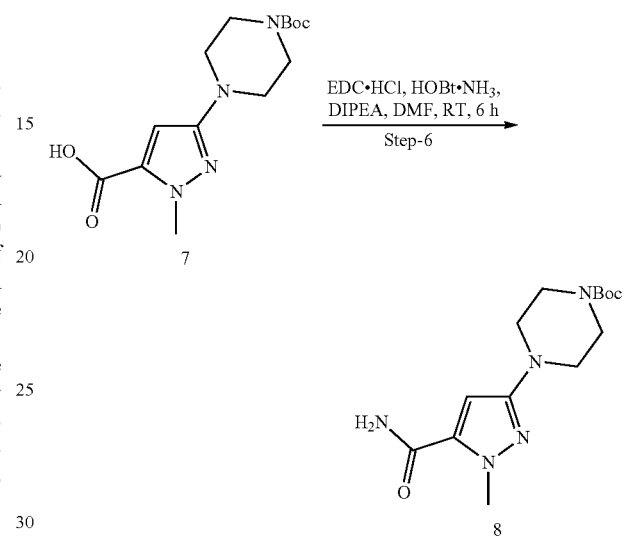

To a stirred solution of 5-(4-tert-butoxycarbonylpiperazin-1-yl)-2-methyl-pyrazole-3-carboxylic acid (0.47 g, 1.51 mmol) in THF (20 mL), EDC HCl (0.43 g, 2.27 mmol), HOBt-NH$_3$ (0.34 g, 2.27 mmol) and DIPEA (0.8 mL, 4.55 mmol) were added under argon atmosphere and stirred at RT for 6 h (TLC indicated complete consumption of starting material). The volatiles were removed under reduced pressure and the residue was diluted with water (40 mL) and EtOAc (100 mL). The organic layer was separated, washed with cold water (2×20 mL), brine (2×20 mL), dried over Na$_2$SO$_4$ and concentrated under reduced pressure to give the crude residue which was purified by column chromatography (100-200 silica gel, 20 g, 2.5% MeOH-DCM) to furnish tert-butyl 4-(5-carbamoyl-1-methyl-pyrazol-3-yl)piperazine-1-carboxylate (0.40 g, 86%) as a white solid.

LCMS: m/z: 310.7 [M+H]$^+$.

Step-7

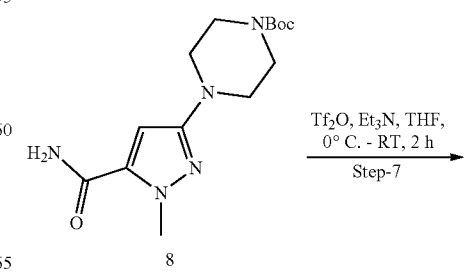

-continued

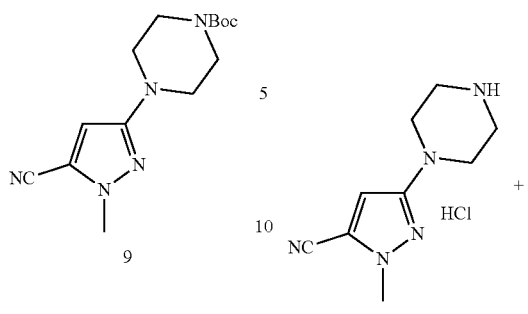

To a stirred solution of tert-butyl 4-(5-carbamoyl-1-methyl-pyrazol-3-yl)piperazine-1-carboxylate (0.17 g, 0.55 mmol) in THF (5.0 mL), cooled to 0° C., Et₃N (0.19 mL, 1.37 mmol) followed by Tf₂O (0.27 mL, 1.90 mmol) were added. The reaction mixture was slowly brought to RT and stirred for 1 h (TLC indicated complete consumption of the starting material). The reaction mixture was diluted with water (10 mL) and extracted with EtOAc (2×25 mL). The combined organic extracts were washed with saturated NaHCO₃ solution (10 mL), dried over Na₂SO₄ and concentrated under reduced pressure to afford tert-butyl 4-(5-cyano-1-methyl-pyrazol-3-yl)piperazine-1-carboxylate (0.11 g, 68%) as a pale yellow solid.

LCMS: m/z: 292.5 [M+H−100]⁺.

Step-8

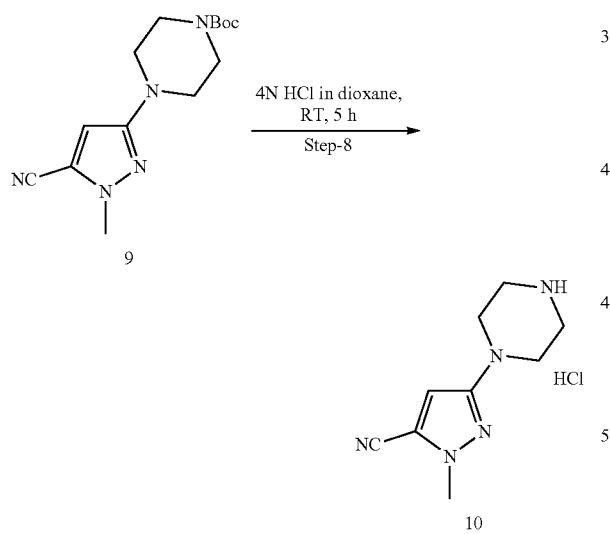

To a stirred solution of tert-butyl 4-(5-cyano-1-methyl-pyrazol-3-yl)piperazine-1-carboxylate (0.11 g, 0.37 mmol) in 1,4-dioxane (5 mL), cooled to 0° C., 4 N HCl in dioxane (3 mL) was added. The reaction mixture was brought to RT, stirred for 5 h (TLC indicates complete consumption of starting material), concentrated under reduced pressure to give the crude residue which was washed with Et₂O (5 mL) and dried under high vacuum to afford 2-methyl-5-piperazin-1-yl-pyrazole-3-carbonitrile hydrochloride (70 mg, 73%) as a white solid.

LCMS: m/z: 192.5 [M+H]⁺.

Step-9

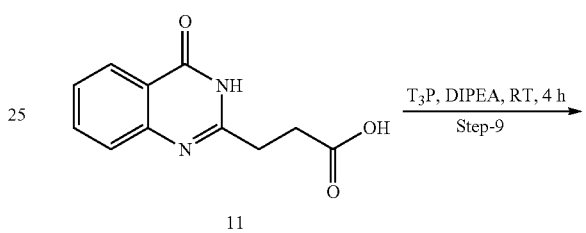

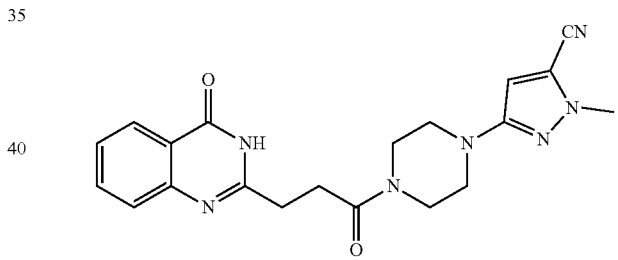

To a stirred solution of 2-methyl-5-piperazin-1-yl-pyrazole-3-carbonitrile; hydrochloride (0.06 g, 0.28 mmol) and 3-(4-oxo-3H-quinazolin-2-yl)propanoic acid (0.075 g, 0.34 mmol) in DMF (2 mL) at RT, 50% T₃P in EtOAc (0.36 mL, 0.57 mmol) and DIPEA (0.1 mL, 0.57 mmol) were added and stirred for 4 h (TLC showed complete consumption of starting material). The reaction mixture was concentrated under high vacuo to give the crude residue which was diluted with 5% MeOH-DCM (75 mL) and washed with cold water (2×10 mL). The organic layer was separated, dried over Na₂SO₄ and concentrated under reduced pressure to give crude residue (110 mg, 37% LCMS) which was prep purified to afford 2-methyl-5-[4-[3-(4-oxo-3H-quinazolin-2-yl)propanoyl]piperazin-1-yl]pyrazole-3-carbonitrile (22 mg, 16%) as a white solid.

¹H NMR [400 MHz, DMSO-d₆]: δ 12.15 (brs, 1H), 8.07 (d, J=6.8, 1.2 Hz, 1H), 7.76-7.72 (m, 1H), 7.53 (d, J=8.0 Hz, 1H), 7.44 (t, J=7.2 Hz, 1H), 6.62 (s, 1H), 3.83 (s, 3H), 3.61 (t, J=4.8 Hz, 2H), 3.54 (t, J=5.2 Hz, 2H), 3.18 (t, J=6.4 Hz, 2H), 3.06 (t, J=4.8 Hz, 2H), 2.87 (s, 4H).

LCMS: m/z: 392.7 [M+H]⁺.

Example 47—Synthesis of 3-chloro-N,N-dimethyl-4-[4-[3-(4-oxo-3H-quinazolin-2-yl)propanoyl]piperazin-1-yl]benzamide Step-1

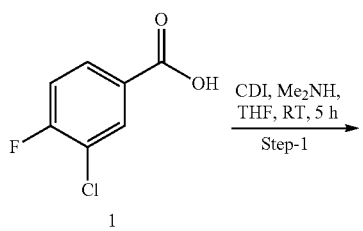

To a stirred solution of 3-chloro-4-fluoro-benzoic acid (0.5 g, 2.87 mmol) in THF (5 mL), Me₂NH (0.3 mL, 5.74 mmol, 1M in THF) and CDI (0.7 g, 4.31 mmol) were added at RT and stirred for 5 h (TLC indicated complete consumption of starting material). The reaction mixture was quenched with water (40 mL) and extracted with EtOAc (3×30 mL). The combined organic extracts were dried over Na₂SO₄, volatiles were removed under reduced pressure to give the residue which was washed with Et₂O and dried to furnish 3-chloro-4-fluoro-N,N-dimethyl-benzamide (450 mg, 78%) as a white solid.

LCMS: m/z: 202.40 [M+H]⁺.

Step-2

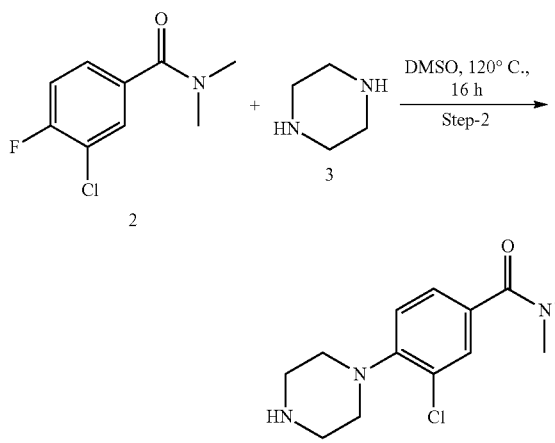

The solution of 3-chloro-4-fluoro-N,N-dimethyl-benzamide (0.4 g, 1.99 mmol) and piperazine (0.8 g, 9.38 mmol) in DMSO (5 mL) was stirred under argon atmosphere at 120° C. for 16 h (TLC indicated complete consumption of starting material). The reaction mixture was quenched with water (40 mL) and extracted with EtOAc (3×10 mL). The combined organic extracts were dried over Na₂SO₄, concentrated under reduced pressure and the residue was washed with Et₂O (10 mL) to give 3-chloro-N,N-dimethyl-4-piperazin-1-yl-benzamide (550 mg, 65%) as an off white solid.

LCMS: m/z: 268.56 [M+H]⁺.

Step-3

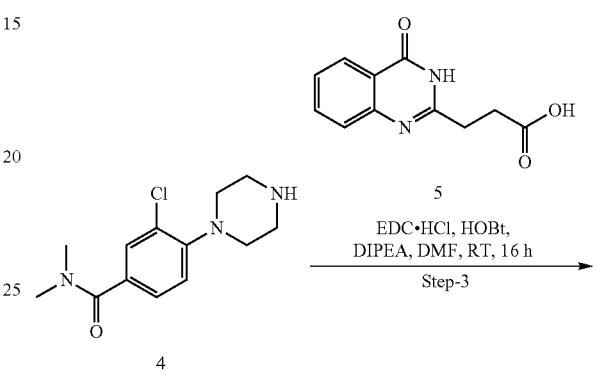

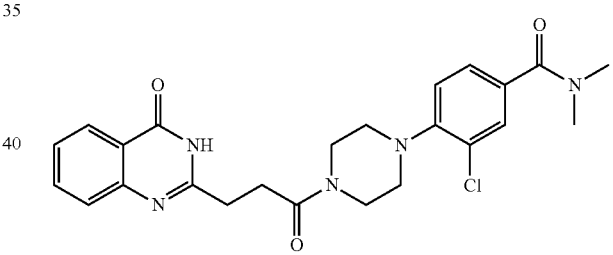

To a stirred solution of 3-chloro-N,N-dimethyl-4-piperazin-1-yl-benzamide (150 mg, 0.55 mmol) and 3-(4-oxo-3H-quinazolin-2-yl)propanoic acid (122 mg, 0.55 mmol) in dry DMF (2 mL), EDC HCl (160 mg, 0.83 mmol), HOBt (113 mg, 0.83 mmol) and DIPEA (0.2 mL, 1.16 mmol) were added at RT and stirred for 16 h (TLC indicated the complete consumption of starting material). The reaction mixture was quenched with water (20 mL) and extracted with EtOAc (3×10 mL). The combined organic extracts were dried over Na₂SO₄, concentrated under reduced pressure and the residue was purified by flash chromatography (100-200 silica gel, 5 g, 5% of MeOH-DCM) to provide 3-chloro-N,N-dimethyl-4-[4-[3-(4-oxo-3H-quinazolin-2-yl)propanoyl]piperazin-1-yl]benzamide (80 mg, 43%) as a white solid.

¹H NMR [400 MHz, DMSO-d₆]: δ 12.20 (s, 1H), 8.07 (dd, J=8, 1.2 Hz, 1H), 7.78-7.74 (m, 1H), 7.57 (d, J=8 Hz, 1H), 7.47-7.43 (m, 2H), 7.36 (dd, J=8.4, 2 Hz, 1H), 7.15 (d, J=8.4 Hz, 1H), 3.70 (brs, 2H), 3.61 (brs, 2H), 3.05 (brs, 2H), 2.94 (s, 8H), 2.89 (s, 4H).

LCMS: m/z: 468.73 [M+H]⁺.

Example 48—Synthesis of N-methyl-6-[4-[3-(4-oxo-3H-quinazolin-2-yl)propanoyl]piperazin-1-yl]pyridine-3-carboxamidine hydrochloride Step-1

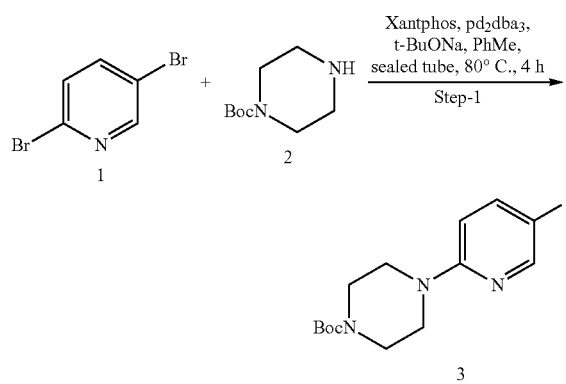

To a stirred solution of 2,5-dibromopyridine (2 g, 10.7 mmol), sodium tert-butoxide (1.6 g, 16.6 mmol), xantphos (400 mg, 0.7 mmol) and toluene (100 mL) in sealed tube argon was purged for 5 min. To the reaction mixture tert-butyl piperazine-1-carboxylate (3.4 g, 14.30 mmol) followed by Pd$_2$(dba)$_3$ (200 mg, 0.21 mmol) was added and heated at 80° C. for 4 h (TLC indicated complete consumption of starting material). The reaction mixture was diluted with EtOAc (200 mL), water (100 mL), filtered through Celite bed and washed with EtOAc (2×30 mL). The combined organic extracts were washed with brine (50 mL), dried over Na$_2$SO$_4$ and concentrated under reduced pressure to give the crude product which was purified by column chromatography (100-200 silica gel, 50 g, 10-20% EtOAc-hexanes) to afford tert-butyl 4-(5-bromo-2-pyridyl)piperazine-1-carboxylate (3 g, 82%) as a yellow solid.

LCMS (ESI+): m/z: 342.57 [M+H]$^+$.

Step-2

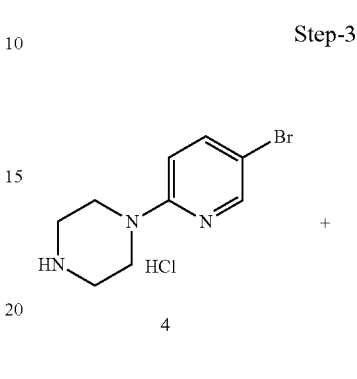

To a stirred solution of tert-butyl 4-(5-bromo-2-pyridyl)piperazine-1-carboxylate (3 g, 8.77 mmol) in dioxane (30 mL), 4 N HCl in dioxane (10 mL) was added at RT and stirred for 4 h (TLC indicated complete consumption of starting material). EtOAc (50 mL) was added to the reaction mixture, stirred for 30 min., the solid was filtered, washed with ether (20 mL) and dried under reduced pressure to afford 1-(5-bromo-2-pyridyl)piperazine hydrochloride (2.1 g, 93%) as an off-white solid.

LCMS (ESI+): m/z: 242.43 [M+H]$^+$.

Step-3

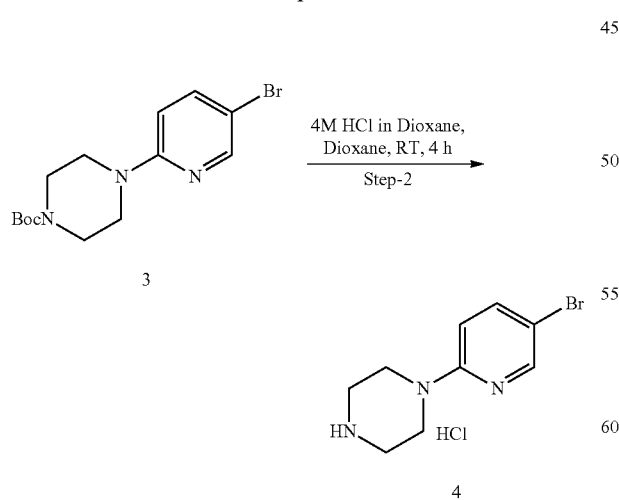

To a stirred solution of 1-(5-bromo-2-pyridyl)piperazine hydrochloride (2.1 g, 8.12 mmol) in DMF (20 mL), DIPEA (3.8 mL, 22.01 mmol), 3-(4-oxo-3H-quinazolin-2-yl)propanoic acid (1.6 g, 7.34 mmol) followed by 50% T$_3$P solution in EtOAc (7 mL, 11.00 mmol) were added at RT and stirred for 12 h (LCMS indicated complete consumption of starting material). The reaction mixture was quenched with ice-water (200 mL), stirred for 2 h, solid obtained was filtered washed with water (50 mL), acetone (20 mL) and dried under vacuo to obtain 2-[3-[4-(5-bromo-2-pyridyl)piperazin-1-yl]-3-oxo-propyl]-3H-quinazolin-4-one (1.6 g, 50%) as an off-white solid.

LCMS (ESI+): m/z: 442.59 [M+H]$^+$.

Step-4

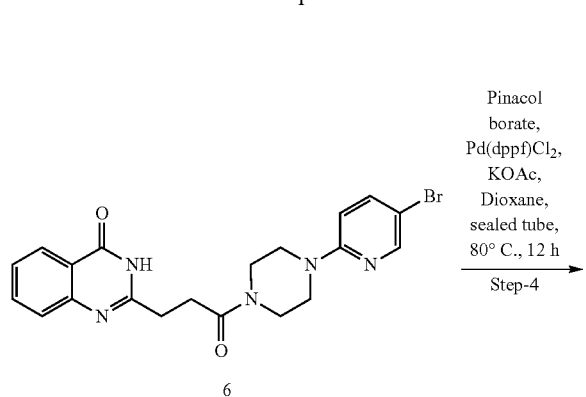

6

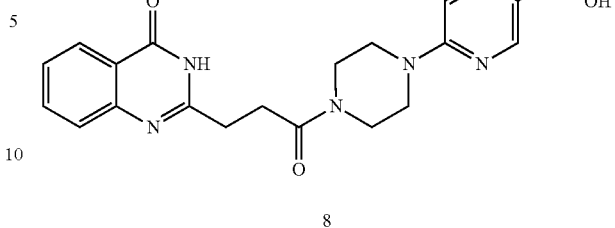

5

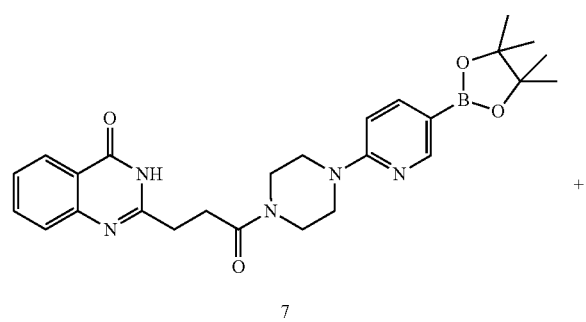

7

To a stirred solution of 2-[3-[4-(5-bromo-2-pyridyl)piperazin-1-yl]-3-oxo-propyl]-3H-quinazolin-4-one (1.6 g, 3.62 mmol) in dioxane (30 mL) in a sealed tube, potassium acetate (1.1 g, 11.21 mmol) was added under argon atmosphere followed by bis(pinacolato)diboron (1.3 g, 5.12 mmol) and Pd(dppf)Cl$_2$ (89 mg, 0.11 mmol). The reaction was heated at 80° C. for 12 h (LCMS indicated complete consumption of starting material). The reaction mixture was diluted with EtOAc (75 mL), filtered through Celite® bed, washed with EtOAc (2×50 mL); the combined organic extracts were washed with brine (25 mL), dried over sodium sulfate and concentrated under reduced pressure to give the crude product which was washed with pentane (2×10 mL) to afford a mixture of both 2-[3-oxo-3-[4-[5-(4,4,5,5-tetramethyl-1,3,2-dioxaborolan-2-yl)-2-pyridyl]piperazin-1-yl]propyl]-3H-quinazolin-4-one and [6-[4-[3-(4-oxo-3H-quinazolin-2-yl)propanoyl]piperazin-1-yl]-3-pyridyl]boronic acid (1.16 g), which was used in the next reaction without further purification.

LCMS (ESI$^+$): m/z: 408.69 [M+H]$^+$. (Boronic acid)

Step-5

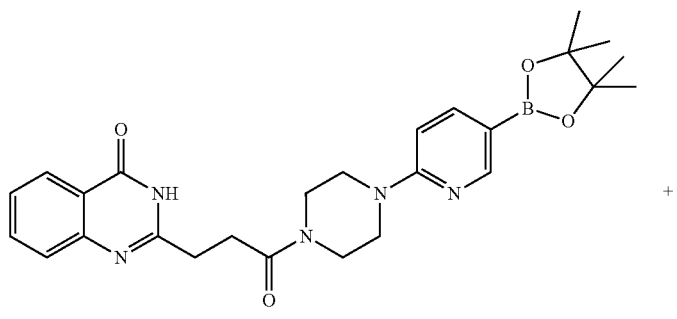

7

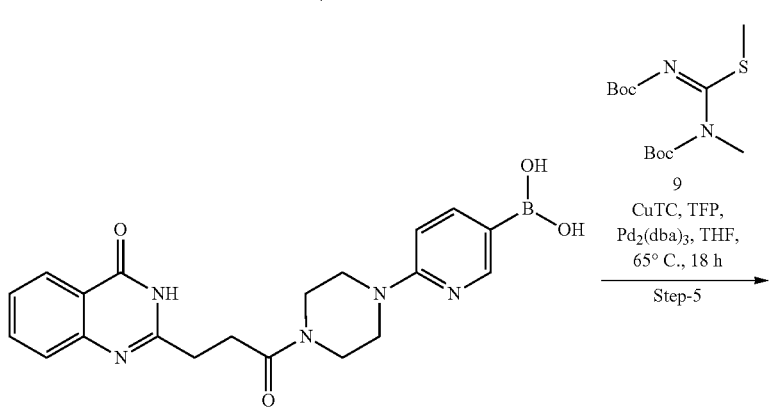

8

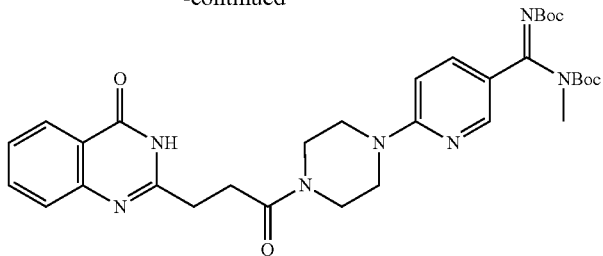

10

To a stirred solution of a mixture of 2-[3-oxo-3-[4-[5-(4,4,5,5-tetramethyl-1,3,2-dioxaborolan-2-yl)-2-pyridyl]piperazin-1-yl]propyl]-3H-quinazolin-4-one & [6-[4-[3-(4-oxo-3H-quinazolin-2-yl)propanoyl]piperazin-1-yl]-3-pyridyl] boronic acid (1.16 g), copper (I) thiophene-2-carboxylate (1.1 g, 5.77 mmol), tri-2-furyl phosphine (140 mg, 0.60 mmol) in THF under argon atmosphere, Pd$_2$(dba)$_3$ (91 mg, 0.10 mmol) was added. The reaction mixture was purged with argon for 5 min, then N,N'-Bis(tert-butoxycarbonyl)-S-methylisothiourea (600 mg, 1.97 mmol) in THF (18 mL) was added under argon atmosphere during which thick homogeneous solution was formed. The reaction mixture was heated at 65° C. for 18 h (LCMS indicated 16% of boronic acid), then brought to RT, saturated aqueous NaHCO$_3$ solution (20 mL) and EtOAc (30 mL) were added. The organic layer was separated, washed with brine (25 mL), dried over Na$_2$SO$_4$ and concentrated under reduced pressure to give the crude product which was purified by column chromatography (100-200 silica gel, 100 g, 2-5% MeOH-DCM) to afford tert-butyl N-[(E)-N-tert-butoxycarbonyl-C-[6-[4-[3-(4-oxo-3H-quinazolin-2-yl)propanoyl]piperazin-1-yl]-3-pyridyl]carbonimidoyl]-N-methyl-carbamate (240 mg, 12% LCMS), which was re-purified by Prep-HPLC to furnish pure compound (13 mg) as a white solid.

LCMS (ESI+): m/z: 620.92 [M+H]$^+$.

Step-6

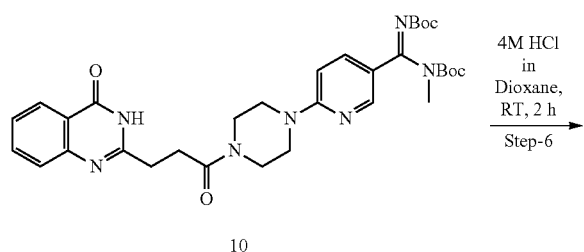

To a stirred solution of tert-butyl N-[(E)-N-tert-butoxycarbonyl-C-[6-[4-[3-(4-oxo-3H-quinazolin-2-yl)propanoyl]piperazin-1-yl]-3-pyridyl]carbonimidoyl]-N-methyl-carbamate (13 mg, 0.021 mmol) in dioxane (0.5 mL), 4 N HCl in dioxane (0.4 mL, 1.744 mmol) was and stirred at RT for 2 h (LCMS indicated complete consumption of starting material). The reaction mixture was concentrated under reduced pressure to give the crude product which was washed with EtOAc (2×5 mL), followed by Et$_2$O (2×5 mL) then lyophilized in a mixture of CH$_3$CN (5 mL) and water (5 mL) to afford N-methyl-6-[4-[3-(4-oxo-3H-quinazolin-2-yl)propanoyl]piperazin-1-yl]pyridine-3-carboxamidine hydrochloride (12 mg, 99%) as an off-white solid.

$^1$H NMR [400 MHz, DMSO-d$_6$]: δ 8.58 (brs, 1H), 8.14 (d, J=7.6 Hz, 2H), 7.99 (brs, 1H), 7.92-7.78 (m, 2H), 7.63-7.57 (m, 1H), 7.35 (brs, 1H), 7.13-7.08 (m, 1H), 4.26 (brs, 5H), 3.81 (s, 2H), 3.68 (s, 4H), 3.60 (s, 2H), 3.06 (s, 3H).

LCMS (ESI+): m/z: 420.70 [M+H]$^+$.

Step-7

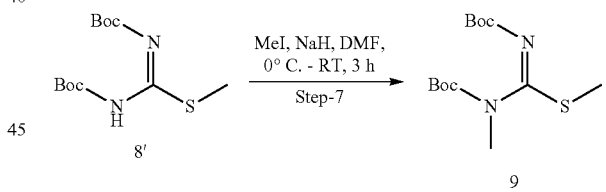

To a solution of tert-butyl N-[(tert-butoxycarbonylamino)-methylsulfanyl-methylene]carbamate (1 g, 3.44 mmol) in DMF (20 mL), cooled to 0° C., 60% sodium hydride (276 mg, 6.916 mmol) was added portionwise followed by MeI (0.32 mL, 5.162 mmol). The reaction mixture was warmed to RT and stirred for 3 h (TLC indicated complete consumption of starting material). The reaction mixture was quenched with ice-water (30 mL) and extracted with EtOAc (2×50 mL). The combined organic extracts were washed with brine (30 mL), dried over Na$_2$SO$_4$ and concentrated under reduced pressure to give the residue which was purified by column chromatography (100-200 silica gel, 20 g, 5-10% EtOAc-hexanes) to furnish tert-butyl N—(N-tert-butoxycarbonyl-C-methylsulfanylcarbonimidoyl)-N-methyl-carbamate (650 mg, 63%) as a colorless oil.

LCMS (ESI+): m/z: 305.66 [M+H]$^+$.

Example 49—Synthesis of 2-[3-[4-[5-(4,5-dihydro-1H-imidazol-2-yl)-2-pyridyl]piperazin-1-yl]-3-oxopropyl]-3H-quinazolin-4-one

Step-1

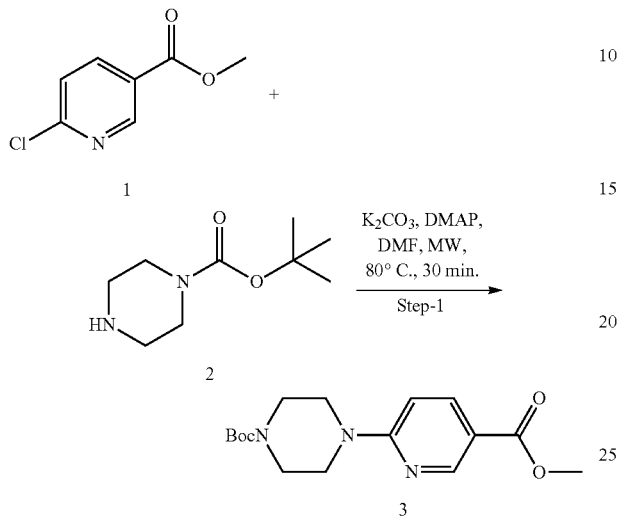

To a stirred solution of methyl 6-chloropyridine-3-carboxylate (500 mg, 2.91 mmol) in DMF (5 mL), tert-butyl piperazine-1-carboxylate (720 mg, 3.87 mmol), K₂CO₃ (1.2 g, 8.74 mmol) and DMAP (35 mg, 0.29 mmol) were added at RT. The reaction mixture was heated in a CEM microwave at 80° C. for 30 min (TLC showed the complete consumption of starting material) and diluted with water (20 mL) during which solid was precipitated out. The solid was filtered and dissolved in EtOAc (50 mL), dried over Na₂SO₄, concentrated under reduced pressure to give the crude compound which was purified by flash chromatography (100-200 silica gel, 5 g, 30% EtOAc-Hexane) to afford tert-butyl 4-(5-methoxycarbonyl-2-pyridyl)piperazine-1-carboxylate (510 mg, 54%) as a white solid.

LCMS: m/z: 322.63 [M+H]⁺.

Step-2

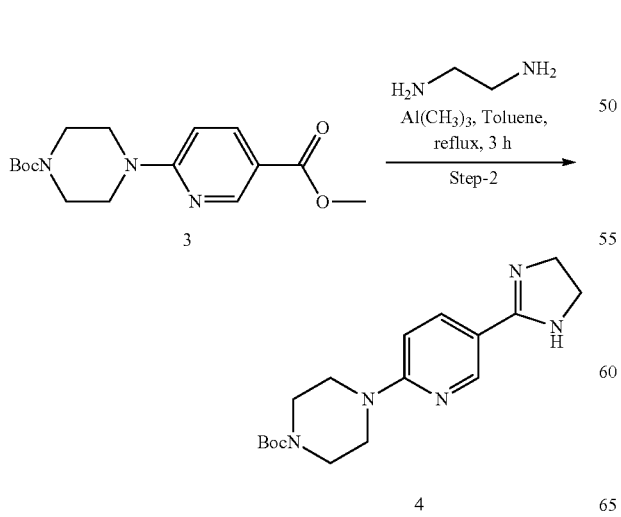

To a stirred solution of trimethyl aluminium (1.86 mL, 3.73 mmol, 2 M in toluene) in toluene (12 mL), cooled to 0° C., ethylenediamine (0.25 mL, 3.73 mmol) was added. The reaction mixture was warmed to RT, stirred for 5 min and tert-butyl 4-(5-methoxycarbonyl-2-pyridyl)piperazine-1-carboxylate (200 mg, 0.62 mmol) in toluene (4 mL) was added at RT. The reaction mixture was refluxed for 3 h (TLC showed the complete consumption of starting material), slowly brought to RT, quenched with water (5 mL) and dissolved in MeOH (15 mL) & DCM (15 mL). The reaction mixture was filtered through Na₂SO₄; the obtained filtrate was evaporated under vacuum to get the crude residue. The residue was dissolved in EtOAc (50 mL), heated at 80° C. for 5 min, filtered through Na₂SO₄ and concentrated under vacuum to give the crude compound. The crude residue was purified by column chromatography (100-200 silica gel, 4 g, 10% MeOH-80% DCM-10% aq. NH₃) to afford tert-butyl 4-[5-(4,5-dihydro-1H-imidazol-2-yl)-2-pyridyl]piperazine-1-carboxylate (160 mg, 78%) as a white solid.

LCMS: m/z: 332.70 [M+H]⁺.

Step-3

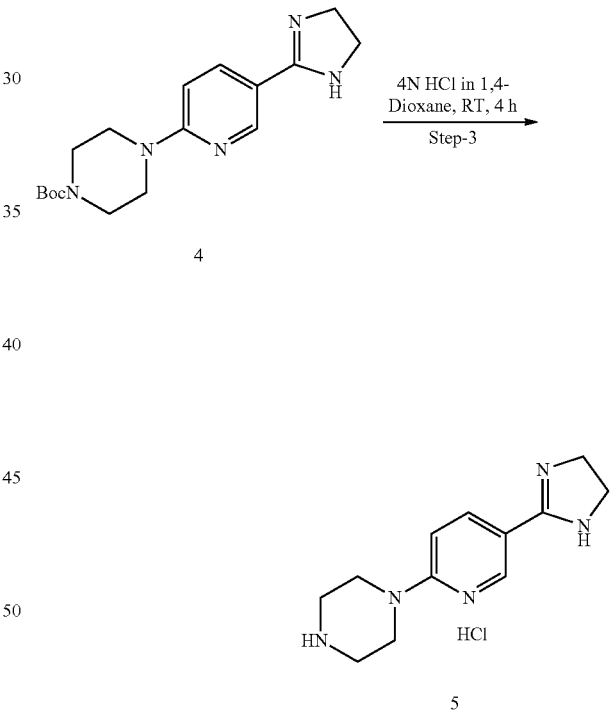

To a stirred solution of tert-butyl 4-[5-(4,5-dihydro-1H-imidazol-2-yl)-2-pyridyl]piperazine-1-carboxylate (160 mg, 0.48 mmol) in 1,4-dioxane (3 ml), cooled to 0° C., 4 N HCl in 1,4-dioxane (0.48 mL, 1.93 mmol) was added. The reaction mixture was warmed to RT and stirred for 4 h (TLC showed the complete consumption of starting material). The volatiles were evaporated under reduced pressure to give 1-[5-(4,5-dihydro-1H-imidazol-2-yl)-2-pyridyl]piperazine hydrochloride (130 mg, 100%) which was used for the next step without further purification.

LCMS: m/z: 232.56 [M+H]⁺.

Step-4

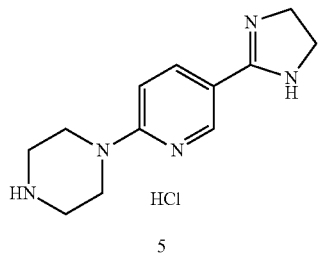

+

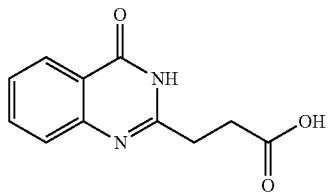

EDC·HCl, HOBt, DIPEA, DMF, RT, 16 h
Step-4
→

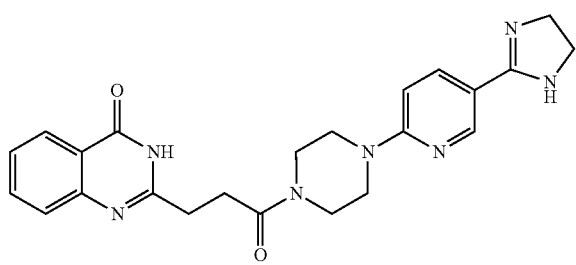

To a stirred solution of 3-(4-oxo-3H-quinazolin-2-yl)propanoic acid (100 mg, 0.458 mmol) in DMF (5 mL), 1-[5-(4,5-dihydro-1H-imidazol-2-yl)-2-pyridyl]piperazine hydrochloride (127 mg, 0.55 mmol), EDC HCl (131 mg, 0.68 mmol), HOBt (93 mg, 0.68 mmol) and DIPEA (0.32 mL, 1.83 mmol) were added at RT and stirred for 16 h (TLC showed the complete consumption of starting material). The volatiles were removed under reduced pressure to give the crude residue which was diluted with cold water (30 ml) during which solid was precipitated out. The precipitate was filtered, dried under vacuum to get crude product (120 mg, 92% LCMS) and purified by preparative HPLC to obtain 2-[3-[4-[5-(4,5-dihydro-1H-imidazol-2-yl)-2-pyridyl]piperazin-1-yl]-3-oxo-propyl]-3H-quinazolin-4-one (55 mg, 28%) as a white solid.

$^1$H NMR [400 MHz, DMSO-d$_6$]: δ 12.0 (s, 1H), 8.54 (d, J=2.0 Hz, 1H), 8.07 (dd, J=1.6, 8.0 Hz, 1H), 7.92 (dd, J=2.4, 9.2 Hz, 1H), 7.76-7.71 (m, 1H), 7.54 (d, J=8.0 Hz, 1H), 7.46-7.42 (m, 1H), 6.87 (d, J=9.2 Hz, 1H), 3.70-3.65 (m, 4H), 3.56 (brs, 8H), 2.89 (brs, 4H).

LCMS: m/z: 432.73[M+H]$^+$.

Example 50—Synthesis of 8-chloro-2-(3-(4-(4-fluorophenyl)-3,6-dihydropyridin-1(2H)-yl)-3-oxopropyl)quinazolin-4(3H)-one Step-1

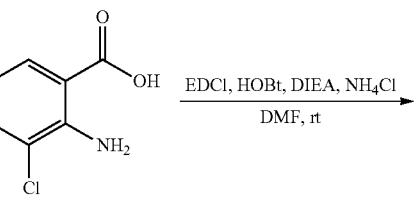

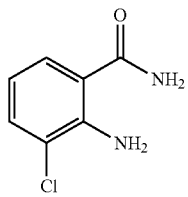

2-Amino-3-chlorobenzoic acid (10 g, 58.3 mmol) was dissolved in DMF (30 mL) and followed by addition of HOBt (10.2 g, 75.8 mmol), EDCI (13.4 g, 69.9 mmol), ammonium chloride (12.5 g, 233 mmol) and DIEA (40.6 mL, 233 mmol) in that order. The resulting mixture was stirred at room temperature for 20 hr. The mixture was partitioned between H$_2$O (200 mL) and EtOAc (200 mL) and phases were separated. The aqueous layer was extracted with EtOAc (2×150 mL). The combined organic extracts were washed with 50% saturated brine, dried (MgSO$_4$), and filtered. The filtrate was concentrated to give a yellow/white solid residue. The solid residue was dissolved in DMF (10 mL). Addition of DCM (10 mL) led to a white precipitation, which was collected by filtration. This process was repeated two more times to provide 2-amino-3-chloro-benzamide (5.1 g) as a white fluffy solid.

LC-MS: m/z: 171.1 [M+H]$^+$

Step-2

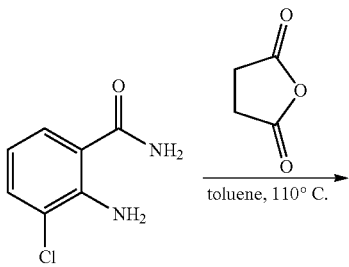

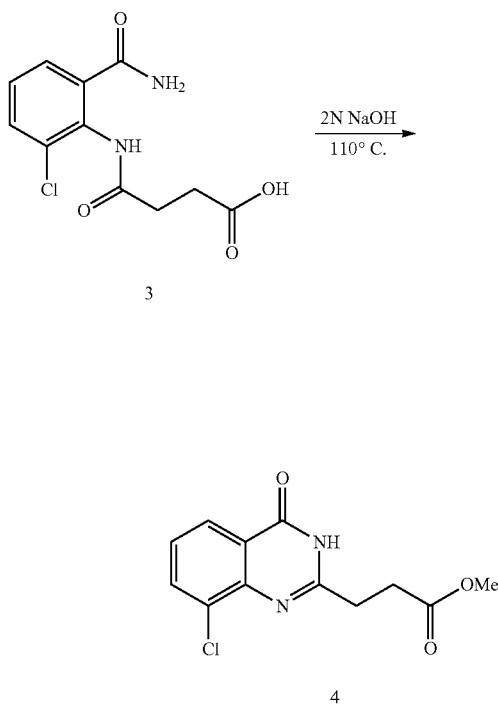

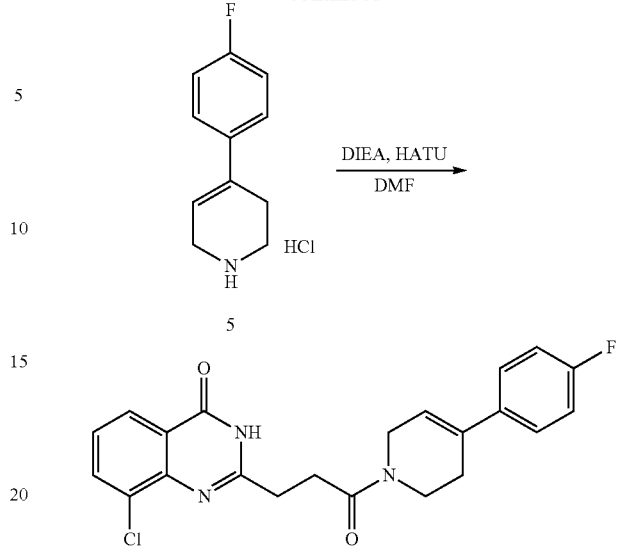

A suspension of 2-amino-3-chloro-benzamide (500 mg, 2.93 mmol) and succinic anhydride (293 mg, 2.93 mmol) in toluene (5 mL) was stirred at 110° C. The mixture became homogeneous after 1 hr. After an additional 16 hr, precipitation was formed. The mixture was cooled to room temperature and concentrated in vacuo. 1 N NaOH (10 mL) was added to the residue and the resulting mixture was heated at 110° C. for 10 min, then cooled to room temperature. 1 N HCl was added until pH reached ~ 1. White precipitation was formed and collected by filtration. The solids were washed with water (2×5 mL) and dried to give 3-(8-chloro-4-oxo-3H-quinazolin-2-yl)propanoic acid (294 mg) as a white solid.

LC-MS: m/z 253.0 [M+H]$^+$ $^1$H NMR (500 MHz, DMSO-d$_6$) δ 12.45 (s, 1H), 12.20 (br.s, 1H), 8.04 (dd, J=7.9, 1.5 Hz, 1H), 7.92 (dd, J=7.8, 1.4 Hz, 1H), 7.43 (t, J=7.8 Hz, 1H), 2.89 (dd, J=10.6, 3.7 Hz, 2H), 2.78 (dd, J=10.6, 3.6 Hz, 2H).

To a solution of 4-(4-fluorophenyl)-1,2,3,6-tetrahydropyridine hydrochloride (18.6 mg, 0.087 mmol) and 3-(8-chloro-4-oxo-3H-quinazolin-2-yl)propanoic acid (20.0 mg, 0.079 mmol) in DMF (3 mL) was added HATU (33.1 mg, 0.087 mmol), followed by DIEA (33.9 L, 0.190 mmol). The resulting mixture was stirred at room temperature for 3 hr, then diluted with EtOAc (40 mL) and washed with sat. NaHCO$_3$ (aq) (10 mL), 50% sat. brine (3×5 mL), dried (MgSO4), filtered and concentrated in vacuo. The residue was purified by silica gel flash chromatography to give crude product (13 mg) as a white solid which is 90% pure material by LC-MS and NMR. This solid was triturated with EtOAc (3 mL) and the solids collected by decanting off liquid to give 8-chloro-2-(3-(4-(4-fluorophenyl)-3,6-dihydropyridin-1(2H)-yl)-3-oxopropyl)quinazolin-4(3H)-one (1.2 mg) as a white solid.

LC-MS: m/z 412.1 [M+H]$^+$ $^1$H NMR (500 MHz, CDCl3) δ 11.08 (s, 1H), 8.18 (d, J=8.0 Hz, 1H), 7.79 (d, J=7.7 Hz, 1H), 7.38-7.28 (m, 3H), 7.03 (td, J=8.7, 2.0 Hz, 2H), 5.98 (d, J=45.0 Hz, 1H), 4.23 (d, J=77.1 Hz, 2H), 3.80 (dt, J=100.6, 5.7 Hz, 2H), 3.17 (dd, J=13.7, 7.8 Hz, 2H), 3.02-2.84 (m, 2H), 2.65-2.48 (m, 2H).

Example 51—Synthesis of 2-(3-(4-(4-fluorophenyl)-3,6-dihydropyridin-1(2H)-yl)-3-oxopropyl)quinazolin-4(3H)-one Step-3

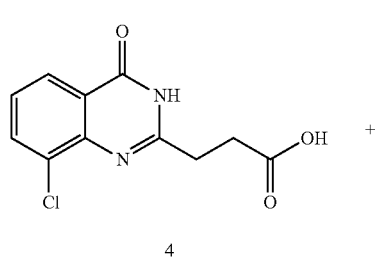

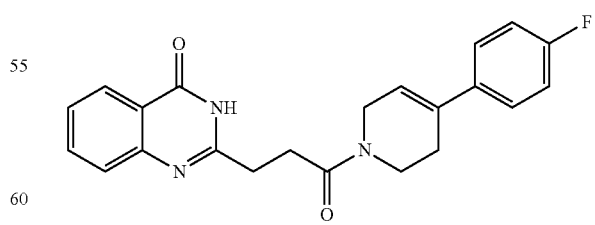

The compound was synthesized according the same sequence for 8-chloro-2-(3-(4-(4-fluorophenyl)-3,6-dihydropyridin-1(2H)-yl)-3-oxopropyl)quinazolin-4(3H)-one (Example 50) with appropriate starting material.

LC-MS: m/z 378.4 [M+H]$^+$ $^1$H NMR (500 MHz, DMSO-d$_6$) δ 12.19 (s, 1H), 8.07 (d, J=7.9 Hz, 1H), 7.72 (ddd, J=8.5, 7.2, 1.6 Hz, 1H), 7.53 (d, J=8.1 Hz, 1H), 7.50-7.46 (m, 2H), 7.46-7.41 (m, 1H), 7.18 (t, J=8.8 Hz, 2H), 6.20-6.12 (m, 1H), 4.24 (d, J=2.6 Hz, 1H), 4.09 (d, J=2.7 Hz, 1H), 3.72 (t, J=5.6 Hz, 1H), 3.66 (t, J=5.7 Hz, 1H), 2.98-2.85 (m, 4H), 2.58 (s, 1H), 2.42 (s, 1H).

Example 52—Synthesis of 2-(3-(4-(4-fluorophenyl)piperazin-1-yl)-3-oxopropyl)quinazolin-4(3H)-one

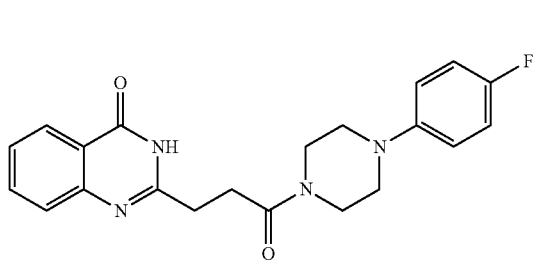 [SMILES: O=C(CCc1nc2ccccc2c(=O)[nH]1)N1CC=C(c2ccc(F)cc2)CC1]

The compound was synthesized according the same sequence for 8-chloro-2-(3-(4-(4-fluorophenyl)-3,6-dihydropyridin-1(2H)-yl)-3-oxopropyl)quinazolin-4(3H)-one (Example 50) with appropriate starting material.
LC-MS: m/z 381.4 [M+H]$^+$
$^1$H NMR (500 MHz, DMSO-d$_6$) δ 12.18 (s, 1H), 8.07 (dd, J=8.0, 1.2 Hz, 1H), 7.77-7.71 (m, 1H), 7.55 (d, J=8.0 Hz, 1H), 7.44 (ddd, J=8.1, 7.3, 1.1 Hz, 1H), 7.10-7.04 (m, 2H), 7.01-6.95 (m, 2H), 3.70-3.63 (m, 2H), 3.63-3.54 (m, 2H), 3.15-3.10 (m, 2H), 3.04-2.98 (m, 2H), 2.89 (s, 4H).

Example 53—Synthesis of 2-(3-(4-(4-fluorophenyl)-3,6-dihydropyridin-1(2H)-yl)-3-oxopropyl)-7-methyl-3,7-dihydro-4H-pyrrolo[2,3-d]pyrimidin-4-one

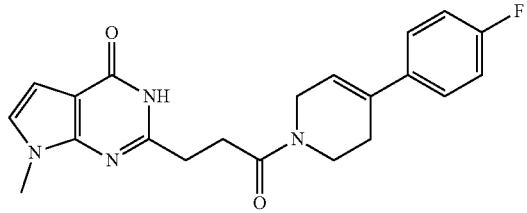 [SMILES: Cn1ccc2c(=O)[nH]c(CCC(=O)N3CC=C(c4ccc(F)cc4)CC3)nc21]

The compound was synthesized according the same sequence for 8-chloro-2-(3-(4-(4-fluorophenyl)-3,6-dihydropyridin-1(2H)-yl)-3-oxopropyl)quinazolin-4(3H)-one (Example 50) with appropriate starting material (2-amino-1-methyl-1H-pyrrole-32-carboxanide, CAS No: 1894093-24-3).
LC-MS: m/z 381.4 [M+H]$^+$
$^1$H NMR (500 MHz, DMSO) δ 11.70 (s, 1H), 7.48 (ddd, J=8.7, 5.6, 2.1 Hz, 2H), 7.21-7.14 (m, 2H), 6.98 (d, J=3.3 Hz, 1H), 6.37 (d, J=3.3 Hz, 1H), 6.16 (t, J=3.3 Hz, 1H), 4.23 (d, J=2.5 Hz, 1H), 4.10 (d, J=2.6 Hz, 1H), 3.71 (t, J=5.6 Hz, 1H), 3.67 (t, J=5.7 Hz, 1H), 3.61 (d, J=6.5 Hz, 3H), 2.92-2.80 (m, 4H), 2.60-2.54 (m, 1H), 2.46-2.40 (m, 1H).

Example 54 Human PARP Assay

Poly (ADP-ribose) polymerase-1 (PARP-1) and Poly (ADP-ribose) polymerase-2 (PARP-2) are two nuclear enzymes involved in many of cellular activities including DNA repair and play a key role in maintaining the integrity of DNA and chromatin structure. This assay is designed to assess the potential of a test substance to inhibit the activity of PARP-1 or PARP-2 and uses scintillation proximity assay (SPA) format.

The scintillation proximity assay (SPA) is designed to measure PARP activity using purified recombinant PARP-1 enzyme and is ideal for high throughput screening of small molecular inhibitors for drug discovery. Here, recombinant human PARP-1 or PARP-2 enzyme was incubated with substrate mix (NAD, $^3$H-NAD and biotinylated-NAD) and the [$^3$H] and biotin-labeled ADP-ribose polymers were captured using Streptavidin-conjugated PVT SPA beads. In the absence of enzyme inhibition, 100% signal was obtained. Inhibitors are identified by a decrease in signal when PARP-1 or PARP-2 mediated poly-ADP ribose polymer formation is reduced.

Chemicals and reagents used in this protocol are listed below with the source and catalogue numbers.

| Sl. No. | Material & Reagents | Supplier | Catalogue No. |
|---|---|---|---|
| 1 | recombinant human PARP-1 enzyme (High Specific Activity) | Trevigen | 4668-500-01 |
| 2 | rh-PARP-2 enzyme, 10 μg/vial | BPS Bioscience | 80502 |
| 3 | 96 Well Microplate, white, FB | Corning | 3600 or CLS3600- |
| 4 | 96 Well Microplate, polypropylene, | Corning | 3365 or P070 |
| 5 | Activated Calf Thymus DNA | Amersham | 27-4575 |
| 6 | Nicotinamide-Adenine Dinucleotide | Sigma | N1511-250MG |
| 7 | Biotinylated NAD (6-biotin-17-NAD) | Trevigen | 4670-500-01 |
| 8 | [Adenine-2,8-3H]-NAD, 250 μCi/vial | Perkin Elmer | NET443H250UC |
| 9 | Streptavidin-SPA beads | Perkin Elmer | RPNQ 0007 |
| 10 | DL-Dithiothreitol | Sigma | 43815-1G |
| 11 | Trizma ® base | Sigma | T6791-100G |
| 12 | Magnesium chloride | Sigma | 449172-10G |
| 13 | Spermine | Sigma | 85590-5G |
| 14 | Potassium chloride | Sigma | 746436-500G |
| 15 | NONIDET ® P-40 Substitute | Amresco | M158 |
| 16 | Dimethyl sulfoxide ACS reagent, ≥99.9% | Sigma | 472301-500 mL |
| 17 | 4-Amino-1,8-Naphthalimide (4-ANI) | Alfa Aesar | J64358 |
| 18 | TOPSEAL-A 96 | Perkin Elmer | 6005185 |
| 19 | Pipettes | Eppendorf | |

Note:
Weigh all chemicals using weighing balance with sensitivity of 0.01 mg.

Instruments: Perkin Elmer; TopCount NXT
Reagents & Buffer Preparation
Buffer A 4×:
Tris pH 8: 100 mM; MgCl$_2$: 4 mM; Spermine: 4 mM; KCl: 200 mM; Nonidet P-40 substitutent: 0.04%.
Assay Mix a Per Well
  Buffer A 4×: 12.5 μL
  DTT 100 mM: 0.5 μL
  PARP-1 enzyme: 1 unit/well, volume depends on the lot specific activity
  PARP-2 enzyme: 30 ng/well, volume depends on the lot specific activity
  H$_2$O: to 35 μL
Assay Mix B per well
  [Adenine-2,8-3H]-NAD 100 uCi/ml: 1 μL (0.1 μCi/well)
  3H-NAD 100 uCi/ml: 2 μl (0.2 μCi/well)
  NAD 1.5 mM: 0.05 μL Biotinylated-NAD 2501.iM: 0.03 μL
Activated Calf Thymus DNA: 50 μg
H$_2$O: to 10 μL
Assay Mix C
Streptavidin-SPA beads: 2.5 mg/mL in 200 mM EDTA pH 8.0 (for PARP-1 assay)
Streptavidin-SPA beads: 2.5 mg/ml dH$_2$O (for PARP-2 assay)
Assay Procedure A 10 mM solution of reference compound, 4-amino-1,8-naphthalimide (4-ANI) was prepared by using 100% DMSO. The 10 mM 4-ANI was diluted to 2 mM and further diluted to 200 μM using 100% DMSO. Serial dilution of 200 μM 4-ANI in 100% DMSO was carried out to obtain 3 fold diluted, ten concentrations. A 5p L of serial dilutions was transferred to 95 μL of water to obtain 10× of final concentration in assay. Top concentration of 4-ANI in the Assay was 1 μM.

A solution of 2 mM 4-ANI prepared earlier was diluted to 100 μM in water. 5 μL of this 100 μM 4-ANI was added to "NC" (negative control) wells. Final concentration of 4-ANI in "NC" wells was 10 μM. "NC" well are defined as the wells that have the lowest signal.

A 10 mM solution of test compound was prepared by using 100% DMSO. The 10 mM solution was diluted to 200× of the desired final concentration in assay. Serial dilution of 200× compound solution in 100% DMSO was carried out to obtain 3 fold diluted, ten concentrations. Pre-dilution Plate: 5 μL of serial dilutions was transferred to 95 μL of water in a polypropylene plate to obtain 10× of final desired concentration in assay.

PARP Reaction Development: Assay Plate

5 μL/well from predilution microplate was transferred into 96 well white microplate (Corning 3600). 35 μL/well of Assay Mix A was added and incubated for 5 minutes at room temperature. 10 μL/well of Assay Mix B was added to start the reaction. The assay plate was incubated for 3 hours at room temperature.

Assay Plate Detection:

50 μL/well of Assay Mix C was added. The plate with TOPSEAL-A 96 was sealted. The assay was incubated for 15 minutes with gentle shaking. The assay plate was read on TopCount using a protocol optimized for Tritium and PVT SPA beads.

Assay Conditions
  TRIS pH 8: 25 mM
  MgCl$_2$: 1 mM
  Spermine: 1 mM
  KCl: 50 mM
  Nonidet P-40: 0.01%
  DTT: 1 mM
  PARP-1: 1 unit/well
  PARP-2: 20-30 ng (depending on the specific activity of each lot)
  Activated calf Thymus: 1 ug/ml
  Cold NAD: 1.5 uM
  Biotinylated NAD: 150 nM
  3H-NAD: 0.2 uCi
  Streptavidin-SPA beads: 1.25 mg/ml Results and Data Analysis:

Raw data was collected as CPM. A 4-Paramaetric Non-linear regression was used to fit a concentration-response curve and to calculate IC$_{50}$ values. The duplicate CPM values for NC, PC groups were averaged. The average of NC was subtracted from all raw CPM counts. These background-subtracted values were then divided by the Average Positive Control to generate the % of Activity. The % Activity was subtracted from 100 to generate the % Inhibition. The data was plotted and fit to the following equation:

$$\% \text{ Inhibition} = \text{MIN} + \frac{(\text{MAX} - \text{MIN})}{1 + \frac{IP^{(HillSlope)}}{[X]}}$$

Example 55 PARP-1 Cell Based Assay

In response to DNA damage, poly-(ADP-ribose) polymerase-1 (PARP-1), which is the main isoform of the PARP family, is rapidly activated by DNA strand breaks occurring from exposure to environmental agents, cancer therapy, inflammation, ischemia-reperfusion and neurodegeneration. Once activated, NAD is consumed for the synthesis of the highly negatively charged polymer poly-ADPribose (PAR), which is found on target nuclear proteins including PARP-1 as a major acceptor. As a consequence of PARP activation, extensive DNA damage can lead to the depletion of NAD$^+$ in the cell, and lead to cell death. Therefore, PARP-1 is regarded as a promising target for the development of drugs useful in various regimens of cancer therapy, inflammation, ischemia and neurodegeneration.

In this assay, to monitor PARP activity within cells, HeLa cells were treated with PARP-1 inhibitors followed by induction of DNA damage with H$_2$O$_2$. The final PARP1 activity was accessed by measuring the levels of NAD$^+$ and NADH in the cell lysates collected from the treated and non-treated cells.

Materials & Reagents

| Sl. No. | Material & Reagents | Supplier | Catalogue No. |
|---|---|---|---|
| 1 | HeLa Cells | ATCC | ATCC ® CCL-2TM |
| 2 | Fetal Bovine Serum, HI | Invitrogen | 10438-026 |
| 3 | Penicillin-Streptomycin (10,000 U/mL), 100 mL | Invitrogen | 15140-122 |
| 4 | DMEM, High Glucose, Pyruvate, 6 × 1,000 mL | Invitrogen | 11995-065 |
| 5 | 0.25% Trypsin-EDTA (1X), Phenol Red, 100 ml | Invitrogen | 25200-056 |
| 6 | 175 cm2, Tissue Culture Flask, 100/case | Corning | CLS431306-84EA |
| 7 | 1X PBS, pH 7.4, 500 mL | Invitrogen | 10010-023 |
| 8 | 96-well, white, flat bottom, sterile, 100/case | Corning | CLS3917-100EA |
| 9 | 96 Well Microplate, polypropylene, clear | Corning | P070 |
| 10 | Dimethyl sulfoxide ACS reagent, ≥99.9% | Sigma | 472301-500 mL |
| 11 | Universal tips, Clear, 0.5-10 UL, 1000/pack | Axygen | T-300 |
| 12 | Universal tips, CLEAR, 1-200 UL, 1000/Pack | Axygen | T-200-C |
| 13 | NAD/NADH Glo Kit | Promega | G9072 |
| 14 | Dodecyltrimethylammonium bromide | Sigma | D5047-5G |
| 15 | NaOH | Sigma | S8045-500G |
| 16 | Sodium Bicarbonate | Sigma | S5761-500G |
| 17 | Sodium Carbonate | Sigma | S7795-500G |
| 18 | Nicotinamide | Sigma | N5535-100G |
| 19 | TritonX-100 | Sigma | T9284-100 mL |
| 20 | Trizma ® base | Sigma | 93362-250G |

-continued

| Sl. No. | Material & Reagents | Supplier | Catalogue No. |
|---|---|---|---|
| 21 | Hydrochloric acid | Sigma | H1758-100 mL |
| 22 | Olaparib | Medchem Express | HY-10162 |
| 23 | Envision Plate Reader | Perkin Elmer | 2104 |
| 24 | CO2 Incubator humidifier | Thermo Scientific | |
| 25 | Pipettes/Serological pipettes | Eppendorf/ Corning | |

Instruments: Detection: Luminescence detection in Envision Plate Reader/TopCount (Perkin Elmer)
Reagent & Media Preparation
Culture Media Preparation
    DMEM Media: 1×
    FBS (Heat Inactivated): 10%
    Pen-Strep (10,000 U/mL): 0.1 mg/mL
    L-Glutamine: 2 mM
Preparing the Luciferin Detection Reagent The reconstitution buffer was thawed. The reconstitution buffer and luciferin detection reagent were equilibrated to room temperature. The entire content of the reconstitution buffer bottle was transferred to the amber bottle of lyophilized luciferin detection reagent. The two reagents were mixed by swirling or inversion to obtain a uniform solution. No vortex. The luciferin detection reagent should go into solution easily in less than 1 minute.
Preparing the NAD/NADH-Glo™ Detection Reagent An equal volume of NAD/NADH-Glo™ Detection Reagent was added to each sample containing $NAD^+$ or NADH.

The reconstituted luciferin detection reagent was equilibrated to room temperature. The reductase, reductase substrate and $NAD^+$ cycling substrate were thawed at room temperature or on ice just prior to use. The $NAD^+$ cycling enzyme was reconstituted by adding 275 μL of water. The mixture was gently swirled the vial, and stored on ice. The required amount of NAD/NADH-Glo™ detection reagent was prepared by adding 5 μL of reductase, 5 μL of reductase substrate, 5 μL of $NAD^+$ cycling enzyme and 25 μL of $NAD^+$ cycling substrate per 1 mL of reconstituted luciferin detection reagent. The mixture was gently inverted five times.
Final Assay Conditions:
    Assay Volume: 100 μL
    Cell Type: HeLa Cells
    Cell Seeding Density: 10,000 cells/well
    Media: DMEM, 10% FBS, 0.1 mg/mL Pen-Strep, 2 mM L-Glutamine
    DMSO Concentration: 0.5%
    Assay Plate: 96 well White, TC, Sterile, with lid
    Compound Incubation Time: 18 hrs
    $CO_2$ Level: 5%
    Humidity: 95%
    Temperature: 37° C.
    $H_2O_2$ Concentration: 200 μM Cell Seeding & Compound Treatment:

HeLa cells in 96-well cell culture microplate were seeded at a density of 10,000 cells/well in 90 μL culture media. The plates was incubated for 4 h at 37° C. under 5% $CO_2$ atmosphere. 10 μL of 10× compounds (5% DMSO) with serial dilutions over eight points (concentration range: 0.3-100 nM) were added. The treated plates was incubated for 18 h at 37° C. in 5% $CO_2$. 5 μL of $H_2O_2$ solution in $H_2O$ (final concentration 200 μM) was added to provoke DNA damage. Cells untreated with $H_2O_2$ were kept in negative control wells. The plate was incubated at 37° C. for 5 min, and then was inverted to gently remove medium. A 50 μL of 1×PBS was added to all the wells.

PARP Activity Determination: Measure NAD+ and NADH Separately

This protocol is for assaying cells in 50 μl of PBS per well in 96-well white luminometer plates. Each well of cells was split into two samples: One sample was treated with acid to quantify NAD, and the other was treated with base to quantify NADH. When plating cells, wells on the plate were reserved for splitting samples. Alternatively, use a second plate when splitting samples.

A 50 μl of base solution with 1% DTAB was added to each well of cells in 50 μl of PBS. The plate was briefly mixed on a plate shaker to ensure homogeneity and cell lysis. A 50 μl of each sample was removed to an empty well for acid treatment. To these samples, a 25 μl of 0.4 N HCl per well was added; these wells contained the acid-treated samples. The original sample wells are the base-treated samples. The plate was covered and incubated for 15 minutes at 60° C. The plate was then equilibrated for 10 minutes at room temperature. A 25 μl of 0.5 M Trizma© base was added to each well of acid-treated cells to neutralize the acid. A 50 μl of HCl/Trizma© solution was added to each well containing base-treated samples. The NAD/NADH-Glo™ Detection Reagent was prepared as described above. An equal volume of NAD/NADH-Glo™ Detection Reagent (e.g., 100 μl) was added to each well. The plate was gently shaken to mix. The plate was incubated for 30-60 minutes at room temperature. Luminescence was recorded by using a luminometer (Envision, PerkinElmer). The Luminescence values were collected. A non-linear regression was used to generate dose response curves and to calculate $IC_{50}$ values.

The Table below lists inhibitory effects of representative compounds of the present invention against PARP1-1 and PARP-2 activities. The results indicate that the compounds of the present invention selectively inhibited PARP1-1 over PARP-2 and are useful for increasing the amount of NAD+ in cells.

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 1 | 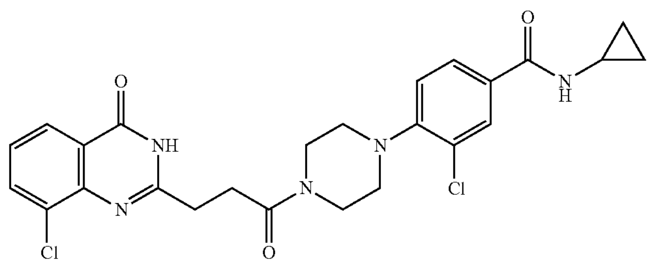 [SMILES: O=C(NC1CC1)c1ccc(N2CCN(C(=O)CCc3nc4c(Cl)cccc4c(=O)[nH]3)CC2)c(Cl)c1] | 27 | 181 | 909 |
| Ex. 2 | 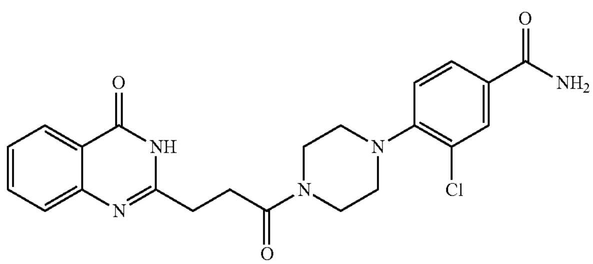 [SMILES: NC(=O)c1ccc(N2CCN(C(=O)CCc3nc4ccccc4c(=O)[nH]3)CC2)c(Cl)c1] | 7 | 69 | |
| Ex. 3 | 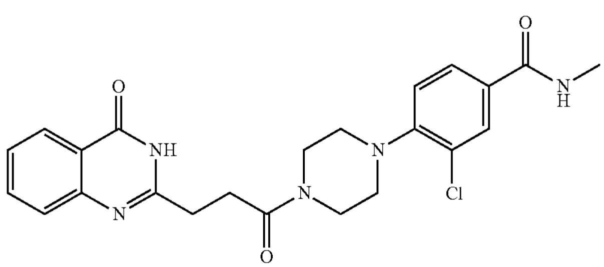 [SMILES: CNC(=O)c1ccc(N2CCN(C(=O)CCc3nc4ccccc4c(=O)[nH]3)CC2)c(Cl)c1] | 16 | 196 | 1322 |
| Ex. 4 | 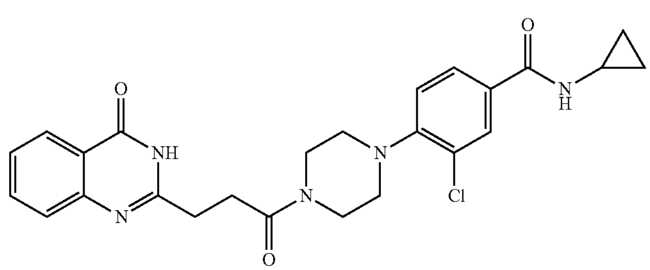 [SMILES: O=C(NC1CC1)c1ccc(N2CCN(C(=O)CCc3nc4ccccc4c(=O)[nH]3)CC2)c(Cl)c1] | 26 | | 1658 |
| Ex. 5 | 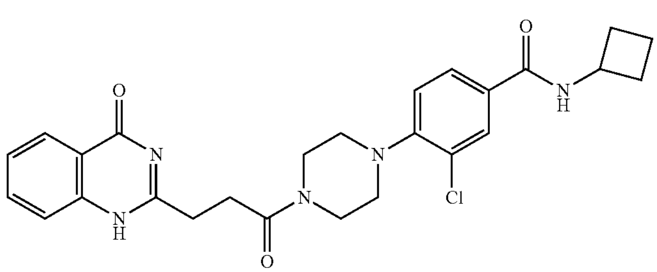 [SMILES: O=C(NC1CCC1)c1ccc(N2CCN(C(=O)CCc3nc(=O)c4ccccc4[nH]3)CC2)c(Cl)c1] | 51 | | 1096 |

-continued
| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 6 | 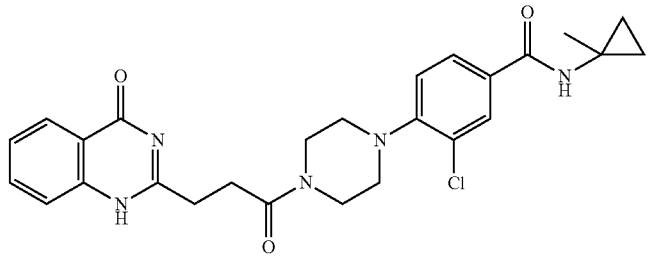 [SMILES: CC1(NC(=O)c2ccc(N3CCN(C(=O)CCc4nc(=O)c5ccccc5[nH]4)CC3)c(Cl)c2)CC1] | 29 | | 1271 |
| Ex. 7 | 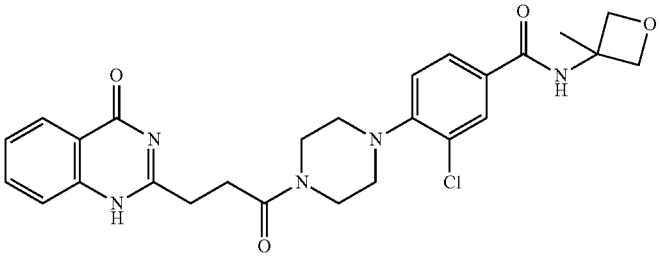 [SMILES: CC1(NC(=O)c2ccc(N3CCN(C(=O)CCc4nc(=O)c5ccccc5[nH]4)CC3)c(Cl)c2)COC1] | 30 | | 2630 |
| Ex. 8 | 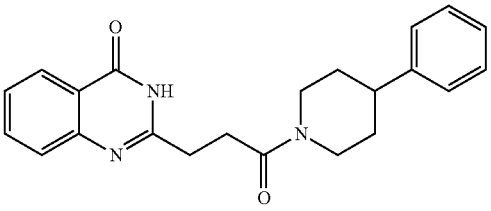 [SMILES: O=C(CCc1nc2ccccc2c(=O)[nH]1)N1CCC(c2ccccc2)CC1] | 325 | | |
| Ex. 9 | 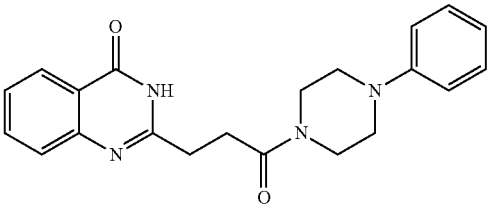 [SMILES: O=C(CCc1nc2ccccc2c(=O)[nH]1)N1CCN(c2ccccc2)CC1] | 160 | | |
| Ex. 10 | 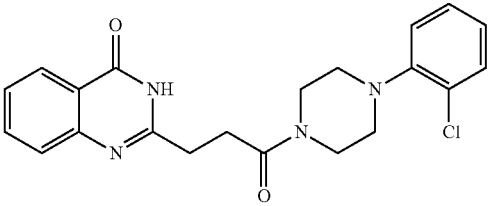 [SMILES: O=C(CCc1nc2ccccc2c(=O)[nH]1)N1CCN(c2ccccc2Cl)CC1] | 180 | | |
| Ex. 11 | 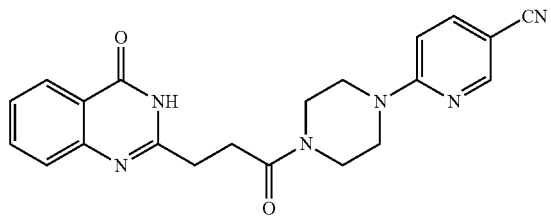 [SMILES: N#Cc1ccc(N2CCN(C(=O)CCc3nc4ccccc4c(=O)[nH]3)CC2)nc1] | 6 | 338 | 50 |

-continued

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 12 | 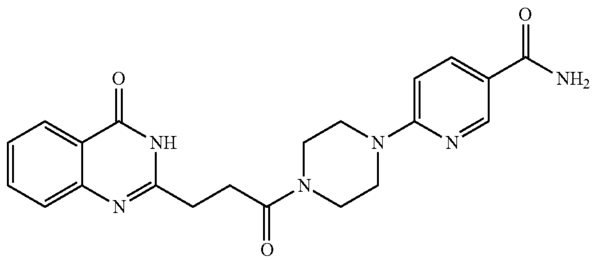 [SMILES: NC(=O)c1ccc(N2CCN(C(=O)CCc3nc4ccccc4c(=O)[nH]3)CC2)nc1] | 25 | | |
| Ex. 13 | 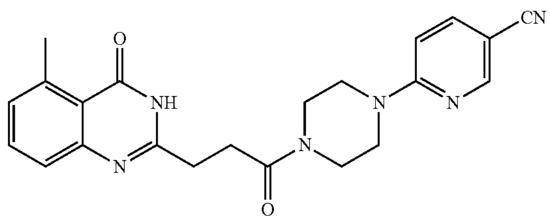 [SMILES: Cc1cccc2nc(CCC(=O)N3CCN(c4ccc(C#N)cn4)CC3)[nH]c(=O)c12] | 54 | | |
| Ex. 14 | 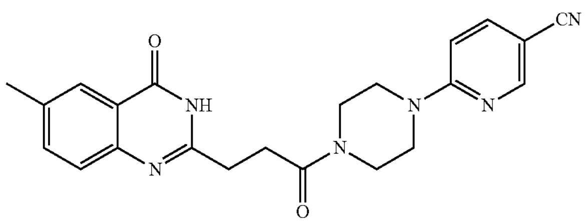 [SMILES: Cc1ccc2nc(CCC(=O)N3CCN(c4ccc(C#N)cn4)CC3)[nH]c(=O)c2c1] | 23 | | 974 |
| Ex. 15 | 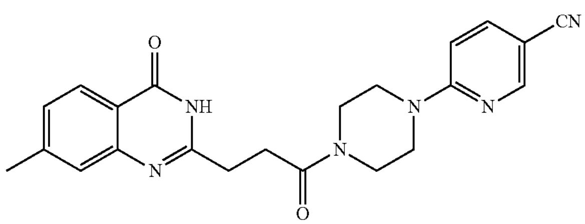 [SMILES: Cc1ccc2c(=O)[nH]c(CCC(=O)N3CCN(c4ccc(C#N)cn4)CC3)nc2c1] | 196 | | |
| Ex. 16 | 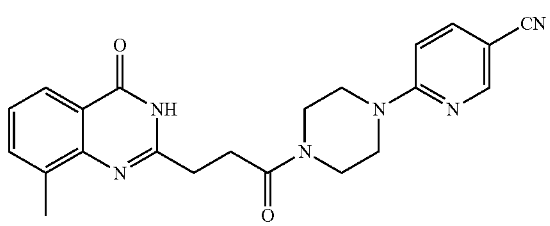 [SMILES: Cc1cccc2c(=O)[nH]c(CCC(=O)N3CCN(c4ccc(C#N)cn4)CC3)nc12] | 7 | 40 | 163 |
| Ex. 17 | 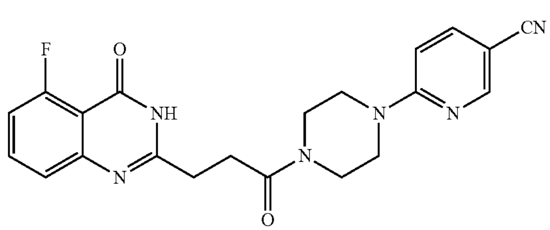 [SMILES: N#Cc1ccc(N2CCN(C(=O)CCc3nc4cccc(F)c4c(=O)[nH]3)CC2)nc1] | 8 | 215 | 16 |

-continued

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 18 | 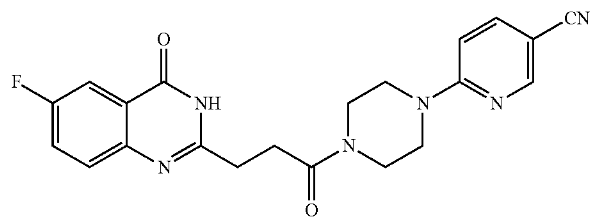 [SMILES: N#Cc1ccc(N2CCN(C(=O)CCc3nc4ccc(F)cc4c(=O)[nH]3)CC2)nc1] | 7 | 216 | 24 |
| Ex. 19 | 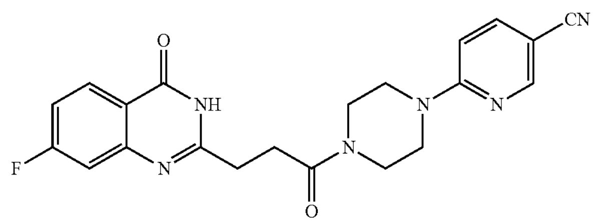 [SMILES: N#Cc1ccc(N2CCN(C(=O)CCc3nc4cc(F)ccc4c(=O)[nH]3)CC2)nc1] | 83 | | |
| Ex. 20 | 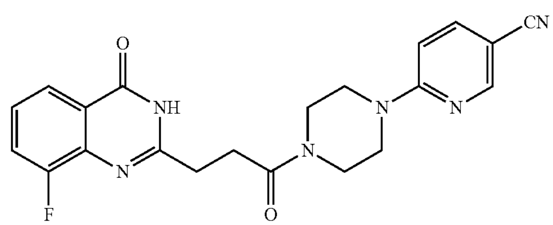 [SMILES: N#Cc1ccc(N2CCN(C(=O)CCc3nc4c(F)cccc4c(=O)[nH]3)CC2)nc1] | 12 | | 288 |
| Ex. 21 | 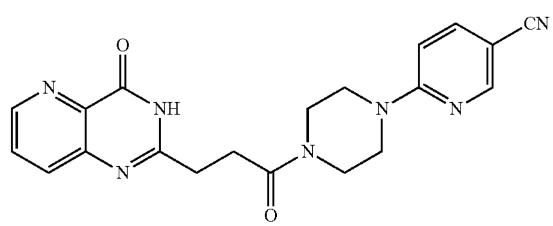 [SMILES: N#Cc1ccc(N2CCN(C(=O)CCc3nc4cccnc4c(=O)[nH]3)CC2)nc1] | 99 | | |
| Ex. 22 | 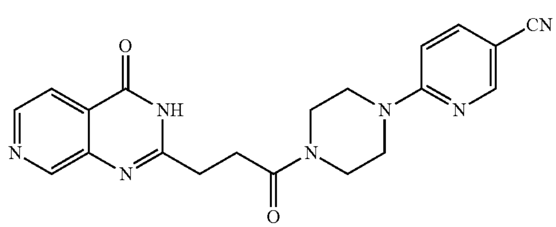 [SMILES: N#Cc1ccc(N2CCN(C(=O)CCc3nc4cnccc4c(=O)[nH]3)CC2)nc1] | 395 | | |
| Ex. 23 | 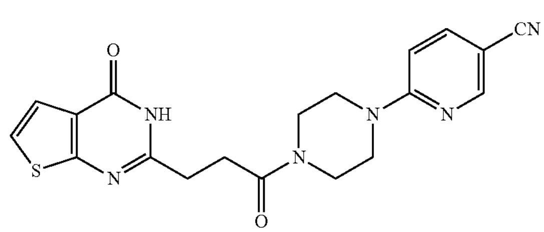 [SMILES: N#Cc1ccc(N2CCN(C(=O)CCc3nc4sccc4c(=O)[nH]3)CC2)nc1] | 35 | 10294 | 552 |

-continued

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 24 | 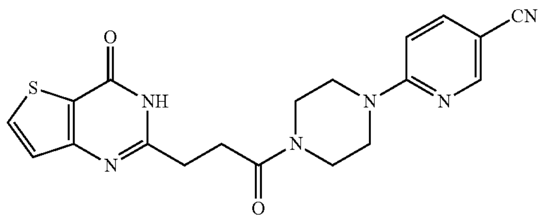 [SMILES: N#Cc1ccc(N2CCN(C(=O)CCc3nc4ccsc4c(=O)[nH]3)CC2)nc1] | 11 | 1591 | 341 |
| Ex. 25 | 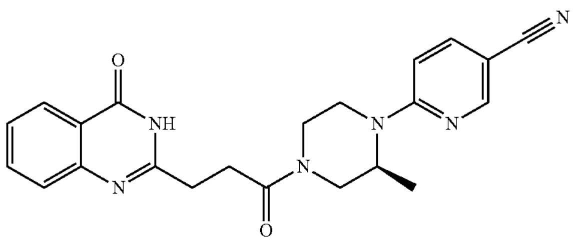 [SMILES: C[C@H]1CN(C(=O)CCc2nc3ccccc3c(=O)[nH]2)CCN1c1ccc(C#N)cn1] | 70 | | |
| Ex. 26 | 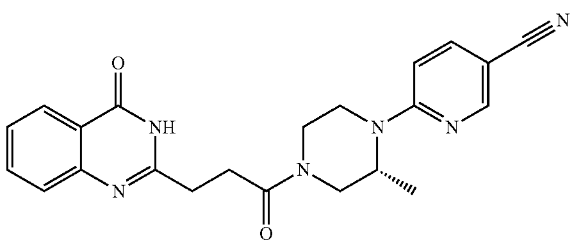 [SMILES: C[C@@H]1CN(C(=O)CCc2nc3ccccc3c(=O)[nH]2)CCN1c1ccc(C#N)cn1] | 47 | | 770 |
| Ex. 27 | 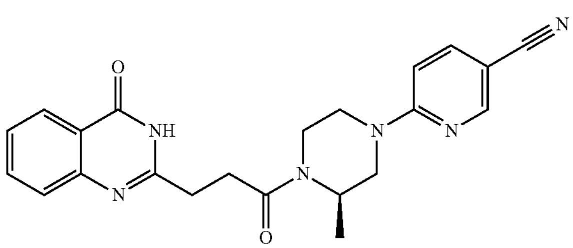 [SMILES: C[C@@H]1CN(c2ccc(C#N)cn2)CCN1C(=O)CCc1nc2ccccc2c(=O)[nH]1] | 94 | | |
| Ex. 28 | 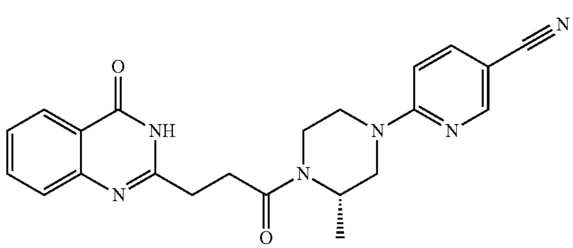 [SMILES: C[C@H]1CN(c2ccc(C#N)cn2)CCN1C(=O)CCc1nc2ccccc2c(=O)[nH]1] | 10 | 910 | 138 |
| Ex. 29 | 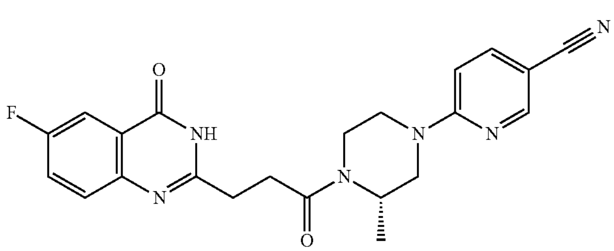 [SMILES: C[C@H]1CN(c2ccc(C#N)cn2)CCN1C(=O)CCc1nc2ccc(F)cc2c(=O)[nH]1] | 12 | 611 | 156 |

-continued

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 30 | 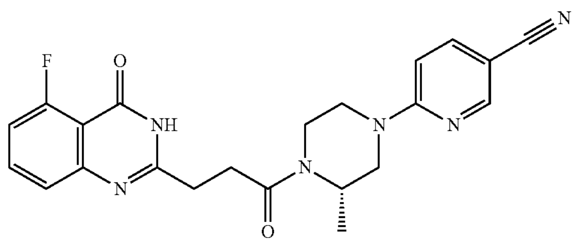 [SMILES: C[C@H]1CN(c2ccc(C#N)cn2)CCN1C(=O)CCc1nc2cccc(F)c2c(=O)[nH]1] | 12 | 624 | 110 |
| Ex. 31 | 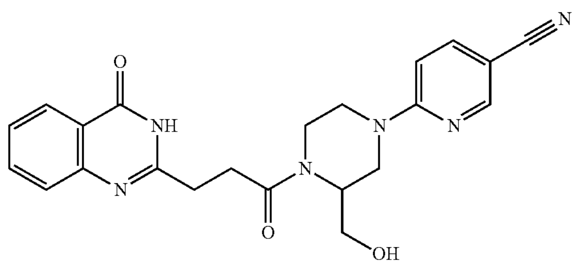 [SMILES: N#Cc1ccc(N2CCN(C(=O)CCc3nc4ccccc4c(=O)[nH]3)C(CO)C2)nc1] | 6 | 42 | 440 |
| Ex. 32 | 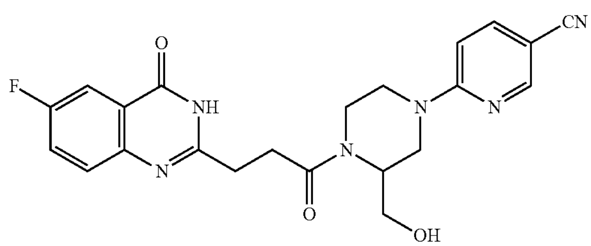 [SMILES: N#Cc1ccc(N2CCN(C(=O)CCc3nc4ccc(F)cc4c(=O)[nH]3)C(CO)C2)nc1] | 5 | | 1232 |
| Ex. 33 | 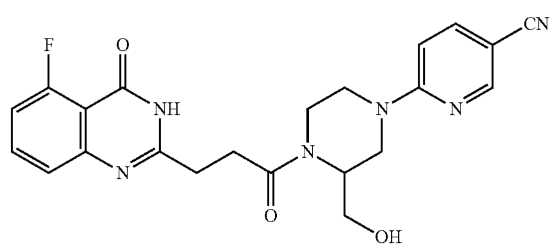 [SMILES: N#Cc1ccc(N2CCN(C(=O)CCc3nc4cccc(F)c4c(=O)[nH]3)C(CO)C2)nc1] | 7 | | 2736 |
| Ex. 34 | 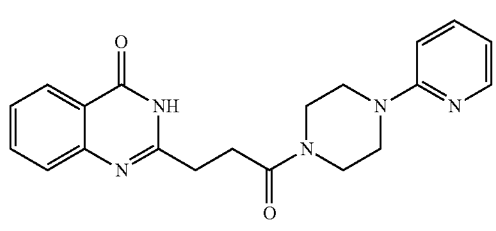 [SMILES: O=C(CCc1nc2ccccc2c(=O)[nH]1)N1CCN(c2ccccn2)CC1] | 54 | | |
| Ex. 35 | 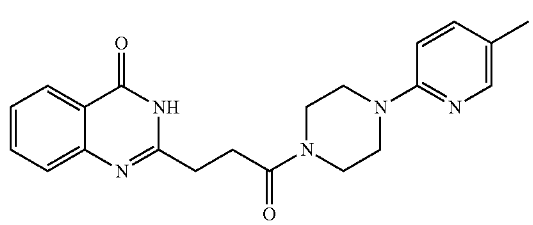 [SMILES: Cc1ccc(N2CCN(C(=O)CCc3nc4ccccc4c(=O)[nH]3)CC2)nc1] | 35 | | 562 |

-continued

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 36 | 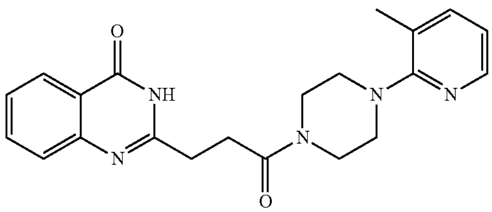 [SMILES: Cc1cccnc1N1CCN(C(=O)CCc2nc3ccccc3c(=O)[nH]2)CC1] | 120 | | |
| Ex. 37 | 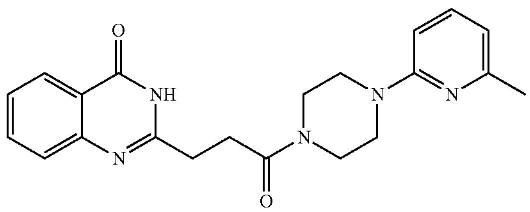 [SMILES: Cc1cccc(N2CCN(C(=O)CCc3nc4ccccc4c(=O)[nH]3)CC2)n1] | 359 | | |
| Ex. 38 | 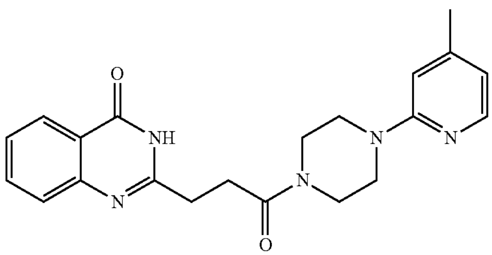 [SMILES: Cc1ccnc(N2CCN(C(=O)CCc3nc4ccccc4c(=O)[nH]3)CC2)c1] | 129 | | |
| Ex. 39 | 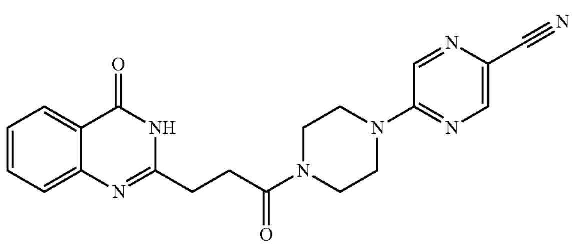 [SMILES: N#Cc1cnc(N2CCN(C(=O)CCc3nc4ccccc4c(=O)[nH]3)CC2)cn1] | 14 | 468 | 754 |
| Ex. 40 | 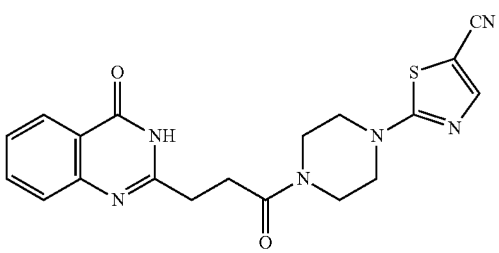 [SMILES: N#Cc1cnc(N2CCN(C(=O)CCc3nc4ccccc4c(=O)[nH]3)CC2)s1] | 53 | | 1502 |
| Ex. 41 | 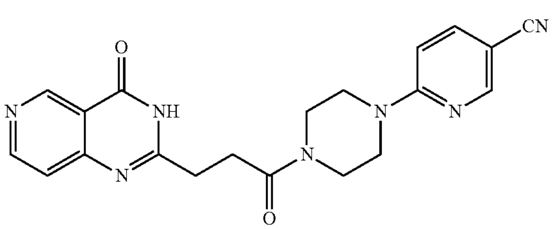 [SMILES: N#Cc1ccc(N2CCN(C(=O)CCc3nc4ccncc4c(=O)[nH]3)CC2)nc1] | 97 | | |

-continued

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 42 | 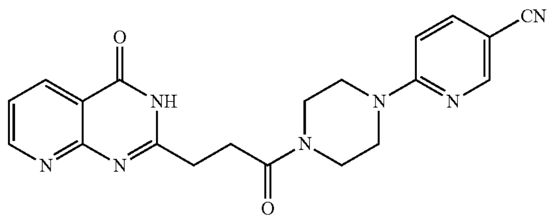 [SMILES: N#Cc1ccc(N2CCN(C(=O)CCc3nc4ncccc4c(=O)[nH]3)CC2)nc1] | 58 | | 12271 |
| Ex. 43 | 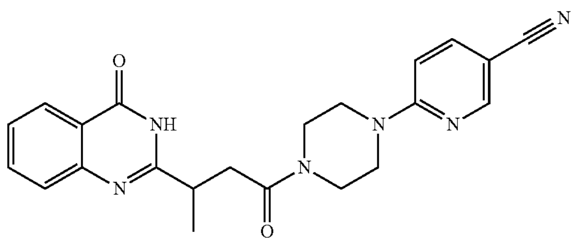 [SMILES: CC(CC(=O)N1CCN(c2ccc(C#N)cn2)CC1)c1nc2ccccc2c(=O)[nH]1] | 42 | 3817 | 440 |
| Ex. 44 | 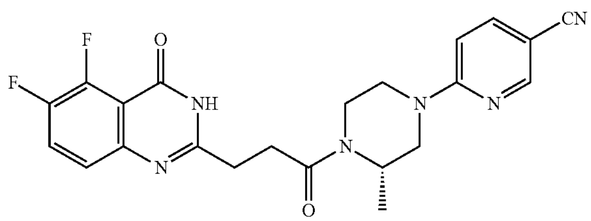 [SMILES: C[C@H]1CN(c2ccc(C#N)cn2)CCN1C(=O)CCc1nc2ccc(F)c(F)c2c(=O)[nH]1] | 11 | | 345 |
| Ex. 45 | 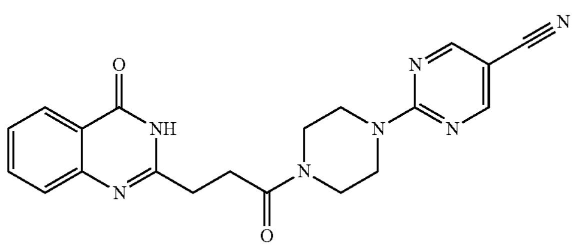 [SMILES: N#Cc1cnc(N2CCN(C(=O)CCc3nc4ccccc4c(=O)[nH]3)CC2)nc1] | 92 | | |
| Ex. 46 | 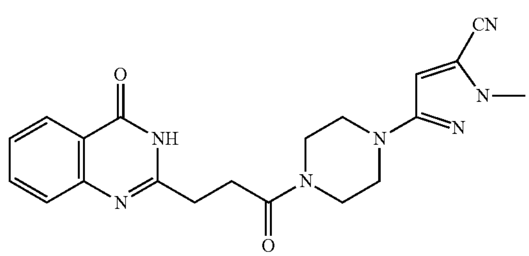 [SMILES: CN/C(C#N)=C\C(=N)N1CCN(C(=O)CCc2nc3ccccc3c(=O)[nH]2)CC1] | 278 | | |
| Ex. 47 | 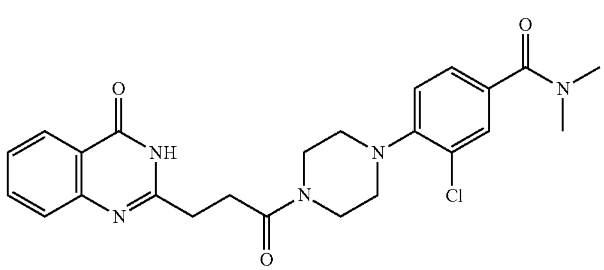 [SMILES: CN(C)C(=O)c1ccc(N2CCN(C(=O)CCc3nc4ccccc4c(=O)[nH]3)CC2)c(Cl)c1] | 922 | | |

-continued

| Example No. | Structure | Avg. PARP-1 IC$_{50}$ (top conc. 10 uM) (nM) | Avg. PARP-2 IC$_{50}$ (top conc. 10 uM) (nM) | H$_2$O$_2$ NAD$^+$ HeLa cellular assy EC$_{50}$ (nM) |
|---|---|---|---|---|
| Ex. 48 | 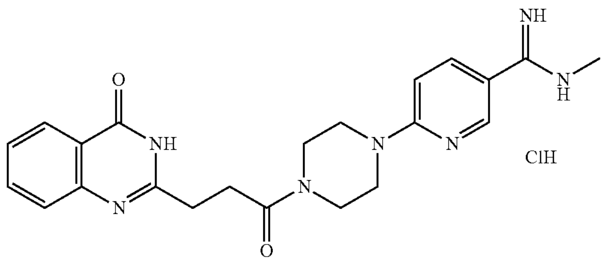 [SMILES: CNC(=N)c1ccc(N2CCN(C(=O)CCc3nc4ccccc4c(=O)[nH]3)CC2)nc1 ; Cl] | 30 | | 7564 |
| Ex. 49 | 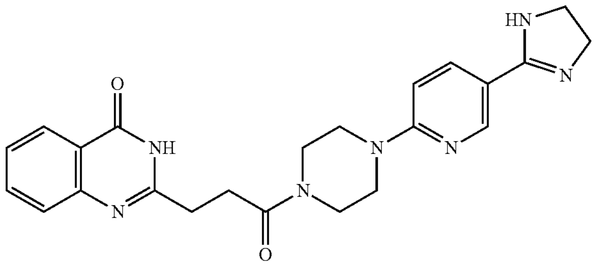 [SMILES: O=C(CCc1nc2ccccc2c(=O)[nH]1)N1CCN(c2ccc(C3=NCCN3)cn2)CC1] | 36 | | 22383 |
| Ex. 50 | 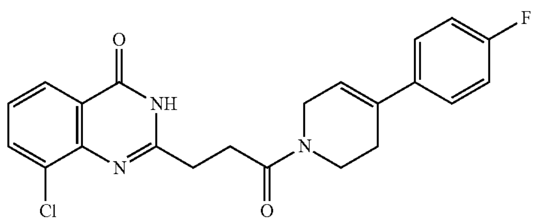 [SMILES: O=C(CCc1nc2c(Cl)cccc2c(=O)[nH]1)N1CC=C(c2ccc(F)cc2)CC1] | 255 | | |
| Ex. 51 | 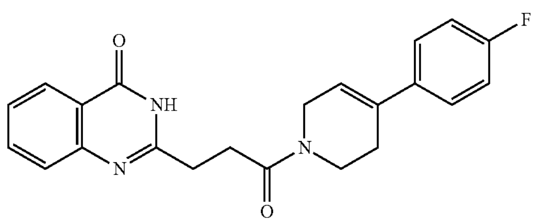 [SMILES: O=C(CCc1nc2ccccc2c(=O)[nH]1)N1CC=C(c2ccc(F)cc2)CC1] | 83 | 339 | |
| Ex. 52 | 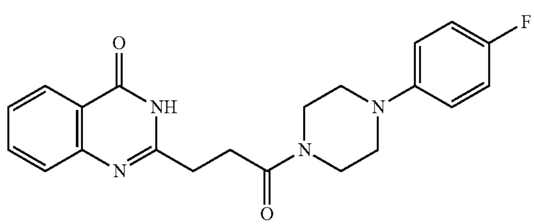 [SMILES: O=C(CCc1nc2ccccc2c(=O)[nH]1)N1CCN(c2ccc(F)cc2)CC1] | 68 | 999 | |
| Ex. 53 | 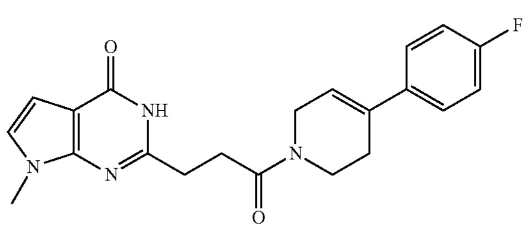 [SMILES: Cn1ccc2c(=O)[nH]c(CCC(=O)N3CC=C(c4ccc(F)cc4)CC3)nc21] | 189 | | |

173

Example 56 Acute Kidney Injury (AKI) Rat Model

Animals, surgery and dosing: Sprague-Dawley male rats weighing approximately 300-350 g, with ad libitum access to standard feed and water were used in these experiments. Rats were anesthetized with isoflurane and placed ventrally on a temperature controlled heated surgical platform. A skin incision was made on the dorsal surface, exposing both kidneys through flank incisions. Vascular clips were applied to both renal pedicles and occlusion lasted 45 minutes. After 45 min, the clips were removed, kidneys were monitored for successful reperfusion, and surgical sites were sutured. The sham-operated group was subjected to similar surgical procedures, except that the occluding clamp was not applied. Compounds were formulated as a fresh daily clear solution of Example 29 or Example 30 in N-methyl pyrrolidone:PEG300:Propylene glycol:normal saline (10:30:20:40). Compounds or vehicle were IV dosed via tail vein at 15 mg/kg (3 mL/kg) 4 hours after reperfusion on day of surgery. On day 1 (day after surgery) animals were administered vehicle or 15 mg/kg of Example 29 or Example 30 (3 mL/kg IV) at the start of the light cycle. Sham surgery control animals were similarly dosed with vehicle.

Plasma collection and biomarker measurement: Twenty-four (24) hours after reperfusion, blood was collected in K2 EDTA tubes by retro-orbital bleeding from all groups under mild isoflurane anesthesia. Plasma was separated by centrifugation at 3000 rpm for 10 minutes at 4° C. Plasma creatinine and blood urea nitrogen (BUN) were analyzed using a fully automated clinical biochemistry analyzer (Siemens Dimension® Xpand® Plus Integrated Chemistry System)

Data Analysis and Statistical analysis: GraphPad Prism software, Version 6.05 was used for graphing and statistical testing. Creatinine and BUN were tested for normal distribution in all groups via a D'Agostino-Pearson omnibus normality test or a Shapiro-Wilk normality test. Statistical significance (p<0.05) was determined by a student's t-test comparing sham-vehicle to IR-vehicle or IR-vehicle to Compound treated group. ##p<0.01, ###p<0.001, ####p<0.0001 Sham vs. IR vehicle; *p<0.05, **p<0.01 IR-vehicle vs. compound treated group (Example 29 or Example 30).

Results: PARP1-inhibitors Example 29 and Example 30, dosed IV after ischemia-reperfusion, reduced kidney injury. Both compounds significantly reduced plasma creatinine and BUN when dosed at 15 mg/kg (FIG. 1).

Example 57 In Vitro and In Vivo Micronucleus Assay

Certain compounds of this invention showed no clastogenic activity at the in vitro and/or in vivo micronucleus assay.

What is claimed is:

1. A method of treating cell death in a subject after surgery, comprising administering to the subject an effective amount of a compound, or a pharmaceutically acceptable salt thereof, or a pharmaceutical composition comprising the compound, or a pharmaceutically acceptable salt thereof, and a pharmaceutically acceptable carrier; and wherein said compound is represented by the following structural formula:

174

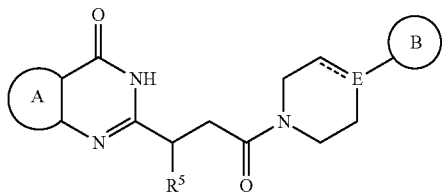

or a pharmaceutically acceptable salt thereof, wherein:
Ring A is phenyl or 5-6 membered heteroaryl; each of which is optionally substituted with one or two substituents selected from the group consisting of -halogen, —CN, —NO$_2$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, —C(=O)R$^b$, halo(C$_1$-C$_5$)alkyl and (C$_1$-C$_5$)alkyl, wherein the (C$_1$-C$_5$)alkyl is optionally substituted one or two groups selected from —CN, —NO$_2$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, and —C(=O)R$^a$;
each R$^a$ and each R$^b$ are independently selected from —H and (C$_1$-C$_5$)alkyl optionally substituted with hydroxyl or (C$_1$-C$_3$)alkoxy;
R$^c$ is —H, halo(C$_1$-C$_5$)alkyl or (C$_1$-C$_5$)alkyl, wherein the (C$_1$-C$_5$)alkyl is optionally substituted with hydroxyl or (C$_1$-C$_3$)alkoxy;
i is 0, 1, or 2;
Ring B is phenyl, 5-6 membered heteroaryl or 5-6 membered heterocyclyl, each optionally substituted with one or two substituents represented by R$^3$;
----- is absent or a bond;
E is N or CH when ----- is absent or E is C when ----- is a bond;

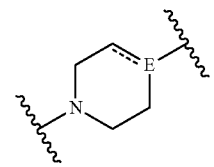

is optionally substituted with (C$_1$-C$_5$)alkyl or hydroxy (C$_1$-C$_5$)alkyl;
each R$^3$ is independently selected from the group consisting of -halogen, —CN, —NO$_2$, —OR$^d$, —S(O)$_i$R$^e$, —C(=NR$^e$)NR$^e$R$^f$, —NR$^e$S(O)$_i$R$^f$, —S(O)$_i$NR$^e$R$^f$, —C(=O)OR$^e$, —OC(=O)OR$^e$, —C(=S)OR$^e$, —O(C=S)R$^e$, —C(=O)NR$^e$R$^f$, —NR$^e$C(=O)R$^f$, —C(=S)NR$^e$R$^f$, —NR$^e$C(=S)R$^f$, —NR$^e$(C=O)OR$^f$, —O(C=O)NR$^e$R$^f$, —NR$^e$(C=S)OR$^f$, —O(C=S)NR$^e$R$^f$, —NR$^e$(C=O)NR$^e$R$^f$, —NR$^e$(C=S)NR$^e$R$^f$, —C(=S)R$^e$, —C(=O)R$^e$, halo(C$_1$-C$_5$)alkyl, and (C$_1$-C$_5$)alkyl, wherein the (C$_1$-C$_5$)alkyl represented by $R^3$ is optionally substituted with —CN, —$NO_2$, —$OR^e$, —$NR^eR^f$, —$S(O)_iR^e$, —$NR^eS(O)_iR^f$, —$S(O)_iNR^eR^f$, —$C(=O)OR^e$, —$OC(=O)OR^e$, —$C(=S)OR^e$, —$O(C=S)R^e$, —$C(=O)NR^eR^f$, —$NR^eC(=O)R^f$, —$C(=S)NR^eR^f$, —$NR^eC(=S)R^f$, —$NR^e(C=O)OR^f$, —$O(C=O)NR^eR^f$, —$NR^e(C=S)OR^f$, —$O(C=S)NR^eR^f$, —$NR^e(C=O)NR^eR^f$, —$NR^e(C=S)NR^eR^f$, —$C(=S)R^e$, or —$C(=O)R^e$;

$R^d$ is —H, halo($C_1$-$C_5$)alkyl or ($C_1$-$C_5$)alkyl, wherein the ($C_1$-$C_5$)alkyl is optionally substituted with hydroxyl or ($C_1$-$C_3$)alkoxy;

each $R^e$ is independently selected from the group consisting of —H and ($C_1$-$C_5$)alkyl optionally substituted with hydroxyl or ($C_1$-$C_3$)alkoxy;

each $R^f$ is independently selected from the group consisting of —H, ($C_1$-$C_5$)alkyl optionally substituted with hydroxyl or ($C_1$-$C_3$)alkoxy, ($C_3$-$C_6$)cycloalkyl optionally substituted with ($C_1$-$C_2$) alkyl, and 4-6 membered oxygen-containing heterocyclyl optionally substituted with ($C_1$-$C_2$) alkyl; or —$NR^eR^f$ taken together is a 4-6 membered heterocyclyl optionally substituted with ($C_1$-$C_2$) alkyl; or —$C(=NR^e)NR^eR^f$ taken together is a 4-6 membered heterocyclyl optionally substituted with $R^e$;

$R^5$ is —H or ($C_1$-$C_5$)alkyl; and i is 0, 1, or 2, wherein 5-6 membered heteroaryl refers to a monocyclic aromatic ring group having five or six ring atoms selected from carbon and 1 to 4 heteroatoms selected from oxygen, nitrogen and sulfur; and 5-6 membered heterocyclyl refers to a monocyclic non-aromatic ring radical containing 5-6 ring atoms selected from carbon atom and 1 or 2 heteroatoms, each heteroatom is independently selected from nitrogen, quaternary nitrogen, oxidized nitrogen (NO), oxygen, sulfur, sulfoxide and sulfone.

2. The method of claim 1, wherein said compound, said pharmaceutically acceptable salt thereof, or said pharmaceutical composition is administered orally.

3. The method of claim 1, wherein the compound is represented by the following structural formula:

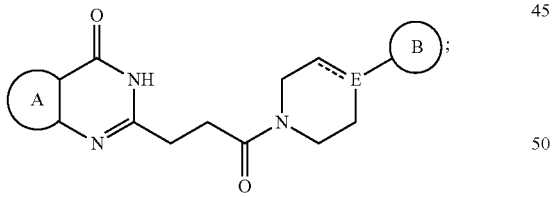

or a pharmaceutically acceptable salt thereof, wherein:

Ring A is phenyl or 5-6 membered heteroaryl; each of which is optionally substituted with one or two substituents selected from the group consisting of -halogen, —CN, —$NO_2$, —$NR^aR^b$, —$S(O)_iR^a$, —$NR^aS(O)_iR^b$, —$S(O)_iNR^aR^b$, —$C(=O)OR^a$, —$OC(=O)OR^a$, —$C(=S)OR^a$, —$O(C=S)R^a$, —$C(=O)NR^aR^b$, —$NR^aC(=O)R^b$, —$C(=S)NR^aR^b$, —$NR^aC(=S)R^b$, —$NR^a(C=O)OR^b$, —$O(C=O)NR^aR^b$, —$NR^a(C=S)OR^b$, —$O(C=S)NR^aR^b$, —$NR^a(C=O)NR^aR^b$, —$NR^a(C=S)NR^aR^b$, —$C(=S)R^a$, —$C(=O)R^b$, halo($C_1$-$C_5$)alkyl and ($C_1$-$C_5$)alkyl, wherein the ($C_1$-$C_5$)alkyl is optionally substituted one or two groups selected from —CN, —$NO_2$, —$NR^aR^b$, —$S(O)_iR^a$, —$NR^aS(O)_iR^b$, —$S(O)_iNR^aR^b$, —$C(=O)OR^a$, —$OC(=O)OR^a$, —$C(=S)OR^a$, —$O(C=S)R^a$, —$C(=O)NR^aR^b$, —$NR^aC(=O)R^b$, —$C(=S)NR^aR^b$, —$NR^aC(=S)R^b$, —$NR^a(C=O)OR^b$, —$O(C=O)NR^aR^b$, —$NR^a(C=S)OR^b$, —$O(C=S)NR^aR^b$, —$NR^a(C=O)NR^aR^b$, —$NR^a(C=S)NR^aR^b$, —$C(=S)R^a$, and —$C(=O)R^a$;

each $R^a$ and each $R^b$ are independently selected from —H and ($C_1$-$C_5$)alkyl optionally substituted with hydroxyl or ($C_1$-$C_3$)alkoxy;

$R^e$ is —H, halo($C_1$-$C_5$)alkyl or ($C_1$-$C_5$)alkyl, wherein the ($C_1$-$C_5$)alkyl is optionally substituted with hydroxyl or ($C_1$-$C_3$)alkoxy;

i is 0, 1, or 2;

Ring B is phenyl, 5-6 membered heteroaryl or 5-6 membered heterocyclyl, each optionally substituted with one or two substituents represented by $R^3$;

----- is absent or a bond;

E is N or CH when ----- is absent or E is C when ----- is a bond;

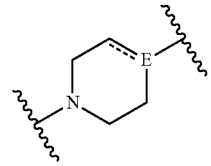

is optionally substituted with ($C_1$-$C_5$)alkyl or hydroxy ($C_1$-$C_5$)alkyl;

each $R^3$ is independently selected from the group consisting of -halogen, —CN, —$NO_2$, —$OR^d$, —$S(O)_iR^e$, —$C(=NR^e)NR^eR^f$, —$NR^eS(O)_iR^f$, —$S(O)_iNR^eR^f$, —$C(=O)OR^e$, —$OC(=O)OR^e$, —$C(=S)OR^e$, —$O(C=S)R^e$, —$C(=O)NR^eR^f$, —$NR^eC(=O)R^f$, —$C(=S)NR^eR^f$, —$NR^eC(=S)R^f$, —$NR^e(C=O)OR^f$, —$O(C=O)NR^eR^f$, —$NR^e(C=S)OR^f$, —$O(C=S)NR^eR^f$, —$NR^e(C=O)NR^eR^f$, —$NR^e(C=S)NR^eR^f$, —$C(=S)R^e$, —$C(=O)R^e$, halo($C_1$-$C_5$)alkyl and ($C_1$-$C_5$)alkyl, wherein the ($C_1$-$C_5$)alkyl represented by $R^3$ is optionally substituted with —CN, —$NO_2$, —$OR^e$, —$NR^eR^f$, —$S(O)_iR^e$, —$NR^eS(O)_iR^f$, —$S(O)_iNR^eR^f$, —$C(=O)OR^e$, —$OC(=O)OR^e$, —$C(=S)OR^e$, —$O(C=S)R^e$, —$C(=O)NR^eR^f$, —$NR^eC(=O)R^f$, —$C(=S)NR^eR^f$, —$NR^eC(=S)R^f$, —$NR^e(C=O)OR^f$, —$O(C=O)NR^eR^f$, —$NR^e(C=S)OR^f$, —$O(C=S)NR^eR^f$, —$NR^e(C=O)NR^eR^f$, —$NR^e(C=S)NR^eR^f$, —$C(=S)R^e$, or —$C(=O)R^e$;

$R^d$ is —H, halo($C_1$-$C_5$)alkyl or ($C_1$-$C_5$)alkyl, wherein the ($C_1$-$C_5$)alkyl is optionally substituted with hydroxyl or ($C_1$-$C_3$)alkoxy;

each $R^e$ is independently selected from the group consisting of —H and ($C_1$-$C_5$)alkyl optionally substituted with hydroxyl or ($C_1$-$C_3$)alkoxy;

each $R^f$ is independently selected from the group consisting of —H, ($C_1$-$C_5$)alkyl optionally substituted with hydroxyl or ($C_1$-$C_3$)alkoxy, ($C_3$-$C_6$)cycloalkyl optionally substituted with ($C_1$-$C_2$) alkyl, and 4-6 membered oxygen-containing heterocyclyl optionally substituted with ($C_1$-$C_2$) alkyl; or —$NR^eR^f$ taken together is a 4-6 membered heterocyclyl optionally substituted with ($C_1$-$C_2$) alkyl; or C(=NR$^e$)NR$^e$R$^f$ taken together is a 4-6 membered heterocyclyl optionally substituted with R$^e$; and i is 0, 1, or 2.

4. The method of claim 3, wherein the compound is represented by the following structural formula:

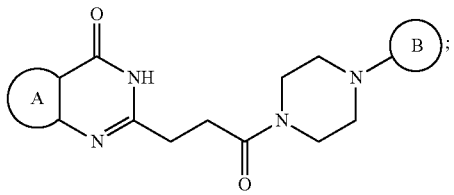

or a pharmaceutically acceptable salt thereof, wherein:

Ring A is phenyl or 5-6 membered heteroaryl; each of which is optionally substituted with one or two substituents selected from the group consisting of -halogen, —CN, —NO$_2$, —OR$^e$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, —C(=O)R$^a$, halo(C$_1$-C$_5$)alkyl and (C$_1$-C$_5$)alkyl, wherein the (C$_1$-C$_5$)alkyl is optionally substituted one or two groups selected from —CN, —NO$_2$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, and —C(=O)R$^a$;

each R$^a$ and each R$^b$ are independently selected from —H and (C$_1$-C$_5$)alkyl optionally substituted with hydroxyl or (C$_1$-C$_3$)alkoxy;

R$^c$ is —H, halo(C$_1$-C$_5$)alkyl or (C$_1$-C$_5$)alkyl, wherein the (C$_1$-C$_5$)alkyl is optionally substituted with hydroxyl or (C$_1$-C$_3$)alkoxy;

i is 0, 1, or 2;

Ring B is phenyl, 5-6 membered heteroaryl or 5-6 membered heterocyclyl, each optionally substituted with one or two substituents represented by R$^3$; and

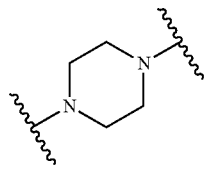 [SMILES: *N1CCN(*)CC1]

is optionally substituted with (C$_1$-C$_5$)alkyl or hydroxy(C$_1$-C$_5$)alkyl.

5. The method of claim 1, wherein the compound is represented by a structural formula selected from the group consisting of:

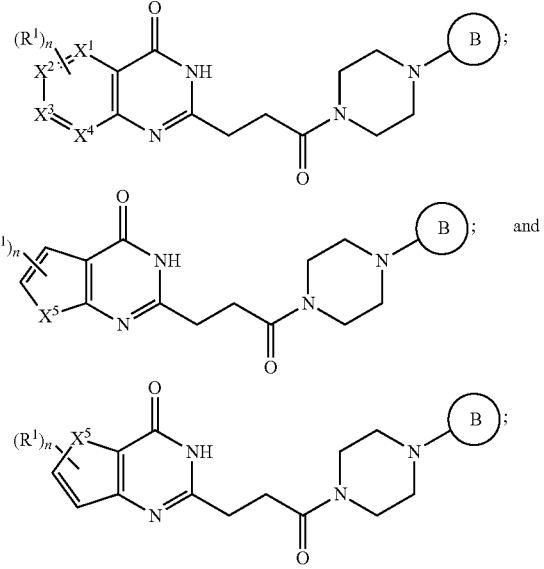

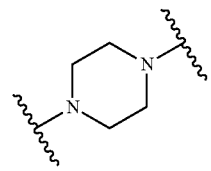 [SMILES: *N1CCN(*)CC1]

or a pharmaceutically acceptable salt thereof, wherein:

X$^1$, X$^2$, X$^3$ and X$^4$ are each independently selected from the group consisting of N and CH, provided no more than two of X$^1$, X$^2$, X$^3$ and X$^4$ is N;

X$^5$ is NR$^2$, O, or S;

Ring B is phenyl, 5-6 membered heteroaryl or 5-6 membered heterocyclyl, each optionally substituted with one or two substituents represented by R$^3$;

is optionally substituted with (C$_1$-C$_5$)alkyl or hydroxy(C$_1$-C$_5$)alkyl;

each R$^1$ is independently selected from the group consisting of -halogen, —CN, —NO$_2$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, —C(=O)R$^b$, halo(C$_1$-C$_5$)alkyl and (C$_1$-C$_5$)alkyl, wherein the (C$_1$-C$_5$)alkyl represented by R$^1$ is optionally substituted with —CN, —NO$_2$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, or —C(=O)R$^a$;

R$^2$ is —H, C$_1$-5 alkyl, phenyl, —C(O)(C$_1$-C$_5$ alkyl), —C(O)(phenyl), —C(O)O(C$_1$-5 alkyl), —C(O)O (phenyl), —S(O)$_2$(C$_1$-C$_5$ alkyl) or —S(O)$_2$(phenyl), wherein each alkyl in the groups represented by R$^2$ independently is optionally substituted with one or two substituents selected from the group consisting of halogen, hydroxy, cyano, phenyl, 5-6 membered heteroaryl, $(C_1-C_5)$ alkoxy, and halo$(C_1-C_5)$alkoxy, and wherein each phenyl in the groups represented by $R^2$ independently is optionally substituted with one or two substituents selected from the group consisting of halogen, hydroxy, nitro, cyano, amino, $(C_1-C_5)$alkyl, halo$(C_1-C_5)$alkyl, $(C_1-C_5)$alkoxy and halo$(C_1-C_5)$alkoxy;

each $R^a$ and each $R^b$ are independently selected from —H and $(C_1-C_5)$alkyl optionally substituted with hydroxyl or $(C_1-C_3)$alkoxy;

$R^c$ is —H, halo$(C_1-C_5)$alkyl or $(C_1-C_5)$alkyl, wherein the $(C_1-C_5)$alkyl is optionally substituted with hydroxyl or $(C_1-C_3)$alkoxy;

i is 0, 1, or 2; and n is 0, 1 or 2.

6. The method of claim 1, wherein the compound is represented by a structural formula selected from the group consisting of:

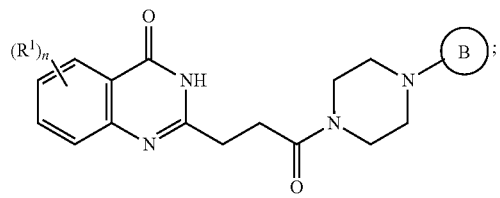

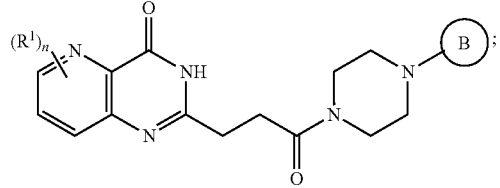

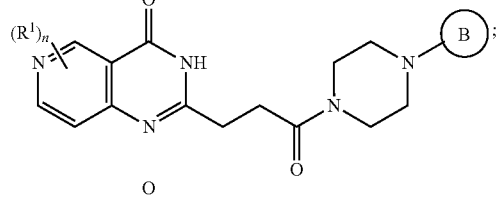

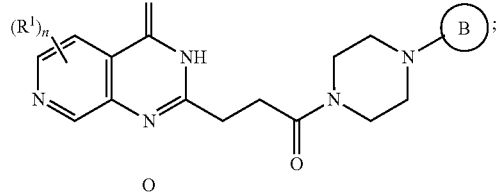

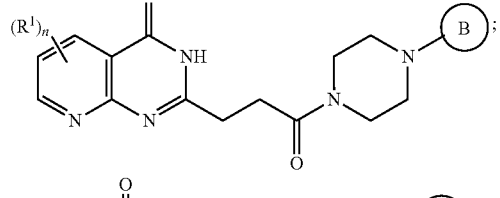

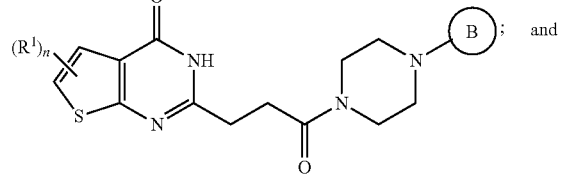

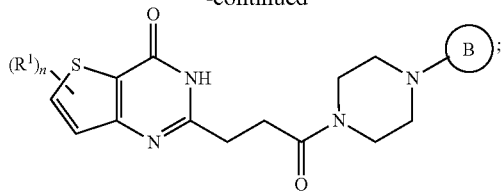

or a pharmaceutically acceptable salt thereof, wherein:

Ring B is aryl, 5-6 membered heteroaryl, or 5-6 membered heterocyclyl, each optionally substituted with one or more substituents represented by $R^3$; and

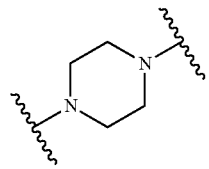 [SMILES: *N1CCN(*)CC1]

is optionally substituted with $(C_1-C_5)$alkyl or hydroxy$(C_1-C_5)$alkyl.

7. The method of claim 5, wherein:

each $R^1$ is independently halogen, $(C_1-C_5)$alkyl, halo$(C_1-C_5)$alkyl, $(C_1-C_5)$alkoxy, halo$(C_1-C_5)$alkoxy or cyano;

each $R^3$ is independently selected from the group consisting of -halogen, —CN, —C(=NR$^e$)NHR$^f$, —S(O)$_i$NR$^e$R$^f$, —C(=O)NR$^e$R$^f$, —C(=S)NR$^e$R$^f$, —O(C=O)NR$^e$R$^f$, —O(C=S)NR$^e$R$^f$, —NR$^e$(C=O)NR$^e$R$^f$, —NR$^e$(C=S)NR$^e$R$^f$, and $(C_1-C_5)$alkyl.

8. The method of claim 7, wherein:

each $R^1$ is independently halogen or $(C_1-C_5)$alkyl;

each $R^3$ is independently selected from the group consisting of -halogen, —CN, —C(=O)NR$^e$R$^f$, —C(=NR$^e$)NHR$^f$ and $(C_1-C_5)$alkyl.

9. The method of claim 8, wherein:

each $R^1$ is independently chloro, fluoro or methyl;

each $R^3$ is independently selected from the group consisting of chloro, fluoro, —CN, —C(=NR$^e$)NHR$^f$, —C(=O)NR$^e$R$^f$ and methyl;

the

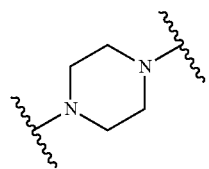 [SMILES: *N1CCN(*)CC1]

group is optionally substituted with methyl or hydroxymethyl.

10. The method of claim 1, wherein Ring B is selected from the group consisting of:

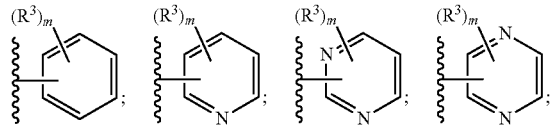

-continued

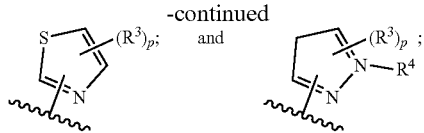

each $R^4$ is —H, $(C_1$-$C_5)$alkyl, or hydroxy $(C_1$-$C_5)$alkyl;
each p is independently 0 or 1; and
each m is 0 or 1, or 2.

11. The method of claim 10, wherein Ring B is selected from the group consisting of

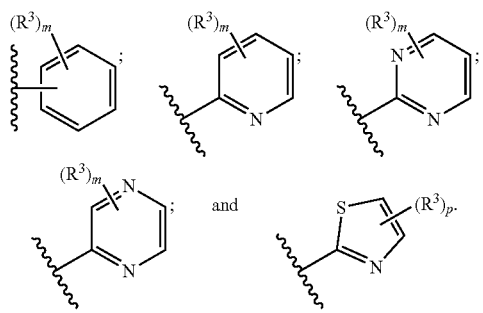

12. The method of claim 7, wherein each $R^e$ and each $R^f$ are independently selected from the group consisting of —H and methyl; or $R^e$ is —H and $R^f$ is —$(C_3$-$C_6)$cycloalkyl or 4-6 membered oxygen-containing heterocyclyl each optionally substituted with $(C_1$-$C_2)$ alkyl.

13. The method of claim 12, wherein each $R^e$ and each $R^f$ are independently selected from the group consisting of —H and methyl; or $R^e$ is —H and $R^f$ is cyclopropyl, cyclobutyl or oxetanyl each optionally substituted with methyl.

14. The method of claim 7, wherein ach $R^3$ is independently selected from the group consisting of chloro, fluoro, —CN, —C(O)NH(cyclopropyl), —C(O)NH$_2$, —C(O)NH(CH$_3$), —C(O)N(CH$_3$)$_2$,

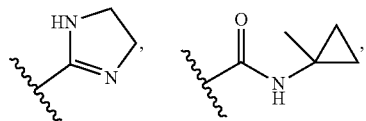

—C(O)NH(cyclobutyl),

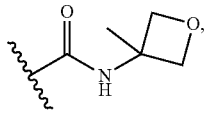 [SMILES: *C(=O)NC1(C)COC1]

—C(=NH)NHCH$_3$, and methyl.

15. The method of claim 5, wherein $R^2$ is —H or $(C_1$-$C_5)$alkyl.

16. The method of claim 15, wherein $R^2$ is —H or methyl.

17. The method of claim 1, wherein the compound is of the following structural formula:

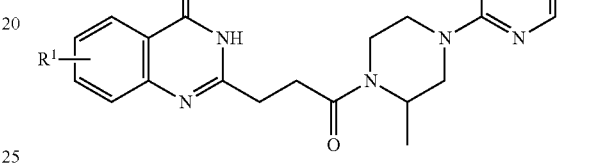

or a pharmaceutically acceptable salt thereof, wherein:
$R^1$ is F or methyl; and
$R^3$ is —CN, —C(=NH)NHCH$_3$,

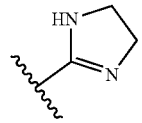 [SMILES: *C1=NCCN1]

or methyl.

18. The method of claim 17, wherein:
$R^1$ is F; and
$R^3$ is —CN.

19. The method of claim 1, wherein the compound is 6-[(3S)-4-[3-(6-fluoro-4-oxo-3H-quinazolin-2-yl)propanoyl]-3-methyl-piperazin-1-yl]pyridine-3-carbonitrile.

20. The compound of claim 1, wherein the compound is 6-[(3S)-4-[3-(5-fluoro-4-oxo-3H-quinazolin-2-yl)propanoyl]-3-methyl-piperazin-1-yl]pyridine-3-carbonitrile.

* * * * *

UNITED STATES PATENT AND TRADEMARK OFFICE
CERTIFICATE OF CORRECTION

PATENT NO. : 11,993,585 B2
APPLICATION NO. : 17/342873
DATED : May 28, 2024
INVENTOR(S) : Taisuke Takahashi et al.

It is certified that error appears in the above-identified patent and that said Letters Patent is hereby corrected as shown below:

In the Claims

In Claim 1, Column 174, Line number 15, please add the term "-$OR^c$" between the terms "-$NO_2$" and "-$NR^aR^b$".

In Claim 1, Column 174, Line number 25, please add the term "-$OR^c$" between the terms "-$NO_2$" and "-$NR^aR^b$".

In Claim 3, Column 175, Line number 58, please add the term "-$OR^c$" between the terms "-$NO_2$" and "-$NR^aR^b$".

In Claim 3, Column 176, Line number 1, please add the term "-$OR^c$" between the terms "-$NO_2$" and "-$NR^aR^b$".

In Claim 3, Column 176, Line number 13, please replace the term "$R^c$" with the term --$R^c$--.

In Claim 4, Column 177, Line number 22, please replace the term "$OR^c$" with the term --$OR^c$--.

In Claim 4, Column 177, Line number 32, please add the term "-$OR^c$" between the terms "-$NO_2$" and "-$NR^aR^b$".

In Claim 5, Column 178, Line number 46, please add the term "-$OR^c$" between the terms "-$NO_2$" and "-$NR^aR^b$".

In Claim 5, Column 178, Line number 56, please add the term "-$OR^c$" between the terms "-$NO_2$" and "-$NR^aR^b$".

In Claim 5, Column 178, Line number 64, please replace the term "-$C_1$-5 alkyl" with the term --$C_{1-5}$ alkyl--.

Signed and Sealed this
Tenth Day of December, 2024

Katherine Kelly Vidal
*Director of the United States Patent and Trademark Office*

CERTIFICATE OF CORRECTION (continued)
U.S. Pat. No. 11,993,585 B2

In Claim 5, Column 178, Line number 65, please replace the term "-C(O)O($C_1$-5 alkyl)" with the term -- -C(O)O($C_{1-5}$ alkyl)--.